US008748107B2

(12) United States Patent
Kavlie et al.

(10) Patent No.: US 8,748,107 B2
(45) Date of Patent: Jun. 10, 2014

(54) ISOLATED ANTIBODIES WHICH BIND TO CXC CHEMOKINE RECEPTOR 4

(75) Inventors: Anita Kavlie, Oslo (NO); Sergej Michailovic Kiprijanov, Oslo (NO)

(73) Assignee: Affitech Research AS, Oslo (NO)

( * ) Notice: Subject to any disclaimer, the term of this patent is extended or adjusted under 35 U.S.C. 154(b) by 0 days.

(21) Appl. No.: 13/024,698

(22) Filed: Feb. 10, 2011

(65) Prior Publication Data

US 2011/0311449 A1  Dec. 22, 2011

Related U.S. Application Data

(60) Provisional application No. 61/303,060, filed on Feb. 10, 2010.

(30) Foreign Application Priority Data

Feb. 10, 2010 (GB) .................................. 1002238.2

(51) Int. Cl.
*G01N 33/53* (2006.01)
*C07K 16/00* (2006.01)
*C12P 21/08* (2006.01)

(52) U.S. Cl.
USPC ............... 435/7.1; 530/388.1; 530/388.22; 530/387.3

(58) Field of Classification Search
None
See application file for complete search history.

(56) References Cited

U.S. PATENT DOCUMENTS

| 6,485,929 | B1 | 11/2002 | Krammer et al. | |
|---|---|---|---|---|
| 6,863,887 | B1 | 3/2005 | Murphy et al. | |
| 7,776,564 | B2 * | 8/2010 | Chu et al. ................ | 435/69.5 |
| 2003/0152913 | A1 | 8/2003 | Hua et al. | |
| 2008/0274100 | A1 | 11/2008 | Ben-Levy et al. | |
| 2010/0104508 | A1 * | 4/2010 | Kuhne et al. ............. | 424/1.49 |
| 2010/0150935 | A1 | 6/2010 | Klinguer-Hamour | |

FOREIGN PATENT DOCUMENTS

| WO | 0135980 | A1 | 5/2001 |
|---|---|---|---|
| WO | 03066830 | A2 | 8/2003 |
| WO | 2004024178 | A1 | 3/2004 |
| WO | 2006089141 | A2 | 8/2006 |
| WO | 2008060367 | A2 | 5/2008 |
| WO | 2009140124 | A1 | 11/2009 |

OTHER PUBLICATIONS

Plett, P. Arthur, et al., "Treatment of circulating CD34+ cells with SDF-1 alpha or anti-CXCR4 antibody enhances migration and NOD/SCID repopulating potential" Exp. Hematol., 30, (2002), 1061-9.
Wei, Lei, et al., "Chondrocyte Death Induced by Pathological Concentration of Chemokine Stromal Cell-Derived Factor-1" J. Rheumatol., 33, (2006), 1818-26.
Zhang, Tianqian, et al., "Preferential Involvement of CX Chemokine Receptor 4 and CX Chemokine Ligand 12 in T-cell Migration toward Melanoma Cells" Cancer Biol. & Therapy, 5, (2006), 1304-12.
Huang, Ming-Bo, et al., "Characterization of Nef-CXCR4 Interactions Important for Apoptosis Induction", J. Virol., 78, (2004), 11084-96.
Database Geneseq [Online], Oct. 16, 2008, "Human 13M57 antibody VH region, h-germline.", XP000002657974, retrieved from EBI accession No. GSP:ATD32841, Database accession No. ATD32841.
Database Geneseq [Online], Mar. 9, 2006, "Human clone 124-152 antibody Vkappa region.", XP000002657975, retrieved from EBI accession No. GSP:AEF11056, Database accession No. AEF11056.
Database Geneseq [Online], Nov. 20, 2003, "Human antibody 1D7 heavy chain amino acid sequence SEQ ID N0:26.", XP002663182, retrieved from EBI accession No. GSP:ADA89182, Database accession No. ADA89182.
Database Geneseq [Online], Jun. 25, 2009, "Human RANTES monoclonal antibody 1D9 VL protein, SEQ 4," XP002663183, retrieved from EBI accession No. GSP:AWV33860, Database accession No. AWV33860.
Database Geneseq [Online], Mar. 5, 2009, "Human anti-PAR-2 antibody Vh protein, SEQ ID 27," XP002663184, retrieved from EBI accession No. GSP:AUP72289, Database accession No. AUP72289.
Database Geneseq [Online], Feb. 7, 2008, "Anti-staphylococci human IgGl light chain protein sequence, SEQ ID 219," XP002663185, retrieved from EBI accession No. GSP:A0D34885, Database accession No. A0D34885.
Database Geneseq [Online], Mar. 20, 2008, "Human CLqR specific antibody VH SEQ ID No. 451," XP002663186, retrieved from EBI accession No. GSP:AQF29829, Database accession No. AQF29829.
Database Geneseq [Online], Sep. 7, 2006, "WNV specific scFv SC04-283 protein," XP002663187, retrieved from EBI accession No. GSP:AE192363 Database accession No. AEI92363.
Database Geneseq [Online], Oct. 29, 2009, "PCSK9-specific antagonist antibody 1B20 VL protein SEQ ID:27," XP002663188, retrieved from ABI accession No. GSP:AXQ60251, Database accession No. AXQ60251.
Dorsam, Robert T. & Gutkind, J. Silvio, "G-protein-coupled receptors and cancer", Nat. Rev. Cancer, 7 (2007), 79-94.
Hoogenboom, Hennie R., et al., "Selection-dominant and nonaccessible epitopes on cell-surface receptors revealed by cell-panning with a large phage antibody library", Eur. J. Biochem, 260, (1999), 774-84.
Sui, Jianhua, et al., "Identification of CD4 and transferrin receptor antibodies by CXCR4 antibody-guided Pathfinder selection", Eur. J. Biochem., 270, (2003), 4497-506.
Baribaud, Frederic, et al., "Antigenically Distinct Conformations of CXCR4", J. Virol., 75 (2001), 8957-67.

(Continued)

*Primary Examiner* — Shulamith H Shafer
(74) *Attorney, Agent, or Firm* — Rothwell, Figg, Ernst & Manbeck, p.c.

(57) ABSTRACT

The present invention provides antibodies which bind to CXC chemokine receptor 4 (CXCR4) and which do not induce significant apoptosis of CXCR4 expressing cells. Also provided are inter alia immunoconjugates and compositions comprising such antibodies and methods and uses involving such antibodies, particularly in the medical and diagnostic fields.

36 Claims, 22 Drawing Sheets

(56) References Cited

OTHER PUBLICATIONS

Figure 6A:
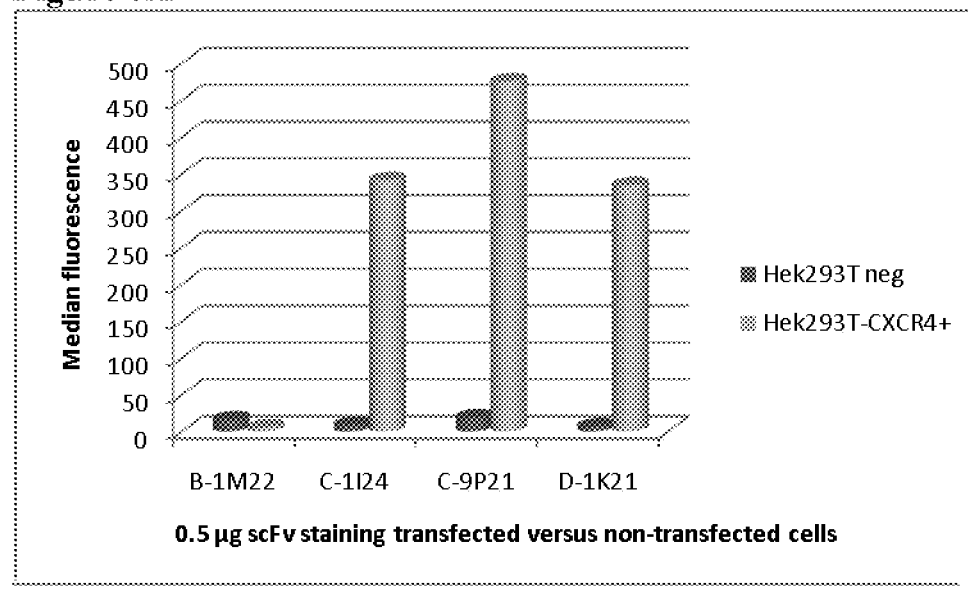

Muller, Anja, et al., "Involvement of chemokine receptors in breast cancer metastasis." Nature, 410, (2001), 50-6.

Liang, Zhongxing, et al., "Blockade of invasion and metastasis of breast cancer cells via targeting CXCR4 with an artificial microRNA." Biochem Biophys Res Commun, 363, (2007), 542-6.

Kim, et al., "Inhibition of the CXCR4/CXCL12 chemokine pathway reduces the development of murine pulmonary metastases." Clin Exp Metastasis, 25, (2008), 201-11.

Xu, Lei, et al., "Direct Evidence that Bevacizumab, an Anti-VEGF Antibody, Up-regilates SDF1α, CXCR4, CXCL6 and Neuropilin 1 in Tumors from Patients with Rectal Cancer." Cancer Res., 69 (2009), 7905-10.

Guleng, Bayasi, et al., "Blockade of the stromal cell-derived factor-1/CXCR4 axis attenuates in vivo tumor growth by inhibiting angiogenesis in a vascular endothelial growth factor-independent manner". Cancer Res., 65 (2005) 5864-71.

Orimo, Akira, et al., "Stromal fibroblasts present in invasive human breast carcinomas promote tumor growth and angiogenesis through elevated SDF-1/CXCL12 secretion." Cell, 121 (2005) 335-48.

Kwong, J., et al., "An antagonist of the chemokine receptor CXCR4 induces mitotic catastrophe in ovarian cancer cells." Mol. Cancer. Ther., 8, (2009) 1893-1905.

Hu, Jinyue, et al., "The expression of functional chemokine receptor CXCR4 is associated with the metastatic potential of human nasopharyngeal carcinoma." Clin. Cancer Res., 11, (2005) 4658-65.

Jacoby, Edgar, et al. "The 7TM G-Protein-Coupled Receptor Target Family", Chem. Med. Chem., 1, (2006), 760-82.

Lee, Hyo Jin, et al. "Chemokine receptor CXCR4 expression, function, and clinical implications in gastric cancer", Int. J. Oncol., 34, (2009), 473-80.

Ehtesham, Moneeb, et al. "CXCR4 expression mediates glioma cell invasiveness", Oncogene, 25, (2006), 2801-6.

* cited by examiner

Figure 1
scFv C-9P21 Nucleotide sequence

CCATGGCCCAGGTGCAGCTGCAGGAGTCCGGGGGAGGCTTAGTTCACCCTGGGGGGTCC
  NcoI    |---------V$_H$ Start (SEQ ID No.34 Start)

CTGAGACTCTCCTGTGCAGCCTCTGGATTCACCTTCAGTAGCTACTGGATGCACTGGGT

CCGCCAAGCTCCAGGGAAGGGGCTGGTGTGGGTCTCACGTATTAATAGTGATGGGAGTA

GCACAAGCTACGCGGACTCCGTGAAGGGCCGATTCACCATCTCCAGAGACAACGCCAAG

AACACGCTGTATCTGCAAATGAACAGTCTGAGAGCCGAGGACACGGCTGTGTATTACTG

TGCGAGAAAAATCTTGGGGGTGGGAGCTAGGTCTCGTCGTTACTTTGACTACTGGGGCC

AGGGAACAATGGTCACCGTCTCTTCA*AAGCTTTCAGGGAGTGCATCCGCCCCAAAACTT*
                          V$_H$ End-----|HindIII--Linker Start
*GAAGAAGGTGAATTTTCAGAAGCACGCGTA*GAAACGACACTCACGCAGTCTCCAGGCAC
          Linker End ------ MluI--|------V$_L$ Start
CCTGTCTTTGTCTCCAGGGGAAAGAGCCACCCTCTCCTGCAGGGCCAGTCAGAGTGTTG

TCAGCAACTATTTAGCCTGGTACCAGCAGAAGCCTGGCCAGGCTCCCAGGCTCCTCATC

TCTGGTGCATCCAACAGGGCCACTGGCATCTCAGACAGGTTCAGTGGCAGTGGGTCTGG

GGCAGACTTCACTCTCACCATCAGCAGAGTCGAGCCTGAAGACTCAGCAGTGTATTACT

GTCAACAGTTTGATAAGTCCACGTGGACGTTCGGCCAAGGGACCAAGGTGGAAATCAAA
                                         (SEQ ID No. 34 End)V$_L$End-----|
GCGGCCGCTGGATCCGAACAAAAGCTGATCTCAGAAGAAGACCTAAACTCACATCACCA
  NotI                    cMyc-tag
TCACCATCAC
 His$_6$-tag scFv C-9P21 Amino acid sequence QVQLQESGGGLVHPGGSLRLSCAASGFTFSSYWMHWVRQAPGKGLVWVSRINSD
|---------V$_H$ Start (SEQ ID No.35 Start)

GSSTSYADSVKGRFTISRDNAKNTLYLQMNSLRAEDTAVYYCARKILGVGARSR

RYFDYWGQGTMVTVSS*KLSGSASAPKLEEGEFSEARV*ETTLTQSPGTLSLSPGE
         V$_H$ End-|-----------Linker--------|------V$_L$ Start
RATLSCRASQSVVSNYLAWYQQKPGQAPRLLISGASNRATGISDRFSGSGSGAD FTLTISRVEPEDSAVYYCQQFDKSTWTFGQGTKVEIKAAAGSEQKLISEEDLNS
         (SEQ ID No. 35 End)V$_L$End------|
HHHHHH

Figure 2
scFv B-1M22 Nucleotide sequence

<u>CCATGGCC</u>CAGGTCCAGCTTGTGCAGTCTGGGGCTGAGGTGAAGAAGCCTGGGTCCTCG
   NcoI   |---------V<sub>H</sub> Start (SEQ ID No.45 Start)

GTGAAGGTCTCCTGCAAGGCTTCTGGAGGCACCTTCAGCAGCTATGCTATCAGCTGGGT

GCGACAGGCCCCTGGACAAGGGCTTGAGTGGATGGGAGGGATCATCCCTATCTTTGGTA

CAGCAAACTACGCACAGAAGTTCCAGGGCAGAGTCACGATTACCGCGGACGAATCCACG

AGCACAGCCTACATGGAGCTGAGGAGCCTGAGATCTGACGACACGGCCGTGTATTACTG

TGCGAGAGATCGGGAGAGATGGCTACAATCCGCGGGCGACTACTGGGGCCAGGGAACCC

TGGTCACTGTCTCCTCA*AAGCTTTCAGGGAGTGCATCCGCCCCAAAACTTGAAGAAGGT*
         V<sub>H</sub> End----|HindIII--Linker Start
*GAATTTTCAGAAGC<u>ACGCGT</u>A*CAGCCTGTGCTGACTCAGTCACCCTCGGTGTCAGTGGC
   Linker End --- MluI---|------V<sub>L</sub> Start
CCCAGGACAGACGGCCAGGATTACCTGTGGGGAAACAACATTGGAAGTAAAAGTGTGC

ACTGGTACCAGCAGAAGCCAGGCCAGGCCCCTGTGCTGGTCGTCTATGATGATAGCGAC

CGGCCCTCAGGGATCCCTGAGCGATTCTCTGGCTCCAACTCTGGGAACACGGCCACCCT

GACCATCAGCAGGGTCGAAGCCGGGGATGAGGCCGACTATTACTGTCAGGTGTGGGATA

GTAGTAGTGATCATTGGGTGTTCGGCGGAGGGACCAAGCTGACCGTCCTAGCGGCCGCT
                             (SEQ ID No. 45 End)V<sub>L</sub>End ----| NotI
GGATCC<u>GAACAAAAGCTGATCTCAGAAGAAGACCTA</u>AACTCA<u>CATCACCATCACCATCAC</u>
            cMyc-tag                           His<sub>6</sub>-tag scFv B-1M22 Amino acid sequence QVQLVQSGAEVKKPGSSVKVSCKASGGTFSSYAISWVRQAPGQGLEWMGGIIPI
|---------V<sub>H</sub> Start (SEQ ID No.46 Start)
FGTANYAQKFQGRVTITADESTSTAYMELRSLRSDDTAVYYCARDRERWLQSAG DYWGQGTLVTVSS*KLSGSASAPKLEEGEFSEARV*QPVLTQSPSVSVAPGQTARI
     V<sub>H</sub> End- |-----------Linker--- ---|------V<sub>L</sub> Start
TCGGNNIGSKSVHWYQQKPGQAPVLVVYDDSDRPSGIPERFSGSNSGNTATLTI SRVEAGDEADYYCQVWDSSSDHWVFGGGTKLTVLAAAGSEQKLISEEDLNSHHH
       (SEQ ID No. 46 End)V<sub>L</sub>End------|
HHH

Figure 3
scFv C-1I24 Nucleotide sequence

<u>CCATGGCC</u>CAGGTCCAGCTGGTACAGTCTGGGGGAGGCGTGGTCCAGCCTGGGAGGTCC
  <u>NcoI</u>    |---------V<sub>H</sub> Start (SEQ ID No.56 Start)

CTGAGACTCTCCTGTGCAGCCTCTGGATTCACCTTCAGTAGCTATGGCATGCACTGGGT

CCGCCAGGCTCCAGGCAAGGGGCTGGAGTGGGTGGCAGTTATATCATATGATGGAAGTA

ATAAATACTATGCAGACTCCGTGAAGGGCCGATTCACCATCTCCAGAGACAATTCCAAG

AACACGCTGTATCTGCAAATGAACAGCCTGAGAGCTGAGGACACGGCTGTGTATTACTG

TGCGAAAGATCTTCCGATTACCCGCGGGACAGGGGCTGACTACTGGGGCCAGGGAACCC

TGGTCACTGTCTCCTCA_AAGCTTTCAGGGAGTGCATCCGCCCCAAAACTTGAAGAAGGT_
          V<sub>H</sub> End----|HindIII--Linker Start
_GAATTTTCAGAAG_<u>_ACGCGTA_</u>CAGTCTGTCCTGATTCAGCCTGCCTCCGTGTCTGGGTC
   Linker End ---- MluI---|------V<sub>L</sub> Start
TCCTGGACAGTCGATCACCATCTCCTGCACTGGAACCAGCAGTGACGTTGGTGGTTATA

ACTATGTCTCCTGGTATCAACAACACCCAGGCAAAGCCCCCAGACTCATGATTTACGAT

GTCACTAGTCGGCCCTCAGGGGTTTCGAATCGCTTCTCTGGCTCCAAGTCTGGCAACAC

GGCCTCCCTGACCATCTCTGGGCTCCAGGCTGAGGACGAGGCTGATTATTACTGCAGTT

CATATGCAGGCAGCTACAGCGTGGTATTCGGCGGAGGGACCAAGGTCACCGTCCTA<u>GCG</u>
                                                                 (SEQ ID No. 56 End)V<sub>L</sub>End----|NotI
<u>GCCGCTGGATCC</u>GAACAAAAGCTGATCTCAGAAGAAGACCTAAACTCA<u>CATCACCATCA</u>
<u>NotI</u>                         cMyc-tag                       His<sub>6</sub>-tag
<u>CCATCAC</u> scFv C-1I24 Amino acid sequence

QVQLVQSGGGVVQPGRSLRLSCAASGFTFSSYGMHWVRQAPGKGLEWVAVISYD
|---------V<sub>H</sub> Start (SEQ ID No.57 Start)
GSNKYYADSVKGRFTISRDNSKNTLYLQMNSLRAEDTAVYYCAKDLPITRGTGA

DYWGQGTLVTVSS_KLSGSASAPKLEEGEFSEARV_QSVLIQPASVSGSPGQSITI
       V<sub>H</sub> End|-----------Linker--------|------V<sub>L</sub> Start
SCTGTSSDVGGYNYVSWYQQHPGKAPRLMIYDVTSRPSGVSNRFSGSKSGNTAS

LTISGLQAEDEADYYCSSYAGSYSVVFGGGTKVTVLAAAGSEQKLISEEDLNSH
          (SEQ ID No. 57 End)V<sub>L</sub>End------|
HHHHH Figure 4
scFv D-1K21 Nucleotide sequence CCATGGCCCAGGTCCAGCTTGTGCAGTCTGGGGCTGAGGTGAAGAAGCCTGGGGCCTCA
  NcoI   |---------V_H Start (SEQ ID No.67 Start)

GTGAAGGTCTCCTGCAAGGCTTCTGGATACACCTTCACCGGCTACTATATGCACTGGGT

GCGACAGGCCCCTGGACAAGGGCTTGAGTGGATGGGACGGATCAACCCTAACAGTGGTG

GCACAAACTATGCACAGAAGTTTCAGGGCAGGGTCACCATGACCAGGGACACGTCCATC

AGCACAGCCTACATGGAGCTGAGCAGGCTGAGATCTGACGACACGGCCGTGTATTACTG

CGCGAGGCGTAACCTGATAGCAGCTCGTCCCCGGAATCGGGGCAGGGATGCTTTTGATA

TCTGGGGCCAAGGGACAATGGTCACCGTCTCTTCA*AAGCTTTCAGGGAGTGCATCCGCC*
                              V_H End-----|HindIII--Linker Start
*CCAAAACTTGAAGAAGGTGAATTTTCAGAAGCACGCGTA*GACATCCAGATGACCCAGTC
              Linker End ------- MluI--|------V_L Start
TCCTTCCACCCTGTCTGCATCTGTAGGAGACAGAGTCACCATCACTTGCCGGGCCAGTC

AGAGTATTGGTGGCTCGTTGGCCTGGTATCAGCAGAAACCAGGGAAAGGCCCTAACCTC

CTGATCTATGCTGCATCCACTTTGCAAAGTGGGGTCCCATCAAGGTTCAGCGGCAGTGG

ATCTGGGACAGAATTCACTCTCACAATCAGCAGCCTGCAGCCTGAAGATTCTGCAACTT

ACTACTGCCAACACTATGAAAGTTATCCCCTCTCTTTCGGCGGCGGGACCAAGCTGGAG
                                        (SEQ ID No. 67 End)V_LEnd-----
ATCAAAGCGGCCGCTGGATCCGAACAAAAGCTGATCTCAGAAGAAGACCTAAACTCACA
------|  NotI                           cMyc-tag
TCACCATCACCATCAC
    His_6-tag scFv D-1K21 Amino acid sequence QVQLVQSGAEVKKPGASVKVSCKASGYTFTGYYMHWVRQAPGQGLEWMGRINPN
|---------V_H Start (SEQ ID No.68 Start)

SGGTNYAQKFQGRVTMTRDTSISTAYMELSRLRSDDTAVYYCARRNLIAARPRN

RGRDAFDIWGQGTMVTVSS*KLSGSASAPKLEEGEFSEARV*DIQMTQSPSTLSAS
              V_H End- |-----------Linker-------|------V_L Start
VGDRVTITCRASQSIGGSLAWYQQKPGKGPNLLIYAASTLQSGVPSRFSGSGSG TEFTLTISSLQPEDSATYYCQHYESYPLSFGGGTKLEIKAAAGSEQKLISEEDL
            (SEQ ID No. 68 End)V_LEnd------|
NSHHHHHH

Figure 5
scFv 9N10 Nucleotide sequence

<u>CCATGGCC</u>CAGGTGCAGCTGCAGGAGTCCGGGGGAGGCTTAGTTCACCCTGGGGGGTCC
  NcoI    |---------V<sub>H</sub> Start (SEQ ID No.100 Start)

CTGAGACTCTCCTGTGCAGCCTCTGGATTCACCTTCAGTAGCTACTGGATGCACTGGGT

CCGCCAAGCTCCAGGGAAGGGGCTGGTGTGGGTCTCACGTATTAATAGTGATGGGAGTA

GCACAAGCTACGCGGACTCCGTGAAGGGCCGATTCACCATCTCCAGAGACAACGCCAAG

AACACGCTGTATCTGCAAATGAACAGTCTGAGAGCCGAGGACACGGCTGTGTATTACTG

TGCGAGAAAAATCTTGGGGGTGGGAGCTAGGTCTCGTCGTTACTTTGACTACTGGGGCC

AGGGAACAATGGTCACCGTCTCTTCA*AAGCTTTCAGGGAGTGCATCCGCCCCAAAACTT*
                 V<sub>H</sub> End----|HindIII--Linker Start
*GAAGAAGGTGAATTTTCAGAAGCACGCGTA*GATATTGTGCTGACCCAGACTCCAGACTC
          Linker End ----- MluI--|------V<sub>L</sub> Start
CCTGGCTGTGTCTCTGGGCGAGACGACCACCATCAACTGCAAGTCCAGCCAGAGTGTTT

TACACAGCTCCAACAATAAGAACTACTTAGCTTGGTACCAGCAGAAACCAGGACAGCCT

CCTAAGCTGCTCATTTACTGGGCATCTACCCGGGAATCCGGGGTCCCTGACCGATTCAG

TGGCAGCGGGTCTGGGACAGATTTCACTCTCACCATCAGCAACCTGCAGCCTGAAGATG

TGGCTTTTTACTACTGTCTGCAATATTCTACTTTTCCTCGGACGTTCGGCCAAGGGACC
                                                                     (SEQ ID No. 100----
AAGGTGGAGATCAAAGCGGCCGCTGGATCC<u>GAACAAAAGCTGATCTCAGAAGAAGACCT</u>
-----End)V<sub>L</sub>End----|   NotI                       cMyc-tag
<u>AAACTCA</u><u>CATCACCATCACCATCAC</u>
             His<sub>6</sub>-tag scFv 9N10 Amino acid sequence

QVQLQESGGGLVHPGGSLRLSCAASGFTFSSYWMHWVRQAPGKGLVWVSRINSD
|---------V<sub>H</sub> Start (SEQ ID No.101 Start)
GSSTSYADSVKGRFTISRDNAKNTLYLQMNSLRAEDTAVYYCARKILGVGARSR RYFDYWGQGTMVTVSS*KLSGSASAPKLEEGEFSEARV*DIVLTQTPDSLAVSLGE
        V<sub>H</sub> End-|-----------Linker-------|------V<sub>L</sub> Start
TTTINCKSSQSVLHSSNNKNYLAWYQQKPGQPPKLLIYWASTRESGVPDRFSGS GSGTDFTLTISNLQPEDVAFYYCLQYSTFPRTFGQGTKVEIKAAAGSEQKLISE
                (SEQ ID No. 101 End)V<sub>L</sub>End-----|
EDLNSHHHHHH

ISOLATED ANTIBODIES WHICH BIND TO CXC CHEMOKINE RECEPTOR 4

This application is a non-provisional application of U.S. provisional patent application No. 61/303,060, filed Feb. 10, 2010 and also claims priority from GB application 1002238.2, filed Feb. 10, 2010. These prior applications are incorporated herein by reference.

FIELD OF THE INVENTION

The present invention relates generally to the fields of antibodies, CXCR4 biology and related therapies. More particularly, it provides antibodies that bind to CXCR4. Such anti-CXCR4 antibodies have diagnostic and therapeutic uses in diseases and conditions associated with CXCR4, such as the treatment of cancer and viral infections, especially HIV, treatment of inflammatory and immune diseases, monitoring or predicting tumor growth and progression e.g. by imaging tumor blood vessels, inhibiting or reducing the formation of metastasis and inhibiting or reducing angiogenesis. The antibody-based compositions and methods of the invention also extend to the use of immunoconjugates and other therapeutic combinations, kits and methods.

BACKGROUND

With more than 800 members, G-protein-coupled receptors (GPCRs) represent the largest family of cell surface molecules involved in signal transmission, accounting for >2% of the total genes encoded by human genome. Members of the GPCR superfamily share a common membrane topology: an extracellular N-terminus, an intracellular C-terminus and seven transmembrane (TM) helices, which are connected by three intracellular loops and three extracellular loops. On the basis of their shared topological structure, GPCRs are also referred to as seven transmembrane (7TM) receptors. These receptors control key physiological functions, including neurotransmission, hormone and enzyme release from endocrine and exocrine glands, immune responses, cardiac- and smooth-muscle contraction and blood pressure regulation. Their dysfunction contributes to some of the most prevalent human diseases. Emerging experimental and clinical data indicate that GPCRs have a crucial role in cancer progression and metastasis. Hence, there is the possibility that some GPCRs may be suitable targets for anti-cancer drugs.

Chemokines play an important role inter alia in immune and inflammatory responses in various diseases and disorders, including cancer, viral infections, asthma and allergic diseases, as well as autoimmune pathologies such as rheumatoid arthritis and atherosclerosis. Depending on their structure, chemokines are classified as C-C chemokines (containing a cysteine-cysteine motif) or C-X-C chemokines (containing a cysteine-X-cysteine motif). Receptors that bind such chemokines are thus classified as members of the CCR or CXCR family, respectively.

CXCR4 (also called fusin, HM89, LESTR, HUMSTR) is an alpha-chemokine receptor specific for stromal-derived-factor-1 (SDF-1, also called CXCL12 and PBSF), a molecule endowed with potent chemotactic activity for lymphocytes. This receptor is one of several chemokine receptors that HIV isolates can use to infect CD4$^+$ T cells. Several normal tissues express CXCR4. Notable examples of cells where expression has been demonstrated, both in terms of mRNA and the functional protein, include: hematopoietic cells/bone marrow progenitor cells; cells of the immune system, e.g. T cells, pre-B and plasma cells, dendritic cells, NK cells; other blood cells, e.g. monocytes, mast cells, platelets; cells of the nervous system, e.g. neurons, astrocytes, microglia; other cells, e.g. endothelial cells, vascular smooth muscle, gastrointestinal epithelium, and certain other epithelial cells.

CXCR4 is expressed in a variety of tumours and plays a decisive role in the pathophysiology of cancer, particularly in cancer metastasis (Dorsam and Gutkind, 2007, G-protein-coupled receptors and cancer. Nat Rev Cancer 7: 79-94). CXCR4 expression has been found in almost all tumours studied. It is also of interest that SDF-1 is expressed at particularly high levels in liver, lung, bone marrow, lymph nodes, and (at somewhat lower levels) in brain, i.e. sites to which cancers typically metastasize. Potential indications for an agent such as an antibody targeting CXCR4 include cancers (e.g. metastatic cancers), e.g. of breast, prostate, pancreas, esophagus, colorectal, liver and lung (both SCLC and NSCLC), as well as malignant or metastatic melanoma, brain tumours (glioma), head-and-neck cancers, certain leukemias, lymphomas such as non-Hodgkins lymphoma, childhood tumours (e.g. neuroblastoma), renal cancer, hemangioblastoma. Overexpressed CXCR4 has been found in several other cancers, including lung tumours, non-small cell lung cancer, ovarian cancer, cervical cancer, papillary thyroid carcinomas, osteosarcomas, and other malignancies. An anti-CXCR4 antibody can also be used for treatment of viral infections such as HIV or other retroviral infections, and in the treatment of immune diseases such as autoimmune diseases, inflammatory diseases and in the inhibition of angiogenesis and vascularization.

Due to their complex structures, GPCRs are considered as "difficult targets" for raising specific antibodies. They can neither be easily purified from the membrane fraction of lysed cells, nor be recombinantly produced in different expression systems as correctly folded soluble proteins.

The difficulties associated with generating antibodies against GPCRs are set out in Hoogenboom et al. Eur. J. Biochem 260, 774-784 (1999). Furthermore, Sui et al. Eur. J. Biochem 270, 4497-4506 (2003) explain the difficulties associated with trying to obtain human antibodies against the GPCR chemokine receptor CXCR4 and report that even using the pathfinder method combined with step-back selection no specific antibodies could be identified. Thus, in the field of GPCRs, the generation of specific antibodies remains a major challenge.

Northwest Biotherapeutics Inc. is developing monoclonal antibodies against CXCR4, some of which are in late stage preclinical development. Data suggesting the potential efficacy of CXCR4 antibodies were gathered in animal models by NWB and others. Subsequent development may include humanization of selected antibodies and toxicity studies in preparation for Phase I clinical trials.

MDX-1338 is an anti-human CXCR4-specific, fully human monoclonal antibody from Medarex. In vitro studies demonstrated that MDX-1338 binds to CXCR4-expressing cells with low nanomolar affinity. MDX-1338 blocks CXCL12 ligand binding to CXCR4 expressing cells and inhibits CXCL12 induced migration and calcium flux with low nanomolar EC$_{50}$ values. MDX-1338 is an IgG4, and thus lacks ADCC and CDC activity. MDX-1338 induces apoptosis in a range of CXCR4 expressing cell lines and also has anti-tumor activity in multiple AML and lymphoma tumor xenograft models.

In addition, there are a number of small molecule compounds and peptides at different stages of development that target CXCR4/SDF-1.

The inventors have recognized that the identification of additional antibodies that recognize CXCR4 would be of benefit in expanding the number of therapeutic options. As discussed above however, the nature of GPCRs such as CXCR4 means that the development of such antibodies poses real challenges.

In particular, there is a need for human antibodies to CXCR4 which recognise CXCR4 in its native membrane bound form. Although human antibodies are generally recognized to display advantages, it is known that the development of human antibodies that have high enough affinities and appropriate functional properties to make them candidates for successful human therapy is by no means straightforward. This is even more so the case with GPCRs, due to their complex and transmembrane nature.

DESCRIPTION OF THE INVENTION

The present invention overcomes certain limitations in the prior art by providing new therapeutic compositions and methods for use in the safe and effective treatment of tumors, viral infections and other diseases and conditions in which CXCR4+ cells are involved such as inflammatory or immune disorders. The invention provides antibodies that bind to CXCR4, preferably to an epitope within one or more of the extracellular domains of CXCR4, particularly human antibodies. Such antibodies are effective in treating tumors and viral infections and other diseases and conditions in which CXCR4+ cells are involved, such as inflammatory or immune disorders. The compositions and methods of the invention also extend to the use of immunoconjugates and combinations using this particular category of antibodies.

A particular advantage of the antibodies of the present invention is that the antibodies do not induce significant apoptosis of CXCR4 expressing cells. This contrasts with leading antibodies in the clinical field (for example, the Medarex antibodies as described in WO 2008/060367), which do induce such apoptosis. As CXCR4 is expressed on a significant number of normal cells, this lack of induction of apoptosis is a real therapeutic advantage to prevent too much unwanted cell killing and such antibodies thus have a favourable safety profile.

An additional or alternative preferred property of the antibodies of the invention described herein is that the antibodies are antagonistic antibodies. Thus, the property of not inducing significant apoptosis is preferably also combined with the property that the antibodies are antagonistic antibodies, i.e. they block or inhibit the function of CXCR4, by for exampling blocking or inhibiting the receptor-ligand interaction and/or blocking or inhibiting downstream signalling events from the CXCR4 receptor, e.g. blocking or inhibiting ligand induced or mediated signalling via CXCR4. This property is important for use of the antibodies in therapy as opposed to their use merely for labelling CXCR4 expressing cells, e.g. for diagnosis.

In this regard, it is known that CXCR4 is expressed on a large range of healthy/normal cells and that both CXCR4 and its ligand SDF-1 are important in development. However, as discussed above, it has also been shown that CXCR4 is overexpressed in almost all malignant tumors, and contributes to their growth. Perhaps even more importantly, SDF-1 is usually expressed strongly in those tissues which are the most likely to carry metastases, such as lymph nodes, bone marrow, lung, liver, etc., and it is largely accepted that the tumor cells migrate along a SDF-1 gradient. The main purpose of the antibodies of the invention is therefore to limit tumor growth and to prevent formation of metastasis by inhibiting the function of CXCR4, e.g. by blocking or inhibiting the receptor-ligand interaction. CXCR4 is also believed to be involved in angiogenesis, so blocking or inhibiting the function of CXCR4 can also be used to effect angiogenesis and tumor vascularization.

The blocking or inhibition of function, in particular by blocking or inhibiting the receptor-ligand interaction, is also important in the use of the antibodies of the invention to treat inflammatory and autoimmune disease. Again, the primary goal is not to kill CXCR4+ cells, but to downregulate their activity (in autoimmune diseases) and to prevent or reduce the migration of CXCR4+ cells to sites of inflammation (useful in both inflammatory and autoimmune diseases).

The antagonistic activity (blocking or inhibition of function of CXCR4) is also important in the use of the antibodies of the invention to treat infections, e.g. viral, bacterial, fungal or parasitic infections in which CXCR4 plays a functional role. Examples of such viral infections are retroviral infections, and in particular HIV, where some strains (CXCR4 tropic strains) have been shown to use the CXCR4 receptor to infect host cells. Thus, blocking or inhibiting the CXCR4 receptor can limit the spread of HIV, e.g. by blocking or inhibiting infection of CXCR4+ cells by HIV.

Although, as discussed above, it is believed that the primary mode of action of the antibodies of the invention is via their antagonistic properties (advantageously combined with their ability not to induce significant apoptosis of CXCR4+ cells), in some embodiments the antibodies of the invention are capable of inducing selective elimination (killing) of CXCR4+ cells. Such selective elimination may be via mechanisms such as ADCC, CDC, or the induction of mitotic catastrophe (in particular in dividing cells such as tumor cells) but does not appear to involve the induction of significant apoptosis.

The present inventors have prepared CXCR4-specific antibodies that bind to CXCR4.

For example, the antibodies bind to CXCR4+ cells such as cells transfected with CXCR4 and cells which naturally express CXCR4. In particular, the antibodies bind to HEK293T-cells transfected with CXCR4, DT40-cells transfected with CXCR4 and Ramos (B-cells), Jurkat (T-cell leukaemia) and CCRF-CEM (human T-cell leukemia) which naturally express CXCR4 (see Examples 2, 3 and 4).

Importantly, the antibodies do not significantly bind to CXCR4– cells, i.e. cells which do not express CXCR4. In particular, the antibodies do not significantly bind to non-CXCR4-transfected cells or to cells which naturally do not express CXCR4.

The antibodies also inhibit the binding of ligands which are known to bind CXCR4, e.g. the natural ligand SDF-1a (also referred to herein as SDF-1) and/or other ligands (e.g. non-native ligands) which bind to CXCR4, such as AMD-3100 (a chemical compound with very high specificity for CXCR4 and which inhibits CXCR4) (see Example 3).

Thus, the antibodies disclosed herein bind specifically to CXCR4, making them suitable candidates for diagnostics and therapy of the conditions discussed herein.

Amino acid and/or DNA sequences of preferred antibody molecules of the invention which bind to CXCR4, their $V_H$ and $V_L$ domains including complementarity determining regions (CDRs), are set forth in the various SEQ ID NOs. listed herein.

Thus, the present invention provides an antibody which binds to CXCR4 and has the property of not inducing significant apoptosis of CXCR4 expressing cells. Preferably the antibody is an antagonistic antibody which blocks or inhibits one or more of the functions of CXCR4, for example, blocks or inhibits the binding of SDF-1 (or other CXCR4 ligands such as AMD-3100) to CXCR4, blocks or inhibits migration of CXCR4+ cells in response to SDF-1 (or other CXCR4 ligand), blocks or inhibits Ca²⁺ flux induced by addition of SDF-1 (or other CXCR4 ligand) to CXCR4+ cells, or blocks or inhibits any other downstream signalling events from the CXCR4 receptor.

Preferably, the antibody is isolated. Also preferably, the antibody is human and/or the CXCR4 is preferably human. Preferably, the antibody binds to an epitope in the extracellular domain of CXCR4. Thus, any reference to "binding to CXCR4" includes the preferred embodiment of "binding to an epitope in the extracellular domain of CXCR4". Other preferred properties of the antibodies of the invention are one or more of the ability to induce ADCC of CXCR4 expressing cells (CXCR4+ cells), the ability to induce CDC of CXCR4 expressing cells and the ability to bind at least to human CXCR4, more preferably to human and monkey CXCR4 or to human and mouse CXCR4, most preferably to human, mouse and monkey CXCR4. When cross species reactivity is observed, even more preferably the antibodies bind to human and monkey or to human and mouse CXCR4 with similar affinities. Preferably the antibodies of the invention display anti-tumor activity, e.g. growth inhibition of tumor cells, in vivo.

Thus, the invention preferably provides an isolated human antibody which binds to an epitope in the extracellular domain of human CXCR4 and which preferably has the property of not inducing significant apoptosis of CXCR4 expressing cells. Thus, in all the embodiments described herein, the property of not inducing significant apoptosis of CXCR4 expressing cells is a preferred feature.

In one embodiment, the present invention provides an antibody that binds to CXCR4 and which has the property of not inducing significant apoptosis of CXCR4 expressing cells, comprising a heavy chain CDR1 domain comprising the amino acid sequence of SEQ ID NO: 1, 7, 13, or 19, or a sequence substantially homologous to any one of these sequences.

Alternatively or in addition, in an embodiment of the invention, the antibody that binds to CXCR4 and which has the property of not inducing significant apoptosis of CXCR4 expressing cells comprises a heavy chain CDR2 domain comprising the amino acid sequence of SEQ ID NO: 2, 8, 14, or 20, or a sequence substantially homologous to any one of these sequences.

Alternatively or in addition, in an embodiment of the invention, the antibody that binds to CXCR4 and which has the property of not inducing significant apoptosis of CXCR4 expressing cells comprises a heavy chain CDR3 domain comprising the amino acid sequence of SEQ ID NO: 3, 9, 15 or 21, or a sequence substantially homologous to any one of these sequences.

Alternatively or in addition, in an embodiment of the invention, the antibody that binds to CXCR4 and which has the property of not inducing significant apoptosis of CXCR4 expressing cells comprises a light chain CDR1 domain comprising the amino acid sequence of SEQ ID NO: 4, 10, 16, 22 or 88, or a sequence substantially homologous to any one of these sequences.

Alternatively or in addition, in an embodiment of the invention, the antibody that binds to CXCR4 and which has the property of not inducing significant apoptosis of CXCR4 expressing cells comprises a light chain CDR2 domain comprising the amino acid sequence of SEQ ID NO: 5, 11, 17, 23, or 89, or a sequence substantially homologous to any one of these sequences.

Alternatively or in addition, in an embodiment of the invention, the antibody that binds to CXCR4 and which has the property of not inducing significant apoptosis of CXCR4 expressing cells comprises a light chain CDR3 domain comprising the amino acid sequence of SEQ ID NO: 6, 12, 18, 24 or 90, or a sequence substantially homologous to any one of these sequences.

Thus, in certain embodiments, the invention provides an antibody that binds to CXCR4 and which has the property of not inducing significant apoptosis of CXCR4 expressing cells, comprising one or more heavy chain CDR domains, wherein the heavy chain CDR domain is selected from the group consisting of:
(a) a heavy chain CDR1 domain comprising the amino acid sequence of SEQ ID NO: 1, 7, 13, or 19, or a sequence substantially homologous thereto;
(b) a heavy chain CDR2 domain comprising the amino acid sequence of SEQ ID NO: 2, 8, 14, or 20, or a sequence substantially homologous thereto; and
(c) a heavy chain CDR3 domain comprising the amino acid sequence of SEQ ID NO: 3, 9, 15 or 21, or a sequence substantially homologous thereto.

The invention also provides, in certain embodiments an antibody that binds to binds to CXCR4 and which has the property of not inducing significant apoptosis of CXCR4 expressing cells, comprising one or more light chain CDR domains, wherein the light chain CDR domain is selected from the group consisting of:
(a) a light chain CDR1 domain comprising the amino acid sequence of SEQ ID NO: 4, 10, 16, 22 or 88, or a sequence substantially homologous thereto;
(b) a light chain CDR2 domain comprising the amino acid sequence of SEQ ID NO: 5, 11, 17, 23 or 89, or a sequence substantially homologous thereto; and
(c) a light chain CDR3 domain comprising the amino acid sequence of SEQ ID NO: 6, 12, 18, 24 or 90, or a sequence substantially homologous thereto.

In certain preferred embodiments, the antibody that binds to CXCR4 and which has the property of not inducing significant apoptosis of CXCR4 expressing cells comprises both
(a) a heavy chain CDR3 comprising the amino acid sequence of SEQ ID NO: 3, or a sequence substantially homologous thereto and
(b) a light chain CDR3 comprising the amino acid sequence of SEQ ID NO: 6, or a sequence substantially homologous thereto.

More preferably, a heavy chain CDR1 domain comprising the amino acid sequence of SEQ ID NO: 1, or a sequence substantially homologous thereto, and/or a light chain CDR1 domain comprising the amino acid sequence of SEQ ID NO: 4, or a sequence substantially homologous thereto, and/or a heavy chain CDR2 domain comprising the amino acid sequence of SEQ ID NO: 2, or a sequence substantially homologous thereto, and/or a light chain CDR2 domain comprising the amino acid sequence of SEQ ID NO: 5, or a sequence substantially homologous thereto, are also present.

In certain preferred embodiments, the antibody that binds to CXCR4 and which has the property of not inducing significant apoptosis of CXCR4 expressing cells comprises both
(a) a heavy chain CDR3 comprising the amino acid sequence of SEQ ID NO: 9, or a sequence substantially homologous thereto, and
(b) a light chain CDR3 comprising the amino acid sequence of SEQ ID NO: 12, or a sequence substantially homologous thereto.

More preferably, a heavy chain CDR1 domain comprising the amino acid sequence of SEQ ID NO: 7, or a sequence substantially homologous thereto, and/or a light chain CDR1 domain comprising the amino acid sequence of SEQ ID NO:

10 or a sequence substantially homologous thereto, and/or a heavy chain CDR2 domain comprising the amino acid sequence of SEQ ID NO: 8, or a sequence substantially homologous thereto, and/or a light chain CDR2 domain comprising the amino acid sequence of SEQ ID NO: 11, or a sequence substantially homologous thereto, are also present.

In certain preferred embodiments, the antibody that binds to CXCR4 and which has the property of not inducing significant apoptosis of CXCR4 expressing cells comprises both (a) a heavy chain CDR3 comprising the amino acid sequence of SEQ ID NO: 15, or a sequence substantially homologous thereto, and
(b) a light chain CDR3 comprising the amino acid sequence of SEQ ID NO: 18, or a sequence substantially homologous thereto.

More preferably, a heavy chain CDR1 domain comprising the amino acid sequence of SEQ ID NO: 13, or a sequence substantially homologous thereto, and/or a light chain CDR1 domain comprising the amino acid sequence of SEQ ID NO: 16, or a sequence substantially homologous thereto, and/or a heavy chain CDR2 domain comprising the amino acid sequence of SEQ ID NO: 14, or a sequence substantially homologous thereto, and/or a light chain CDR2 domain comprising the amino acid sequence of SEQ ID NO: 17, or a sequence substantially homologous thereto, are also present.

In certain preferred embodiments, the antibody that binds to CXCR4 and which has the property of not inducing significant apoptosis of CXCR4 expressing cells comprises both (a) a heavy chain CDR3 comprising the amino acid sequence of SEQ ID NO: 21, or a sequence substantially homologous thereto, and
(b) a light chain CDR3 comprising the amino acid sequence of SEQ ID NO: 24, or a sequence substantially homologous thereto.

More preferably, a heavy chain CDR1 domain comprising the amino acid sequence of SEQ ID NO: 19, or a sequence substantially homologous thereto, and/or a light chain CDR1 domain comprising the amino acid sequence of SEQ ID NO: 22, or a sequence substantially homologous thereto, and/or a heavy chain CDR2 domain comprising the amino acid sequence of SEQ ID NO: 20, or a sequence substantially homologous thereto, and/or a light chain CDR2 domain comprising the amino acid sequence of SEQ ID NO: 23, or a sequence substantially homologous thereto, are also present.

In certain preferred embodiments, the antibody that binds to CXCR4 and which has the property of not inducing significant apoptosis of CXCR4 expressing cells comprises both (a) a heavy chain CDR3 comprising the amino acid sequence of SEQ ID NO: 3, or a sequence substantially homologous thereto, and
(b) a light chain CDR3 comprising the amino acid sequence of SEQ ID NO: 90, or a sequence substantially homologous thereto.

More preferably, a heavy chain CDR1 domain comprising the amino acid sequence of SEQ ID NO: 1, or a sequence substantially homologous thereto, and/or a light chain CDR1 domain comprising the amino acid sequence of SEQ ID NO: 88, or a sequence substantially homologous thereto, and/or a heavy chain CDR2 domain comprising the amino acid sequence of SEQ ID NO: 2, or a sequence substantially homologous thereto, and/or a light chain CDR2 domain comprising the amino acid sequence of SEQ ID NO: 89, or a sequence substantially homologous thereto, are also present.

In one preferred embodiment, the heavy chain CDR1 comprising the amino acid sequence of SEQ ID NO: 1, or a sequence substantially homologous thereto, CDR2 comprising the amino acid sequence of SEQ ID NO: 2, or a sequence substantially homologous thereto, and CDR3 comprising the amino acid sequence of SEQ ID NO: 3, or a sequence substantially homologous thereto, are present individually or in combination.

In yet another preferred embodiment, the light chain CDR1 comprising the amino acid sequence of SEQ ID NO: 4, or a sequence substantially homologous thereto, CDR2 comprising the amino acid sequence of SEQ ID NO: 5, or a sequence substantially homologous thereto, and CDR3 comprising the amino acid sequence of SEQ ID NO: 6, or a sequence substantially homologous thereto, are present individually or in combination.

In one preferred embodiment, the heavy chain CDR1 comprising the amino acid sequence of SEQ ID NO: 7, or a sequence substantially homologous thereto, CDR2 comprising the amino acid sequence of SEQ ID NO: 8, or a sequence substantially homologous thereto, and CDR3 comprising the amino acid sequence of SEQ ID NO: 9, or a sequence substantially homologous thereto, are present individually or in combination.

In yet another preferred embodiment, the light chain CDR1 comprising the amino acid sequence of SEQ ID NO: 10, or a sequence substantially homologous thereto, CDR2 comprising the amino acid sequence of SEQ ID NO: 11, or a sequence substantially homologous thereto, and CDR3 comprising the amino acid sequence of SEQ ID NO: 12, or a sequence substantially homologous thereto, are present individually or in combination.

In one preferred embodiment, the heavy chain CDR1 comprising the amino acid sequence of SEQ ID NO: 13, or a sequence substantially homologous thereto, CDR2 comprising the amino acid sequence of SEQ ID NO: 14, or a sequence substantially homologous thereto, and CDR3 comprising the amino acid sequence of SEQ ID NO: 15, or a sequence substantially homologous thereto, are present individually or in combination.

In yet another preferred embodiment, the light chain CDR1 comprising the amino acid sequence of SEQ ID NO: 16, or a sequence substantially homologous thereto, CDR2 comprising the amino acid sequence of SEQ ID NO: 17, or a sequence substantially homologous thereto, and CDR3 comprising the amino acid sequence of SEQ ID NO: 18, or a sequence substantially homologous thereto, are present individually or in combination.

In one preferred embodiment, the heavy chain CDR1 comprising the amino acid sequence of SEQ ID NO: 19, or a sequence substantially homologous thereto, CDR2 comprising the amino acid sequence of SEQ ID NO: 20, or a sequence substantially homologous thereto, and CDR3 comprising the amino acid sequence of SEQ ID NO: 21, or a sequence substantially homologous thereto, are present individually or in combination.

In yet another preferred embodiment, the light chain CDR1 comprising the amino acid sequence of SEQ ID NO: 22, or a sequence substantially homologous thereto, CDR2 comprising the amino acid sequence of SEQ ID NO: 23, or a sequence substantially homologous thereto, and CDR3 comprising the amino acid sequence of SEQ ID NO: 24, or a sequence substantially homologous thereto, are present individually or in combination.

In yet another preferred embodiment, the light chain CDR1 comprising the amino acid sequence of SEQ ID NO: 88, or a sequence substantially homologous thereto, CDR2 comprising the amino acid sequence of SEQ ID NO: 89, or a sequence substantially homologous thereto, and CDR3 comprising the amino acid sequence of SEQ ID NO: 90, or a sequence substantially homologous thereto, are present individually or in combination.

Viewed alternatively, in certain embodiments, the present invention provides an antibody that binds to CXCR4 and which has the property of not inducing significant apoptosis of CXCR4 expressing cells, comprising a heavy chain CDR3 domain comprising the amino acid sequence of SEQ ID NO: 3, or a sequence substantially homologous thereto and/or a light chain CDR3 domain comprising the amino acid sequence of SEQ ID NO: 6, or a sequence substantially homologous thereto.

Said antibody optionally further comprises a heavy chain CDR2 domain comprising the amino acid sequence of SEQ ID NO: 2, or a sequence substantially homologous thereto, and/or a light chain CDR2 domain comprising the amino acid sequence of SEQ ID NO: 5, or a sequence substantially homologous thereto, and/or further comprises a heavy chain CDR1 domain comprising the amino acid sequence of SEQ ID NO:1, or a sequence substantially homologous thereto, and/or a light chain CDR1 domain comprising the amino acid sequence of SEQ ID NO:4, or a sequence substantially homologous thereto.

In certain embodiments, the present invention provides an antibody that binds to CXCR4 and which has the property of not inducing significant apoptosis of CXCR4 expressing cells, comprising a heavy chain CDR3 domain comprising the amino acid sequence of SEQ ID NO:9, or a sequence substantially homologous thereto, and/or a light chain CDR3 domain comprising the amino acid sequence of SEQ ID NO: 12, or a sequence substantially homologous thereto.

Said antibody optionally further comprises a heavy chain CDR2 domain comprising the amino acid sequence of SEQ ID NO: 8, or a sequence substantially homologous thereto, and/or a light chain CDR2 domain comprising the amino acid sequence of SEQ ID NO: 11, or a sequence substantially homologous thereto, and/or further comprises a heavy chain CDR1 domain comprising the amino acid sequence of SEQ ID NO: 7, or a sequence substantially homologous thereto, and/or a light chain CDR1 domain comprising the amino acid sequence of SEQ ID NO: 10, or a sequence substantially homologous thereto.

In certain embodiments, the present invention provides an antibody that binds to CXCR4 and which has the property of not inducing significant apoptosis of CXCR4 expressing cells, comprising a heavy chain CDR3 domain comprising the amino acid sequence of SEQ ID NO: 15, or a sequence substantially homologous thereto, and/or a light chain CDR3 domain comprising the amino acid sequence of SEQ ID NO: 18, or a sequence substantially homologous thereto.

Said antibody optionally further comprises a heavy chain CDR2 domain comprising the amino acid sequence of SEQ ID NO: 14, or a sequence substantially homologous thereto, and/or a light chain CDR2 domain comprising the amino acid sequence of SEQ ID NO: 17, or a sequence substantially homologous thereto, and/or further comprises a heavy chain CDR1 domain comprising the amino acid sequence of SEQ ID NO: 13, or a sequence substantially homologous thereto, and/or a light chain CDR1 domain comprising the amino acid sequence of SEQ ID NO: 16, or a sequence substantially homologous thereto.

In certain embodiments, the present invention provides an antibody that binds to CXCR4 and which has the property of not inducing significant apoptosis of CXCR4 expressing cells, comprising a heavy chain CDR3 domain comprising the amino acid sequence of SEQ ID NO: 21, or a sequence substantially homologous thereto, and/or a light chain CDR3 domain comprising the amino acid sequence of SEQ ID NO: 24, or a sequence substantially homologous thereto.

Said antibody optionally further comprises a heavy chain CDR2 domain comprising the amino acid sequence of SEQ ID NO: 20, or a sequence substantially homologous thereto, and/or a light chain CDR2 domain comprising the amino acid sequence of SEQ ID NO: 23, or a sequence substantially homologous thereto, and/or further comprises a heavy chain CDR1 domain comprising the amino acid sequence of SEQ ID NO: 19, or a sequence substantially homologous thereto, and/or a light chain CDR1 domain comprising the amino acid sequence of SEQ ID NO: 22, or a sequence substantially homologous thereto.

In certain embodiments, the present invention provides an antibody that binds to CXCR4 and which has the property of not inducing significant apoptosis of CXCR4 expressing cells, comprising a heavy chain CDR3 domain comprising the amino acid sequence of SEQ ID NO: 3, or a sequence substantially homologous thereto, and/or a light chain CDR3 domain comprising the amino acid sequence of SEQ ID NO: 90, or a sequence substantially homologous thereto.

Said antibody optionally further comprises a heavy chain CDR2 domain comprising the amino acid sequence of SEQ ID NO: 2, or a sequence substantially homologous thereto, and/or a light chain CDR2 domain comprising the amino acid sequence of SEQ ID NO: 89, or a sequence substantially homologous thereto, and/or further comprises a heavy chain CDR1 domain comprising the amino acid sequence of SEQ ID NO: 1, or a sequence substantially homologous thereto, and/or a light chain CDR1 domain comprising the amino acid sequence of SEQ ID NO: 88, or a sequence substantially homologous thereto.

Viewed alternatively, in certain embodiments, the present invention provides an antibody that binds to binds to CXCR4 and which has the property of not inducing significant apoptosis of CXCR4 expressing cells, comprising a heavy chain CDR2 domain comprising the amino acid sequence of SEQ ID NO: 2, or a sequence substantially homologous thereto, and/or a light chain CDR2 domain comprising the amino acid sequence of SEQ ID NO: 5, or a sequence substantially homologous thereto.

Said antibody optionally further comprises a heavy chain CDR3 domain comprising the amino acid sequence of SEQ ID NO: 3, or a sequence substantially homologous thereto, and/or a light chain CDR3 domain comprising the amino acid sequence of SEQ ID NO: 6, or a sequence substantially homologous thereto, and/or further comprises a heavy chain CDR1 domain comprising the amino acid sequence of SEQ ID NO: 1, or a sequence substantially homologous thereto, and/or a light chain CDR1 domain comprising the amino acid sequence of SEQ ID NO: 4, or a sequence substantially homologous thereto.

In certain embodiments, the present invention provides an antibody that binds to binds to CXCR4 and which has the property of not inducing significant apoptosis of CXCR4 expressing cells, comprising a heavy chain CDR2 domain comprising the amino acid sequence of SEQ ID NO: 8, or a sequence substantially homologous thereto, and/or a light chain CDR2 domain comprising the amino acid sequence of SEQ ID NO: 11, or a sequence substantially homologous thereto.

Said antibody optionally further comprises a heavy chain CDR3 domain comprising the amino acid sequence of SEQ ID NO: 9, or a sequence substantially homologous thereto, and/or a light chain CDR3 domain comprising the amino acid sequence of SEQ ID NO: 12, or a sequence substantially homologous thereto, and/or further comprises a heavy chain CDR1 domain comprising the amino acid sequence of SEQ ID NO: 7, or a sequence substantially homologous thereto, and/or a light chain CDR1 domain comprising the amino acid sequence of SEQ ID NO: 10, or a sequence substantially homologous thereto.

In certain embodiments, the present invention provides an antibody that binds to binds to CXCR4 and which has the property of not inducing significant apoptosis of CXCR4 expressing cells, comprising a heavy chain CDR2 domain comprising the amino acid sequence of SEQ ID NO: 14, or a sequence substantially homologous thereto, and/or a light chain CDR2 domain comprising the amino acid sequence of SEQ ID NO: 17, or a sequence substantially homologous thereto.

Said antibody optionally further comprises a heavy chain CDR3 domain comprising the amino acid sequence of SEQ ID NO: 15, or a sequence substantially homologous thereto, and/or a light chain CDR3 domain comprising the amino acid sequence of SEQ ID NO: 18, or a sequence substantially homologous thereto, and/or further comprises a heavy chain CDR1 domain comprising the amino acid sequence of SEQ ID NO: 13, or a sequence substantially homologous thereto, and/or a light chain CDR1 domain comprising the amino acid sequence of SEQ ID NO: 16, or a sequence substantially homologous thereto.

Viewed alternatively, in certain embodiments, the present invention provides an antibody that binds to binds to CXCR4 and which has the property of not inducing significant apoptosis of CXCR4 expressing cells, comprising a heavy chain CDR2 domain comprising the amino acid sequence of SEQ ID NO: 20, or a sequence substantially homologous thereto, and/or a light chain CDR2 domain comprising the amino acid sequence of SEQ ID NO: 23, or a sequence substantially homologous thereto.

Said antibody optionally further comprises a heavy chain CDR3 domain comprising the amino acid sequence of SEQ ID NO: 21, or a sequence substantially homologous thereto, and/or a light chain CDR3 domain comprising the amino acid sequence of SEQ ID NO: 24, or a sequence substantially homologous thereto, and/or further comprises a heavy chain CDR1 domain comprising the amino acid sequence of SEQ ID NO: 19, or a sequence substantially homologous thereto, and/or a light chain CDR1 domain comprising the amino acid sequence of SEQ ID NO: 22, or a sequence substantially homologous thereto.

Viewed alternatively, in certain embodiments, the present invention provides an antibody that binds to binds to CXCR4 and which has the property of not inducing significant apoptosis of CXCR4 expressing cells, comprising a heavy chain CDR2 domain comprising the amino acid sequence of SEQ ID NO: 2, or a sequence substantially homologous thereto, and/or a light chain CDR2 domain comprising the amino acid sequence of SEQ ID NO: 89, or a sequence substantially homologous thereto.

Said antibody optionally further comprises a heavy chain CDR3 domain comprising the amino acid sequence of SEQ ID NO: 3, or a sequence substantially homologous thereto, and/or a light chain CDR3 domain comprising the amino acid sequence of SEQ ID NO: 90, or a sequence substantially homologous thereto, and/or further comprises a heavy chain CDR1 domain comprising the amino acid sequence of SEQ ID NO: 1, or a sequence substantially homologous thereto, and/or a light chain CDR1 domain comprising the amino acid sequence of SEQ ID NO: 88, or a sequence substantially homologous thereto.

Viewed alternatively, in certain embodiments, the present invention provides an antibody that binds to CXCR4 and which has the property of not inducing significant apoptosis of CXCR4 expressing cells, comprising a heavy chain CDR1 domain comprising the amino acid sequence of SEQ ID NO: 1, or a sequence substantially homologous thereto, and/or a light chain CDR1 domain comprising the amino acid sequence of SEQ ID NO: 4, or a sequence substantially homologous thereto.

Said antibody optionally further comprises a heavy chain CDR3 domain comprising the amino acid sequence of SEQ ID NO: 3, or a sequence substantially homologous thereto, and/or a light chain CDR3 domain comprising the amino acid sequence of SEQ ID NO: 6, or a sequence substantially homologous thereto, and/or further comprises a heavy chain CDR2 domain comprising the amino acid sequence of SEQ ID NO: 2, or a sequence substantially homologous thereto, and/or a light chain CDR2 domain comprising the amino acid sequence of SEQ ID NO: 5, or a sequence substantially homologous thereto.

In certain embodiments, the present invention provides an antibody that binds to CXCR4 and which has the property of not inducing significant apoptosis of CXCR4 expressing cells, comprising a heavy chain CDR1 domain comprising the amino acid sequence of SEQ ID NO: 7, or a sequence substantially homologous thereto, and/or a light chain CDR1 domain comprising the amino acid sequence of SEQ ID NO: 10, or a sequence substantially homologous thereto.

Said antibody optionally further comprises a heavy chain CDR3 domain comprising the amino acid sequence of SEQ ID NO: 9, or a sequence substantially homologous thereto, and/or a light chain CDR3 domain comprising the amino acid sequence of SEQ ID NO: 12, or a sequence substantially homologous thereto, and/or further comprises a heavy chain CDR2 domain comprising the amino acid sequence of SEQ ID NO: 8, or a sequence substantially homologous thereto, and/or a light chain CDR2 domain comprising the amino acid sequence of SEQ ID NO: 11, or a sequence substantially homologous thereto.

In certain embodiments, the present invention provides an antibody that binds to CXCR4 and which has the property of not inducing significant apoptosis of CXCR4 expressing cells, comprising a heavy chain CDR1 domain comprising the amino acid sequence of SEQ ID NO: 13, or a sequence substantially homologous thereto, and/or a light chain CDR1 domain comprising the amino acid sequence of SEQ ID NO: 16, or a sequence substantially homologous thereto.

Said antibody optionally further comprises a heavy chain CDR3 domain comprising the amino acid sequence of SEQ ID NO: 15, or a sequence substantially homologous thereto, and/or a light chain CDR3 domain comprising the amino acid sequence of SEQ ID NO: 18, or a sequence substantially homologous thereto, and/or further comprises a heavy chain CDR2 domain comprising the amino acid sequence of SEQ ID NO: 14, or a sequence substantially homologous thereto, and/or a light chain CDR2 domain comprising the amino acid sequence of SEQ ID NO: 17, or a sequence substantially homologous thereto.

In certain embodiments, the present invention provides an antibody that binds to CXCR4 and which has the property of not inducing significant apoptosis of CXCR4 expressing cells, comprising a heavy chain CDR1 domain comprising the amino acid sequence of SEQ ID NO: 19, or a sequence substantially homologous thereto, and/or a light chain CDR1 domain comprising the amino acid sequence of SEQ ID NO: 22, or a sequence substantially homologous thereto.

Said antibody optionally further comprises a heavy chain CDR3 domain comprising the amino acid sequence of SEQ ID NO: 21, or a sequence substantially homologous thereto, and/or a light chain CDR3 domain comprising the amino acid sequence of SEQ ID NO: 24, or a sequence substantially homologous thereto, and/or further comprises a heavy chain CDR2 domain comprising the amino acid sequence of SEQ ID NO: 20, or a sequence substantially homologous thereto, and/or a light chain CDR2 domain comprising the amino acid sequence of SEQ ID NO: 23, or a sequence substantially homologous thereto.

In certain embodiments, the present invention provides an antibody that binds to CXCR4 and which has the property of not inducing significant apoptosis of CXCR4 expressing cells, comprising a heavy chain CDR1 domain comprising the amino acid sequence of SEQ ID NO: 1, or a sequence substantially homologous thereto, and/or a light chain CDR1 domain comprising the amino acid sequence of SEQ ID NO: 88, or a sequence substantially homologous thereto.

Said antibody optionally further comprises a heavy chain CDR3 domain comprising the amino acid sequence of SEQ ID NO: 3, or a sequence substantially homologous thereto, and/or a light chain CDR3 domain comprising the amino acid sequence of SEQ ID NO: 90, or a sequence substantially homologous thereto, and/or further comprises a heavy chain CDR2 domain comprising the amino acid sequence of SEQ ID NO: 2, or a sequence substantially homologous thereto, and/or a light chain CDR2 domain comprising the amino acid sequence of SEQ ID NO: 89, or a sequence substantially homologous thereto.

Certain preferred antibodies of the invention comprise one or more of the CDRs selected from the group consisting of SEQ ID NOs: 1, 2, 3, 4, 5 and 6, or a sequence substantially homologous to any one of the foregoing SEQ ID NOs.

Certain preferred antibodies of the invention comprise one or more of the CDRs selected from the group consisting of SEQ ID NOs: 7, 8, 9, 10, 11 and 12, or a sequence substantially homologous to any one of the foregoing SEQ ID NOs.

Certain preferred antibodies of the invention comprise one or more of the CDRs selected from the group consisting of SEQ ID NOs: 13, 14, 15, 16, 17 and 18, or a sequence substantially homologous to any one of the foregoing SEQ ID NOs.

Certain preferred antibodies of the invention comprise one or more of the CDRs selected from the group consisting of SEQ ID NOs: 19, 20, 21, 22, 23 and 24, or a sequence substantially homologous to any one of the foregoing SEQ ID NOs.

Certain preferred antibodies of the invention comprise one or more of the CDRs selected from the group consisting of SEQ ID NOs: 1, 2, 3, 88, 89 and 90, or a sequence substantially homologous to any one of the foregoing SEQ ID NOs.

Certain preferred antibodies comprise two or more of the light chain CDRs of SEQ ID NOs: 4, 5 and 6; or 10, 11 and 12; or 16, 17 and 18; or 22, 23 and 24; or 88, 89 and 90, or sequences substantially homologous to any one of the foregoing SEQ ID NOs.

Especially preferred binding molecules comprise 3 of the light chain CDRs of SEQ ID NOs: 4, 5 and 6; or 10, 11 and 12; or 16, 17 and 18; or 22, 23 and 24; or 88, 89 and 90, or sequences substantially homologous to any one of the foregoing SEQ ID NOs (i.e. one of each of the aforementioned light chain CDR1 and CDR2 and CDR3 or sequences substantially homologous thereto).

Other certain preferred antibodies comprise two or more of the heavy chain CDRs of SEQ ID NOs: 1, 2 and 3; or 7, 8 and 9; or 13, 14 and 15; or 19, 20 and 21, or sequences substantially homologous to any one of the foregoing SEQ ID NOs.

Especially preferred antibodies comprise 3 of the heavy chain CDRs of SEQ ID NOs: 1, 2 and 3; or 7, 8 and 9; or 13, 14 and 15; or 19, 20 and 21, or sequences substantially homologous to any one of the foregoing SEQ ID NOs (i.e. one of each of the aforementioned heavy chain CDR1 and CDR2 and CDR3 or sequences substantially homologous thereto).

Certain more especially preferred antibodies comprise 3 of the light chain CDRs of SEQ ID NOs: 4, 5 and 6, or sequences substantially homologous to any one of these sequences (i.e. one of each of the aforementioned light chain CDR1 and CDR2 and CDR3 or sequences substantially homologous thereto), and 3 of the heavy chain CDRs of SEQ ID NOs: 1, 2 and 3, or sequences substantially homologous any one of these sequences (i.e. one of each of the aforementioned heavy chain CDR1 and CDR2 and CDR3 or sequences substantially homologous thereto).

Certain more especially preferred antibodies comprise 3 of the light chain CDRs of SEQ ID NOs: 10, 11 and 12, or sequences substantially homologous to any one of these sequences (i.e. one of each of the aforementioned light chain CDR1 and CDR2 and CDR3 or sequences substantially homologous thereto), and 3 of the heavy chain CDRs of SEQ ID NOs: 7, 8 and 9, or sequences substantially homologous any one of these sequences (i.e. one of each of the aforementioned heavy chain CDR1 and CDR2 and CDR3 or sequences substantially homologous thereto).

Certain more especially preferred antibodies comprise 3 of the light chain CDRs of SEQ ID NOs: 16, 17 and 18, or sequences substantially homologous to any one of these sequences (i.e. one of each of the aforementioned light chain CDR1 and CDR2 and CDR3 or sequences substantially homologous thereto), and 3 of the heavy chain CDRs of SEQ ID NOs: 13, 14 and 15, or sequences substantially homologous any one of these sequences (i.e. one of each of the aforementioned heavy chain CDR1 and CDR2 and CDR3 or sequences substantially homologous thereto).

Certain more especially preferred antibodies comprise 3 of the light chain CDRs of SEQ ID NOs: 22, 23 and 24, or sequences substantially homologous to any one of these sequences (i.e. one of each of the aforementioned light chain CDR1 and CDR2 and CDR3 or sequences substantially homologous thereto), and 3 of the heavy chain CDRs of SEQ ID NOs: 19, 20 and 21, or sequences substantially homologous any one of these sequences (i.e. one of each of the aforementioned heavy chain CDR1 and CDR2 and CDR3 or sequences substantially homologous thereto).

Certain more especially preferred antibodies comprise 3 of the light chain CDRs of SEQ ID NOs: 88, 89 and 90, or sequences substantially homologous to any one of these sequences (i.e. one of each of the aforementioned light chain CDR1 and CDR2 and CDR3 or sequences substantially homologous thereto), and 3 of the heavy chain CDRs of SEQ ID NOs: 1, 2 and 3, or sequences substantially homologous any one of these sequences (i.e. one of each of the aforementioned heavy chain CDR1 and CDR2 and CDR3 or sequences substantially homologous thereto).

Certain especially preferred antibodies comprise a heavy chain CDR1 domain of SEQ ID NO: 1, a heavy chain CDR2 domain of SEQ ID NO: 2, and a heavy chain CDR3 domain of SEQ ID NO: 3, or sequences substantially homologous to any one of the aforementioned sequences; and/or comprise a light chain CDR1 domain of SEQ ID NO: 4, a light chain CDR2 domain of SEQ ID NO: 5, and a light chain CDR 3 domain of SEQ ID NO: 6, or sequences substantially homologous to any one of the aforementioned sequences.

Certain especially preferred antibodies comprise a heavy chain CDR1 domain of SEQ ID NO: 7, a heavy chain CDR2 domain of SEQ ID NO: 8, and a heavy chain CDR3 domain of SEQ ID NO: 9, or sequences substantially homologous to any one of the aforementioned sequences; and/or comprise a light chain CDR1 domain of SEQ ID NO: 10, a light chain CDR2 domain of SEQ ID NO: 11, and a light chain CDR 3 domain of SEQ ID NO: 12, or sequences substantially homologous to any one of the aforementioned sequences.

Certain especially preferred antibodies comprise a heavy chain CDR1 domain of SEQ ID NO: 13, a heavy chain CDR2 domain of SEQ ID NO: 14, and a heavy chain CDR3 domain of SEQ ID NO: 15, or sequences substantially homologous to any one of the aforementioned sequences; and/or comprise a light chain CDR1 domain of SEQ ID NO: 16, a light chain CDR2 domain of SEQ ID NO: 17, and a light chain CDR 3 domain of SEQ ID NO: 18, or sequences substantially homologous to any one of the aforementioned sequences.

Certain especially preferred antibodies comprise a heavy chain CDR1 domain of SEQ ID NO: 19, a heavy chain CDR2 domain of SEQ ID NO: 20, and a heavy chain CDR3 domain of SEQ ID NO: 21, or sequences substantially homologous to any one of the aforementioned sequences; and/or comprise a light chain CDR1 domain of SEQ ID NO: 22, a light chain CDR2 domain of SEQ ID NO: 23, and a light chain CDR 3 domain of SEQ ID NO: 24, or sequences substantially homologous to any one of the aforementioned sequences.

Certain especially preferred antibodies comprise a heavy chain CDR1 domain of SEQ ID NO: 1, a heavy chain CDR2 domain of SEQ ID NO: 2, and a heavy chain CDR3 domain of SEQ ID NO: 3, or sequences substantially homologous to any one of the aforementioned sequences; and/or comprise a light chain CDR1 domain of SEQ ID NO: 88, a light chain CDR2 domain of SEQ ID NO: 89, and a light chain CDR 3 domain of SEQ ID NO: 90, or sequences substantially homologous to any one of the aforementioned sequences.

In a further embodiment, the invention provides an antibody that binds to CXCR4 and which has the property of not inducing significant apoptosis of CXCR4 expressing cells and that comprises at least one heavy chain variable region that comprises three CDRs and at least one light chain variable region that comprises three CDRs, wherein said heavy chain variable region comprises:
(i) a variable heavy (VH) CDR1 that has the amino acid sequence of SEQ ID NO: 1,
(ii) a VH CDR2 that has the amino acid sequence of SEQ ID NO: 2, and
(iii) a VH CDR3 that has the amino acid sequence of SEQ ID NO: 3.

In a preferred aspect of this embodiment, one or more of said light chain variable region CDRs are selected from the group consisting of:
(i) a VL CDR1 that has the amino acid sequence of SEQ ID NO: 4,
(ii) a VL CDR2 that has the amino acid sequence of SEQ ID NO: 5, and
(iii) a VL CDR3 that has the amino acid sequence of SEQ ID NO: 6. Preferably, 2 or 3 of said light chain variable region CDRs are selected from the above group. Antibodies comprising sequences which are substantially homologous to one or more of the aforementioned sequences are also provided in this embodiment.

In a further embodiment, the invention provides an antibody that binds to CXCR4 and which has the property of not inducing significant apoptosis of CXCR4 expressing cells and that comprises at least one heavy chain variable region that comprises three CDRs and at least one light chain variable region that comprises three CDRs, wherein said heavy chain variable region comprises:
(i) a variable heavy (VH) CDR1 that has the amino acid sequence of SEQ ID NO: 7,
(ii) a VH CDR2 that has the amino acid sequence of SEQ ID NO: 8, and
(iii) a VH CDR3 that has the amino acid sequence of SEQ ID NO: 9.

In a preferred aspect of this embodiment, one or more of said light chain variable region CDRs are selected from the group consisting of:
(i) a VL CDR1 that has the amino acid sequence of SEQ ID NO: 10,
(ii) a VL CDR2 that has the amino acid sequence of SEQ ID NO: 11, and
(iii) a VL CDR3 that has the amino acid sequence of SEQ ID NO: 12. Preferably, 2 or 3 of said light chain variable region CDRs are selected from the above group. Antibodies comprising sequences which are substantially homologous to one or more of the aforementioned sequences are also provided in this embodiment.

In a further embodiment, the invention provides an antibody that binds to CXCR4 and which has the property of not inducing significant apoptosis of CXCR4 expressing cells and that comprises at least one heavy chain variable region that comprises three CDRs and at least one light chain variable region that comprises three CDRs, wherein said heavy chain variable region comprises:
(i) a variable heavy (VH) CDR1 that has the amino acid sequence of SEQ ID NO: 13,
(ii) a VH CDR2 that has the amino acid sequence of SEQ ID NO: 14, and
(iii) a VH CDR3 that has the amino acid sequence of SEQ ID NO: 15.

In a preferred aspect of this embodiment, one or more of said light chain variable region CDRs are selected from the group consisting of:
(i) a VL CDR1 that has the amino acid sequence of SEQ ID NO: 16,
(ii) a VL CDR2 that has the amino acid sequence of SEQ ID NO: 17, and
(iii) a VL CDR3 that has the amino acid sequence of SEQ ID NO: 18. Preferably, 2 or 3 of said light chain variable region CDRs are selected from the above group. Antibodies comprising sequences which are substantially homologous to one or more of the aforementioned sequences are also provided in this embodiment.

In a further embodiment, the invention provides an antibody that binds to CXCR4 and which has the property of not inducing significant apoptosis of CXCR4 expressing cells and that comprises at least one heavy chain variable region that comprises three CDRs and at least one light chain variable region that comprises three CDRs, wherein said heavy chain variable region comprises:
(i) a variable heavy (VH) CDR1 that has the amino acid sequence of SEQ ID NO: 19,
(ii) a VH CDR2 that has the amino acid sequence of SEQ ID NO: 20, and
(iii) a VH CDR3 that has the amino acid sequence of SEQ ID NO: 21.

In a preferred aspect of this embodiment, one or more of said light chain variable region CDRs are selected from the group consisting of:
(i) a VL CDR1 that has the amino acid sequence of SEQ ID NO: 22,
(ii) a VL CDR2 that has the amino acid sequence of SEQ ID NO: 23, and
(iii) a VL CDR3 that has the amino acid sequence of SEQ ID NO: 24. Preferably, 2 or 3 of said light chain variable region CDRs are selected from the above group. Antibodies comprising sequences which are substantially homologous to one or more of the aforementioned sequences are also provided in this embodiment.

In a further embodiment, the invention provides an antibody that binds to CXCR4 and which has the property of not inducing significant apoptosis of CXCR4 expressing cells and that comprises at least one heavy chain variable region that comprises three CDRs and at least one light chain variable region that comprises three CDRs, wherein said heavy chain variable region comprises:
(i) a variable heavy (VH) CDR1 that has the amino acid sequence of SEQ ID NO: 1,
(ii) a VH CDR2 that has the amino acid sequence of SEQ ID NO: 2, and
(iii) a VH CDR3 that has the amino acid sequence of SEQ ID NO: 3.

In a preferred aspect of this embodiment, one or more of said light chain variable region CDRs are selected from the group consisting of:
(i) a VL CDR1 that has the amino acid sequence of SEQ ID NO: 88,
(ii) a VL CDR2 that has the amino acid sequence of SEQ ID NO: 89, and
(iii) a VL CDR3 that has the amino acid sequence of SEQ ID NO: 90. Preferably, 2 or 3 of said light chain variable region CDRs are selected from the above group. Antibodies comprising sequences which are substantially homologous to one or more of the aforementioned sequences are also provided in this embodiment.

Certain further preferred embodiments of the invention provide an antibody that binds to CXCR4 and which has the property of not inducing significant apoptosis of CXCR4 expressing cells and that comprises:
a VH domain that comprises one, two or three of the heavy chain CDRs of SEQ ID NOs: 1, 2 or 3, or sequences substantially homologous to one or more of SEQ ID NOs: 1, 2 or 3, and/or a VL domain that comprises one, two or three of the light chain CDRs of SEQ ID NOs: 4, 5 or 6, or sequences substantially homologous to one or more of SEQ ID NOs: 4, 5 or 6.

Certain further preferred embodiments of the invention provide an antibody that binds to CXCR4 and which has the property of not inducing significant apoptosis of CXCR4 expressing cells and that comprises: a VH domain that comprises one, two or three of the heavy chain CDRs of SEQ ID NOs: 7, 8 or 9, or sequences substantially homologous to one or more of SEQ ID NOs: 7, 8 or 9, and/or a VL domain that comprises one, two or three of the light chain CDRs of SEQ ID NOs: 10, 11 or 12, or sequences substantially homologous to one or more of SEQ ID NOs: 10, 11 or 12.

Certain further preferred embodiments of the invention provide an antibody that binds to CXCR4 and which has the property of not inducing significant apoptosis of CXCR4 expressing cells and that comprises: a VH domain that comprises one, two or three of the heavy chain CDRs of SEQ ID NOs: 13, 14 or 15, or sequences substantially homologous to one or more of SEQ ID NOs: 13, 14 or 15, and/or a VL domain that comprises one, two or three of the light chain CDRs of SEQ ID NOs: 16, 17 or 18, or sequences substantially homologous to one or more of SEQ ID NOs: 16, 17 or 18.

Certain further preferred embodiments of the invention provide an antibody that binds to CXCR4 and which has the property of not inducing significant apoptosis of CXCR4 expressing cells and that comprises: a VH domain that comprises one, two or three of the heavy chain CDRs of SEQ ID NOs: 19, 20 or 21, or sequences substantially homologous to one or more of SEQ ID NOs: 19, 20 or 21, and/or a VL domain that comprises one, two or three of the light chain CDRs of SEQ ID NOs: 22, 23 or 24, or sequences substantially homologous to one or more of SEQ ID NOs: 22, 23 or 24.

Certain further preferred embodiments of the invention provide an antibody that binds to CXCR4 and which has the property of not inducing significant apoptosis of CXCR4 expressing cells and that comprises: a VH domain that comprises one, two or three of the heavy chain CDRs of SEQ ID NOs: 1, 2 or 3, or sequences substantially homologous to one or more of SEQ ID NOs: 1, 2 or 3, and/or a VL domain that comprises one, two or three of the light chain CDRs of SEQ ID NOs: 88, 89 or 90, or sequences substantially homologous to one or more of SEQ ID NOs: 88, 89 or 90.

In preferred embodiments one, two or three of the light chain CDRs are as defined in SEQ ID NOs: 4, 5 and 6; or 88, 89 and 90, and/or one, two or three of the heavy chain CDRs are as defined in SEQ ID NOs: 1, 2 and 3.

Certain preferred embodiments of the invention provide an antibody that binds to CXCR4 and which has the property of not inducing significant apoptosis of CXCR4 expressing cells, comprising a VH domain that has the amino acid sequence of SEQ ID NO: 69, 71, 73 or 75, or a sequence substantially homologous thereto, and/or a VL domain that has the amino acid sequence of SEQ ID NO: 70, 72, 74, 76 or 103, or a sequence substantially homologous thereto.

Further preferred embodiments provide an antibody that binds to CXCR4 and which has the property of not inducing significant apoptosis of CXCR4 expressing cells, comprising a VH domain that has the amino acid sequence of SEQ ID NO: 69, 71, 73 or 75 and a VL domain that comprises 3 light chain CDRs. Preferably said light chain CDRs have SEQ ID NOs 4, 5 and 6; or 10, 11 and 12; or 16, 17 and 18; or 22, 23 and 24; or 88, 89 and 90.

Further preferred embodiments provide an antibody that binds to CXCR4 and which has the property of not inducing significant apoptosis of CXCR4 expressing cells, comprising a VH domain that has the amino acid sequence of SEQ ID NO: 69, or a sequence substantially homologous thereto, and/or a VL domain that has the amino acid sequence of SEQ ID NO: 70, or a sequence substantially homologous thereto.

Further preferred embodiments provide an antibody that binds to CXCR4 and which has the property of not inducing significant apoptosis of CXCR4 expressing cells, comprising a VH domain that has the amino acid sequence of SEQ ID NO: 71, or a sequence substantially homologous thereto, and/or a VL domain that has the amino acid sequence of SEQ ID NO: 72, or a sequence substantially homologous thereto.

Further preferred embodiments provide an antibody that binds to CXCR4 and which has the property of not inducing significant apoptosis of CXCR4 expressing cells, comprising a VH domain that has the amino acid sequence of SEQ ID NO: 73, or a sequence substantially homologous thereto, and/or a VL domain that has the amino acid sequence of SEQ ID NO: 74, or a sequence substantially homologous thereto.

Further preferred embodiments provide an antibody that binds to CXCR4 and which has the property of not inducing significant apoptosis of CXCR4 expressing cells, comprising a VH domain that has the amino acid sequence of SEQ ID NO: 75, or a sequence substantially homologous thereto, and/or a VL domain that has the amino acid sequence of SEQ ID NO: 76, or a sequence substantially homologous thereto.

Further preferred embodiments provide an antibody that binds to CXCR4 and which has the property of not inducing significant apoptosis of CXCR4 expressing cells, comprising a VH domain that has the amino acid sequence of SEQ ID NO: 69, or a sequence substantially homologous thereto, and/or a VL domain that has the amino acid sequence of SEQ ID NO: 103, or a sequence substantially homologous thereto.

Antibodies comprising a VH domain that has the amino acid sequence of SEQ ID NO: 69, or a sequence substantially homologous thereto, and/or a VL domain that has the amino acid sequence of SEQ ID NO: 103 or 70, or a sequence substantially homologous thereto, are particularly preferred.

In a yet further embodiment, the present invention provides an antibody that binds CXCR4 and which has the property of not inducing significant apoptosis of CXCR4 expressing cells, comprising the amino acid sequence of SEQ ID NO: 35 (said antibody also being referred to herein as C-9P21 scFv), SEQ ID NO: 46 (said antibody also being referred to herein as B-1M22 scFv), SEQ ID NO: 57 (said antibody also being referred to herein as C-1I24 scFv), SEQ ID NO: 68 (said antibody also being referred to herein as D-1K21 scFv), or SEQ ID NO: 101 (said antibody also being referred to herein as 9N10 scFv) or comprising a fragment of any thereof that binds CXCR4 and which has the property of not inducing significant apoptosis of CXCR4 expressing cells, or a sequence substantially homologous to any of the above sequences.

Antibodies based on the C-9P21 or 9N10 sequences are particularly preferred.

The invention is exemplified by monoclonal antibodies C-9P21, B-1M22, C-1I24, D-1K21 and 9N10, single chain forms of which are shown in Tables 1, 2, 3, 4 and 5 (SEQ ID NOs: 35, 46, 57, 68 and 101, respectively). Full length IgG forms of antibodies C-9P21, B-1M22, C-1I24, D-1K21 and 9N10 have been made and their sequences are shown in Tables 6, 7, 8, 9 and 10, respectively. The CDR domains, VH and VL domains of the C-9P21, B-1M22, C-1I24, D-1K21 and 9N10 antibodies are shown in Tables 1 to 5 and FIGS. 1 to 5. Antibodies comprising these CDR domains or VH and VL domains (or sequences substantially homologous thereto) are preferred aspects of the invention. Antibodies based on the C-9P21 or 9N10 sequences are particularly preferred.

A preferred embodiment of the invention is a scFv form of the C-9P21 antibody comprising or consisting of SEQ ID NO: 35, which is preferably encoded by SEQ ID NO: 34. More preferably, the antibody comprises or consists of the amino acid sequence shown in FIG. 1 and preferably this antibody is encoded by the nucleic acid sequence shown in FIG. 1.

Another preferred embodiment of the invention is a scFv form of the B-1M22 antibody comprising or consisting of SEQ ID NO: 46, which is preferably encoded by SEQ ID NO: 45. More preferably, the antibody comprises or consists of the amino acid sequence shown in FIG. 2 and preferably this antibody is encoded by the nucleic acid sequence shown in FIG. 2.

Another preferred embodiment of the invention is a scFv form of the C-1I24 antibody comprising or consisting of SEQ ID NO: 57, which is preferably encoded by SEQ ID NO: 56. More preferably, the antibody comprises or consists of the amino acid sequence shown in FIG. 3 and preferably this antibody is encoded by the nucleic acid sequence shown in FIG. 3.

Another preferred embodiment of the invention is a scFv form of the D-1K21 antibody comprising or consisting of SEQ ID NO: 68, which is preferably encoded by SEQ ID NO: 67. More preferably, the antibody comprises or consists of the amino acid sequence shown in FIG. 4 and preferably this antibody is encoded by the nucleic acid sequence shown in FIG. 4.

Another preferred embodiment of the invention is a scFv form of the 9N10 antibody comprising or consisting of SEQ ID NO: 101, which is preferably encoded by SEQ ID NO: 100. More preferably, the antibody comprises or consists of the amino acid sequence shown in FIG. 5 and preferably this antibody is encoded by the nucleic acid sequence shown in FIG. 5.

Other preferred embodiments are IgG forms of the C-9P21, B-1M22, C-1I24, D-1K21 and 9N10 antibodies, preferably full length IgG forms. The IgG1 form of any of these antibodies is most preferred.

Thus, another preferred embodiment of the invention is a full length IgG antibody which comprises a heavy chain of SEQ ID NO: 108 (amino acid) and/or a light chain of SEQ ID NO: 109 (amino acid). Also preferred is an IgG antibody which comprises a heavy chain encoded by SEQ ID NO: 106 and/or a light chain encoded by SEQ ID NO: 107. It is of course understood that full IgG antibodies will comprise two substantially identical heavy chains and two substantially identical light chains.

Another preferred embodiment of the invention is a full length IgG antibody which comprises a heavy chain of SEQ ID NO: 112 (amino acid) and/or a light chain of SEQ ID NO: 113 (amino acid). Also preferred is an IgG antibody which comprises a heavy chain encoded by SEQ ID NO: 110 and/or a light chain encoded by SEQ ID NO: 111.

Another preferred embodiment of the invention is a full length IgG antibody which comprises a heavy chain of SEQ ID NO: 116 (amino acid) and/or a light chain of SEQ ID NO: 117 (amino acid). Also preferred is an IgG antibody which comprises a heavy chain encoded by SEQ ID NO: 114 and/or a light chain encoded by SEQ ID NO: 115.

Another preferred embodiment of the invention is a full length IgG antibody which comprises a heavy chain of SEQ ID NO: 120 (amino acid) and/or a light chain of SEQ ID NO: 121 (amino acid). Also preferred is an IgG antibody which comprises a heavy chain encoded by SEQ ID NO: 118 and/or a light chain encoded by SEQ ID NO: 119.

Another preferred embodiment of the invention is a full length IgG antibody which comprises a heavy chain of SEQ ID NO: 108 (amino acid) and/or a light chain of SEQ ID NO: 125 (amino acid). Also preferred is an IgG antibody which comprises a heavy chain encoded by SEQ ID NO: 106 and/or a light chain encoded by SEQ ID NO: 123.

Antibodies based on the C-9P21 or 9N10 sequences are particularly preferred.

In further embodiments of the present invention, the VH CDR1 has or comprises an amino acid sequence of SEQ ID NO: 126 (S/G Y $X_3$ M/I H/S) or SEQ ID NO: 127 ($X_1$ Y $X_3$ M H) or SEQ ID NO: 128 (S Y $X_3$ M H).

In these embodiments $X_1$ can be S or G, preferably S. $X_3$ can be any amino acid, preferably G or W or Y or A, most preferably W. Preferred VH CDR1 sequences of this embodiment are SEQ ID NOs: 1, 7, 13 or 19. A particularly preferred VH CDR1 has or comprises the amino acid sequence of SEQ ID NO: 1.

In further embodiments of the present invention, the VH CDR2 has or comprises an amino acid sequence of SEQ ID NO: 129 ($X_1$ I $X_3$ $X_4$ D G S $X_8$ $X_9$ $X_{10}$ Y A D S V K G). In these embodiments $X_1$, $X_3$, $X_4$, $X_8$, $X_9$ and $X_{10}$ can be any amino acid. Preferably one or more, most preferably all, of these X residues are selected from the following group: $X_1$ is V or R (preferably R), $X_3$ is S or N (preferably N), $X_4$ is Y or S (preferably S), $X_8$ is N or S (preferably S), $X_9$ is K or T (preferably T) and $X_{10}$ is Y or S (preferably S). Thus, a preferred VH CDR2 has or comprises the amino acid sequence of SEQ ID NO: 130 (V/R I S/N Y/S D G S N/S K/T Y/S Y A D S V K G). For example, preferred VH CDR2 sequences of this embodiment have or comprise SEQ ID NOs: 2 or 14. SEQ ID NO:2 is particularly preferred.

In further embodiments of the present invention, the VH CDR2 has or comprises an amino acid sequence of SEQ ID NO: 131 ($X_1$ I $X_3$ P $X_5$ $X_6$ G $X_8$ $X_9$ N Y A Q K F Q G). In these embodiments $X_1$, $X_3$, $X_5$ $X_6$, $X_8$ and $X_9$ can be any amino acid. Preferably one or more, most preferably all, of these X residues are selected from the following group: $X_1$ is R or G (preferably R), $X_3$ is N or I (preferably N), $X_5$ is N or I (preferably N), $X_6$ is S or F (preferably S), $X_8$ is G or T (preferably G) and $X_9$ is T or A (preferably T). Thus, a preferred VH CDR2 has or comprises the amino acid sequence of SEQ ID NO: 132 (R/G I N/I P N/I S/F G G/T T/A N Y A Q K F Q G). For example, preferred VH CDR2 sequences of this embodiment have or comprise SEQ ID NOs: 8 and 20. SEQ ID NO:20 is particularly preferred.

Due to the ability of the antibodies of the invention to not induce significant apoptosis of CXCR4 expressing cells (an ability which has not been described previously for CXCR4 antibodies), it is believed that the antibodies of the invention may bind to a different epitope to known anti-CXCR4 antibodies (for example, an epitope which protects the CXCR4+ cell from apoptosis or an epitope which is not involved in the apoptosis mechanism or which does not trigger apoptosis, but which is still involved in the binding of ligand to CXCR4).

Thus, also provided are antibodies which can compete with any of the antibodies described herein (e.g. C-9 P21, C1I24, D-1K21, B-1M22 or 9N10) for binding to CXCR4.

The term "competing antibodies", as used herein, refers to antibodies that bind to about, substantially or essentially the same, or even the same, epitope as a "reference antibody". "Competing antibodies" include antibodies with overlapping epitope specificities. Competing antibodies are thus able to effectively compete with a reference antibody for binding to CXCR4. Preferably, the competing antibody can bind to the same epitope as the reference antibody. Alternatively viewed, the competing antibody preferably has the same epitope specificity as the reference antibody.

"Reference antibodies" as used herein are antibodies which can bind to an epitope in the extracellular domain of human CXCR4 and which have one or more of the CDR sequences are defined herein, preferably a VH and a VL domain as defined herein, more preferably a VH of SEQ ID NO: 69 and a VL of SEQ ID NO: 70, or a VH of SEQ ID NO: 71 and a VL of SEQ ID NO: 72, or a VH of SEQ ID NO: 73 and a VL of SEQ ID NO: 74, or a VH of SEQ ID NO: 75 and a VL of SEQ ID NO: 76, or a VH of SEQ ID NO: 69 and a VL of SEQ ID NO: 103. Most preferred reference antibodies are selected from C-9P21, B-1M22, C-1I24, D-1K21 and 9N10.

The identification of one or more competing antibodies is a straightforward technical matter now that reference antibodies such as C-9P21, B-1M22, C-1I24, D-1K21 and 9N10 have been provided. As the identification of competing antibodies is determined in comparison to a reference antibody, it will be understood that actually determining the epitope to which either or both antibodies bind is not in any way required in order to identify a competing antibody. However, epitope mapping can be performed using standard techniques, if desired.

By way of example, the following methods for the identification and definition of epitopes are mentioned herein. The amino acid sequence of CXCR4 is known, so synthetic peptides may be used for epitope mapping, e.g. using the Pepscan assay. Site directed mutagenesis is also a powerful tool in epitope mapping and can be used to evaluate the role of single amino acids in immune complex formation. Protein footprinting relies on the fact that the epitope is protected from cleavage when bound as an antibody-antigen complex. Enzyme linked immunosorbent assay (ELISA) and haemaglutination and slot-blotting may also be used in epitope mapping. Crystallisation of the antigen with the antibody may be used to map a non-linear epitope. Protocols for carrying out such methods are widely available and the skilled person will be aware of suitable alternative methods of epitope mapping.

The identification of competing antibodies can be readily determined using any one of variety of immunological screening assays in which antibody competition can be assessed. All such assays are routine in the art and are further described herein in detail. Each of U.S. Pat. Nos. 6,342,219, 6,524,583, 7,056,509, 6,887,468, 6,342,221, 6,676,941, 6,703,020 and 6,416,758 are specifically incorporated herein by reference for purposes including even further supplementing the present teaching concerning how to identify competing antibodies.

For example, where the test antibodies to be examined are obtained from different source animals, or are even of a different isotype, a simple competition assay may be employed in which the reference and test antibodies are admixed (or pre-adsorbed) and applied to a CXCR4-containing composition, preferably cells expressing CXCR4, phage displaying CXCR4, or biochips containing immobilised CXCR4. Protocols based upon ELISAs are particularly suitable for use in such simple competition studies.

In certain embodiments, one would pre-mix the reference antibodies (e.g., C-9 P21, C1I24, D1K21, B-1M22 or 9N10) with varying amounts of the test antibodies (e.g., 1:10, 1:100 or 1:1000) for a period of time prior to applying to an antigen composition. In other embodiments, the reference and varying amounts of test antibodies can simply be admixed during exposure to the antigen composition. In any event, by using species or isotype secondary antibodies one will be able to detect only the bound reference antibodies, the binding of which will be reduced by the presence of a test antibody that "competes" for binding.

In conducting an antibody competition study between a reference antibody and any test antibody (irrespective of species or isotype), one may first label the reference (e.g., C-9 P21, C1I24, D1K21, B-1M22 or 9N10) with a detectable label, such as, e.g., biotin or an enzymatic or radioactive label to enable subsequent identification. In these cases, one would pre-mix or incubate the labeled reference antibodies with the test antibodies to be examined at various ratios (e.g., 1:10, 1:100 or 1:1000) and (optionally after a suitable period of time) then assay the reactivity of the labeled reference antibodies and compare this with a control value in which no potentially competing test antibody was included in the incubation.

The assay may be any one of a range of immunological assays based upon antibody binding, and the reference antibodies would be detected by means of detecting their label, e.g., using streptavidin in the case of biotinylated antibodies or by using a chromogenic substrate in connection with an enzymatic label (such as 3,3'5,5'-tetramethylbenzidine (TMB) substrate with peroxidase enzyme) or by simply detecting a radioactive label. An antibody that competes with the reference antibodies for binding to CXCR4 will be able to effectively or significantly reduce reference antibody binding to CXCR4, as evidenced by a reduction in bound label.

The reactivity of the (labeled) reference antibodies in the absence of a completely irrelevant antibody would be the control high value. The control low value would be obtained by incubating the labeled reference (e.g., C-9 P21, C1I24, D1K21, B-1M22 or 9N10) antibodies with unlabelled antibodies of exactly the same type, when competition would occur and reduce binding of the labeled antibodies. In a test assay, a significant reduction in labeled antibody reactivity in the presence of a test antibody is indicative of a test antibody that "competes" with the labeled antibody for binding to CXCR4.

A significant reduction is a "reproducible", i.e., consistently observed, reduction in binding. A "significant reduction" in terms of the present application is defined as a reproducible reduction (in binding of the reference antibody to CXCR4 in an ELISA or other suitable assay) of at least about 20%, more preferably at least about 25, 30, 35, 40, 45, 50, 55, 60 or 65%, even more preferably at least about 70%, about 75% or about 80% at any ratio between about 1:10 and about 1:100. Antibodies with even more stringent competing activities will exhibit a reproducible reduction (in binding of the reference antibody to CXCR4 in an ELISA or other suitable assay) of at least about 82%, about 85%, about 88%, about 90%, about 92% or about 95% or so at any ratio between about 1:10 and about 1:100. Complete or near-complete competition, such as exhibiting a reproducible reduction in binding of the reference antibody to CXCR4 of about 99%, about 98%, about 97% or about 96% or so, although by no means required to practice the invention, is certainly not excluded.

The method described above is only one example of a suitable competition assay. The skilled person will be aware of other suitable methods and variations. An alternative competition assay is described below.

Before the alternative competition assay is performed using flow cytometry, some quantities of the tested antibody should be labeled, e.g. by biotinylation. The functionality (retention of the cell-binding properties) of the biotinylated product and the minimal concentration of the biotinylated antibody of the invention (Ab1) that gives sub-maximal binding against a fixed number of CXCR4+ cells is determined. A total of $10^6$ cells are harvested from exponentially growing cultures and incubated with various antibody concentrations for a suitable period of time at a suitable temperature, e.g. 1 hr at 4° C. The cells are washed and incubated with a suitable detection antibody for a suitable period of time at a suitable temperature, e.g. an additional hour at 4° C. After washing, the cells are analyzed by flow cytometry. For each test antibody, a saturation curve is generated from the data by plotting median fluorescence intensity (MFI) against the antibody concentration.

For the alternative competition assay, CXCR4+ cells may be prepared as above and treated in duplicate with a mixture of fixed concentration of labeled (biotinylated) antibody (bio-Ab1) and increasing concentrations of non-labeled competitive antibody. The fixed concentration is the minimal concentration of antibody that generates reasonable fluorescence signal against a fixed number of tumor cells as determined above. Ideally, this fixed concentration in nM should be below the affinity of the tested antibody at equilibrium ($K_D$). In this case the described method can be used for estimation of affinities of competitive antibodies (Schodin and Kranz, 1993, Binding affinity and inhibitory properties of a single-chain anti-T cell receptor antibody. J Biol Chem 268: 25722-7). The antibody mixture is incubated with target cells for a suitable period of time at a suitable temperature, e.g. 1 hr at 4° C. The cells are washed and the cell binding of biotinylated antibody is revealed by incubation with FITC-labeled streptavidin. After subtracting the background fluorescence (PBS-5% FCS) from the median fluorescence reading for each test sample (bio-Ab1+Ab2), the percent of inhibition is calculated for each Ab2 concentration "c" according to the formula:

$$\% \text{ inhibition} = (1 - \text{MFI}^{bio-Ab1+Ab2\text{"}c\text{"}} / \text{MFI}^{bio-Ab1}) \times 100$$

is calculated.

Any antibodies which can bind to CXCR4 and which can compete with any of the antibodies described herein are contemplated, but preferred antibodies are set out below. Accordingly, in some preferred embodiments there is provided the following.

An antibody which binds to an epitope in the extracellular domain of human CXCR4 and which preferably has the property of not inducing significant apoptosis of CXCR4 expressing cells, wherein said antibody
(a) comprises at least one heavy chain variable region that comprises three CDRs and at least one light chain variable region that comprises three CDRs,
wherein said light chain variable region comprises:
(i) a variable light (VL) CDR1 that has the amino acid sequence of SEQ ID NO: 4;
(ii) a VL CDR2 that has the amino acid sequence of SEQ ID NO: 5; and/or
(iii) a VL CDR3 that has the amino acid sequence of SEQ ID NO: 6; and/or wherein said heavy chain variable region comprises
(iv) a variable heavy (VH) CDR1 that has the amino acid sequence of SEQ ID NO: 1;
(v) a VH CDR2 that has the amino acid sequence of SEQ ID NO: 2; and/or
(vi) a VH CDR3 that has the amino acid sequence of SEQ ID NO: 3; or
(b) is an antibody which can compete with antibody (a) for binding to CXCR4.

An antibody which binds to an epitope in the extracellular domain of human CXCR4 and which preferably has the property of not inducing significant apoptosis of CXCR4 expressing cells, wherein said antibody
(a) comprises at least one heavy chain variable region that comprises three CDRs and at least one light chain variable region that comprises three CDRs,
wherein said light chain variable region comprises:
(i) a variable light (VL) CDR1 that has the amino acid sequence of SEQ ID NO: 10;
(ii) a VL CDR2 that has the amino acid sequence of SEQ ID NO: 11; and/or
(iii) a VL CDR3 that has the amino acid sequence of SEQ ID NO: 12; and/or wherein said heavy chain variable region comprises
(iv) a variable heavy (VH) CDR1 that has the amino acid sequence of SEQ ID NO: 7;
(v) a VH CDR2 that has the amino acid sequence of SEQ ID NO: 8; and/or
(vi) a VH CDR3 that has the amino acid sequence of SEQ ID NO: 9; or
(b) is an antibody which can compete with antibody (a) for binding to CXCR4.

An antibody which binds to an epitope in the extracellular domain of human CXCR4 and which preferably has the property of not inducing significant apoptosis of CXCR4 expressing cells, wherein said antibody
(a) comprises at least one heavy chain variable region that comprises three CDRs and at least one light chain variable region that comprises three CDRs,
wherein said light chain variable region comprises:
(i) a variable light (VL) CDR1 that has the amino acid sequence of SEQ ID NO: 16;
(ii) a VL CDR2 that has the amino acid sequence of SEQ ID NO: 17; and/or
(iii) a VL CDR3 that has the amino acid sequence of SEQ ID NO: 18; and/or wherein said heavy chain variable region comprises (iv) a variable heavy (VH) CDR1 that has the amino acid sequence of SEQ ID NO: 13;
(v) a VH CDR2 that has the amino acid sequence of SEQ ID NO: 14; and/or
(vi) a VH CDR3 that has the amino acid sequence of SEQ ID NO: 15; or
(b) is an antibody which can compete with antibody (a) for binding to CXCR4.

An antibody which binds to an epitope in the extracellular domain of human CXCR4 and which preferably has the property of not inducing significant apoptosis of CXCR4 expressing cells, wherein said antibody
(a) comprises at least one heavy chain variable region that comprises three CDRs and at least one light chain variable region that comprises three CDRs,
wherein said light chain variable region comprises:
(i) a variable light (VL) CDR1 that has the amino acid sequence of SEQ ID NO: 22;
(ii) a VL CDR2 that has the amino acid sequence of SEQ ID NO: 23; and/or
(iii) a VL CDR3 that has the amino acid sequence of SEQ ID NO: 24; and/or wherein said heavy chain variable region comprises
(iv) a variable heavy (VH) CDR1 that has the amino acid sequence of SEQ ID NO: 19;
(v) a VH CDR2 that has the amino acid sequence of SEQ ID NO: 20; and/or
(vi) a VH CDR3 that has the amino acid sequence of SEQ ID NO: 21; or
(b) is an antibody which can compete with antibody (a) for binding to CXCR4.

An antibody which binds to an epitope in the extracellular domain of human CXCR4 and which preferably has the property of not inducing significant apoptosis of CXCR4 expressing cells, wherein said antibody
(a) comprises at least one heavy chain variable region that comprises three CDRs and at least one light chain variable region that comprises three CDRs,
wherein said light chain variable region comprises:
(i) a variable light (VL) CDR1 that has the amino acid sequence of SEQ ID NO: 88;
(ii) a VL CDR2 that has the amino acid sequence of SEQ ID NO: 89; and/or
(iii) a VL CDR3 that has the amino acid sequence of SEQ ID NO: 90; and/or wherein said heavy chain variable region comprises
(iv) a variable heavy (VH) CDR1 that has the amino acid sequence of SEQ ID NO: 1;
(v) a VH CDR2 that has the amino acid sequence of SEQ ID NO: 2; and/or
(vi) a VH CDR3 that has the amino acid sequence of SEQ ID NO: 3; or
(b) is an antibody which can compete with antibody (a) for binding to CXCR4.

In one embodiment, the antibody
(a) has a VH domain of SEQ ID NO: 69 and a VL domain of SEQ ID NO: 70; or
(b) is an antibody which can compete with antibody (a) for binding to CXCR4.

In one embodiment, the antibody
(a) has a VH domain of SEQ ID NO: 71 and a VL domain of SEQ ID NO: 72; or
(b) is an antibody which can compete with antibody (a) for binding to CXCR4.

In one embodiment, the antibody
(a) has a VH domain of SEQ ID NO: 73 and a VL domain of SEQ ID NO: 74; or
(b) is an antibody which can compete with antibody (a) for binding to CXCR4.

In one embodiment, the antibody
(a) has a VH domain of SEQ ID NO: 75 and a VL domain of SEQ ID NO: 76; or
(b) is an antibody which can compete with antibody (a) for binding to CXCR4.

In one embodiment, the antibody
(a) has a VH domain of SEQ ID NO: 69 and a VL domain of SEQ ID NO: 103; or
(b) is an antibody which can compete with antibody (a) for binding to CXCR4.

Preferably, antibody (b) has one or more of the CDR sequences, VH domains and/or VL domains described herein.
Preferably, antibody (b) can bind to the same epitope as antibody (a).

Certain examples of substantially homologous sequences are sequences that have at least 70% identity to the amino acid sequences disclosed. In certain embodiments, the antibodies of the invention that bind to CXCR4 and have the property of not inducing significant apoptosis of CXCR4 expressing cells comprise at least one light chain variable region that includes an amino acid sequence region of at least about 75%, more preferably at least about 80%, more preferably at least about 85%, more preferably at least about 90% or 95% and most preferably at least about 97%, 98% or 99% amino acid sequence identity to the amino acid sequence of SEQ ID NO: 70, 72, 74, 76 or 103; and/or at least one heavy chain variable region that includes an amino acid sequence region of at least about 75%, more preferably at least about 80%, more preferably at least about 85%, more preferably at least about 90% or 95% and most preferably at least about 97%, 98% or 99% amino acid sequence identity to the amino acid sequence of SEQ ID NO: 69, 71, 73 or 75.

Other preferred examples of substantially homologous sequences are sequences containing conservative amino acid substitutions of the amino acid sequences disclosed.

Other preferred examples of substantially homologous sequences are sequences containing up to 1, 2, 3 or 4 preferably up to 1 or 2, altered amino acids in one or more of the CDR regions disclosed. Such alterations might be conservative or non-conservative amino acid substitutions, or a mixture thereof.

In all such embodiments, preferred alterations are conservative amino acid substitutions.

In all embodiments, the antibodies containing substantially homologous sequences retain the ability to bind to CXCR4 and preferably retain one or more of the other properties described herein, e.g. the property of not inducing significant apoptosis of CXCR4 expressing cells and/or the property of being antagonistic.

Other embodiments of the present invention provide binding proteins that bind to CXCR4 and preferably have one or more of the other properties described herein, e.g. have the property of not inducing significant apoptosis of CXCR4 expressing cells and/or the property of being antagonistic and that comprise an antibody of the invention, a VH or VL domain of the invention, or one or more of the CDRs of the invention. In a preferred embodiment, such binding proteins are antibodies.

Preferred antibodies of the invention comprise at least one heavy chain variable region that comprises three CDRs and at least one light chain variable region that comprises three CDRs. Exemplary and preferred sequences for these CDRs are described herein.

As used herein, the succinct term "CXCR4", unless otherwise specifically stated or made clear from the scientific terminology, means CXC chemokine receptor 4 (also known as fusin, HM89, LESTR or HUMSTR).

CXCR4 may be free CXCR4, e.g. recombinant or purified CXCR4, but preferably it is present in a native form, e.g. on the surface of a cell.

The antibodies or binding proteins of the invention can also bind to fragments of CXCR4, in particular fragments comprising or consisting of all or part of the extracellular domain of CXCR4, or can bind to entities comprising CXCR4 or fragments of CXCR4. Indeed, the epitopes of the antibodies of the invention are located in the extracellular domain of CXCR4.

"CXCR4" may also refer to any form of CXCR4, particularly as CXCR4 is conserved across mammalian species. The antibodies or antibody fragments of the invention may thus bind to human, monkey (e.g. cynomolgus monkey or *Macaca mulatta*/rhesus monkey), mouse (murine), cow (bovine), rat, hamster, ferret, guinea pig and/or rabbit CXCR4, for example. Preferably, the antibodies or antibody fragments of the invention will bind at least to human CXCR4. Thus, unless stated otherwise, any reference herein to "CXCR4" may be read to mean "human CXCR4". In certain preferred embodiments, the antibodies or antibody fragments of the invention will bind at least to human and monkey (e.g. cynomologus monkey or *Macaca mulatta*/rhesus monkey) CXCR4. In other preferred embodiments the antibodies or antibody fragments of the invention will bind at least to human and mouse CXCR4. In other preferred embodiments the antibodies or antibody fragments of the invention will bind at least to human, monkey and mouse CXCR4.

As used herein, the term "that binds to CXCR4" or "anti-CXCR4" in the context of antibodies or antibody fragments of the present invention, means antibodies or antibody fragments that are capable of one or more of the following; preferably, of more than one of the following; and most preferably, of all of the following:

(a) bind to CXCR4 expressed on the surface of a cell, e.g. a cell transfected with CXCR4 or a cell which naturally expresses CXCR4, e.g. as assessed by flow cytometry or immunohistochemistry;
(b) bind to a conformationally dependent (e.g. non linear) CXCR4 epitope, e.g. as assessed by binding to CXCR4 in a Western blot under non-reducing conditions;
(c) bind at least to human CXCR4, more preferably to human and monkey CXCR4 or to human and mouse CXCR4, most preferably to human, monkey and mouse CXCR4;
(d) bind to human and monkey CXCR4 or to human and mouse CXCR4 with similar affinities, e.g. with a Kd of 10 nM or less, preferably 5 nM or less, more preferably 3 nM or less or 2 nM or less, for example 1 nM or less as also discussed elsewhere herein.

Preferred antibodies or antibody fragments of the present invention are also capable of one or more of the following; preferably, of more than one of the following; and most preferably, of all of the following functional properties:

(e) do not induce significant apoptosis of CXCR4 expressing cells;
(f) block or inhibit the binding of CXCR4 to one or more of its ligands, e.g. block or inhibit the binding of CXCR4 to at least SDF-1 or an alternative ligand for CXCR4, e.g. the chemical compound AMD-3100, and preferably inhibit the binding of CXCR4 to at least both of SDF-1 and AMD-3100;
(g) block or inhibit downstream signalling events from the CXCR4 receptor, e.g. inhibit CXCR4-mediated cellular responses to a CXCR4 ligand such as SDF-1, for example preferably to inhibit the release of calcium ions in response to a CXCR4 ligand such as SDF-1 or to block or inhibit ligand (e.g. SDF-1) induced migration of CXCR4+ cells;
(h) induce ADCC of CXCR4+ cells as described elsewhere herein;
(i) induce anti tumour effects in vivo;
(j) localize to tumours upon administration to an animal with a tumour;
(k) induce CDC of CXCR4+ cells;
(l) induce anti-viral effects, in particular anti-HIV effects, in vitro or in vivo;
(m) not exhibit agonistic activity in respect of the CXCR4 receptor;

In the context of binding to CXCR4+ cells, it should be understood that the antibodies of the present invention bind to CXCR4+ cells and do not significantly bind to CXCR4$^-$ cells (as shown in Example 2).

The term "do not significantly bind to CXCR4$^-$ cells" should be understood such that any binding of the antibody to CXCR4$^-$ cells does not prohibit the use of said antibody for therapeutic or diagnostic purposes. Thus, "insignificant" binding to CXCR4$^-$ cells includes the situation that the binding of the antibody to CXCR4$^-$ cells is significantly weaker than its binding to one or more CXCR4$^+$ cells or can be considered to be at a background level, e.g. comparative to or not significantly different from a level observed in a negative control experiment.

For therapeutic or diagnostic purposes the main consideration is that the antibody must bind more strongly to one or more types of CXCR4$^+$ cells than to any CXCR4$^-$ cells with which the antibody may come into contact during the therapeutic or diagnostic application.

The antibodies of the invention may be referred to as "CXCR4-specific". The term "CXCR4-specific" should be interpreted such that the binding of the antibody to CXCR4 expressing cells is specific enough to allow the use of said antibody for therapeutic or diagnostic purposes. A CXCR4-specific antibody as described herein has the ability to bind CXCR4 (e.g. on the surface of a cell) but does not significantly bind to non-CXCR4 proteins (e.g. does not significantly bind to CXCR4– cells). The skilled person can readily determine if any given antibody is CXCR4-specific by comparing the binding strength to a target CXCR4$^+$ cell (e.g. a cell transfected with and expressing CXCR4, or a cell which naturally expresses CXCR4, e.g. Ramos cells, Jurkat cells, CCRF-CEM cells, Raji cells), with the binding strength to one or more types of CXCR4$^-$ cells, e.g. wild-type cells not transformed with CXCR4 such as HEK293T-cells or DT40-cells.

It is described in the art that CXCR4 has a tendency to develop somewhat different conformations depending on the cell type expressing it (see for example Baribaud et al., 2001). Thus, antibodies of the invention are regarded as having the ability to bind to CXCR4 on the surface of a cell when they can bind to one or more cell types which have been transfected with CXCR4 or which naturally express CXCR4. Preferred antibodies have the ability to bind to CXCR4 on multiple cell types and thus have the ability to bind multiple conformations of CXCR4. For example, the C-9P21, 9N10 and C-1I24 antibodies described herein show such abilities.

The skilled person will be aware that binding to CXCR4$^+$ cells compared to CXCR4$^-$ cells may be assessed, for example, using flow cytometry and a suitable assay is described in Examples 2 and 3.

Immunohistochemistry techniques, which are well known in the art, may be used to score the binding of antibodies to cells or samples. Such assays may be used to test the specificity of a particular antibody, or to detect CXCR4 expression in tissue samples. Briefly, the antibody may be tested for example on a high-density array of human tissues including a positive control (cells known to be CXCR4-positive) and a negative control (cells known to be CXCR4-negative). The membranous staining intensity may be estimated by visual inspection in a four step scale (0, 1, 2, 3). Preferred antibodies show weak or strong (i.e. scores above 0), preferably strong immunohistochemical scores for CXCR4+ tissues.

As discussed above, the antibodies of the invention have the property of not inducing significant apoptosis of CXCR4+ cells (CXCR4 expressing cells). By the term "not inducing significant apoptosis of CXCR4+ cells" is meant that levels of apoptosis induced in the presence of an antibody are comparable to or not significantly different from levels of apoptosis induced in the absence of an antibody, e.g. under negative control conditions or background level, for example in the presence of growth medium alone. Thus, preferably the antibodies of the invention do not induce a measurable or significant increase in apoptosis over natural, or background, or control levels of apoptosis. This is in contrast to prior art antibodies such as the Medarex antibodies described in WO 2008/060367 (e.g. F7) which induce measurable and significant apoptosis compared to apoptosis observed in the absence of antibody (see also Example 10 herein). Preferably, the antibodies of the invention do not induce significant apoptosis at antibody concentrations of >0.4 µg/ml, for example, at concentrations of at or at least 0.4 µg/ml, 1 µg/ml, 2 µg/ml, 3 µg/ml, 4 µg/ml, 5 µg/ml, 6 µg/ml, 7 µg/ml, 8 µg/ml, 9 µg/ml 10 µg/ml, 11 µg/ml, 12 µg/ml, 15 µg/ml, 20 µg/ml, 25 µg/ml, 30 µg/ml, 40 µg/ml, 50 µg/ml, 75 µg/ml and 100 µg/ml (preferably in IgG, e.g. IgG1 form). More preferably, the antibodies of the invention do not induce significant apoptosis when assessed on the CXCR4+ Ramos cell line in vitro (e.g. when assessed using an assay as described in Example 10). Preferably, the antibodies of the invention do not induce significant apoptosis when used at concentrations of ≥0.14 µg/1×10$^5$ cells, for example, at concentrations of at or at least 0.14 µg/1×10$^5$ cells, 0.25 µg/1×10$^5$ cells, 0.5 µg/1×10$^5$ cells, 1 µg/1×10$^5$ cells, 2 µg/1×10$^5$ cells, 3 µg/1×10$^5$ cells, 3.5 µg/1×10$^5$ cells, 4 µg/1×10$^5$ cells, 5 µg/1×10$^5$ cells, 10 µg/1×10$^5$ cells, 15 µg/1×10$^5$ cells, 20 µg/1×10$^5$ cells, 25 µg/1×10$^5$ cells, 30 µg/1×10$^5$ cells and 35 µg/1×10$^5$ cells, more preferably the cells are RAMOS cells. Preferably, the antibodies of the invention do not induce significant apoptosis when used at a therapeutically useful concentration (e.g. at an antibody concentration of ≥0.4 µg/ml, for example, at concentrations of at or at least 0.4 µg/ml, 1 µg/ml, 2 µg/ml, 3 µg/ml, 4 µg/ml, 5 µg/ml, 6 µg/ml, 7 µg/ml, 8 µg/ml, 9 µg/ml 10 µg/ml, 11 µg/ml, 12 µg/ml, 15 µg/ml, 20 µg/ml, 25 µg/ml, 30 µg/ml, 40 µg/ml, 50 µg/ml, 75 µg/ml and 100 µg/ml (preferably in IgG, e.g. IgG1 form, preferably the antibody concentration is the antibody concentration in serum). By way of example, an antibody which does not induce significant apoptosis of CXCR4+ cells is an antibody which does not cause more than 10% cells to become apoptotic upon incubation with the antibody in an assay which defines apoptotic cells as those which are positive to Annexin V binding. A preferred assay is described in Example 10 and involves the use of Ramos cells and IgG1 antibodies up to a concentration of 10 µg/ml. Viewed alternatively, an antibody which does not induce significant apoptosis of CXCR4+ cells is an antibody where any increase in apoptosis above background or control level is an increase of a maximum of 50% over said background or control level in an assay which defines apoptotic cells as those which are positive to Annexin V binding. A preferred assay is described in Example 10 and involves the use of Ramos cells and IgG1 antibodies up to a concentration of 10 µg/ml.

The induction of apoptosis may be assayed using well-known standard methods, for example methods which assay Annexin V staining (for an exemplary method involving Annexin staining see Example 10). Briefly, cells (e.g. Ramos cells) may be incubated with an antibody (e.g. an antibody in IgG1 format) for a suitable period of time, e.g. 24 or 48 hours and the effect, after cell harvesting and Annexin V staining may be measured by FACS analysis (e.g. using EasyCyte). Annexin V staining is indicative of apoptotic cells, whereas dead cells can be identified (and distinguished from apoptotic cells) by for example PI staining The antibodies C-9P21, B-1M22, C-1I24, D-1K21 and 9N10 have been shown to be capable of inhibiting ligand induced signalling via CXCR4, e.g. inhibiting CXCR4-mediated cellular responses to a CXCR4 ligand such as SDF-1, in particular by inhibiting the release of calcium ions in response to a CXCR4 ligand such as SDF-1 (see Example 6). Thus, the antibodies of the invention are preferably capable of inhibiting CXCR4-mediated cellular responses to a CXCR4 ligand such as SDF-1, in particular by inhibiting the release of calcium ions in response to a CXCR4 ligand such as SDF-1. In particular, the antibodies are preferably capable of inhibiting SDF-1-induced calcium flux. Suitable assay methods are known and one assay is disclosed in Example 6.

The "blocking" or "inhibition" of various CXCR4 mediated events described herein such as downstream signalling events from CXCR4, ligand induced signalling via CXCR4, CXCR4 mediated cellular responses to a CXCR4 ligand, release of calcium ions, ligand induced migration, etc., means that the property in question is measurably or significantly reduced in the presence of the antibody of the invention compared to the absence of the antibody. For example, said property may be reduced by at least 10, 20, 30, or 40%, more preferably at least 45, 50, 55, 60, 65, 70 or 75%, even more preferably at least 80% in the presence of the antibody compared to binding in the absence of the antibody. The reduction by at least 85, 90 or 95% are also contemplated for certain properties.

In the case of the blocking or inhibition of the release of calcium ions (calcium flux) at least 20% or 30% inhibition is often seen with the antibodies of the invention rising up to at least 70%, 75%, 80% or 95% inhibition (see Example 6). Exemplary concentrations of antibody used to achieve such inhibition are 4 µg/ml, 10 µg/ml or 100 µg/ml. In certain embodiments of the invention, the antibody concentration capable of giving rise to 50% inhibition of the release of calcium ions ($IC_{50}$) from CXCR4+ cells, e.g. CCRF-CEM cells, in vitro, is preferably less than 50 nM, 40 nM, 35 nM or 30 nM (or any integer between 30 and 50), 25 nM, 20 nM, 15 nM, 10 nM, 7 nM or 5 nM (or any integer between 5 and 30). For example, the C-9P21 antibody of the invention has been shown to have an $IC_{50}$ of 29 nM for CCRF-CEM cells. The 9N10 antibody has been shown to have an $IC_{50}$ of 3.85 nM for CCRF-CEM cells.

In some embodiments, the antibodies may block or inhibit migration or chemotaxis of CXCR4+ cells towards a ligand of CXCR4 such as SDF-1 (see Example 7). The inhibition of migration or chemotaxis may be assayed using standard methods, for example using a transwell assay. Briefly, cells capable of chemotaxis and which express CXCR4 are contacted with an antibody in one chamber and a ligand of CXCR4 such as SDF-1 is placed in another chamber separated from the first chamber by a membrane of filter having a suitable pore size. The effect of the antibody on cell migration towards the ligand (chemotaxis) is determined by comparing chemotaxis in the presence of the antibody to chemotaxis in the absence of the antibody. A suitable assay is described in Example 7. At least 50% and up to 100% inhibition of migration is seen depending on the concentration of antibody.

In certain embodiments of the invention, the antibody concentration capable of giving rise to 50% inhibition of cell migration ($IC_{50}$) of CXCR4+ cells, e.g. CCRF-CEM cells, in vitro, is preferably less than 20 µg/ml, 15 µg/ml (or any integer between 15 and 20), 10 µg/ml (or any integer between 10 and 15), 5 µg/ml (or any integer between 5 and 10), 4 µg/ml, 3 µg/ml, 2 µg/ml or 1 µg/ml. For example, the C-9P21 antibody of the invention has been shown to have an $IC_{50}$ of 2.9 µg/ml for CCRF-CEM cells. In certain embodiments of the invention, the antibodies are capable of 100% inhibition in vitro at 5 µg/ml, 10 µg/ml, 15 µg/ml, 20 µg/ml, 25 µg/ml or 30 µg/ml (or any integer between 6 and 30 µg/ml).

Preferably the antibodies of the invention (e.g. C-9P21, C-1I24, D-1K21, B-1M22 and 9N10) are capable of inhibiting the binding of CXCR4 to one or more of its ligands. Preferably, the binding to at least SDF-1 is inhibited. More preferably, the binding to SDF-1 and AMD-3100 is inhibited. For example, the antibodies C-9P21, C-1I24, 9N10 and D-1K21 have been shown to be capable of inhibiting the binding of CXCR4 to its ligand SDF-1 (Example 3). The antibodies C-9P21, C-1I24 and D-1K21 have also been shown to be capable of inhibiting the binding of CXCR4 to AMD-3100 (Example 3). Given their effects on calcium flux, it can be expected that B-1M22 also competes with ligand for binding to CXCR4.

By the "blocking of binding" or "inhibition of binding" of a ligand to CXCR4 is meant that binding of the ligand to CXCR4 is measurably or significantly reduced, e.g. is reduced by at least 10, 20, 30, or 40%, more preferably at least 45, 50, 55, 60, 65, 70 or 75%, even more preferably at least 80% in the presence of the antibody compared to binding in the absence of the antibody. Embodiments in which the binding of ligand to CXCR4 is reduced by at least 85, 90 or 95% are also contemplated. Alternatively viewed, when the ligand is first contacted with CXCR4 and the antibody is subsequently added, the ligand can inhibit the binding of the antibody to CXCR4.

Assays for determining whether an antibody can inhibit the binding of a ligand to CXCR4 are well known and would be immediately apparent to a person skilled in the art. A suitable assay is described in Example 3. Briefly, CXCR4+ cells were incubated with SDF-1 (or AMD-3100, as appropriate) or without SDF-1 (or AMD-3100, as appropriate), then antibody was added and the antibody was then detected with labeled anti-human antibody. For antibodies with the ability to inhibit the binding of a ligand to CXCR4, pre-incubation in the presence of SDF-1 (or AMD-3100, as appropriate) resulted in a reduction in antibody binding to CXCR4. Particularly, the binding of antibody to Ramos cells, Jurkat cells or CCRF-CEM cells which naturally express CXCR4 and are pre-incubated with SDF-1 or AMD-3100 is inhibited. Alternatively, the antibodies being tested can be added to the cells at the same time as the ligand, or the antibodies can be added first.

Alternative assays for determining whether an antibody can block the binding of a ligand to CXCR4 include the use of labeled ligand, e.g. radiolabelled ligand.

Although not the main mechanism of action for the antibodies of the invention, the antibodies of the invention preferably have the ability to induce antibody dependent cellular cytotoxicity (ADCC) of CXCR4+ cells. ADCC may be assayed in vitro using methods well known in the art. A suitable method in which CXCR4+ cells, e.g. CCRF-CEM cells, are labelled with a fluorescent label in order to assess ADCC lysis in the presence of PBMCs is described in Example 8. Alternatively, a Chromium-51 release assay may be used, for example. Thus, the antibodies of the invention may for example cause at least 10%, 15%, 20%, 22%, 25%, 30%, 40%, 50%, 60%, 70%, 80%, 90%, 95% or 98% killing of CXCR4+ cells in vitro e.g., in the presence of human PBMCs. Antibodies which can induce 100% or almost 100% killing are also included. For example, the B-1M22 antibody has been shown to induce 100% (or almost 100% given the bounds of experimental error) killing in some experiments (see Example 8 where essentially 100% killing of the CXCR4+ cell line CCRF-CEM in the presence of human PBMCs and the B-1M22 antibody is induced). In addition, at the IgG level, the antibodies C-9P21 and C-1I24 have been shown to cause at least 50%, 55% or 60% killing of the CXCR4+ cell line CCRF-CEM in the presence of human PBMCs, the antibody D-1K21 has been shown to cause at least 15%, 20% or 25% killing of the CXCR4+ cell line CCRF-CEM in the presence of human PBMCs (see Example 8).

Although not the main mechanism of action for the antibodies of the invention, ADCC is advantageous for some applications, particularly some therapeutic applications. Thus, in preferred embodiments the antibody can induce ADCC of CXCR4+ cells, preferably of CXCR4+ tumour cells in the presence of PBMCs. In other embodiments, the antibodies induce little or no significant ADCC.

The antibodies of the invention are preferably also shown to be suitably potent in terms of the concentration of antibody required to achieve such ADCC levels. Again, a suitable in vitro test is described in Example 8.

Thus, the antibody concentration required for half maximal cell lysis ($EC_{50}$) of CXCR4+ cells, e.g. CCRF-CEM cells, in vitro is preferably less than 2000 ng/ml, 1500 ng/ml, 1000 ng/ml, 700 ng/ml, 650 ng/ml, 620 ng/ml, 600 ng/ml, 550 ng/ml, 500 ng/ml, 450 ng/ml, 400 ng/ml, 350 ng/ml, 300 ng/ml, 250 ng/ml, 200 ng/ml, 150 ng/ml, 125 ng/ml, 100 ng/ml, 90 ng/ml, 80 ng/ml, 70 ng/ml, 60 ng/ml, 50 ng/ml, 45 ng/ml, 40 ng/ml, 35 ng/ml, 30 ng/ml, 25 ng/ml, 20 ng/ml, 15 ng/ml, 10 ng/ml, 9 ng/ml, 1 ng/ml, 5 ng/ml, 2 ng/ml, 1 ng/ml, 0.5 ng/ml or 0.25 ng/ml. For example, at the IgG level, the C-9P21 antibody of the invention has been shown to have an $EC_{50}$ of 1852 ng/ml for CCRF-CEM cells, and antibody C1I24 of the invention has been shown to have an $EC_{50}$ of 49.2 ng/ml for CCRF-CEM cells. Antibody D-1K21 of the invention has been shown to have an $EC_{50}$ of 79.9 ng/ml and antibody B-1M22 of the invention has been shown to have an $EC_{50}$ of 115.7 ng/ml.

In some embodiments, the antibodies may induce complement-dependent cytotoxicity (CDC) of CXCR4+ cells, but in other embodiments the antibodies are not capable of inducing CDC. For example, the antibodies B-1M22 and C1I24, in particular C-1I24, have shown a good ability to induce CDC of CXCR4+ cells, e.g. in Ramos cells (see Example 9).

The induction of CDC may be assayed using well-known standard methods, for example by labelling CXCR4+ cells such as Ramos cells with a fluorescent label in order to assess CDC lysis in the presence of human serum. A suitable assay is discussed in Example 9.

Other preferred properties include the absence of significant toxicity in vivo when the antibodies of the invention are administered and the absence of significant other side effects in vivo.

Preferably, the abilities described herein are observed at a measurable or significant level and more preferably at a statistically significant level, when compared to appropriate control levels.

Some antibodies are capable of being internalized into the cells to which they become bound. Thus, in some embodiments of the invention the antibodies are capable of being internalized. This property is particularly advantageous for use in immunoconjugates as any other agent attached to the antibody molecule should be internalized with the antibody molecule. In other embodiments no significant internalization is seen.

The skilled person will be aware of suitable ways to assay internalization, for example using temperature-differential fluorescence labeling on flow cytometry or confocal microscopy. An example of a suitable assay involves a secondary antibody labelled with a pH-sensitive dye (such as CypHer5E), which is minimally fluorescent at a basic pH (as found outside of cells) and maximally fluorescent at an acidic pH (as found inside of cells).

The term "ligand" of CXCR4 includes the natural ligands of CXCR4 such as SDF-1, which may be naturally produced, recombinantly expressed or synthesised in the laboratory. This term also includes non-natural or engineered ligands of CXCR4, such as AMD-3100, which can bind to CXCR4.

By "CXCR4+ cells" or "CXCR4 expressing cells" is meant cells which express CXCR4 on their surface, preferably at least substantially in its wild-type conformation. CXCR4+ cells may be naturally positive for CXCR4, or they may be transformants which express recombinant CXCR4.

In light of this invention, therefore, a range of anti-CXCR4 antibodies can be made and used in a variety of embodiments, including in the treatment of any of the disorders discussed elsewhere herein, particularly cancer (including metastatic cancer), autoimmune disorders, inflammatory disorders and infections, in particular viral infections such as HIV.

As used throughout the entire application, the terms "a" and "an" are used in the sense that they mean "at least one", "at least a first", "one or more" or "a plurality" of the referenced components or steps, except in instances wherein an upper limit is thereafter specifically stated. Therefore, an "antibody", as used herein, means "at least a first antibody". The operable limits and parameters of combinations, as with the amounts of any single agent, will be known to those of ordinary skill in the art in light of the present disclosure.

Preferred embodiments of the invention are compositions comprising at least one anti-CXCR4 antibody of the invention, or antigen binding fragment thereof.

Nucleic acid molecules comprising nucleotide sequences that encode the antibodies of the present invention as defined herein or parts or fragments thereof, or nucleic acid molecules substantially homologous thereto, form yet further aspects of the invention. Preferred nucleic acid molecules comprise sequences which encode the amino acid sequence set out in SEQ ID NO: 35 (which is preferably encoded by SEQ ID NO: 34), SEQ ID NO: 46 (which is preferably encoded by SEQ ID NO: 45), SEQ ID NO: 57 (which is preferably encoded by SEQ ID NO: 56), SEQ ID NO: 68 (which is preferably encoded by SEQ ID NO: 67) or SEQ ID NO: 101 (which is preferably encoded by SEQ ID NO: 100). Other preferred nucleic acid molecules comprise sequences which encode a heavy chain variable region (VH) that has the amino acid sequence of SEQ ID NO: 69, 71, 73 or 75 (which is preferably encoded by SEQ ID NO: 77, 79, 81 or 83) and/or comprise sequences which encode a light chain variable region (VL) which has the amino acid sequence of SEQ ID NO: 70, 72, 74, 76 or 103 (which is preferably encoded by SEQ ID NO: 78, 80, 82, 84 or 105). More preferred are nucleic acids which encode the following combinations: SEQ ID NOs: 69 and 70; or SEQ ID NOs: 71 and 72; or SEQ ID NOs 73 and 74; or SEQ ID NOs 75 and 76; or SEQ ID NOs 69 and 103. Also preferred are nucleic acid molecules which comprise the following combinations: SEQ ID NOs: 77 and 78; or SEQ ID NOs: 79 and 80; or SEQ ID NOs: 81 and 82; or SEQ ID NOs: 83 and 84; or SEQ ID NOs: 77 and 105.

Other preferred nucleic acid molecules comprise sequences that encode IgG forms of the antibodies of the invention, for example those as described in Example 4, or murine chimeric forms.

As indicated above, other nucleic acid molecules encompassed by the present invention are those encoding parts or fragments of the human antibodies of the present invention, e.g., those encoding a heavy chain variable region (VH) of an antibody (e.g., those encoding SEQ ID NO: 69, 71, 73 or 75, such as SEQ ID NOs: 77, 79, 81 or 83 respectively) or those encoding a light chain variable region (VL) of an antibody (e.g., those encoding SEQ ID NO: 70, 72, 74, 76 or 103, such as SEQ ID NO: 78, 80, 82, 84 or 105 respectively). Other preferred nucleic acid molecules are those encoding a heavy chain of an antibody of the present invention (e.g., those encoding SEQ ID NO: 108, 112, 116 or 120, such as SEQ ID NOs: 106, 110, 114 or 118 respectively) or those encoding a light chain of an antibody (e.g., those encoding SEQ ID NO: 109, 113, 117, 121 or 125 such as SEQ ID NOs: 107, 111, 115, 119 or 123 respectively).

Thus, fragments of the antibodies of the invention as defined herein, or sequences substantially homologous thereto, or nucleic acid molecules comprising sequences encoding such fragments form a yet further aspect of the invention.

Advantageously, the antibodies of the present invention, when in IgG format, have a high binding affinity for CXCR4, i.e., have a Kd in the range of $1 \times 10^{-8}$ M or $1 \times 10^{-9}$ M or less. Importantly, antibodies with such an affinity are in the established range that has been shown to be useful for therapy.

In some embodiments, antibodies of the invention may bind to both human CXCR4 and monkey CXCR4. For example, the antibodies C-9P21, C1I24, D1K21, 9N10 and B-1M22 all have this capability. Such cross-reactivity between species and in particular between humans and species commonly used as pre-clinical animal models may be an advantage as it allows a more effective translation from preclinical studies to clinical use. For example, having an antibody which cross reacts with the native CXCR4 present in the particular animal model used means that the results in this model are more likely to reflect the situation in a human patient, thereby allowing a more accurate assessment of for example dosing to be made and an increased likelihood of identifying any potentially relevant or problematic side effects. This is especially the case if the antibody has similar affinity to both monkey and human CXCR4.

For example, the ability of an antibody of the invention to bind to both human CXCR4 and monkey CXCR4 means that such antibodies can be tested in preclinical toxicity studies to assess adverse side effects of the treatment and to find appropriate tolerated dosages.

In addition, the ability to bind both human CXCR4 and mouse CXCR4 means that the results shown by such antibodies of the invention in mouse models, e.g. mouse syngeneic models using immunocompetent mice, are more likely to be representative of the activity of the antibodies in human subjects. The reason for this is that antibodies which can bind to human CXCR4 but not mouse CXCR4 will bind to CXCR4 expressed by the human tumor cells in the mouse model but will not be able to bind to endogenous murine CXCR4. This is of course unlike the situation in a human patient, in which CXCR4 expressed by the tumor and endogenous CXCR4 would be present.

The potential disadvantage with such a situation is that an antibody which binds to human CXCR4 but not, or with significantly lower affinity, to mouse CXCR4 might perform well in a human tumor xenograft model in immunocompromized mice (e.g. nude or SCID mice) but this might not be reflected by a similar performance in a human system where much more CXCR4 was present. In other words, the anti-tumor effect seen in a mouse xenograft system with an antibody which can bind to human CXCR4 but not mouse CXCR4 might look better than the clinical reality. In contrast, when working with an antibody that can bind to both human and mouse CXCR4 then this will bind to all forms of CXCR4 present in the mouse model system and is likely to be more representative of the situation when the antibody is put into humans. This is especially the case if the antibody has similar affinity to both murine and human CXCR4.

In preferred embodiments, antibodies of the invention bind to human and monkey CXCR4 or to human and mouse CXCR4 or to human and monkey and mouse CXCR4 with similar affinities.

By "similar affinity" is also meant that the binding affinity of the antibody for human CXCR4 and for one or more of the other species of interest (e.g. monkey or mouse) is comparable, e.g. is not more than a factor of 20 different. More preferably the difference between the binding affinities is less than a factor of 15, more preferably less than a factor of 10, most preferably less than a factor of 5, 4, 3 or 2. Comparison of binding affinities can be carried out by any appropriate method. For a cell surface ligand such as CXCR4, flow cytometry methods such as FACS provide a convenient method of comparison in which binding curves and, for example, median values, can be compared, in the same experiment. An appropriate method is described in Example 5.

However, in other embodiments, the antibodies of the present invention may not bind to monkey CXCR4 and/or they may not bind to mouse CXCR4.

In the following descriptions of the compositions, immunoconjugates, pharmaceuticals, combinations, cocktails, kits, first and second medical uses and all methods in accordance with this invention, the terms "antibody" and "immunoconjugate", or an antigen-binding region or fragment thereof, unless otherwise specifically stated or made clear from the scientific terminology, refer to a range of anti-CXCR4 antibodies as well as to the specific C-9P21, B-1M22, C-1I24, D-1K21, and 9N10 antibodies.

The terms "antibody" and "immunoglobulin", as used herein, refer broadly to any immunological binding agent or molecule that comprises a human antigen binding domain, including polyclonal and monoclonal antibodies. Depending on the type of constant domain in the heavy chains, whole antibodies are assigned to one of five major classes: IgA, IgD, IgE, IgG, and IgM and the antibodies of the invention may be in any one of these classes. Several of these are further divided into subclasses or isotypes, such as IgG1, IgG2, IgG3, IgG4, and the like. The heavy-chain constant domains that correspond to the difference classes of immunoglobulins are termed α, δ, ε, γ and μ, respectively. The subunit structures and three-dimensional configurations of different classes of immunoglobulins are well known.

Generally, where whole antibodies rather than antigen binding regions are used in the invention, IgG and/or IgM are preferred because they are the most common antibodies in the physiological situation and because they are most easily made in a laboratory setting. IgG1 antibodies are particularly preferred.

The "light chains" of mammalian antibodies are assigned to one of two clearly distinct types: kappa (κ) and lambda (λ), based on the amino acid sequences of their constant domains and some amino acids in the framework regions of their variable domains. There is essentially no preference to the use of κ or λ light chain constant regions in the antibodies of the present invention.

As will be understood by those in the art, the immunological binding reagents encompassed by the term "antibody" extend to all antibodies and antigen binding fragments thereof, including whole antibodies, dimeric, trimeric and multimeric antibodies; bispecific antibodies; chimeric antibodies; recombinant and engineered antibodies, and fragments thereof.

The term "antibody" is thus used to refer to any antibody-like molecule that has an antigen binding region, and this term includes antibody fragments that comprise an antigen binding domain such as Fab', Fab, F(ab)$_2$, single domain antibodies (DABs), T and Abs dimer, Fv, scFv (single chain Fv), dsFv, ds-scFv, Fd, linear antibodies, minibodies, diabodies, bispecific antibody fragments, bibody, tribody (scFv-Fab fusions, bispecific or trispecific, respectively); sc-diabody; kappa (lamda) bodies (scFv-CL fusions); Bispecific T-cell Engager (BiTE) (scFv-scFv tandems to attract T cells); dual variable domain (DVD)-Ig (bispecific format); small immunoprotein (SIP) (kind of minibody); SMIP ("small modular immunopharmaceutical" scFv-Fc dimer; DART (ds-stabilized diabody "Dual Affinity ReTargeting"); small antibody mimetics comprising one or more CDRs and the like.

The techniques for preparing and using various antibody-based constructs and fragments are well known in the art (see Kabat et al., 1991, specifically incorporated herein by reference). Diabodies, in particular, are further described in EP 404, 097 and WO 93/11161; whereas linear antibodies are further described in Zapata et al. (1995).

Antibodies can be fragmented using conventional techniques. For example, F(ab')$_2$ fragments can be generated by treating the antibody with pepsin. The resulting F(ab')$_2$ fragment can be treated to reduce disulfide bridges to produce Fab' fragments. Papain digestion can lead to the formation of Fab fragments. Fab, Fab' and F(ab')$_2$, scFv, Fv, dsFv, Fd, dAbs, T and Abs, ds-scFv, dimers, minibodies, diabodies, bispecific antibody fragments and other fragments can also be synthesized by recombinant techniques or can be chemically synthesized. Techniques for producing antibody fragments are well known and described in the art. For example, each of Beckman et al., 2006; Holliger & Hudson, 2005; Le Gall et al., 2004; Reff & Heard, 2001; Reiter et al., 1996; and Young et al., 1995 further describe and enable the production of effective antibody fragments.

The antibodies or antibody fragments can be produced naturally or can be wholly or partially synthetically produced. Thus the antibody may be from any appropriate source, for example recombinant sources and/or produced in transgenic animals or transgenic plants, or in eggs using the IgY technology. Thus, the antibody molecules can be produced in vitro or in vivo.

Preferably, the antibody or antibody fragment comprises an antibody light chain variable region ($V_L$) that comprises three CDR domains and an antibody heavy chain variable region ($V_H$) that comprises three CDR domains. Said VL and VH generally form the antigen binding site.

An "Fv" fragment is the minimum antibody fragment that contains a complete antigen-recognition and binding site. This region has a dimer of one heavy chain and one light chain variable domain in tight, non-covalent association. It is in this configuration that the three hypervariable regions (CDRs) of each variable domain interact to define an antigen-binding site on the surface of the $V_H$-$V_L$ dimer. Collectively, the six hypervariable regions (CDRs) confer antigen-binding specificity to the antibody.

However, it is well documented in the art that the presence of three CDRs from the light chain variable domain and three CDRs from the heavy chain variable domain of an antibody is not necessary for antigen binding. Thus, constructs smaller than the above classical antibody fragment are known to be effective.

For example, camelid antibodies (Hamers-Casterman et al., 1993; Arbabi Ghahroudi et al., 1997) have an extensive antigen binding repertoire but are devoid of light chains. Also, results with single domain antibodies comprising VH domains alone (Ward et al., 1989; Davies and Riechmann, 1995) or VL domains alone (van den Beucken et al., 2001) show that these domains can bind to antigen with acceptably high affinities. Thus, three CDRs can effectively bind antigen.

It is also known that a single CDR, or two CDRs, can effectively bind antigen. As a first example, a single CDR can be inserted into a heterologous protein and confer antigen binding ability on the heterologous protein, as exemplified by showing that a VH CDR3 region inserted into a heterologous protein, such as GFP, confers antigen binding ability on the heterologous protein (Kiss et al., 2006; Nicaise et al., 2004).

It is further known that two CDRs can effectively bind antigen, and even confer superior properties than possessed by the parent antibody. For example, it has been shown (Qiu et al., 2007) that two CDRs from a parent antibody (a VH CDR1 and a VL CDR3 region) retain the antigen recognition properties of the parent molecule but have a superior capacity to penetrate tumours. Joining these CDR domains with an appropriate linker sequence (e.g., from VH FR2) to orientate the CDRs in a manner resembling the native parent antibody produced even better antigen recognition. Therefore, it is known in the art that it is possible to construct antigen binding antibody mimetics comprising two CDR domains (preferably one from a VH domain and one from a VL domain, more preferably, with one of the two CDR domains being a CDR3 domain) orientated by means of an appropriate framework region to maintain the conformation found in the parent antibody.

Thus, although preferred antibodies of the invention might comprise six CDR regions (three from a light chain and three from a heavy chain), antibodies with fewer than six CDR regions and as few as one or two CDR regions are encompassed by the invention. In addition, antibodies with CDRs from only the heavy chain or light chain are also contemplated.

Preferred antibodies of the invention that bind to CXCR4 comprise at least one heavy chain variable region that comprises three CDRs and at least one light chain variable region that comprises three CDRs, wherein said heavy chain variable region comprises:
  (a) a variable heavy (VH) CDR1 that has the amino acid sequence of SEQ ID NO: 1 or a sequence substantially homologous thereto,
  (b) a VH CDR2 that has the amino acid sequence of SEQ ID NO: 2 or a sequence substantially homologous thereto, and
  (c) a VH CDR3 that has the amino acid sequence of SEQ ID NO: 3 or a sequence substantially homologous thereto; or
  (d) a variable heavy (VH) CDR1 that has the amino acid sequence of SEQ ID NO: 7 or a sequence substantially homologous thereto,
  (e) a VH CDR2 that has the amino acid sequence of SEQ ID NO: 8 or a sequence substantially homologous thereto, and
  (f) a VH CDR3 that has the amino acid sequence of SEQ ID NO: 9 or a sequence substantially homologous thereto; or
  (g) a variable heavy (VH) CDR1 that has the amino acid sequence of SEQ ID NO: 13 or a sequence substantially homologous thereto,
  (h) a VH CDR2 that has the amino acid sequence of SEQ ID NO: 14 or a sequence substantially homologous thereto, and
  (i) a VH CDR3 that has the amino acid sequence of SEQ ID NO: 15 or a sequence substantially homologous thereto; or
  (j) a variable heavy (VH) CDR1 that has the amino acid sequence of SEQ ID NO: 19 or a sequence substantially homologous thereto,
  (k) a VH CDR2 that has the amino acid sequence of SEQ ID NO: 20 or a sequence substantially homologous thereto, and
  (l) a VH CDR3 that has the amino acid sequence of SEQ ID NO: 21 or a sequence substantially homologous thereto; or Preferred light chain CDR regions for use in conjunction with the specified heavy chain CDR regions are described elsewhere herein. However, other light chain variable regions that comprise three CDRs for use in conjunction with the heavy chain variable regions of the invention are also contemplated. Appropriate light chain variable regions which can be used in combination with the heavy chain variable regions of the invention and which give rise to an antibody which binds CXCR4 can be readily identified by a person skilled in the art.

For example, a heavy chain variable region of the invention can be combined with a single light chain variable region or a repertoire of light chain variable regions and the resulting antibodies tested for binding to CXCR4. It would be expected that a reasonable number of such combinations of heavy chain variable regions of the invention with different light chain variable regions would retain the ability to bind CXCR4. Indeed the 9N10 antibody has the same heavy chain variable region as C-9P21 but a different light chain variable region.

Similar methods could be used to identify alternative heavy chain variable regions for use in combination with preferred light chain variable regions of the invention.

In certain embodiments, the antibody or antibody fragment comprises all or a portion of a heavy chain constant region, such as an IgG1, IgG2, IgG3, IgG4, IgA1, IgA2, IgE, IgM or IgD constant region. Preferably, the heavy chain constant region is an IgG1 heavy chain constant region, or a portion thereof. Furthermore, the antibody or antibody fragment can comprise all or a portion of a kappa light chain constant region or a lambda light chain constant region, or a portion thereof. All or part of such constant regions may be produced naturally or may be wholly or partially synthetic. Appropriate sequences for such constant regions are well known and documented in the art. When a full complement of constant regions from the heavy and light chains are included in the antibodies of the invention, such antibodies are typically referred to herein as "full length" antibodies or "whole" antibodies Antibodies containing an Fc region are preferred for certain uses, particularly therapeutic uses in vivo, where the Fc region mediates effector functions such as ADCC. Appropriate Fc regions would be well known to a person skilled in the art and can be selected accordingly.

The term "substantially homologous" as used herein in connection with an amino acid or nucleic acid sequence includes sequences having at least 70% or 75%, preferably at least 80%, and even more preferably at least 85%, 90%, 95%, 96%, 97%, 98% or 99%, sequence identity to the amino acid or nucleic acid sequence disclosed. Substantially homologous sequences of the invention thus include single or multiple base or amino acid alterations (additions, substitutions, insertions or deletions) to the sequences of the invention. At the amino acid level preferred substantially homologous sequences contain only up to 1, 2, 3, 4 or 5, preferably up to 1, 2 or 3, more preferably up to 1 or 2, altered amino acids, in one or more of the framework regions and/or one or more of the CDRs making up the sequences of the invention. Said alterations can be with conservative or non-conservative amino acids. Preferably said alterations are conservative amino acid substitutions.

The substantially homologous nucleic acid sequences also include nucleotide sequences that hybridize to the nucleic acid sequences disclosed (or their complementary sequences), e.g., hybridize to nucleotide sequences encoding one or more of the light chain or heavy chain CDRs of the invention, the light or heavy chain variable regions of the invention, or the antibodies of the invention (or hybridize to their complementary sequences), under at least moderately stringent hybridization conditions.

The term "substantially homologous" also includes modifications or chemical equivalents of the amino acid and nucleotide sequences of the present invention that perform substantially the same function as the proteins or nucleic acid molecules of the invention in substantially the same way. For example, any substantially homologous antibody (or the substantially homologous nucleic acid encoding it) should retain the ability to bind to CXCR4 as described above. Preferably, any substantially homologous antibody should retain one or more of the functional capabilities of the antibody, e.g. as defined elsewhere herein. Preferably, any substantially homologous antibody should retain the ability to specifically bind to the same epitope of CXCR4 as recognized by the antibody in question, for example, the same epitope recognized by the CDR domains of the invention or the VH and VL domains of the invention as described herein. Binding to the same epitope/antigen can be readily tested by methods well known and described in the art, e.g., using binding assays, e.g., a competition assay. Retention of other functional properties can also readily be tested by methods well known and described in the art. For the antibodies of the present invention it is particularly preferred that the antagonistic properties and/or the non-induction of apoptosis property is retained.

Thus, a person skilled in the art will appreciate that binding assays can be used to test whether "substantially homologous" antibodies have the same binding specificities as the antibodies and antibody fragments of the invention, for example, binding assays such as flow cytometry, ELISA assays or BIAcore assays can readily be used to establish whether such "substantially homologous" antibodies can bind to CXCR4. Flow cytometry on cells is the most convenient assay for analysing binding to a cell surface receptor such as CXCR4. As outlined above, a competition binding assay can be used to test whether "substantially homologous" antibodies retain the ability to specifically bind to substantially the same epitope of CXCR4 as recognized by the antibodies of the invention. The method described above is only one example of a suitable competition assay. The skilled person will be aware of other suitable methods and variations.

Substantially homologous sequences of proteins of the invention include, without limitation, conservative amino acid substitutions, or for example alterations that do not effect the VH, VL or CDR domains of the antibodies, e.g., include scFv antibodies where a different linker sequence is used or antibodies where tag sequences or other components are added that do not contribute to the binding of antigen, or alterations to convert one type or format of antibody molecule or fragment to another type or format of antibody molecule or fragment (e.g., conversion from Fab to scFv or vice versa), or the conversion of an antibody molecule to a particular class or subclass of antibody molecule (e.g., the conversion of an antibody molecule to IgG or a subclass thereof, e.g., IgG1 or IgG3).

A "conservative amino acid substitution", as used herein, is one in which the amino acid residue is replaced with another amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., glycine, cysteine, alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

Homology may be assessed by any convenient method. However, for determining the degree of homology between sequences, computer programs that make multiple alignments of sequences are useful, for instance Clustal W (Thompson et al., 1994). If desired, the Clustal W algorithm can be used together with BLOSUM 62 scoring matrix (Henikoff and Henikoff, 1992) and a gap opening penalty of 10 and gap extension penalty of 0.1, so that the highest order match is obtained between two sequences wherein at least 50% of the total length of one of the sequences is involved in the alignment. Other methods that may be used to align sequences are the alignment method of Needleman and Wunsch (1970), as revised by Smith and Waterman (1981) so that the highest order match is obtained between the two sequences and the number of identical amino acids is determined between the two sequences. Other methods to calculate the percentage identity between two amino acid sequences are generally art recognized and include, for example, those described by Carillo and Lipton (1988) and those described in Computational Molecular Biology, Lesk, e.d. Oxford University Press, New York, 1988, Biocomputing: Informatics and Genomics Projects.

Generally, computer programs will be employed for such calculations. Programs that compare and align pairs of sequences, like ALIGN (Myers and Miller, 1988), FASTA (Pearson and Lipman, 1988; Pearson, 1990) and gapped BLAST (Altschul et al., 1997), BLASTP, BLASTN, or GCG (Devereux et al., 1984) are also useful for this purpose. Furthermore, the Dali server at the European Bioinformatics institute offers structure-based alignments of protein sequences (Holm, 1993; 1995; 1998).

By way of providing a reference point, sequences according to the present invention having 70%, 75%, 80%, 85%, 90%, 95%, 96%, 97%, 98% or 99% homology, sequence identity etc. may be determined using the ALIGN program with default parameters (for instance available on Internet at the GENESTREAM network server, IGH, Montpellier, France).

By "at least moderately stringent hybridization conditions" it is meant that conditions are selected that promote selective hybridization between two complementary nucleic acid molecules in solution. Hybridization may occur to all or a portion of a nucleic acid sequence molecule. The hybridizing portion is typically at least 15 (e.g., 20, 25, 30, 40 or 50) nucleotides in length. Those skilled in the art will recognize that the stability of a nucleic acid duplex, or hybrids, is determined by the Tm, which in sodium containing buffers is a function of the sodium ion concentration and temperature (Tm=81.5° C.−16.6 (Log 10 [Na+])+0.41(% (G+C)−600/1), or similar equation). Accordingly, the parameters in the wash conditions that determine hybrid stability are sodium ion concentration and temperature. In order to identify molecules that are similar, but not identical, to a known nucleic acid molecule, a 1% mismatch may be assumed to result in about a 1° C. decrease in Tm. For example, if nucleic acid molecules are sought that have a >95% identity, the final wash temperature will be reduced by about 5° C. Based on these considerations those skilled in the art will be able to readily select appropriate hybridization conditions. In preferred embodiments, stringent hybridization conditions are selected. By way of example the following conditions may be employed to achieve stringent hybridization: hybridization at 5× sodium chloride/sodium citrate (SSC)/5×Denhardt's solution/1.0% SDS at Tm −5° C. based on the above equation, followed by a wash of 0.2×SSC/0.1% SDS at 60° C. Moderately stringent hybridization conditions include a washing step in 3×SSC at 42° C. By way of further example, sequences that "hybridize" are those sequences binding (hybridizing) under non-stringent conditions (e.g., 6×SSC, 50% formamide at room temperature) and washed under conditions of low stringency (e.g., 2×SSC, room temperature, more preferably 2×SSC, 42° C.) or conditions of higher stringency (e.g., 2×SSC, 65° C.) (where SSC=0.15M NaCl, 0.015M sodium citrate, pH 7.2).

It is understood, however, that equivalent stringencies may be achieved using alternative buffers, salts and temperatures. Additional guidance regarding hybridization conditions may be found in: Current Protocols in Molecular Biology, John Wiley & Sons, N.Y., 1989, 6.3.1-6.3.6 and in: Sambrook et al., Molecular Cloning, a Laboratory Manual, Cold Spring Harbor Laboratory Press, 1989, Vol. 3.

Generally speaking, sequences that hybridize under conditions of high stringency are preferred, as are sequences which, but for the degeneracy of the code, would hybridize under high stringency conditions.

In other preferred embodiments, second generation antibodies are provided that have enhanced or superior properties in comparison to an original anti-CXCR4 antibody, such as C-9P21, B-1M22, C-1I24, D-1K21 or 9N10. For example, the second generation antibodies may have a stronger binding affinity for CXCR4, a superior cross reactivity profile, induce even lower levels of apoptosis of CXCR4+ cells, superior ability to target CXCR4+ cells, particularly tumour cells, e.g. an improved ability to inhibit growth of tumor cells, an improved antagonistic ability, e.g. an improved ability to block Ca-influx induced by binding of SDF-1 to CXCR4, an improved inhibition of ligand induced migration, or an improved ability to induce ADCC or CDC, depending on the application, or an improved treatment of the disorders discussed elsewhere herein.

Comparisons to identify effective second generation antibodies are readily conducted and quantified, e.g., using one or more of the various assays described in detail herein or in the art. Second generation antibodies that have an enhanced biological property or activity of at least about 2-fold, 5-fold, 10-fold, 20-fold, and preferably, at least about 50-fold, in comparison to the anti-CXCR4 antibodies of the present invention, as exemplified by the C-9P21, B-1M22, C-1I24, D-1K21, or 9N10 antibodies, are encompassed by the present invention. Particularly preferred second generation antibodies comprise VH chains of the antibodies of the present invention, or the VH CDRs thereof, combined with alternative VL chains (or alternative VL CDRs).

The antibody, binding protein and nucleic acid molecules of the invention are generally "isolated" or "purified" molecules insofar as they are distinguished from any such components that may be present in situ within a human or animal body or a tissue sample derived from a human or animal body. The sequences may, however, correspond to or be substantially homologous to sequences as found in a human or animal body. Thus, the term "isolated" or "purified" as used herein in reference to nucleic acid molecules or sequences and proteins or polypeptides, e.g., antibodies, refers to such molecules when isolated from, purified from, or substantially free of their natural environment, e.g., isolated from or purified from the human or animal body (if indeed they occur naturally), or refers to such molecules when produced by a technical process, i.e., includes recombinant and synthetically produced molecules.

Thus, when used in connection with a nucleic acid molecule, such terms may refer to a nucleic acid substantially free of material with which it is naturally associated such as other nucleic acids/genes or polypeptides. These terms may also refer to a nucleic acid substantially free of cellular material or culture medium when produced by recombinant DNA techniques, or substantially free of chemical precursors, or other chemicals when chemically synthesized. An isolated or purified nucleic acid may also be substantially free of sequences that naturally flank the nucleic acid (i.e., sequences located at the 5' and 3' ends of the nucleic acid) from which the nucleic acid is derived or sequences that have been made to flank the nucleic acid (e.g., tag sequences or other sequence that have no therapeutic value) by, for example, genetic engineering.

Thus, when used in connection with a protein or polypeptide molecule such as light chain CDRs 1, 2 and 3, heavy chain CDRs 1, 2 and 3, light chain variable regions, heavy chain variable regions, and binding proteins or antibodies of the invention, including full length antibodies, the term "isolated" or "purified" typically refers to a protein substantially free of cellular material or other proteins from the source from which it is derived. In some embodiments, particularly where the protein is to be administered to humans or animals, such isolated or purified proteins are substantially free of culture medium when produced by recombinant techniques, or chemical precursors or other chemicals when chemically synthesized. Such isolated or purified proteins may also be free of flanking sequences such as those described above for the isolated nucleic acid molecules.

The term "nucleic acid sequence" or "nucleic acid molecule" as used herein refers to a sequence of nucleoside or nucleotide monomers composed of naturally occurring bases, sugars and intersugar (backbone) linkages. The term also includes modified or substituted sequences comprising non-naturally occurring monomers or portions thereof. The nucleic acid sequences of the present invention may be deoxyribonucleic acid sequences (DNA) or ribonucleic acid sequences (RNA) and may include naturally occurring bases including adenine, guanine, cytosine, thymidine and uracil. The sequences may also contain modified bases. Examples of such modified bases include aza and deaza adenine, guanine, cytosine, thymidine and uracil; and xanthine and hypoxanthine. The nucleic acid molecules may be double stranded or single stranded. The nucleic acid molecules may be wholly or partially synthetic or recombinant.

In preferred embodiments the antibodies of the invention are human antibodies, more preferably fully human antibodies. In this regard, human antibodies generally have at least three potential advantages for use in human therapy. First, the human immune system should not recognize the antibody as foreign. Second, the half-life in the human circulation will be similar to naturally occurring human antibodies, allowing smaller and less frequent doses to be given. Third, because the effector portion is human, in embodiments where the mode of action involves killing of the target cells, it will interact better with the other parts of the human immune system, e.g., to destroy target cells more efficiently by complement-dependent cytotoxicity (CDC) or antibody-dependent cellular cytotoxicity (ADCC).

However, although human antibodies are generally recognized to display these advantages, it is known that the development of human antibodies that have high enough affinities and appropriate functional properties to make them candidates for successful human therapy is by no means straightforward. The art therefore still lacks anti-CXCR4 for the safe and effective treatment of humans, and poses challenges to the development of such agents.

The term "human" as used herein in connection with antibody molecules and binding proteins first refers to antibodies and binding proteins having variable regions (e.g., $V_H$, $V_L$, CDR or FR regions) and, optionally, constant antibody regions, isolated or derived from a human repertoire or derived from or corresponding to sequences found in humans or a human repertoire, e.g., in the human germline or somatic cells. The C-9P21, B-1M22, C-1I24, D-1K21, and 9N10 antibodies of the invention are examples of such human antibody molecules wherein the variable regions have been isolated from a human repertoire.

The "human" antibodies and binding proteins of the invention further include amino acid residues not encoded by human sequences, e.g., mutations introduced by random or site directed mutations in vitro, for example mutations introduced by in vitro cloning or PCR. Particular examples of such mutations are mutations that involve conservative substitutions or other mutations in a small number of residues of the antibody or binding protein, e.g., in up to 5, 4, 3, 2 or 1 of the residues of the antibody or binding protein, preferably e.g., in up to 5, 4, 3, 2 or 1 of the residues making up one or more of the CDRs of the antibody or binding protein. Certain examples of such "human" antibodies include antibodies and variable regions that have been subjected to standard modification techniques to reduce the amount of potentially immunogenic sites.

Thus, the "human" antibodies of the invention include sequences derived from and related to sequences found in humans, but which may not naturally exist within the human antibody germline repertoire in vivo. In addition, the human antibodies and binding proteins of the present invention include proteins comprising human consensus sequences identified from human sequences, or sequences substantially homologous to human sequences.

In addition, the human antibodies and binding proteins of the present invention are not limited to combinations of $V_H$, $V_L$, CDR or FR regions that are themselves found in combination in human antibody molecules. Thus, the human antibodies and binding proteins of the invention can include or correspond to combinations of such regions that do not necessarily exist naturally in humans.

In preferred embodiments, the human antibodies will be fully human antibodies. "Fully human" antibodies, as used herein, are antibodies comprising "human" variable region domains and/or CDRs, as defined above, without substantial non-human antibody sequences or without any non-human antibody sequences. For example, antibodies comprising human variable region domains and/or CDRs "without substantial non-human antibody sequences" are antibodies, domains and/or CDRs in which only up to 5, 4, 3, 2 or 1 amino acids are amino acids that are not encoded by human antibody sequences. Thus, "fully human" antibodies are distinguished from "humanized" antibodies, which are based on substantially non-human variable region domains, e.g., mouse variable region domains, in which certain amino acids have been changed to better correspond with the amino acids typically present in human antibodies.

The "fully human" antibodies of the invention may be human variable region domains and/or CDRs without any other substantial antibody sequences, such as being single chain antibodies. Alternatively, the "fully human" antibodies of the invention may be human variable region domains and/or CDRs integral with or operatively attached to one or more human antibody constant regions. Certain preferred fully human antibodies are IgG antibodies with the full complement of IgG constant regions.

In other embodiments, "human" antibodies of the invention will be part-human chimeric antibodies. "Part-human chimeric" antibodies, as used herein, are antibodies comprising "human" variable region domains and/or CDRs operatively attached to, or grafted onto, a constant region of a non-human species, such as rat or mouse. Such part-human chimeric antibodies may be used, for example, in pre-clinical studies, wherein the constant region will preferably be of the same species of animal used in the pre-clinical testing. These part-human chimeric antibodies may also be used, for example, in ex vivo diagnostics, wherein the constant region of the non-human species may provide additional options for antibody detection.

The term "fragment" as used herein refers to fragments of biological relevance, e.g., fragments that contribute to antigen binding, e.g., form part of the antigen binding site, and/or contribute to the inhibition or reduction in function of the CXCR4 antigen. Certain preferred fragments comprise a heavy chain variable region ($V_H$ domain) and/or a light chain variable region ($V_L$ domain) of the antibodies of the invention. Other preferred fragments comprise one or more of the heavy chain CDRs of the antibodies of the invention (or of the $V_H$ domains of the invention), or one or more of the light chain CDRs of the antibodies of the invention (or of the $V_L$ domains of the invention). Certain preferred fragments are at least 5 amino acids in length and comprise at least one CDR region, preferably a CDR3 region, more preferably a heavy chain CDR3 region.

In embodiments where the antibodies of the invention comprise a fragment of any of the defined sequences (for example comprise a fragment of SEQ ID NO:35, 46, 57, 68 or 101), e.g., are antibodies comprising $V_H$ and/or $V_L$ domains of the invention, or are antibodies or binding proteins comprising one or more CDRs of the invention, then these regions/domains are generally separated within the antibody or binding protein so that each region/domain can perform its biological function and so that the contribution to antigen binding is retained. Thus, the $V_H$ and $V_L$ domains are preferably separated by appropriate scaffold sequences/linker sequences and the CDRs are preferably separated by appropriate framework regions such as those found in naturally occurring antibodies and/or effective engineered antibodies. Thus, the $V_H$, $V_L$ and individual CDR sequences of the invention are preferably provided within or incorporated into an appropriate framework or scaffold to enable antigen binding. Such framework sequences or regions may correspond to naturally occurring framework regions, FR1, FR2, FR3 and/or FR4, as appropriate to form an appropriate scaffold, or may correspond to consensus framework regions, for example identified by comparing various naturally occurring framework regions. Alternatively, non-antibody scaffolds or frameworks, e.g., T cell receptor frameworks can be used.

Appropriate sequences that can be used for framework regions are well known and documented in the art and any of these may be used. Preferred sequences for framework regions are one or more (i.e. one, two, three or four) of the framework regions making up the $V_H$ and/or $V_L$ domains of the invention, i.e., one or more of the framework regions disclosed in Tables 1, 2, 3, 4 or 5, or framework regions substantially homologous thereto, and in particular framework regions that allow the maintenance of antigen specificity, for example framework regions that result in substantially the same or the same 3D structure of the antibody.

In certain preferred embodiments, all four of the variable light chain (SEQ ID NOs:30, 31, 32 and 33) and/or variable heavy chain (SEQ ID NOs: 25, 26, 27 and 28), as appropriate, FR regions of SEQ ID NO: 35 (also shown in Table 1), or FR regions substantially homologous thereto, are found in the antibodies of the invention.

In certain preferred embodiments, all four of the variable light chain (SEQ ID NOs:41, 42, 43 and 44) and/or variable heavy chain (SEQ ID NOs: 36, 37, 38 and 39), as appropriate, FR regions of SEQ ID NO: 46 (also shown in Table 2), or FR regions substantially homologous thereto, are found in the antibodies of the invention.

In certain preferred embodiments, all four of the variable light chain (SEQ ID NOs:52, 53, 54 and 55) and/or variable heavy chain (SEQ ID NOs: 47, 48, 49 and 50), as appropriate, FR regions of SEQ ID NO: 57 (also shown in Table 3), or FR regions substantially homologous thereto, are found in the antibodies of the invention.

In certain preferred embodiments, all four of the variable light chain (SEQ ID NOs: 63, 64, 65 and 66) and/or variable heavy chain (SEQ ID NOs: 58, 59, 60 and 61), as appropriate, FR regions of SEQ ID NO: 68 (also shown in Table 4), or FR regions substantially homologous thereto, are found in the antibodies of the invention.

In certain preferred embodiments, all four of the variable light chain (SEQ ID NOs: 96, 97, 98 and 33) and/or variable heavy chain (SEQ ID NOs: 25, 26, 27 and 28), as appropriate, FR regions of SEQ ID NO: 101 (also shown in Table 5), or FR regions substantially homologous thereto, are found in the antibodies of the invention.

In addition, although preferred antibodies of the invention are made up of $V_H$, $V_L$ or CDRs of the invention, it should be noted that the antibodies of the invention also encompass one or more $V_H$, $V_L$ or CDRs of the invention in combination with other $V_H$, $V_L$ or CDRs not of the invention, provided that the CXCR4 binding properties or anti-CXCR4 properties of the antibodies of the invention as outlined herein are still present.

The term "heavy chain complementarity determining region" ("heavy chain CDR") as used herein refers to regions of hypervariability within the heavy chain variable region ($V_H$ domain) of an antibody molecule. The heavy chain variable region has three CDRs termed heavy chain CDR1, heavy chain CDR2 and heavy chain CDR3 from the amino terminus to carboxy terminus. The heavy chain variable region also has four framework regions (FR1, FR2, FR3 and FR4 from the amino terminus to carboxy terminus). These framework regions separate the CDRs.

The term "heavy chain variable region" ($V_H$ domain) as used herein refers to the variable region of a heavy chain of an antibody molecule.

The term "light chain complementarity determining region" ("light chain CDR") as used herein refers to regions of hypervariability within the light chain variable region ($V_L$ domain) of an antibody molecule. Light chain variable regions have three CDRs termed light chain CDR1, light chain CDR2 and light chain CDR3 from the amino terminus to the carboxy terminus. The light chain variable region also has four framework regions (FR1, FR2, FR3 and FR4 from the amino terminus to carboxy terminus). These framework regions separate the CDRs.

The term "light chain variable region" ($V_L$ domain) as used herein refers to the variable region of a light chain of an antibody molecule.

It should be noted that the Kabat nomenclature is followed herein, where necessary, in order to define the positioning of the CDRs (Kabat et al., 1991, specifically incorporated herein by reference).

A person skilled in the art will appreciate that the proteins and polypeptides of the invention, such as the light and heavy CDRs, the light and heavy chain variable regions, antibodies, antibody fragments, and immunoconjugates, may be prepared in any of several ways well known and described in the art, but are most preferably prepared using recombinant methods.

Nucleic acid fragments encoding the light and heavy chain variable regions of the antibodies of the invention can be derived or produced by any appropriate method, e.g., by cloning or synthesis. Such sequences could, for example, be prepared by cloning appropriate sequences from e.g., human germ line genes and then making any necessary modifications to the germ line sequences to obtain the sequences of the invention using methods well known and described in the art. An alternative and more efficient method would be to synthesize the appropriate light or heavy chain variable region sequence as overlapping primers, and use primer extension to obtain the full sequence. This full sequence could then be amplified via PCR with primers containing appropriate restriction sites for further cloning and manipulation, e.g., for cloning into an appropriate expression vector. Five to seven overlapping primers per variable region are normally be sufficient, thereby making this technique very efficient and precise.

Once nucleic acid fragments encoding the light and heavy chain variable regions of the antibodies of the invention have been obtained, these fragments can be further manipulated by standard recombinant DNA techniques, for example to convert the variable region fragments into full length antibody molecules with appropriate constant region domains, or into particular formats of antibody fragment discussed elsewhere herein, e.g., Fab fragments, scFv fragments, etc. Typically, or as part of this further manipulation procedure, the nucleic acid fragments encoding the antibody molecules of the invention are generally incorporated into an appropriate expression vector in order to facilitate production of the antibodies of the invention.

Possible expression vectors include but are not limited to cosmids, plasmids, or modified viruses (e.g., replication defective retroviruses, adenoviruses and adeno-associated viruses), so long as the vector is compatible with the host cell used. The expression vectors are "suitable for transformation of a host cell", which means that the expression vectors contain a nucleic acid molecule of the invention and regulatory sequences selected on the basis of the host cells to be used for expression, which are operatively linked to the nucleic acid molecule. Operatively linked is intended to mean that the nucleic acid is linked to regulatory sequences in a manner that allows expression of the nucleic acid.

The invention therefore contemplates a recombinant expression vector containing a nucleic acid molecule of the invention, or a fragment thereof, and the necessary regulatory sequences for the transcription and translation of the protein sequence encoded by the nucleic acid molecule of the invention.

Suitable regulatory sequences may be derived from a variety of sources, including bacterial, fungal, viral, mammalian, or insect genes (for example, see the regulatory sequences described in Goeddel, 1990). Selection of appropriate regulatory sequences is dependent on the host cell chosen as discussed below, and may be readily accomplished by one of ordinary skill in the art. Examples of such regulatory sequences include: a transcriptional promoter and enhancer or RNA polymerase binding sequence, a ribosomal binding sequence, including a translation initiation signal. Additionally, depending on the host cell chosen and the vector employed, other sequences, such as an origin of replication, additional DNA restriction sites, enhancers, and sequences conferring inducibility of transcription may be incorporated into the expression vector.

The recombinant expression vectors of the invention may also contain a selectable marker gene that facilitates the selection of host cells transformed or transfected with a recombinant molecule of the invention. Examples of selectable marker genes are genes encoding a protein such as neomycin and hygromycin that confer resistance to certain drugs, β-galactosidase, chloramphenicol acetyltransferase, firefly luciferase, or an immunoglobulin or portion thereof such as the Fc portion of an immunoglobulin preferably IgG. Transcription of the selectable marker gene is monitored by changes in the concentration of the selectable marker protein such as β-galactosidase, chloramphenicol acetyltransferase, or firefly luciferase. If the selectable marker gene encodes a protein conferring antibiotic resistance such as neomycin resistance transformant cells can be selected with G418. Cells that have incorporated the selectable marker gene will survive, while the other cells die. This makes it possible to visualize and assay for expression of recombinant expression vectors of the invention and in particular to determine the effect of a mutation on expression and phenotype. It will be appreciated that selectable markers can be introduced on a separate vector from the nucleic acid of interest.

The recombinant expression vectors may also contain genes that encode a fusion moiety that provides increased expression of the recombinant protein; increased solubility of the recombinant protein; and aid in the purification of the target recombinant protein by acting as a ligand in affinity purification (for example appropriate "tags" to enable purification and/or identification may be present, e.g., His tags or myc tags). For example, a proteolytic cleavage site may be added to the target recombinant protein to allow separation of the recombinant protein from the fusion moiety subsequent to purification of the fusion protein. Typical fusion expression vectors include pGEX (Amrad Corp., Melbourne, Australia), pMal (New England Biolabs, Beverly, Mass.) and pRIT5 (Pharmacia, Piscataway, N.J.) which fuse glutathione S-transferase (GST), maltose E binding protein, or protein A, respectively, to the recombinant protein.

Recombinant expression vectors can be introduced into host cells to produce a transformed host cell. The terms "transformed with", "transfected with", "transformation" and "transfection" are intended to encompass introduction of nucleic acid (e.g., a vector) into a cell by one of many possible techniques known in the art. The term "transformed host cell" as used herein is intended to also include cells capable of glycosylation that have been transformed with a recombinant expression vector of the invention. Prokaryotic cells can be transformed with nucleic acid by, for example, electroporation or calcium-chloride mediated transformation. For example, nucleic acid can be introduced into mammalian cells via conventional techniques such as calcium phosphate or calcium chloride co-precipitation, DEAE-dextran mediated transfection, lipofection, electroporation or microinjection. Suitable methods for transforming and transfecting host cells can be found in Sambrook et al., 1989, and other laboratory textbooks.

Suitable host cells include a wide variety of eukaryotic host cells and prokaryotic cells. For example, the proteins of the invention may be expressed in yeast cells or mammalian cells. Other suitable host cells can be found in Goeddel, 1990. In addition, the proteins of the invention may be expressed in prokaryotic cells, such as *Escherichia coli* (Zhang et al., 2004).

Yeast and fungi host cells suitable for carrying out the present invention include, but are not limited to *Saccharomyces cerevisiae*, the genera *Pichia* or *Kluyveromyces* and various species of the genus *Aspergillus*. Examples of vectors for expression in yeast *S. cerevisiae* include pYepSec1 (Baldari. et al., 1987), pMFa (Kurjan and Herskowitz, 1982), pJRY 88 (Schultz et al., 1987), and pYES2 (Invitrogen Corporation, San Diego, Calif.). Protocols for the transformation of yeast and fungi are well known to those of ordinary skill in the art (see Hinnen et al., 1978; Ito et al., 1983, and Cullen et al. 1987).

Mammalian cells suitable for carrying out the present invention include, among others: COS (e.g., ATCC No. CRL 1650 or 1651), BHK (e.g., ATCC No. CRL 6281), CHO (ATCC No. CCL 61), HeLa (e.g., ATCC No. CCL 2), 293 (ATCC No. 1573), NS-1 cells, NS0 (ATCC CRL-11177), and Per.C6® (Crucell, Leiden, Netherlands). Suitable expression vectors for directing expression in mammalian cells generally include a promoter (e.g., derived from viral material such as polyoma, Adenovirus 2, cytomegalovirus and Simian Virus 40), as well as other transcriptional and translational control sequences. Examples of mammalian expression vectors include pCDM8 (Seed, B., 1987) and pMT2PC (Kaufman et al., 1987).

Given the teachings provided herein, promoters, terminators, and methods for introducing expression vectors of an appropriate type into plant, avian, and insect cells may also be readily accomplished. For example, within one embodiment, the proteins of the invention may be expressed from plant cells (see Sinkar et al., 1987, which reviews the use of *Agrobacterium rhizogenes* vectors; see also Zambryski et al., 1984, which describes the use of expression vectors for plant cells, including, among others, PAPS2022, PAPS2023, and PAPS2034).

Insect cells suitable for carrying out the present invention include cells and cell lines from *Bombyx*, *Trichoplusia* or *Spodotera* species. Baculovirus vectors available for expression of proteins in cultured insect cells (SF 9 cells) include the pAc series (Smith et al., 1983) and the pVL series (Luckow and Summers 1989). Some baculovirus-insect cell expression systems suitable for expression of the recombinant proteins of the invention are described in PCT/US/02442.

Alternatively, the proteins of the invention may also be expressed in non-human transgenic animals such as, rats, rabbits, sheep and pigs (Hammer et al. 1985; Palmiter et al. 1983; Brinster et al. 1985; Palmiter and Brinster 1985, and U.S. Pat. No. 4,736,866).

The proteins of the invention may also be prepared by chemical synthesis using techniques well known in the chemistry of proteins such as solid phase synthesis (Merrifield (1964); Frische et al., 1996) or synthesis in homogenous solution (Houbenweyl, 1987).

N-terminal or C-terminal fusion proteins comprising the antibodies and proteins of the invention conjugated to other molecules, such as proteins, may be prepared by fusing through recombinant techniques. The resultant fusion proteins contain an antibody or protein of the invention fused to the selected protein or marker protein, or tag protein as described herein. The antibodies and proteins of the invention may also be conjugated to other proteins by known techniques. For example, the proteins may be coupled using heterobifunctional thiol-containing linkers as described in WO 90/10457, N-succinimidyl-3-(2-pyridyldithio-proprionate) or N-succinimidyl-5 thioacetate. Examples of proteins that may be used to prepare fusion proteins or conjugates include cell binding proteins such as immunoglobulins, hormones, growth factors, lectins, insulin, low density lipoprotein, glucagon, endorphins, transferrin, bombesin, asialoglycoprotein glutathione-S-transferase (GST), hemagglutinin (HA), and truncated myc.

Irrespective of the manner of preparation of a first anti-CXCR4 antibody nucleic acid segment, further suitable antibody nucleic acid segments may be readily prepared by standard molecular biological techniques. In order to confirm that any variant, mutant or second generation anti-CXCR4 antibody nucleic acid segment is suitable for use in the present invention, the nucleic acid segment will be tested to confirm expression of an anti-CXCR4 antibody in accordance with the present invention. Preferably, the variant, mutant or second generation nucleic acid segment will also be tested to confirm hybridization under standard, more preferably, standard stringent hybridization conditions. Exemplary suitable hybridization conditions include hybridization in about 7% sodium dodecyl sulfate (SDS), about 0.5 M $NaPO_4$, about 1 mM EDTA at about 50° C.; and washing with about 1% SDS at about 42° C.

As a variety of antibodies may be readily prepared, the treatment methods of the invention may be executed by providing to the animal or patient at least a first nucleic acid segment or molecule that expresses a biologically effective amount of at least a first anti-CXCR4 antibody of the invention in the patient. The "nucleic acid segment or molecule that expresses an anti-CXCR4 antibody" will generally be in the form of at least an expression construct or vector, and may be in the form of an expression construct or vector comprised within a virus or within a recombinant host cell. Preferred gene therapy vectors of the present invention will generally be viral vectors, such as comprised within a recombinant retrovirus, herpes simplex virus (HSV), adenovirus, adeno-associated virus (AAV), cytomegalovirus (CMV), and the like.

A yet further aspect provides an expression construct or expression vector comprising one or more of the nucleic acid segments or molecules of the invention. Preferably the expression constructs or vectors are recombinant. Preferably said constructs or vectors further comprise the necessary regulatory sequences for the transcription and translation of the protein sequence encoded by the nucleic acid molecule of the invention.

A yet further aspect provides a host cell or virus comprising one or more expression constructs or expression vectors of the invention. Also provided are host cells or viruses comprising one or more of the nucleic acid molecules of the invention. A host cell or virus expressing an antibody of the invention forms a yet further aspect.

A yet further aspect of the invention provides a method of producing an antibody of the present invention comprising a step of culturing the host cells of the invention. Preferred methods comprise the steps of (i) culturing a host cell comprising one or more of the recombinant expression vectors or one or more of the nucleic acid sequences of the invention under conditions suitable for the expression of the encoded antibody or protein; and optionally (ii) isolating or obtaining the antibody or protein from the host cell or from the growth medium/supernatant. Such methods of production may also comprise a step of purification of the antibody or protein product and/or formulating the antibody or product into a composition including at least one additional component, such as a pharmaceutically acceptable carrier or excipient.

In embodiments when the antibody or protein of the invention is made up of more than one polypeptide chain (e.g., certain fragments such as Fab fragments), then all the polypeptides are preferably expressed in the host cell, either from the same or a different expression vector, so that the complete proteins, e.g., binding proteins of the invention, can assemble in the host cell and be isolated or purified therefrom.

The antibodies of the invention may also be used to produce further antibodies that bind to CXCR4. Such uses involve for example the addition, deletion, substitution or insertion of one or more amino acids in the amino acid sequence of a parent antibody to form a new antibody, wherein said parent antibody is one of the antibodies of the invention as defined elsewhere herein, and testing the resulting new antibody to identify antibodies that bind to CXCR4 and have one or more of the other preferred functional properties described herein. Such methods can be used to form multiple new antibodies that can all be tested for their ability to bind CXCR4 and other functional properties. Preferably said addition, deletion, substitution or insertion of one or more amino acids takes place in one or more of the CDR domains.

Such modification or mutation to a parent antibody can be carried out in any appropriate manner using techniques well known and documented in the art, for example by carrying out methods of random or directed mutagenesis. If directed mutagenesis is to be used then one strategy to identify appropriate residues for mutagenesis utilizes the resolution of the crystal structure of the binding protein-antigen complex, e.g., the Ab-Ag complex, to identify the key residues involved in the antigen binding (Davies and Cohen, 1996). Subsequently, those residues can be mutated to enhance the interaction. Alternatively, one or more amino acid residues can simply be targeted for directed mutagenesis and the effect on binding to CXCR4 assessed.

Random mutagenesis can be carried out in any appropriate way, e.g., by error-prone PCR, chain shuffling or mutator E. coli strains.

Thus, one or more of the $V_H$ domains of the invention can be combined with a single $V_L$ domain or a repertoire of $V_L$ domains from any appropriate source and the resulting new antibodies tested to identify antibodies specific for CXCR4. This is preferred. Conversely, one or more of the $V_L$ domains of the invention can be combined with a single $V_H$ domain or repertoire of $V_H$ domains from any appropriate source and the resulting new antibodies tested to identify antibodies that bind to CXCR4.

Similarly, one or more, or preferably all three CDRs of the $V_H$ and/or $V_L$ domains of the invention can be grafted into a single $V_H$ and/or $V_L$ domain or a repertoire of $V_H$ and/or $V_L$ domains, as appropriate, and the resulting new antibodies tested to identify antibodies that bind to CXCR4.

The targeted mutations of the CDRs, especially CDR3 of the light and/or heavy chains, have been shown to be an effective technique for increasing antibody affinity and are preferred. Preferably, blocks of 3 to 4 amino acids of the CDR3 or specific regions called "hot-spots" are targeted for mutagenesis.

"Hot spots" are the sequences where somatic hypermutation takes place in vivo (and below Neuberger and Milstein, 1995). The hotspot sequences can be defined as consensus nucleotide sequences in certain codons. The consensus sequence is the tetranucleotide, RGYW, in which R can be either A or G, Y can be C or T and W can be either A or T (Neuberger and Milstein, 1995). In addition, the serine residues encoded by the nucleotides AGY are predominantly present in the CDRs regions of the variable domain over those encoded by TCN corresponding to a potential hot-spot sequences (Wagner et al., 1995).

Thus, the nucleotide sequence of the CDRs of the heavy and light chains of each antibody of the invention can be scanned for the presence of the hot-spot sequences and AGY codons. The identified hot-spots of the CDR regions of the light and heavy chain can then optionally be compared to the germinal sequences of the heavy and light chains using the International ImMunoGenTics database (IMGT, http://imgt-.cines.fr/textes/vquest/) (Davies et al., 1990). A sequence, identical to the germ line, suggest that somatic mutation has not occurred; therefore random mutations can be introduced mimicking the somatic events occurring in vivo or alternatively, site directed mutagenesis can be carried out, e.g., at the hot spots and/or AGY codons. In contrast, a different sequence shows that some somatic mutations have already occurred. It will remain to be determined if the in vivo somatic mutation was optimal.

Preferred hot-spots for mutation are those that code for exposed amino acids and preferably those that encode amino acids that form part of the antigen binding sites. Other preferred hot-spots for mutation are those that code for non-conserved amino acids. The hot-spots that code for buried or conserved amino acids within the CDRs are preferably not mutagenized. These residues are usually critical for the overall structure and are unlikely to interact with the antigen since they are buried.

Methods of carrying out the above described manipulation of amino acids and protein domains are well known to a person skilled in the art. For example, said manipulations could conveniently be carried out by genetic engineering at the nucleic acid level wherein nucleic acid molecules encoding appropriate binding proteins and domains thereof are modified such that the amino acid sequence of the resulting expressed protein is in turn modified in the appropriate way.

Testing the ability of one or more antibodies to specifically bind to CXCR4 can be carried out by any appropriate methods which are well known and described in the art. CXCR4+ cell lines may be obtained from culture collections, or they may be prepared by transforming CXCR4-negative cells with a construct that allows expression of recombinant CXCR4. Such cells can readily be used to assay binding, for example by conventional methods such as ELISA, BIACore, FACS etc.

The new antibodies produced by these methods will preferably have improved functional properties, e.g. a higher or enhanced affinity (or at least an equivalent affinity) for CXCR4 as the parent antibodies, and can be treated and used in the same way as the antibodies of the invention as described elsewhere herein (e.g., for therapy, diagnosis, in compositions etc). Alternatively, or additionally, the new antibodies will have one or more other improved functional properties as described elsewhere herein.

New antibodies produced, obtained or obtainable by these methods form a yet further aspect of the invention.

This invention further provides compositions comprising at least one antibody or antibody fragment of the invention, optionally including a diluent. Such compositions may be pharmaceutically acceptable compositions or compositions for use in laboratory studies. In terms of the pharmaceutical compositions, they may preferably be formulated for parenteral, intravenous or even subcutaneous administration.

The present invention provides a number of methods and uses of the human antibodies and antibody fragments of the invention. Concerning all methods, the terms "a" and "an" are used to mean "at least one", "at least a first", "one or more" or "a plurality" of steps in the recited methods, except where specifically stated. This is particularly relevant to the administration steps in the treatment methods. Thus, not only may different doses be employed with the present invention, but different numbers of doses, e.g., injections, may be used, up to and including multiple injections. Combined therapeutics may be used, administered before, after or during administration of the anti-CXCR4 therapeutic antibody.

Various useful in vitro methods and uses of the antibodies or immunoconjugates of the invention are provided that have important biological implications. First provided are methods of, and uses in, binding CXCR4, which generally comprise effectively contacting a composition comprising CXCR4 with at least a first anti-CXCR4 antibody of the invention, or antigen-binding fragment thereof. The antibodies of the invention, or immunoconjugates thereof, can thus be used in binding assays. Suitably useful binding assays include those commonly employed in the art, such as in immunoblots, Western blots, dot blots, RIAs, ELISAs, immunohistochemistry, fluorescent activated cell sorting (FACS), immunoprecipitation, affinity chromatography, and the like.

Methods of, and uses in, detecting CXCR4 are provided, which generally comprise contacting a composition suspected of containing CXCR4 with at least a first antibody or immunoconjugate of the invention, or antigen-binding fragment thereof, under conditions effective to allow the formation of CXCR4/antibody complexes and detecting the complexes so formed. The detection methods and uses may be used in connection with biological samples, e.g., in diagnostics for tumours, and diagnostic kits based thereon are also provided. It is also believed that detection of CXCR4 can be prognostic for some diseases and thus mention of diagnosis herein also includes prognosis, where relevant. In particular, CXCR4 has been indicated to have prognostic value for metastasis recurrence and survival, glioma and some childhood cancers The antibodies or binding proteins of the invention can be used to detect CXCR4 in vivo or in vitro, in particular to detect CXCR4+ cells. For example, as CXCR4 is overexpressed on certain tumour cells, the antibodies or binding proteins of the invention can be used to detect tumour cells in vivo or in vitro. In addition, the ability of the antibodies to localize to CXCR4+ cells means that the antibodies of the invention can target body sites at which CXCR4+ cells are present, whereupon the antibody can act at the target site. In particular, the ability of the antibodies to localize to CXCR4+ tumour cells means that the antibodies of the invention can target body sites at which CXCR4+ tumour cells are present, whereupon the antibody can act at the target site.

The methods and uses of the present invention are particularly intended for use in animals and patients that have, or are at risk for developing, any disease or condition associated with CXCR4 expression or activity or in which CXCR4 plays a biological role. Such diseases and disorders include diseases which are mediated by CXCR4 positive cells, typically immunoregulatory CXCR4+ T-cells, which, upon binding of a ligand to CXCR4, may take part in a signaling pathway which will cause or contribute to a disorder or disease. They also include diseases caused by aberrant proliferation of cells expressing CXCR4. Such aberrantly proliferating cells may naturally be CXCR4+, or they may have mutated/been transformed to express CXCR4. As mentioned above, expression of CXCR4 may help cancer cells to metastasize along a SDF-1 gradient. Also included are diseases characterised by overexpression of CXCR4 on cells which are inherently CXCR4+. In addition, CXCR4 tropic strains of HIV use CXCR4 to enter host cells, so blocking that receptor may limit the spread of this disease.

Thus, there is provided a method of treating a disease or disorder mediated by CXCR4 and/or characterized by aberrant proliferation of CXCR4-positive cells, and/or characterised by overexpression of CXCR4 on cells which are inherently CXCR4+.

Alternatively viewed, there is provided the treatment of a condition which can benefit from one or more of the following:
(i) Inhibition of CXCR4 binding to its ligand.
(ii) Inhibition of CXCR4-mediated cellular responses to a CXCR4 ligand, particularly the inhibition of chemotaxis or migration, e.g. in connection with cancer metastasis/organ invasion or inflammatory response, or increased intracellular calcium ion concentration (cell activation).
(iii)) Selective elimination of CXCR4+ cells.
(iv) Activation and induction of migration of CXCR4+ hematopoietic stem cells, as those cells are kept inactive in the bone marrow by an interaction of their CXCR4 receptor with SDF-1 produced in the bone marrow stroma.
(v) Blocking of infection of CXCR4+ cells by X4 strains of HIV, which use CXCR4 as co-receptor during infection.

Preferably, the CXCR4 ligand is SDF-1.

It is well known to those of ordinary skill in the art that as CXCR4 is involved in a wide range of diseases and disorders, a given anti-CXCR4 therapy, once shown to be effective in any acceptable model system, can be used to treat the entire range of diseases and disorders connected with CXCR4 expression.

In one embodiment, the CXCR4-mediated condition is cancer, and, in particular, the spread, metastasis formation, organ invasion and/or the tumor growth mediated or supported by CXCR4 and the interaction with its ligands.

CXCR4 is expressed in a variety of tumors, and there is now significant documentation for the notion that this expression plays a decisive role in the pathophysiology of cancer particularly in cancer metastasis. Several lines of evidence have led to the now largely accepted idea that expression of CXCR4 enables malignant cells to use SDF-1-based gradients for metastatic migration. CXCR4 is by far the most commonly expressed chemokine receptor in cancer cells. Expression has been found in almost all tumors studied. It is also of interest that SDF-1 (CXCL12) is expressed at particularly high levels in liver, lung, bone marrow, lymph nodes, and (at somewhat lower levels) in brain, i.e. sites to which cancers typically metastasize, or which are invaded by hematological tumors. There is copious evidence that blocking CXCR4 signaling caused by SDF-1 is capable of reducing or preventing formation of metastasis in mouse models. This inhibition of signaling can be achieved by antibodies (Muller et al, 2001 and many others), siRNA to CXCR4 (Liang et al, 2007), and peptides (Kim et al, 2008).

Blocking CXCR4 is also described to have an effect on angiogenesis, for example an inhibitory (anti-angiogenic effect). Thus, in a further embodiment the antibodies of the invention can be used to effect angiogenesis (e.g. have an anti-angiogenic effect). In yet another embodiment, the antagonistic antibody of the invention can be used in conjunction with any anti-angiogenic agent described in the art. In particular, the antibodies of the invention can be used in combination with bevacizumab (Avastin) for the treatment of cancer, or as second line treatment for patients where the tumour has acquired resistance to Avastin.

A study by Xu et al, 2009 show that CXCR4 on tumor cells is upregulated by treatment with Avastin. This will make the tumour cells more susceptible to treatment with antibodies targeting CXCR4. This is of special interest for patients which have become resistant to treatment with Avastin. Alternatively, the two drugs can be given together.

In addition, many of the compounds blocking CXCR4 signaling which are described to have an anti-metastatic effect are also known to inhibit tumor growth. Although the exact effect for limiting tumor growth by blocking the CXCR4 receptor are not fully understood, there is increasing evidence that the interaction between the neoplastic cells and the surrounding stroma is of central importance. One study has shown that, although transfection of pancreatic and colon cancer cells with siRNA against CXCR4 led to little effect on cell growth in vitro, the growth in vivo of tumors derived from these cells was significantly suppressed (Guleng et al, 2005). Furthermore, it was shown that carcinoma-associated fibroblasts, with the traits of myofibroblast, stimulated growth of admixed breast carcinoma cells markedly more than did normal mammary fibroblasts from the same patient, and promoted angiogenesis by recruiting endothelial progenitor cells (Orimo et al, 2005). These effects were mediated through SDF-1 secreted by the tumor fibroblasts/myofibroblasts. Antibody against SDF-1 or siRNA against CXCR4 inhibited the tumor growth. Thus, taken together these studies show that the tumor microenvironment is of importance for the behavior of the cancer, and marked tumor growth inhibition was obtained by targeting the SDF-1/CXCR4 interaction in vivo. Thus, the antibodies of the invention can be used to inhibit the attraction of CXCR4+ cells to the tumor stroma, and/or inhibit the activation of said cells to create a microenvironment favourable to the tumor.

In another embodiment, the CXCR4-mediated condition which is treated is the presence of transformed cells expressing CXCR4.

As already described, CXCR4 is strongly expressed in many tumors. This can be used to kill those cells by means of inducing apoptosis, ADCC or CDC. Of course, as CXCR4 is also expressed on a wide variety of healthy cells, safety aspects and side effects are a reason for concern. The limited number of available phase I studies on small molecule antagonists to CXCR4 showed some side effects, mostly of minor concern. However, there is no data available on longterm use of drugs targeting CXCR4. In addition, there might be some variation depending on the drug used; antibodies like MDX-1338, which induces apoptosis might have a very different safety profile from antibodies which do not. Furthermore, it was recently demonstrated that the peptide-derived drug CTCE-9908 caused death of ovarian cancer cells via induction of multinucleation, $G_2$-M arrest, and abnormal mitosis (mitotic catastrophe) (Kwong et al, 2009). It can be speculated that this mode of action, e.g. mitotic catastrophe, is much more efficient in CXCR4+ tumor cells which are prone to cell division, compared to fully differentiated CXCR4+ neural cells, which rarely if ever undergo mitosis. Thus, in some embodiments, cell killing of CXCR4+ cells is a further mode of action for the antibodies of the invention, although such killing is preferably induced by mechanisms other than apoptosis.

In another embodiment, the CXCR4-mediated condition which is treated is the migration of bone marrow support cells to the tumor site.

A Phase II clinical trial in hepatocellular carcinoma investigating the use of CTCE-9908 (a dimerized peptide blocking CXCR4 signaling) in combination with transarterial chemoembolization is being initiated. The hypothesis is that CTCE-9908 would block the recruitment of bone marrow-derived support cells by the tumor after the transarterial chemoembolization procedure in addition to blocking the metastatic process.

In another embodiment, the CXCR4-mediated condition to be treated is the migration of CXCR4+ cells to a site of inflammation.

CXCR4 is known to play a role in inflammation. Like other cytokines SDF-1 is contributing to inflammation by attracting CXCR4+ cells of the immune system to the site of inflammation. Blocking the interaction might be beneficial for a wide variety of inflammatory and auto-immune disorders, e.g. rheumatoid arthritis. The small molecule drug candidate AMD3465, a CXCR4 antagonist, has been shown to abrogate the Th2-mediated inflammatory response in a schistosomal antigen-elicited model of pulmonary granuloma formation (Hu et al, 2006)

In yet another embodiment, the CXCR4 mediated condition to be treated is a viral infection, in particular a retroviral infection such as HIV infection, or any other viral infection wherein said virus uses CXCR4 as a receptor.

A significant portion of HIV strains use CXCR4 as co-receptor during infection (X4 HIV strains). Blocking the CXCR4 receptor has been shown to be very effective in blocking the infection. AMD3100 has been shown to inhibit entry of X4 HIV strains into CXCR4 strains with a very high efficacy both in vitro and in in vivo in clinical trials in humans. A derivative of this compound with increased bioavailability, AMD070, is currently in phase II clinical trials for treatment of HIV. Several other antagonists to CXCR4 are in various stages of development for this purpose.

In yet another embodiment, the CXCR4 mediated condition to be treated is a condition in which it is desired to mobilize stem cells retained in bone marrow. The mobilization of such stem cells can be achieved by blocking CXCR4/SDF-1 interaction and this allows for example the restoration of the immune system, required e.g. after whole body irradiation or bone marrow transplantation or a blood cancer such as non-Hodgkin's lymphoma or multiple myeloma. Such methods are useful to treat these conditions and any other disease which requires or could benefit from transplants of blood-forming stem cells.

In January 2009, Genzyme received FDA approval to sell a small molecule CXCR4 inhibitor plerixafor (former AMD3100) under the trade name Mozobil™ as an injectable drug for patients with non-Hodgkin's lymphoma and multiple myeloma, which need transplants of blood-forming stem cells. This product is meant to be used for the autologous stem cell mobilization in combination with G-CSF. Blocking the interaction between CXCR4 and SDF-1 has been shown to increase both the white blood cell count and the number of CD34+ cells in the peripheral blood significantly, as SDF-1 secreted by the bone marrow stroma is in this case contributing to keeping the stem cells in the bone marrow in activated form. There are several other CXCR4 antagonists under development for this indication.

In yet another embodiment, blocking the CXCR4 receptor mediated signalling sensitizes tumour cells for treatment with other therapeutic compounds, e.g. chemotherapeutic drugs. Thus, combination therapies with chemotherapeutic drugs are particularly preferred. Such embodiments are particularly useful for the treatment of blood cancers.

In December 2009, Genzyme announced that Phase I/II trial provided early clinical data suggesting that Mozobil® (plerixafor injection) in combination with chemotherapy may offer a therapeutic impact on leukemic cells protected in bone marrow. In the clinical trial, Mozobil was given as a pre-conditioning strategy prior to chemotherapy (MEC regimen: mitoxantrone, etoposide, and cytarabine) to patients with relapsed or refractory acute myeloid leukaemia (AML). Many of the trial participants were either unresponsive to, or had short remissions, following prior treatments. Of the patients available for the first follow-up evaluation, researchers observed a complete remission (CR or CRi) in 50 percent of patients. Similar trials have been initiated for other blood cancers.

The embodiments described above can be used for the treatment of a wide variety of diseases.

Examples of tumor types where increased CXCR4 expression has been shown are breast cancer, prostate cancer, colorectal cancer, pancreatic cancer, malignant or metastatic melanomas, head and neck cancers including but not limited to oral squamous cell carcinomas and nasopharyngeal cancer, oesophagus cancer, brain tumors including but not limited to gliomas and meningiomas, leukemias, lymphomas such as non-Hodgkins lymphoma, neuroblastoma and other childhood cancers, renal cancer, hemangioblastomas, von Hippel-Lindau disease, lung tumors (both SCLC and NSCLC), liver cancers, ovarian cancers, cervical cancers, papillary thyroid carcinomas and osteosarcomas. The treatment of metastatic cancer or the inhibition of cancer cell invasion is particularly preferred.

The CXCR4-mediated disease or disorder may also be a disease or condition associated with inflammation or autoimmune diseases. Preferred diseases or conditions include:

(1) allergic diseases such as systemic anaphylaxis or hypersensitivity responses, drug allergies, allergic bronchopulmonary aspergillosis (ABPA), insect sting allergies and food allergies, (2) inflammatory bowel diseases, such as Crohn's disease, ulcerative colitis, ileitis and enteritis, (3) vaginitis, (4) psoriasis and inflammatory dermatoses such as dermatitis, eczema, atopic dermatitis, allergic contact dermatitis, urticaria and pruritus, (5) vasculitis, (6) spondyloarthropathies, (7) scleroderma, (8) asthma and respiratory allergic diseases such as allergic asthma, allergic rhinitis, chronic obstructive pulmonary disease, hypersensitivity lung diseases and the like, (9) autoimmune diseases, such as arthritis (including rheumatoid and psoriatic), multiple sclerosis, systemic lupus erythematosus, type I diabetes, glomerulonephritis, and the like, (10) graft rejection (including allograft rejection and graft-v-host disease), and (11) other diseases in which undesired inflammatory responses are to be inhibited, such as atherosclerosis, myositis, T-cell mediated neurodegenerative diseases, multiple sclerosis, encephalitis, meningitis, hepatitis, nephritis, sepsis, sarcoidosis, allergic conjunctivitis, otitis, Castleman's disease, sinusitis, LPS-induced endotoxic shock, Behcet's syndrome and gout. Rheumatoid arthritis and Th2 mediated inflammation are particularly preferred diseases to be treated with the antibodies of the invention.

As used herein, the term "aberrant proliferation" means cell proliferation that deviates from the normal, proper, or expected course. For example, aberrant cell proliferation may include inappropriate proliferation of cells whose DNA or other cellular components have become damaged or defective.

Aberrant cell proliferation may include cell proliferation whose characteristics are associated with an indication caused by, mediated by, or resulting in inappropriately high levels of cell division, inappropriately low levels of apoptosis, or both. Such indications may be characterized, for example, by single or multiple local abnormal proliferations of cells, groups of cells, or tissue (s), cancerous or non-cancerous, benign or malignant.

Any reference to "tumor(s)" herein also refers to "cancer(s)" or "carcinoma(s)". Metastatic cancers can also be treated, as can the reduction of metastases from a primary tumor. So-called minimal residual disease (MRD), which is left in post-surgery patients, may be amenable for immunotherapy with anti-CXCR4 antibodies.

The present invention thus further provides methods of, and uses in, treating a disease as defined above, comprising administering to an animal or patient with such a disease, a therapeutically effective amount of an anti-CXCR4 antibody of the invention, or an antigen-binding fragment or immunoconjugate of such an anti-CXCR4 antibody.

A yet further aspect of the invention provides the use of the antibodies of the invention or an antigen-binding fragment or immunoconjugate of such an antibody in the manufacture of a composition or medicament for use in therapy, imaging or diagnosis.

A yet further aspect provides the antibodies of the invention or an antigen-binding fragment or immunoconjugate of such an antibody for use in therapy, diagnosis or imaging.

In addition, the invention provides compositions comprising the antibodies of the invention or an antigen-binding fragment or immunoconjugate of such an antibody with one or more pharmaceutically acceptable excipient, carrier, diluent, buffer or stabilizer.

The in vivo methods as described herein are generally carried out in a mammal. Any mammal may be treated, for example humans and any livestock, domestic or laboratory animal. Specific examples include mice, rats, pigs, cats, dogs, sheep, rabbits, cows and monkey. Preferably, however, the mammal is a human.

Thus, the term "animal" or "patient" as used herein includes any mammal, for example humans and any livestock, domestic or laboratory animal. Specific examples include mice, rats, pigs, cats, dogs, sheep, rabbits, cows and monkey. Preferably, however, the animal or patient is a human subject.

This invention links both methods of treating disorders as defined above using unconjugated or naked antibodies and fragments thereof, and CXCR4+ cell (preferably CXCR4+ tumour cell or CXCR4+ cells of the immune system, for example cells which can be infected by CXCR4 tropic strains of HIV) targeting methods using immunoconjugates in which an antibody of the invention or antigen-binding fragment thereof, is operatively attached to a therapeutic or diagnostic agent. Unless otherwise specifically stated or made clear in scientific terms, the terms "antibody and fragment thereof", as used herein, therefore mean an "unconjugated or naked" antibody or fragment, which is not attached to another agent, particularly a therapeutic or diagnostic agent. These definitions do not exclude modifications of the antibody, such as, by way of example only, modifications to improve the biological half life, affinity, avidity or other properties of the antibody, or combinations of the antibody with other effectors.

The treatment methods and uses of the invention also encompass the use of both unconjugated or naked antibodies and immunoconjugates. In the immunoconjugate-based treatment methods, an antibody of the invention, or antigen-binding fragment thereof, is preferably operatively attached to a second therapeutic agent (the anti-CXCR4 antibody itself being the first therapeutic agent).

An appropriate therapeutic agent can be selected depending on the disease or condition to be treated and/or the desired mode of therapeutic action.

For example, when the desired mode of action is antagonistic, e.g. to modulate cellular signalling of the target CXCR4+ cell, e.g. to modulate signalling inside the target cell or to modulate the signalling of the target cell to other cells, or to down regulate or inhibit the function/signalling of CXCR4+ cells, e.g. tumor cells, or cells of the immune system involved in an inflammatory or autoimmune response, or cells which are susceptible to viral infection such as HIV, then appropriate agents might be immunomodulatry therapeutic agents such as anti-inflammatory agents, e.g. corticosteroids (preferably glucocorticoids) or non-steroidal anti-inflammatory drugs (NSAIDs) such as COX-2 inhibitors, sulphonanilides, licofelone and omega-3 fatty acids, steroid antagonists, cytokine or chemokine antagonists, or inhibitors of cytokine or chemokine expression. Alternative agents might be inhibitors of angiogenesis such as angiostatin, endostatin, any one of the angiopoietins, vasculostatin, canstatin or maspin. Alternative agents might be additional signalling pathway inhibitors such as an inhibitor of a growth factor receptor, e.g. EGFR IGF receptors such as IGF-1 receptor (IGF-1R), IGF-2R, IGF binding protein (IGFBP-3) and FGFR.

Where inhibition of growth of CXCR4+ cells is a desired mode of action (e.g. in the treatment of cancer) then an appropriate agent with growth inhibiting effects can be selected, for example a cytostatic therapeutic agent such as inhibitors of steroid receptors (e.g. the estrogen receptor).

When cell killing is a desired mode of action, then an appropriate cytotoxic agent such as radiotherapeutic agents or ATPase inhibitors can be selected.

For cancer treatment, appropriate anti-cancer drugs might also be used.

Alternatively, in anti-viral applications, e.g. treatment of HIV, an appropriate anti-viral agent can be used as the additional therapeutic.

It is important to note that multiple modes of action might be appropriate for certain diseases or stages of disease, and, if so, multiple additional therapeutics can be used. It is also important to note that many agents have multiple effects, or effects which differ depending on the context. Blocking signalling pathways can have an effect both on migration of tumor cells as well as on tumour growth. Many chemotherapeutic agents also have more than one function. Chemokines and their antagonists may have different effects in connection with cancer compared to anti-inflammatory applications. However, it would be well within the capability of a person skilled in the art to select an appropriate additional therapeutic agent depending on the disease, stage of disease and the desired mode of action.

The additional therapeutics may be provided in the form of an immunoconjugate but may alternatively be provided in a combination therapy, e.g. when the various agents are administered together (e.g. as a mixture), separately or sequentially, if this is more appropriate.

The foregoing treatment methods and uses will generally involve the administration of the pharmaceutically effective composition to the animal or patient systemically, such as by transdermal, intramuscular, intravenous injection and the like. However, any route of administration that allows the therapeutic agent to localize to the tumour site or other appropriate sites, such as sites of inflammation or viral infection will be acceptable. Therefore, other suitable routes of delivery include oral, nasal or respiratory and topical.

"Administration", as used herein, means provision or delivery of anti-CXCR4 antibody therapeutics in an amount(s) and for a period of time(s) effective to exert therapeutic, e.g. anti-tumour, anti-inflammatory or anti-viral effects. The passive administration of proteinaceous therapeutics is generally preferred, in part, for its simplicity and reproducibility.

However, the term "administration" is herein used to refer to any and all means by which anti-CXCR4 antibodies of the invention are delivered or otherwise provided to the target site. "Administration" therefore includes the provision of cells that produce the anti-CXCR4 antibody of the invention in a manner effective to result in delivery to the target site. In such embodiments, it may be desirable to formulate or package the cells in a selectively permeable membrane, structure or implantable device, generally one that can be removed to cease therapy. Exogenous anti-CXCR4 antibody of the invention will still generally be preferred, as this represents a non-invasive method that allows the dose to be closely monitored and controlled.

The therapeutic methods and uses of the invention also extend to the provision of nucleic acids that encode an anti-CXCR4 antibody of the invention in a manner effective to result in their expression in the vicinity of the tumour or their localization to the target site. Any gene therapy technique may be employed, such as naked DNA delivery, recombinant genes and vectors, cell-based delivery, including ex vivo manipulation of patients' cells, and the like.

The anti-CXCR4 antibodies of the invention can also be used to deliver other therapeutic or diagnostic agents to the target site In such embodiments, the other therapeutic or diagnostic agents are generally operatively attached to the anti-CXCR4 antibodies of the invention.

The "therapeutically effective amounts" for use in the invention are amounts of anti-CXCR4 antibody of the invention, or immunoconjugates thereof, effective to inhibit the binding of a CXCR4 ligand to CXCR4; to inhibit CXCR4-mediated cellular responses to a CXCR4 ligand, preferably to inhibit the release of calcium ions in response to a CXCR4 ligand or to inhibit migration of CXCR4+ cells; to reduce inflammation; to inhibit formation of metastasis; to inhibit cancer cell invasion; to inhibit tumor growth; to inhibit tumor angiogenesis; to induce tumour regression or remission upon administration to animals or patients having a CXCR4+ tumour; to limit the spread of CXCR4 tropic HIV strains and/or, when the mechanism of action involves cell killing, to specifically kill at least a portion of target CXCR4+ cells. Such effects are preferably achieved while exhibiting little or no binding to, or little or no killing of cells in normal, healthy tissues and exerting negligible or manageable adverse side effects on normal, healthy tissues of the animal or patient.

By "target site" is meant the location of CXCR4+ cells which mediate a disorder or which proliferate in an aberrant manner causing or exacerbating a disorder. The target site may thus for example be a tumour or the site of CXCR4-mediated inflammation. "Target cells" are CXCR4+ cells which mediate a disorder or which proliferate in an aberrant manner causing or exacerbating a disorder. Thus, target cells may for example include CXCR4+ tumour cells, cells of the immune system e.g. CXCR4+ leucocytes (for anti-inflammatory/anti-autoimmune applications) or CXCR4+ immune cells targeted by CXCR4 tropic HIV strains.

The terms "preferentially" and "specifically", as used herein in the context of killing CXCR4+ cells such as CXCR4+ tumour cells, CXCR4+ leucocytes (for anti-inflammatory/anti-autoimmune applications) or of reducing inflammation or of inducing tumour regression or remission, thus mean that the anti-CXCR4 antibody of the invention or immunoconjugates thereof, function to achieve CXCR4+ target cell destruction, e.g. tumour cell destruction, that is substantially confined to the target site, and does not substantially extend to causing destruction in normal, healthy tissues of the animal or subject.

Anti-CXCR4 antibodies of the invention or therapeutic conjugates are preferably linked to one or more radiotherapeutic agents, chemotherapeutic agents, anti-angiogenic agents, apoptosis-inducing agents, anti-tubulin drugs, anti-cellular or cytotoxic agents, cytokine or chemokine antagonists, inhibitors of cytokine or chemokine expression, ATPase inhibitors, anti-inflammatory agents, other antibodies (e.g. as bispecific antibodies) or coagulants (coagulation factors) or anti-inflammatory agents such as corticosteroids, preferably glucocorticoids, or non-steroidal anti-inflammatory drugs (NSAIDs).

The invention thus provides a range of conjugated antibodies and fragments thereof in which the anti-CXCR4 antibody is operatively attached to at least one other therapeutic or diagnostic agent. The term "immunoconjugate" is broadly used to define the operative association of the antibody with another effective agent and is not intended to refer solely to any type of operative association, and is particularly not limited to chemical "conjugation". Recombinant fusion proteins are particularly contemplated. So long as the delivery or targeting agent is able to bind to the target and the therapeutic or diagnostic agent is sufficiently functional upon delivery, the mode of attachment will be suitable.

Attachment of agents via the carbohydrate moieties on antibodies is also contemplated. Glycosylation, both O-linked and N-linked, naturally occurs in antibodies. Recombinant antibodies can be modified to recreate or create additional glycosylation sites if desired, which is simply achieved by engineering the appropriate amino acid sequences (such as Asn-X-Ser, Asn-X-Thr, Ser, or Thr where X is any amino acid except Pro) into the primary sequence of the antibody.

Currently preferred agents for use in anti-CXCR4 antibody or therapeutic conjugates of the invention and related methods and uses are those that complement or enhance the effects of the antibody and/or those selected for a particular type of disorder (e.g. tumour type) or patient.

"Therapeutic agents that complement or enhance the effects of the antibody" include radiotherapeutic agents, chemotherapeutic agents, anti-angiogenic agents, apoptosis-inducing agents, anti-tubulin drugs, anti-cellular or cytotoxic agents, coagulants, cytokine or chemokine antagonists, inhibitors of cytokine or chemokine expression, ATPase inhibitors, anti-inflammatory agents such as corticosteroids, preferably glucocorticoids, or non-steroidal anti-inflammatory drugs (NSAIDs), other antibodies, (e.g. as bispecific antibodies), any one or more of which are preferred for use herewith.

Currently preferred anti-cancer, particularly anti-leukaemia agents include Anthracycline drugs such as daunorubicin, Doxorubicin, Cytarabine, 6-thioguanine, Mitoxantrone, busulfan (Myleran®), dasatinib (Sprycel™), prednisone, vincristine sulfate (Oncovin®), Chlorambucil, Fludarabine, Pentostatin and Cladribine.

Currently preferred anti-angiogenic agents include angiostatin, endostatin, any one of the angiopoietins, vasculostatin, canstatin and maspin.

"Anti-tubulin drug(s)", as used herein, means any agent, drug, prodrug or combination thereof that inhibits cell mitosis, preferably by directly or indirectly inhibiting tubulin activities necessary for cell mitosis, preferably tubulin polymerization or depolymerization. Currently preferred anti-tubulin drugs include colchicine, taxol, vinblastine, vincristine, vindescine and one or more of the combretastatins.

Currently preferred NSAIDs include COX-2 inhibitors, sulphonanilides, licofelone and omega-3 fatty acids.

The attachment or association of the preferred agents with anti-CXCR4 antibodies of the invention gives "immunoconjugates", wherein such immunoconjugates often have enhanced and even synergistic therapeutic properties, e.g. anti-tumour or anti-inflammatory properties.

The use of anti-cellular and cytotoxic agents (where appropriate) results in anti-CXCR4 antibody "immunotoxins" of the invention, whereas the use of coagulation factors results in anti-CXCR4 antibody "coaguligands" of the invention.

The use of at least two therapeutic agents is also contemplated, such as combinations of one or more of the above agents.

In certain applications, the anti-CXCR4 antibody therapeutics of the invention will be operatively attached to cytotoxic, cytostatic or otherwise anti-cellular agents that have the ability to kill or suppress the growth or cell division of cells. Suitable anti-cellular agents include chemotherapeutic agents, as well as cytotoxins and cytostatic agents. Cytostatic agents are generally those that disturb the natural cell cycle of a target cell, preferably so that the cell is taken out of the cell cycle.

Exemplary chemotherapeutic agents include: hormones, such as steroids; anti-metabolites, such as cytosine arabinoside, fluorouracil, methotrexate or aminopterin; anthracyclines; mitomycin C; vinca alkaloids; antibiotics; demecolcine; etoposide; mithramycin; and anti-tumor alkylating agents, such as chlorambucil or melphalan. Certain preferred anti-cellular agents are DNA synthesis inhibitors, such as daunorubicin, doxorubicin/adriamycin, and the like. Overall, taxol/paclitaxel, docetaxel, cisplatin, gemcitabine, a combretastatin and doxorubicin/adriamycin are currently preferred anti-cancer agents.

V-type ATPase inhibitors are also currently preferred, such as salicylihalamide, concanamycin or bafilomycin, as are protein synthesis inhibitors, such as psymberin, pederin, irciniastatin A.

In certain therapeutic applications, toxin moieties will be preferred, due to the much greater ability of most toxins to deliver a cell killing effect, as compared to other potential agents. Therefore, certain preferred anti-cellular agents for anti-CXCR4 antibody constructs of the invention are plant-, fungus- or bacteria-derived toxins. Exemplary toxins include epipodophyllotoxins; bacterial endotoxin or the lipid A moiety of bacterial endotoxin; ribosome inactivating proteins, such as saporin or gelonin; a-sarcin; aspergillin; restrictocin; ribonucleases, such as placental ribonuclease; diphtheria toxin and *pseudomonas* exotoxin. Currently preferred examples are ricin, gelonin, abrin, diphtheria, *pseudomonas* and pertussis toxins.

Certain preferred toxins are the A chain toxins, such as ricin A chain. The most preferred toxin moiety is often ricin A chain that has been treated to modify or remove carbohydrate residues, so called "deglycosylated A chain" (dgA). Deglycosylated ricin A chain is preferred because of its extreme potency, longer half-life, and because it is economically feasible to manufacture it a clinical grade and scale. Recombinant and/or truncated ricin A chain may also be used.

The anti-CXCR4 antibody therapeutics of the invention may comprise a component that is capable of promoting coagulation, i.e., a coagulant. Here, the targeting antibody may be directly or indirectly, e.g., via another antibody, linked to a factor that directly or indirectly stimulates coagulation.

Preferred coagulation factors for such uses are Tissue Factor (TF) and TF derivatives, such as truncated TF (tTF), dimeric, trimeric, polymeric/multimeric TF, and mutant TF deficient in the ability to activate Factor VII. Other suitable coagulation factors include vitamin K-dependent coagulants, such as Factor II/IIa, Factor VII/VIIa, Factor IX/IXa and Factor X/Xa; vitamin K-dependent coagulation factors that lack the Gla modification; Russell's viper venom Factor X activator; platelet-activating compounds, such as thromboxane $A_2$ and thromboxane $A_2$ synthase; and inhibitors of fibrinolysis, such as α2-antiplasmin. Overall, truncated Tissue Factor (tTF) is currently preferred.

The preparation of immunoconjugates and immunotoxins is generally well known in the art (see, e.g., U.S. Pat. No. 4,340,535). Each of the following patents are further incorporated herein by reference for the purposes of even further supplementing the present teachings regarding immunotoxin generation, purification and use: U.S. Pat. Nos. 6,004,554; 5,855,866; 5,965,132; 5,776,427; 5,863,538; 5,660,827 and 6,051,230.

A variety of chemotherapeutic and other pharmacological agents can also be successfully conjugated to anti-CXCR4 antibody therapeutics of the invention. Exemplary antineoplastic agents that have been conjugated to antibodies include doxorubicin, daunomycin, methotrexate and vinblastine. Moreover, the attachment of other agents such as neocarzinostatin, macromycin, trenimon and α-amanitin has been described (see U.S. Pat. Nos. 5,660,827; 5,855,866; and 5,965,132; each incorporated herein.)

The preparation of coaguligands is also easily practiced. The operable association of one or more coagulation factors with an anti-CXCR4 antibody of the invention may be a direct linkage, such as those described above for the immunotoxins. Alternatively, the operative association may be an indirect attachment, such as where the antibody is operatively attached to a second binding region, preferably an antibody or antigen binding region of an antibody, which binds to the coagulation factor. The coagulation factor should be attached to the anti-CXCR4 antibody of the invention at a site distinct from its functional coagulating site, particularly where a covalent linkage is used to join the molecules.

Bispecific or trispecific antibodies may also be employed in the methods of the invention. In such antibodies one arm binds to CXCR4 and is an antibody of the present invention. Methods for preparing bispecific antibodies are well known and described in the art.

In the preparation of immunoconjugates, immunotoxins and coaguligands, recombinant expression may be employed. The nucleic acid sequences encoding the chosen anti-CXCR4 antibody of the invention, and therapeutic agent, toxin or coagulant, are attached in-frame in an expression vector. Recombinant expression thus results in translation of the nucleic acid to yield the desired immunoconjugate. Chemical cross-linkers and avidin:biotin bridges may also join the therapeutic agents to the anti-CXCR4 antibody of the invention.

The compositions and methods of the present invention may be used in combination with other therapeutics and diagnostics. In terms of biological agents, preferably diagnostic or therapeutic agents, for use "in combination" with an anti-CXCR4 antibody in accordance with the present invention, the term "in combination" is succinctly used to cover a range of embodiments. The "in combination" terminology, unless otherwise specifically stated or made clear from the scientific terminology, thus applies to various formats of combined compositions, pharmaceuticals, cocktails, kits, methods, and first and second medical uses.

The "combined" embodiments of the invention thus include, for example, where the anti-CXCR4 of the invention is a naked antibody and is used in combination with an agent or therapeutic agent that is not operatively attached thereto. In such cases, the agent or therapeutic agent may be used in a non-targeted or targeted form. In "non-targeted form", the agent, particularly therapeutic agents, will generally be used according to their standard use in the art. In "targeted form", the agent will generally be operatively attached to a distinct antibody or targeting region that delivers the agent or therapeutic agent to the target disease site. The use of such targeted forms of biological agents, both diagnostics and therapeutics, is also quite standard in the art.

In other "combined" embodiments of the invention, the anti-CXCR4 antibody of the invention is an immunoconjugate wherein the antibody is itself operatively associated or combined with the agent or therapeutic agent. The operative attachment includes all forms of direct and indirect attachment as described herein and known in the art.

The "combined" uses, particularly in terms of an anti-CXCR4 antibody of the invention in combination with therapeutic agents, also include combined compositions, pharmaceuticals, cocktails, kits, methods, and first and second medical uses wherein the therapeutic agent is in the form of a prodrug. In such embodiments, the activating component able to convert the prodrug to the functional form of the drug may again be operatively associated with the anti-CXCR4 antibodies of the present invention.

In certain preferred embodiments, the therapeutic compositions, combinations, pharmaceuticals, cocktails, kits, methods, and first and second medical uses will be "prodrug combinations". As will be understood by those of ordinary skill in the art, the term "prodrug combination", unless otherwise stated, means that the antibody of the invention is operatively attached to a component capable of converting the prodrug to the active drug, not that the antibody is attached to the prodrug itself. However, there is no requirement that the prodrug embodiments of the invention need to be used as prodrug combinations. Accordingly, prodrugs may be used in any manner that they are used in the art, including in ADEPT and other forms.

Thus, where combined compositions, pharmaceuticals, cocktails, kits, methods, and first and second medical uses are described, preferably in terms of diagnostic agents, and more preferably therapeutic agents, the combinations include anti-CXCR4 antibodies that are naked antibodies and immunoconjugates, and wherein practice of the in vivo embodiments of the invention involves the prior, simultaneous or subsequent administration of the naked antibodies or immunoconjugate and the biological, diagnostic or therapeutic agent; so long as, in some conjugated or unconjugated form, the overall provision of some form of the antibody and some form of the biological, diagnostic or therapeutic agent is achieved.

The foregoing and other explanations of the effects of the present invention on tumors are made for simplicity to explain the combined mode of operation, type of attached agent(s) and such like. This descriptive approach should not be interpreted as either an understatement or an oversimplification of the beneficial properties of the anti-CXCR4 antibodies of the invention. It will therefore be understood that such antibodies themselves have anti-CXCR4 properties and that immunoconjugates of such antibodies will maintain these properties and combine them with the properties of the attached agent; and further, that the combined effect of the antibody and any attached agent will typically be enhanced and/or magnified.

The invention therefore provides compositions, pharmaceutical compositions, therapeutic kits and medicinal cocktails comprising, optionally in at least a first composition or container, a biologically effective amount of at least a first anti-CXCR4 antibody of the invention, or an antigen-binding fragment or immunoconjugate of such an anti-CXCR4 antibody; and a biologically effective amount of at least a second biological agent, component or system.

The "at least a second biological agent, component or system" will often be a therapeutic or diagnostic agent, component or system, but it need not be. For example, the at least a second biological agent, component or system may comprise components for modification of the antibody and/or for attaching other agents to the antibody. Certain preferred second biological agents, components or systems are prodrugs or components for making and using prodrugs, including components for making the prodrug itself and components for adapting the antibodies of the invention to function in such prodrug or ADEPT embodiments.

Where therapeutic or diagnostic agents are included as the at least a second biological agent, component or system, such therapeutics and/or diagnostics will typically be those for use in connection with the treatment or diagnosis of one or more of the disorders defined above.

Thus, in certain embodiments "at least a second therapeutic agent" will be included in the therapeutic kit or cocktail. The term is chosen in reference to the anti-CXCR4 antibody of the invention being the first therapeutic agent. Therapeutic agents which are appropriate for being "at least a second therapeutic agent" in accordance with the invention are discussed above in connection with immunoconjugates.

In terms of compositions, kits and/or medicaments of the invention, the combined effective amounts of the therapeutic agents may be comprised within a single container or container means, or comprised within distinct containers or container means. The cocktails will generally be admixed together for combined use. Agents formulated for intravenous administration will often be preferred. Imaging components may also be included. The kits may also comprise instructions for using the at least a first antibody and the one or more other biological agents included.

Speaking generally, the at least a second therapeutic agent may be administered to the animal or patient substantially simultaneously with the anti-CXCR4 antibody of the invention; such as from a single pharmaceutical composition or from two pharmaceutical compositions administered closely together.

Alternatively, the at least a second therapeutic agent may be administered to the animal or patient at a time sequential to the administration of the anti-CXCR4 antibody of the invention. "At a time sequential", as used herein, means "staggered", such that the at least a second anti-cancer agent is administered to the animal or patient at a time distinct to the administration of the anti-CXCR4 antibody of the invention. Generally, the two agents are administered at times effectively spaced apart to allow the two agents to exert their respective therapeutic effects, i.e., they are administered at "biologically effective time intervals". The at least a second therapeutic agent may be administered to the animal or patient at a biologically effective time prior to the anti-CXCR4 antibody of the invention, or at a biologically effective time subsequent to that therapeutic.

Accordingly, the present invention provides methods for treating an animal or patient with a tumor, comprising:

(a) subjecting the animal or patient to a first treatment that substantially reduces the tumor burden; and (b) subsequently administering at least a first anti-CXCR4 antibody of the invention, or antigen-binding fragment thereof; optionally wherein the antibody or fragment is operatively associated with a second therapeutic agent.

Preferred first treatments include surgical resection and chemotherapeutic intervention.

In other embodiments, the present invention provides methods for treating an animal or patient with a CXCR4-mediated disorder, comprising:
(a) subjecting the animal or patient to a first treatment that substantially reduces the CXCR4-mediated burden such as inflammation; and
(b) subsequently administering at least a first anti-CXCR4 antibody of the invention, or antigen-binding fragment thereof; optionally wherein the antibody or fragment is operatively associated with a second therapeutic agent.

In certain other embodiments, the antibodies and immunoconjugates of the invention may be combined with one or more diagnostic agents, typically diagnostic agents for use in connection with the diagnosis of a disorder as defined above. A range of diagnostic compositions, kits and methods are thus included within the invention.

Yet further aspects are methods of diagnosis or imaging of a subject comprising the administration of an appropriate amount of an antibody or other protein of the invention as defined herein to the subject and detecting the presence and/or amount and/or the location of the antibody or other protein of the invention in the subject.

In one embodiment, the invention provides a method of reducing immunosuppression associated with CXCR4 expression in an animal, comprising administering to said animal the antibody of the invention, or an immunoconjugate thereof, in an amount effective to form complexes between said antibody and CXCR4 in said animal, thereby reducing immunosuppression associated with CXCR4 expression in an animal.

Appropriate diseases to be imaged or diagnosed in accordance with the above described uses and methods include any CXCR4 associated disease as described elsewhere herein and preferably any cancer as described elsewhere herein.

In one embodiment, the invention provides a method of diagnosing disease in an animal comprising the step of:
(a) contacting a test sample taken from said animal with an antibody of the invention or an immunoconjugate thereof.

In a further embodiment, the invention provides a method of diagnosing disease in an animal comprising the steps of:
(a) contacting a test sample taken from said animal with an antibody of the invention or an immunoconjugate thereof;
(b) measuring or detecting the presence and/or amount and/or location of antibody-antigen complex in the test sample; and, optionally
(c) comparing the presence and/or amount of antibody-antigen complex in the test sample to a control.

In the above methods, said contacting step is carried out under conditions that permit the formation of an antibody-antigen complex. Appropriate conditions can readily be determined by a person skilled in the art.

In the above methods any appropriate test sample may be used, for example biopsy cells, tissues or organs suspected of being affected by disease or histological sections.

In certain of the above methods, the presence of any amount of antibody-antigen complex in the test sample would be indicative of the presence of disease. Preferably, for a positive diagnosis to be made, the amount of antibody-antigen complex in the test sample is greater than, preferably significantly greater than, the amount found in an appropriate control sample. More preferably, the significantly greater levels are statistically significant, preferably with a probability value of <0.05. Appropriate methods of determining statistical significance are well known and documented in the art and any of these may be used.

Appropriate control samples could be readily chosen by a person skilled in the art, for example, in the case of diagnosis of a particular disease, an appropriate control would be a sample from a subject that did not have that disease. Appropriate control "values" could also be readily determined without running a control "sample" in every test, e.g., by reference to the range for normal subjects known in the art.

For use in the diagnostic or imaging applications, the antibodies of the invention may be labeled with a detectable marker such as a radio-opaque or radioisotope, such as $^3$H, $^{14}$C, $^{32}$P, $^{35}$S, $^{123}$I, $^{125}$I, $^{131}$I; a radioactive emitter (e.g., $\alpha$, $\beta$ or $\gamma$ emitters); a fluorescent (fluorophore) or chemiluminescent (chromophore) compound, such as fluorescein isothiocyanate, rhodamine or luciferin; an enzyme, such as alkaline phosphatase, beta-galactosidase or horseradish peroxidase; an imaging agent; or a metal ion; or a chemical moiety such as biotin which may be detected by binding to a specific cognate detectable moiety, e.g., labelled avidinistreptavidin. Methods of attaching a label to a binding protein, such as an antibody or antibody fragment, are known in the art. Such detectable markers allow the presence, amount or location of binding protein-antigen complexes in the test sample to be examined.

Preferred detectable markers for in vivo use include an X-ray detectable compound, such as bismuth (III), gold (III), lanthanum (III) or lead (II); a radioactive ion, such as copper$^{67}$, gallium$^{67}$, gallium$^{68}$, indium$^{111}$, indium$^{113}$, iodine$^{123}$, iodine$^{125}$, iodine$^{131}$, mercury$^{197}$, mercury$^{203}$, rhenium$^{186}$, rhenium$^{188}$, rubidium$^{97}$, rubidium$^{103}$, technetium$^{99m}$ or yttrium$^{90}$; a nuclear magnetic spin-resonance isotope, such as cobalt (II), copper (II), chromium (III), dysprosium (III), erbium (III), gadolinium (III), holmium (III), iron (II), iron (III), manganese (II), neodymium (III), nickel (II), samarium (III), terbium (III), vanadium (II) or ytterbium (III); or rhodamine or fluorescein.

The invention also includes diagnostic or imaging agents comprising the antibodies of the invention attached to a label that produces a detectable signal, directly or indirectly. Appropriate labels are described elsewhere herein.

The invention further includes kits comprising one or more of the antibodies, immunoconjugates or compositions of the invention or one or more of the nucleic acid molecules encoding the antibodies of the invention, or one or more recombinant expression vectors comprising the nucleic acid sequences of the invention, or one or more host cells or viruses comprising the recombinant expression vectors or nucleic acid sequences of the invention. Preferably said kits are for use in the methods and uses as described herein, e.g., the therapeutic, diagnostic or imaging methods as described herein, or are for use in the in vitro assays or methods as described herein. The antibody in such kits may preferably be an antibody conjugate as described elsewhere herein, e.g., may be conjugated to a detectable moiety or may be an immumoconjugate. Preferably said kits comprise instructions for use of the kit components, for example in diagnosis. Preferably said kits are for diagnosing or treating diseases as described elsewhere herein and optionally comprise instructions for use of the kit components to diagnose or treat such diseases.

The antibodies of the invention as defined herein may also be used as molecular tools for in vitro or in vivo applications and assays. As the antibodies have an antigen binding site, these can function as members of specific binding pairs and these molecules can be used in any assay where the particular binding pair member is required.

Thus, yet further aspects of the invention provide a reagent that comprises an antibody of the invention as defined herein and the use of such antibodies as molecular tools, for example in in vitro or in vivo assays.

Cancer treatment may also be carried out by:
(a) forming an image of a tumor by administering to an animal or patient having a tumor a diagnostic amount of at least a first detectably-labeled anti-CXCR4 antibody of the invention, comprising a diagnostic agent operatively attached to the anti-CXCR4 antibody of the invention, thereby forming a detectable image of the tumor; and
(b) subsequently administering to the same animal or patient a therapeutically optimized amount of at least a first naked anti-CXCR4 antibody of the invention or therapeutic agent-antibody construct using such an antibody, thereby causing an anti-tumor effect.

The invention will now be described in more detail in the following non-limited examples with reference to the Tables and Figures in which:

Table 1 lists some of the sequences disclosed herein relating to antibody C-9P21

Table 2 lists some of the sequences disclosed herein relating to antibody B-1M22

Table 3 lists some of the sequences disclosed herein relating to antibody C-1I24

Table 4 lists some of the sequences disclosed herein relating to antibody D-1K21

Table 5 lists some of the sequences disclosed herein relating to antibody 9N10

Table 6 lists some of the sequences disclosed herein relating to the IgG form of antibody C-9P21. The variable regions are underlined.

Table 7 lists some of the sequences disclosed herein relating to IgG form of antibody B-1M22. The variable regions are underlined.

Table 8 lists some of the sequences disclosed herein relating to IgG form of antibody C-1I24. The variable regions are underlined.

Table 9 lists some of the sequences disclosed herein relating to IgG form of antibody D-1K21. The variable regions are underlined.

Table 10 lists some of the sequences disclosed herein relating to IgG form of antibody 9N10. The variable regions are underlined.

Table 11 lists some other sequences disclosed herein relating to antibodies of the invention.

FIG. 1 shows the nucleotide and amino acid sequence of inter alia the heavy and light chain of clone C-9P21. ScFv was cloned via NcoI/NotI site into pHOG21. The restriction sites used for initial cloning (NcoI, HindIII, MluI and NotI) are italicized and underlined. The linker sequence between VH and VL is in italic. The c-myc epitope and 6 His are underlined and double underlined, respectively.

FIG. 2 shows the nucleotide and amino acid sequence of inter alia the heavy and light chain of clone B-1M22. ScFv was cloned via NcoI/NotI site into pHOG21. The restriction sites used for initial cloning (NcoI, HindIII, MluI and NotI) are italicized and underlined. The linker sequence between VH and VL is in italic. The c-myc epitope and 6 His are underlined and double underlined, respectively.

FIG. 3 shows the nucleotide and amino acid sequence of inter alia the heavy and light chain of clone C-1I24. ScFv was cloned via NcoI/NotI site into pHOG21. The restriction sites used for initial cloning (NcoI, HindIII, MluI and NotI) are italicized and underlined. The linker sequence between VH and VL is in italic. The c-myc epitope and 6 His are underlined and double underlined, respectively.

FIG. 4 shows the nucleotide and amino acid sequence of inter alia the heavy and light chain of clone D-1K21. ScFv was cloned via NcoI/NotI site into pHOG21. The restriction sites used for initial cloning (NcoI, HindIII, MluI and NotI) are italicized and underlined. The linker sequence between VH and VL is in italic. The c-myc epitope and 6 His are underlined and double underlined, respectively.

FIG. 5 shows the nucleotide and amino acid sequence of inter alia the heavy and light chain of clone 9N10. ScFv was cloned via NcoI/NotI site into pHOG21. The restriction sites used for initial cloning (NcoI, HindIII, MluI and NotI) are italicized and underlined. The linker sequence between VH and VL is in italic. The c-myc epitope and 6 His are underlined and double underlined, respectively.

Figure 6B:
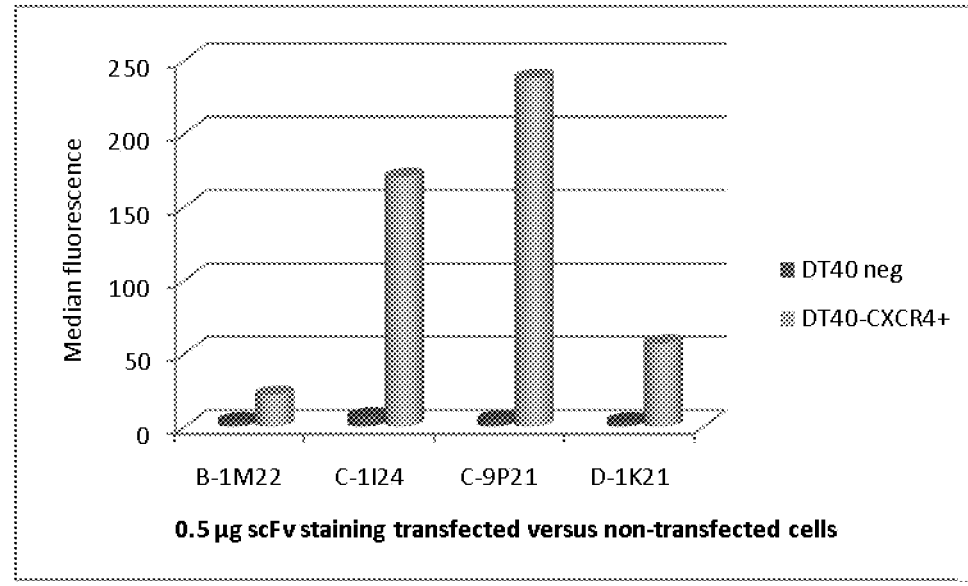
Figure 6C:
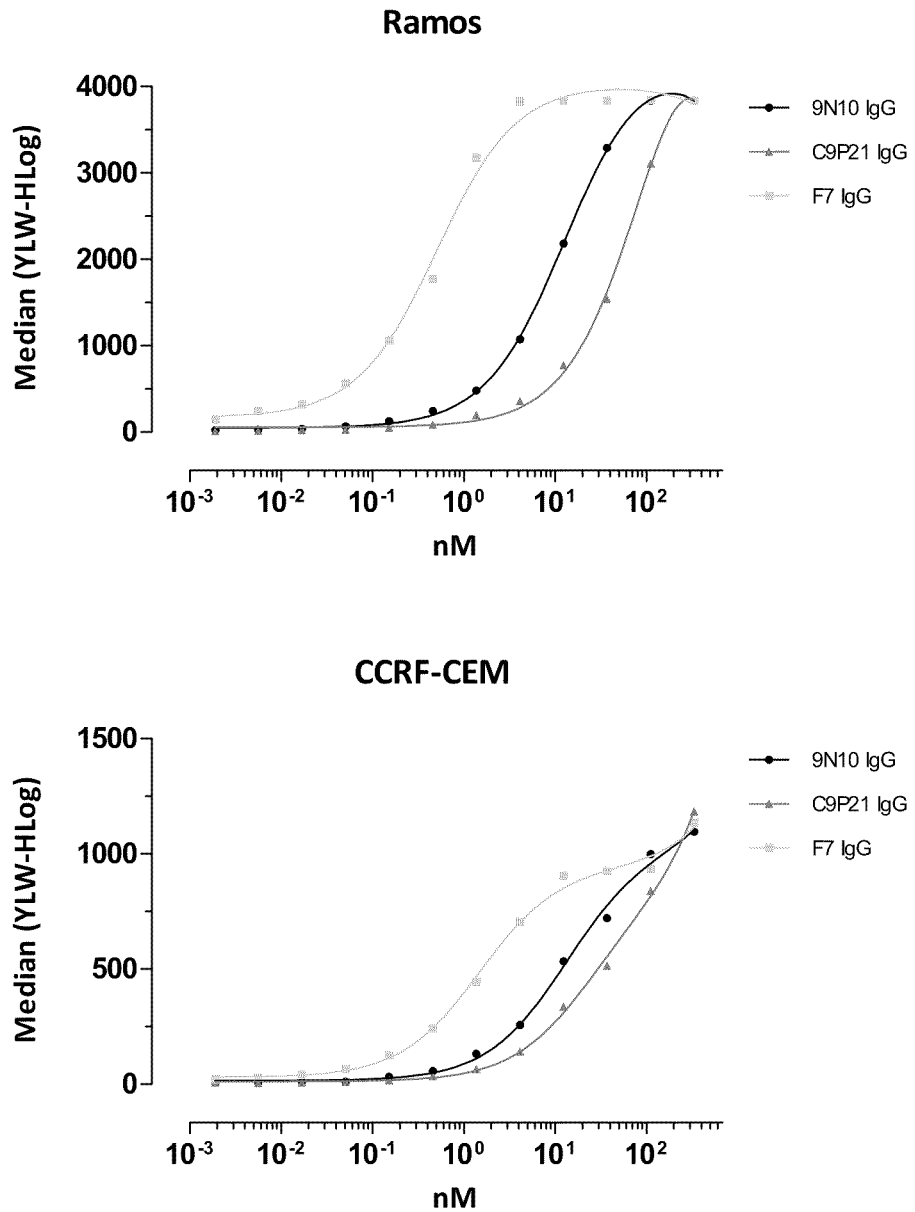

FIG. 6A shows EasyCyte staining demonstrating the binding of B-1M22, C-9P21, C-1I24, and D-1K21scFv clones to CXCR4-transfected versus non-transfected HEK293 cell lines. FIG. 6B shows EasyCyte staining demonstrating the binding of B-1M22, C-9P21, C-1I24, and D-1K21 scFv clones to transfected versus non-transfected DT40 cell lines. FIG. 6C shows EasyCyte staining demonstrating the binding of C-9P21, 9N10, and F7 IgG clones to Ramos and CCRF-CEM cell lines.

Figure 7A:
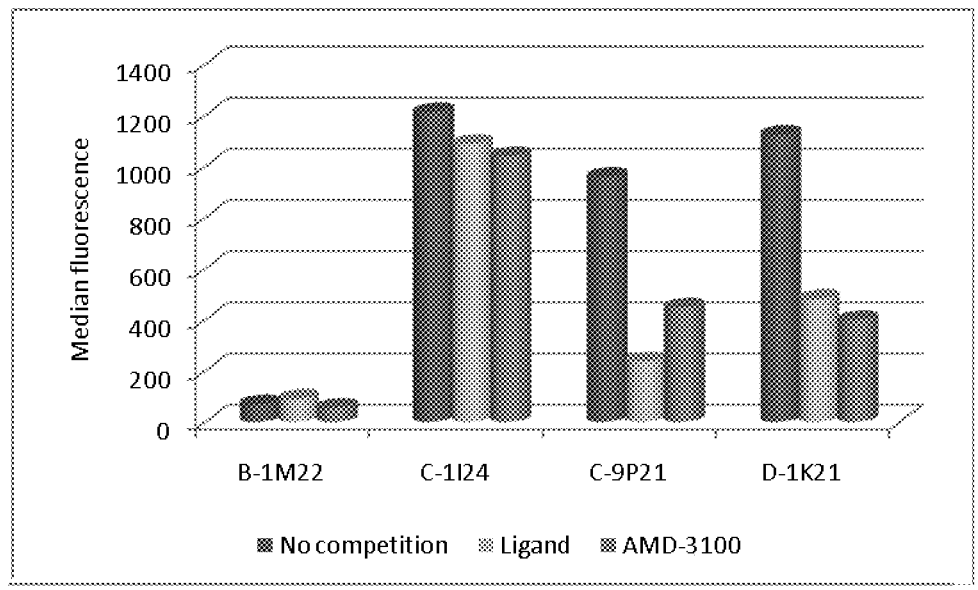
Figure 7B:
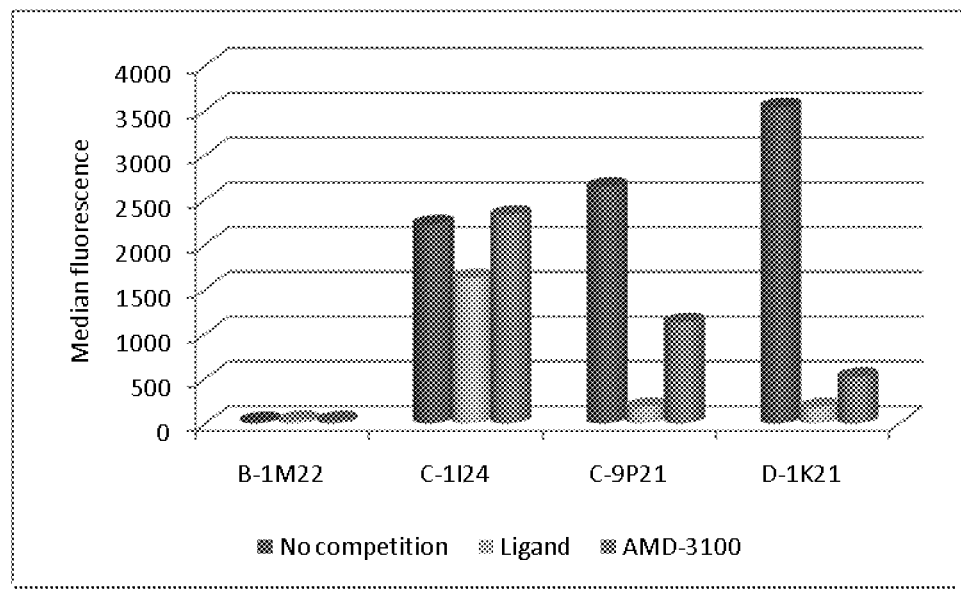
Figure 7C:
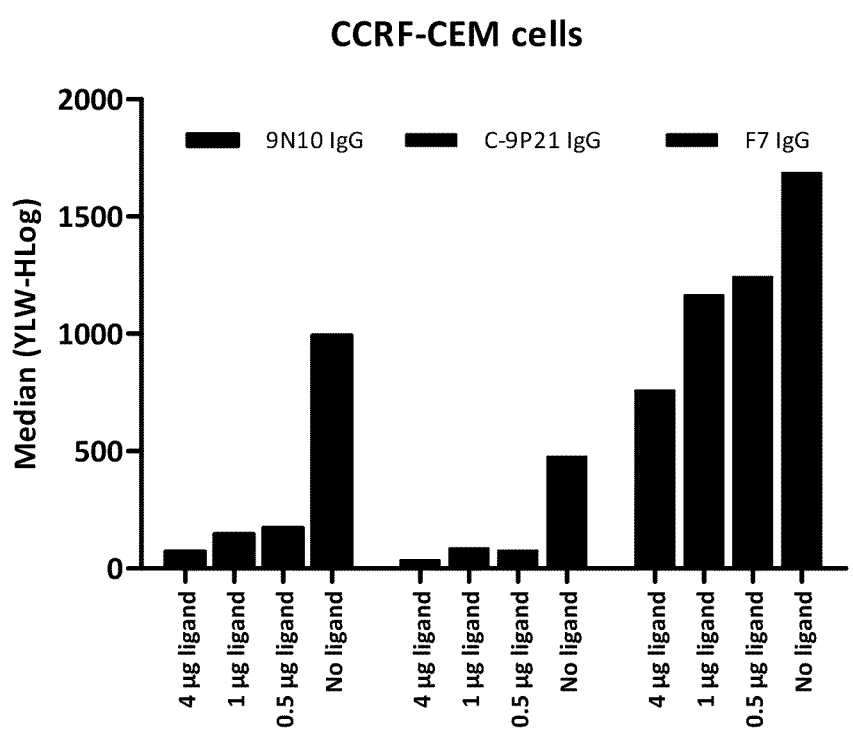

FIG. 7A shows EasyCyte staining of $10^5$ Jurkat cells with 0.5 μg each of B-1M22, C-9P21, C-1I24, and D-1K21 scFv clones without and with competition with ligand and AMD-3100. FIG. 7B shows EasyCyte staining of $10^5$ Ramos cells with 0.5 μg each of B-1M22, C-9P21, C-1I24, and D-1K21 scFv clones without and with competition with ligand and AMD-3100. FIG. 7C shows EasyCyte staining of $10^5$ CCRF-CEM cells with 0.1 μg each of C-9P21, 9N10, and F7 IgG clones without and with competition with 4 μg, 1 μg and 0.5 μg ligand.

Figure 8A:
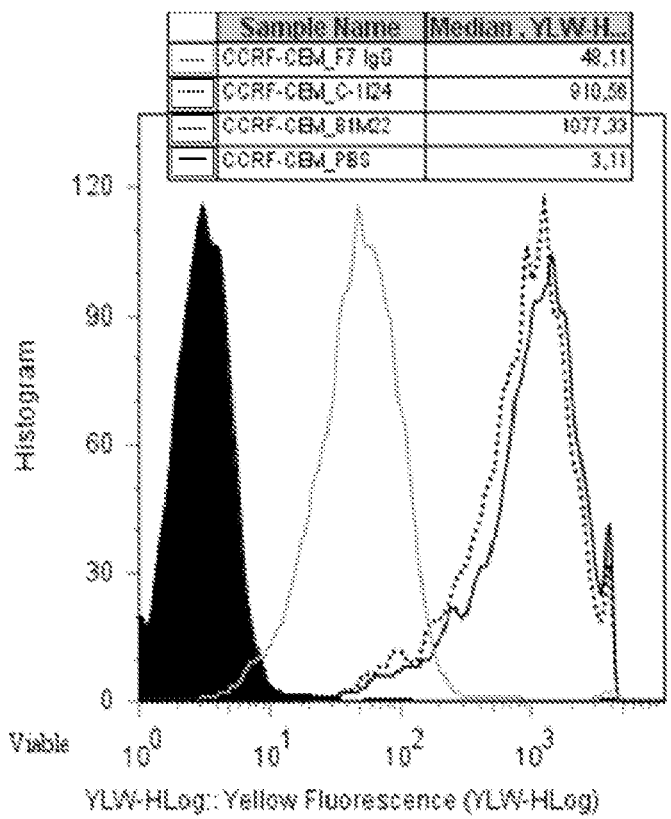
Figure 8B:
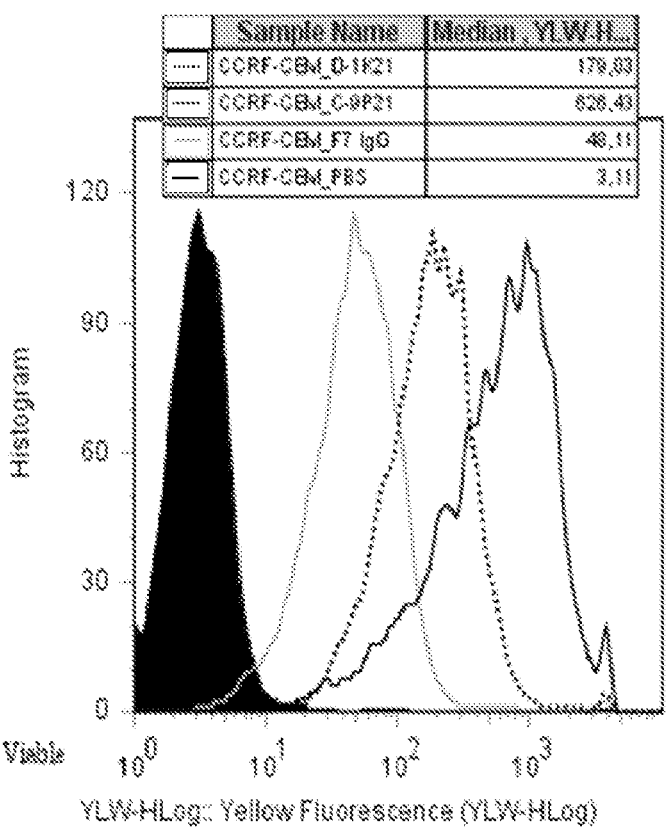

FIG. 8A shows EasyCyte staining of $10^5$ CCRF-CEM cells with 0.5 μg of C-1I24 (dotted line), B-1M22 (dark solid line) and F7 (pale solid line) compared to PBS (black shading). FIG. 8B shows EasyCyte staining of $10^5$ CCRF-CEM cells with 0.5 μg of D-1K21 (dotted line), C-9P21 (dark solid line) and F7 (pale solid line) compared to PBS (black shading). All antibodies were in IgG1 format and binding was detected with goat anti-human IgGrPE secondary antibody.

Figure 9:
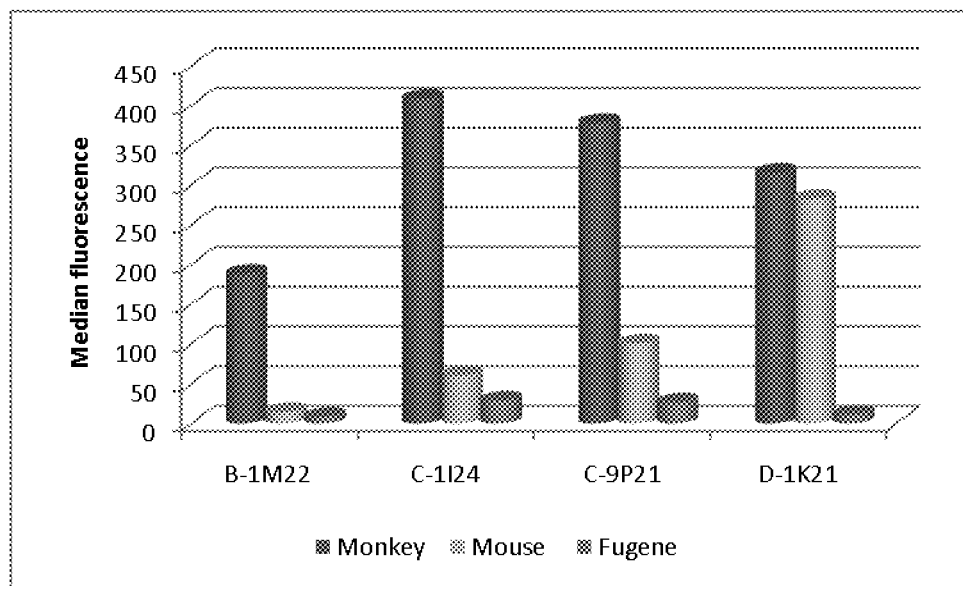

FIG. 9 shows binding of B-1M22, C-9P21, C-1I24, and D-1K21 to HEK293T/17 cells transiently expressing mouse or monkey CXCR4. The columns labelled "Fugene" are cells treated with the transfecting agent applied without DNA. This column serves as negative control.

Figure 10:
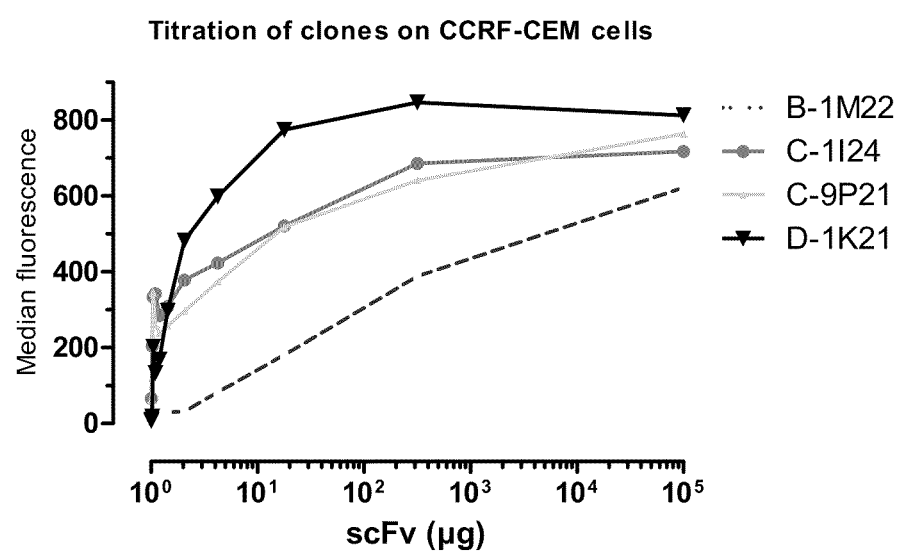

FIG. 10 shows an EasyCyte experiment in which B-1M22, C-9P21, C-1I24, and D-1K21 scFv clones were titrated on CCRF-CEM cells to determine optimal concentration for use in $Ca^{++}$ flux assays.

Figure 11A:
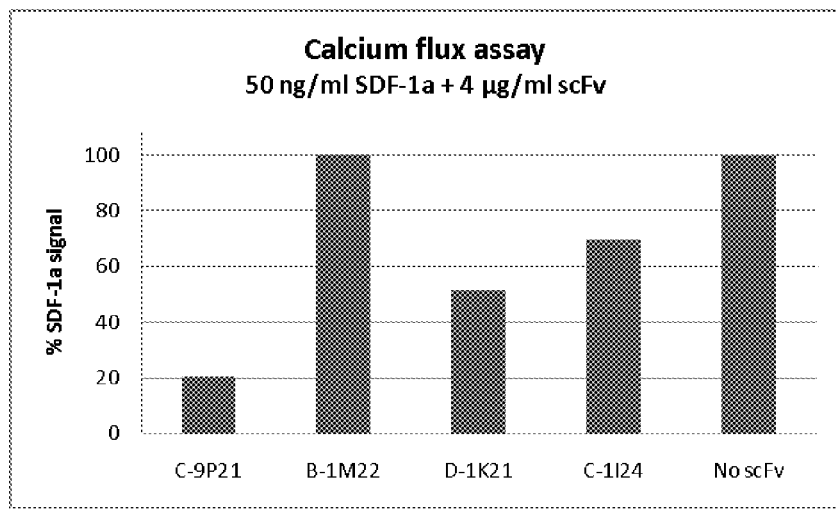
Figure 11B:
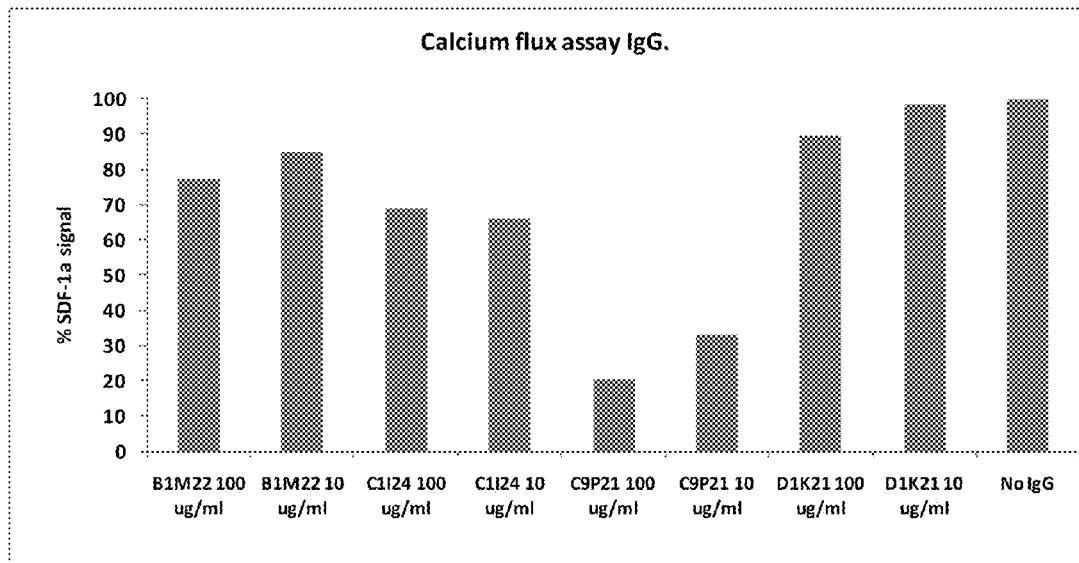
Figure 11C:
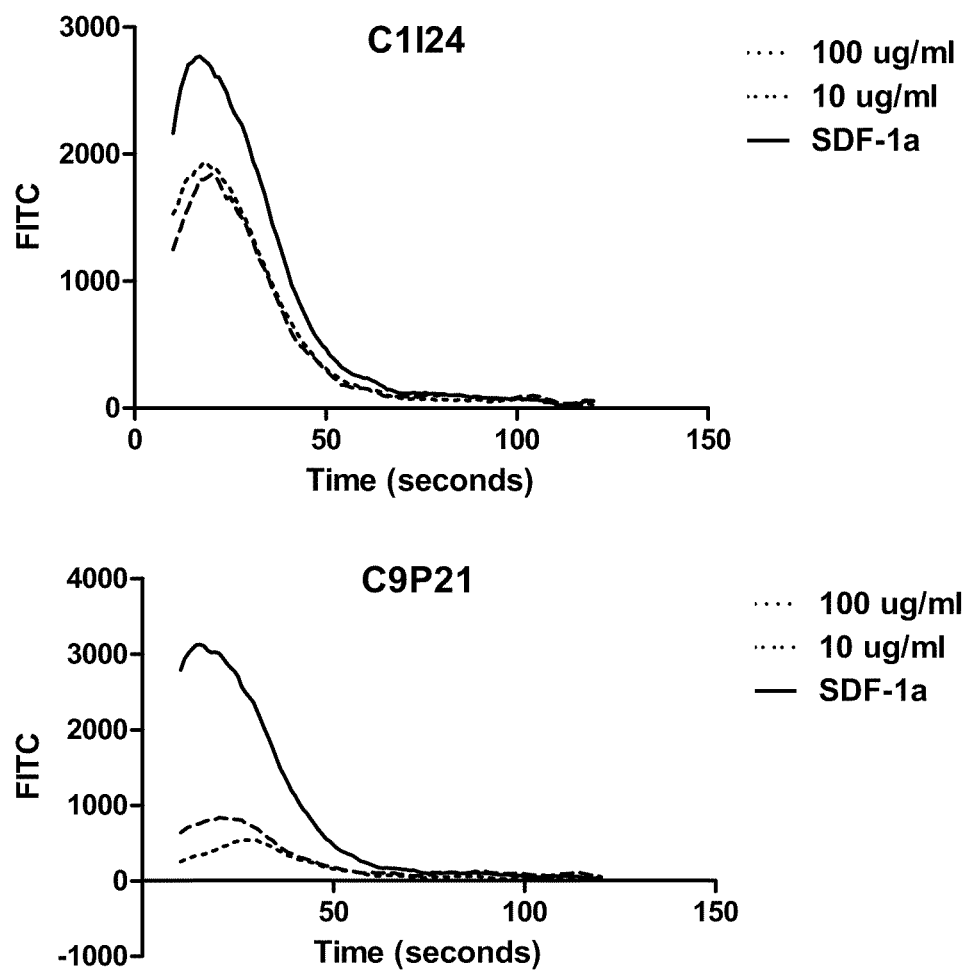
Figure 11D:
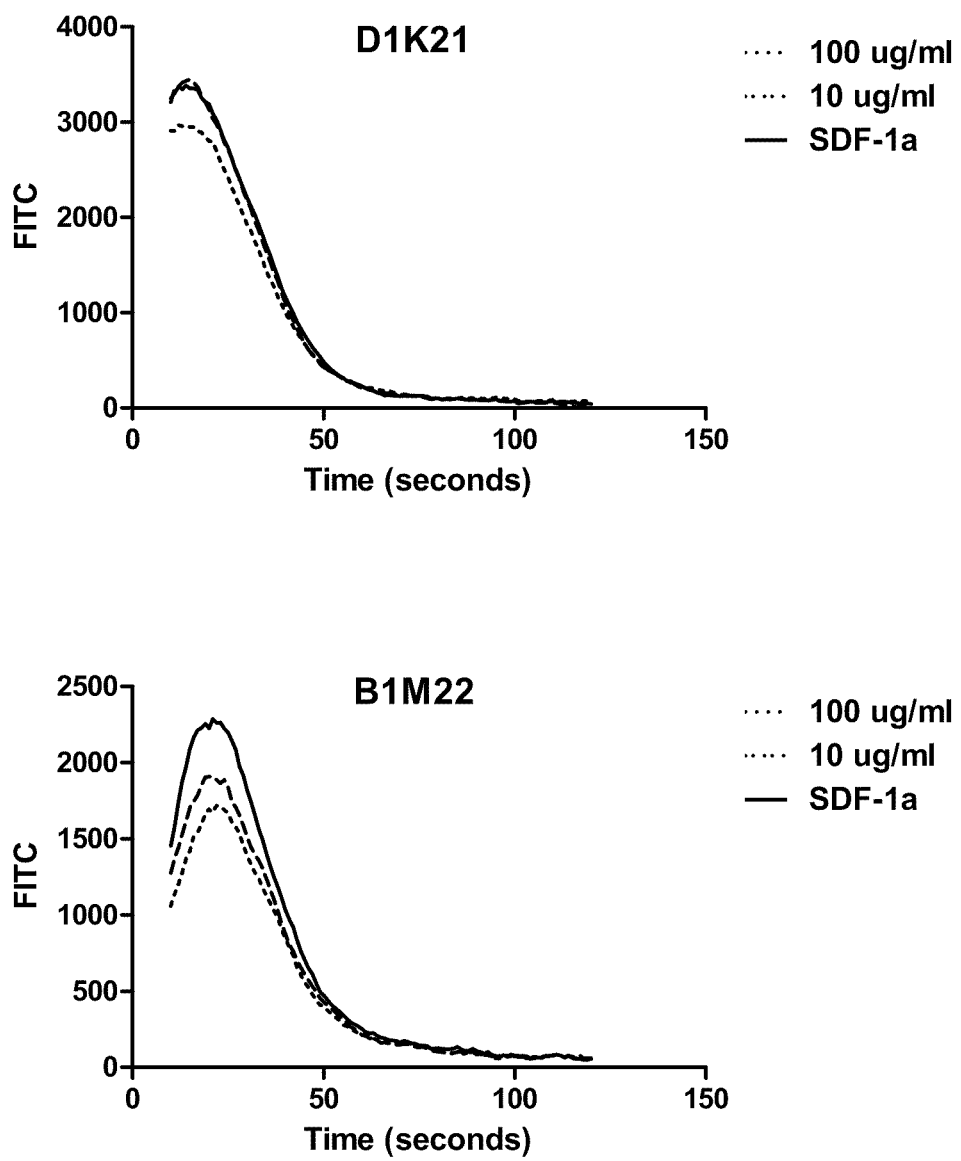
Figure 11E:
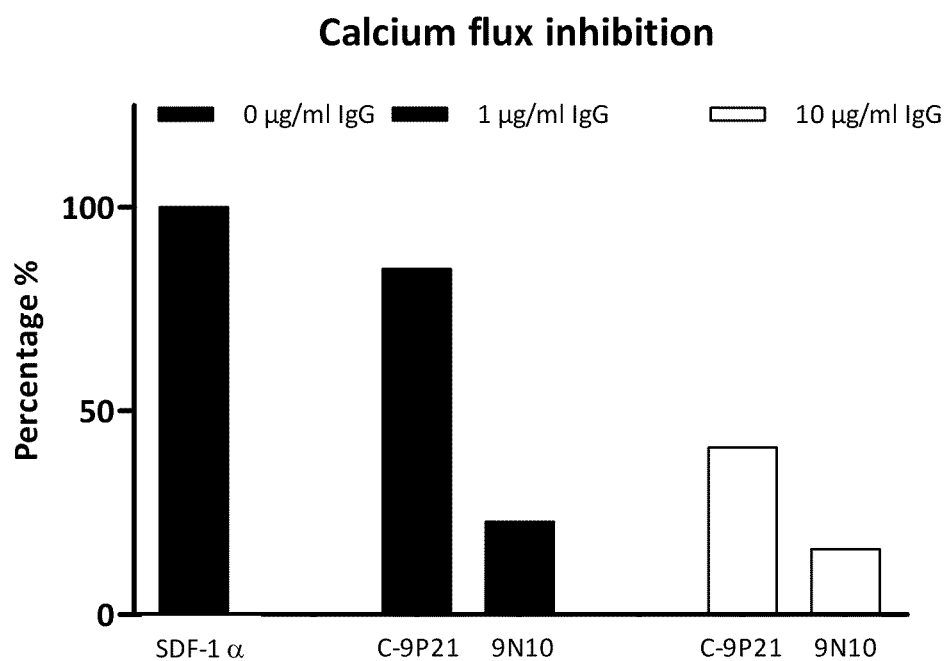

FIG. 11A, FIG. 11B, FIG. 11C and FIG. 11D and FIG. 11E show the results of a $Ca^{++}$-flux assay on CCRF-CEM cells (labelled with Fluo-4). The antibodies B-1M22, C-9P21, C-1I24, and D-1K21 were tested at both the scFv level (FIG. 11A) and the IgG level (FIGS. 11B, 11C and 11D), clone 9N10 was tested at IgG level (FIG. 11E). Cells were pre-incubated with 4 μg/ml scFvs (FIG. 11A) or 10 and 100 μg/ml IgGs (FIGS. 11B, 11C and 11D), or 1 and 10 μg/ml IgGs (FIG. 11E) for 15 min before adding CXCR4-specific ligand SDF-1α. The signal recording started approximately 10 sec after adding the ligand. The areas under the curves (AUC) were integrated and plotted as percentage of AUC for maximal stimulation with SDF-1α alone.

Figure 12A:
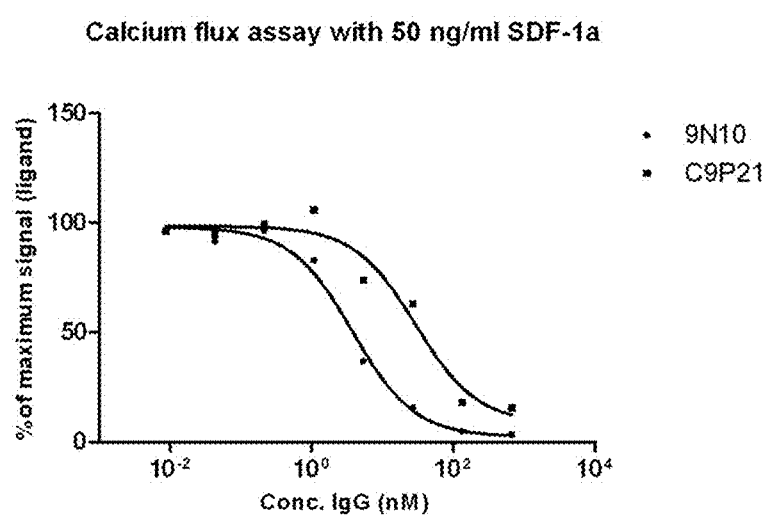
Figure 12:
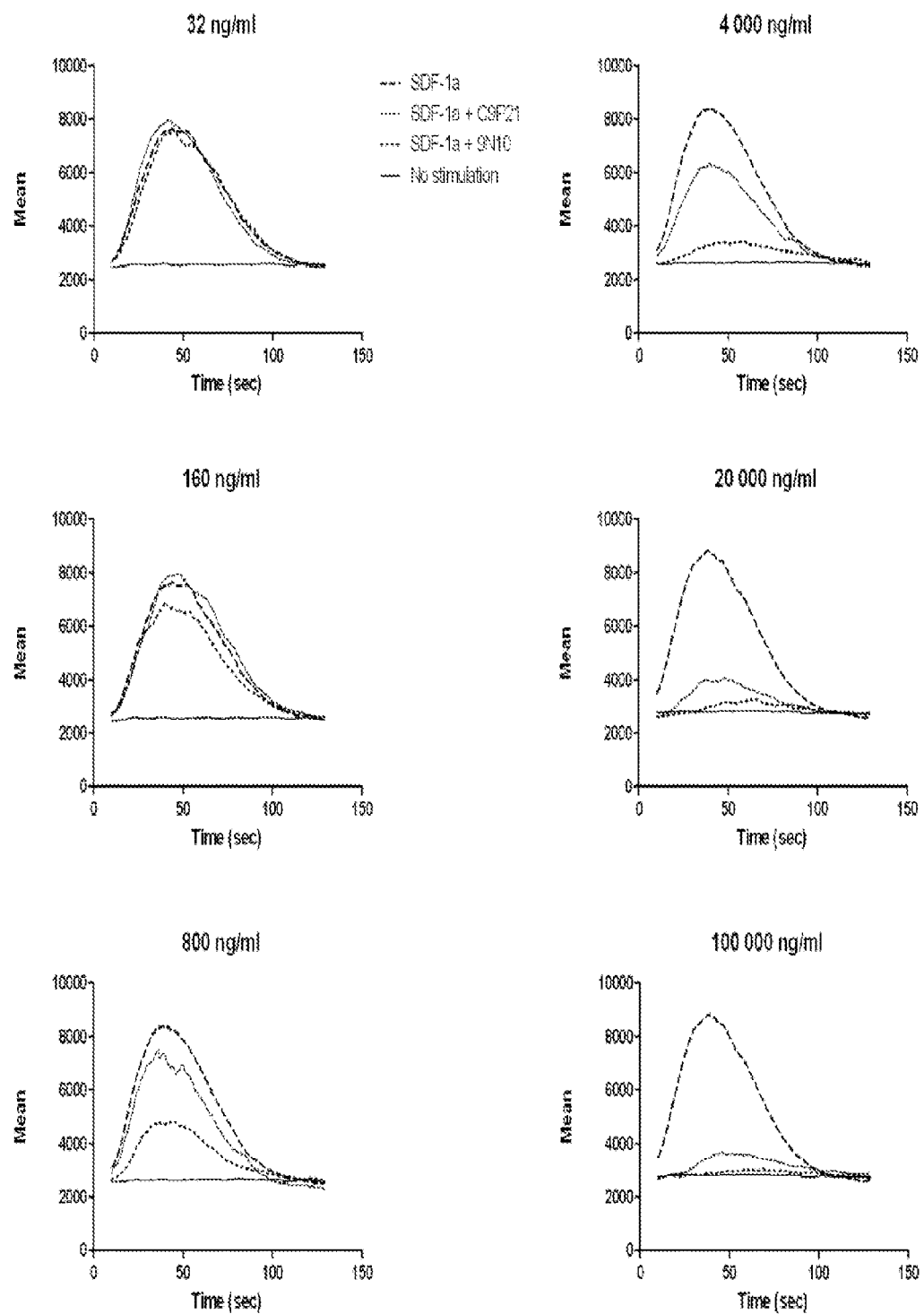

FIG. 12A and FIG. 12B show the results of a $Ca^{++}$-flux assay on CCRF-CEM cells (labelled with Fluo-4). The antibodies C-9P21 and 9N10 were tested at the IgG level. Cells were pre-incubated with varying concentrations of the antibodies for 15 min before adding CXCR4-specific ligand SDF-1α. The signal recording started approximately 10 sec after adding the ligand. FIG. 12A shows the signal reduction at a series of concentrations. FIG. 12B shows the original data.

Figure 13:
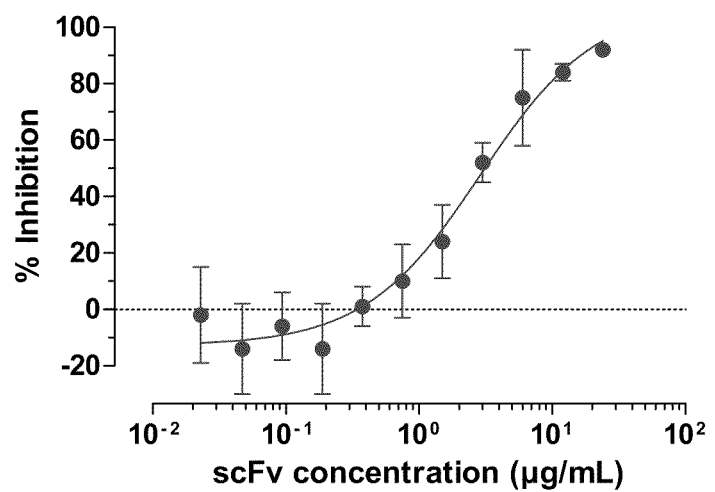

FIG. 13 shows inhibition of ligand (SDF-1α) induced cell migration by anti-CXCR4 scFv C-9P21. Human T-cell leukaemia CCRF-CEM cells labelled with BATDA were induced to migrate in Boyden chambers, where the SDF-1 ligand was placed in the lower chamber and the cells were co-incubated with antibodies or medium only as a control in the upper chambers. Cells which migrated to the lower chamber were detected by fluorescence intensity after Triton X-100 induced cell lysis. Mean and SD values of triplicates are plotted.

Figure 14A:
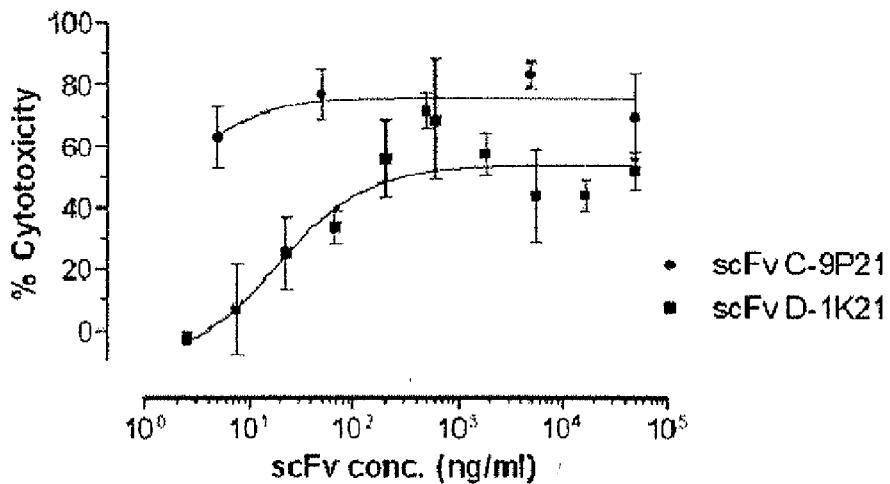
Figure 14B:
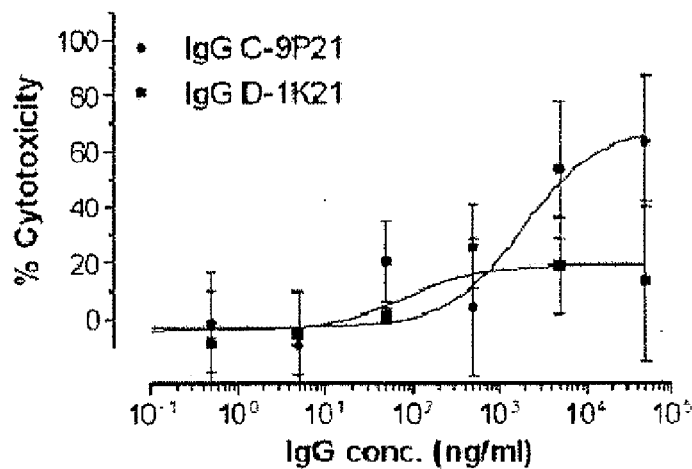
Figure 14C:
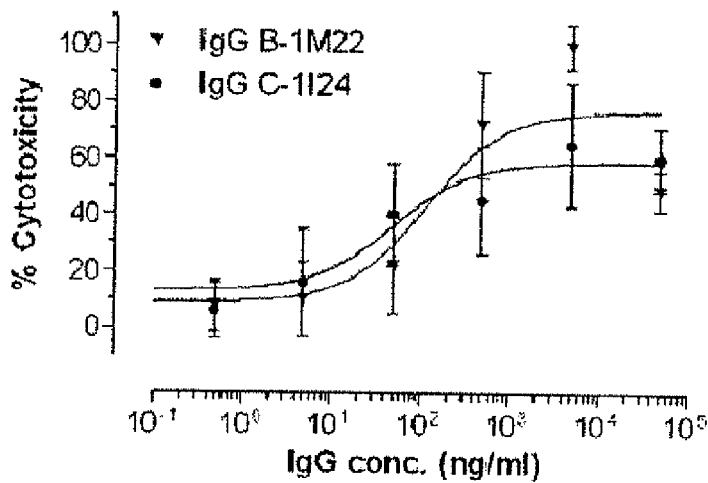

FIG. 14A, FIG. 14B and FIG. 14C shows the induction of ADCC by the anti-CXCR4 antibodies B-1M22, C-9P21, C-1I24, and D-1K21. Dose-response killing of CCRF-CEM cells is shown for scFvs C-9P21 and D-1K21 (a), and IgGs C-9P21 and D-1K21 (b), and IgGs B-1M22 and C-1I24.

Figure 15A:
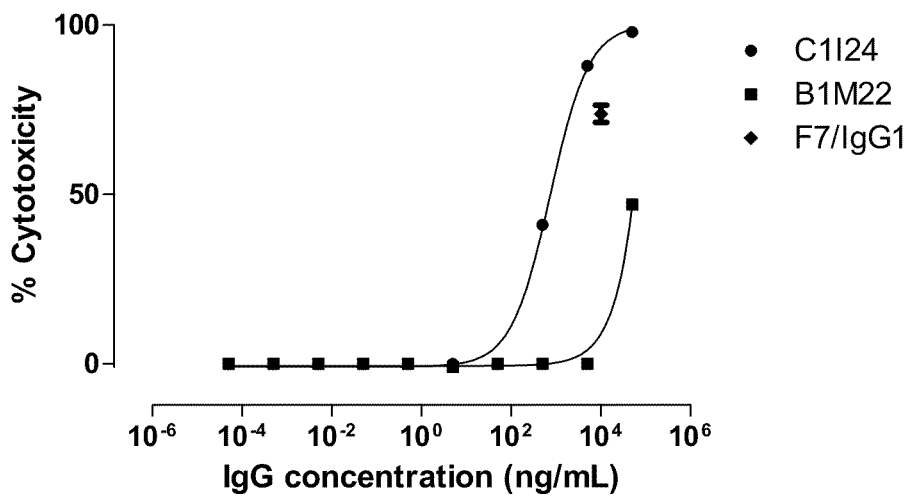
Figure 15B:
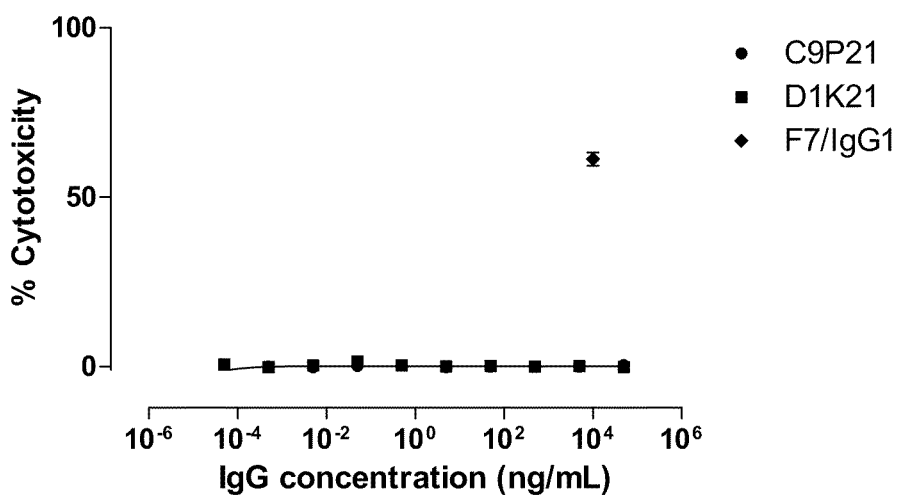

FIG. 15A and FIG. 15B show the results of an assay to test the ability of the antibodies B-1M22, C-9P21, C-1I24, and D-1K21 to induce CDC. Dose-response killing of Ramos cells in the presence of human serum is shown for IgGs B-1M22 and C-1I24 (FIG. 15A). C-9P21 and D-1K21 do not induce CDC (FIG. 15B). As a control, antibody F7 in IgG1 format was used.

Figure 16A:
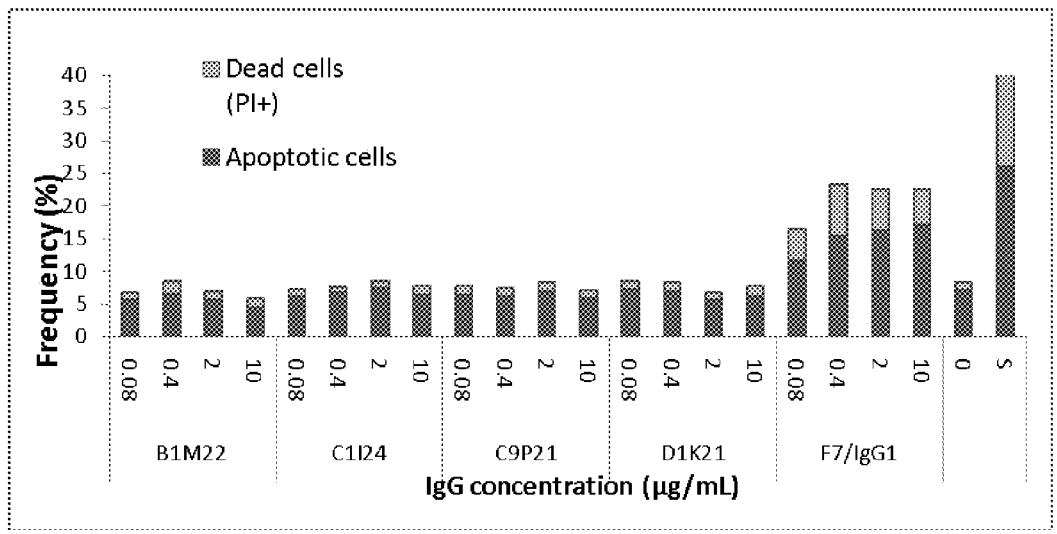
Figure 16B:
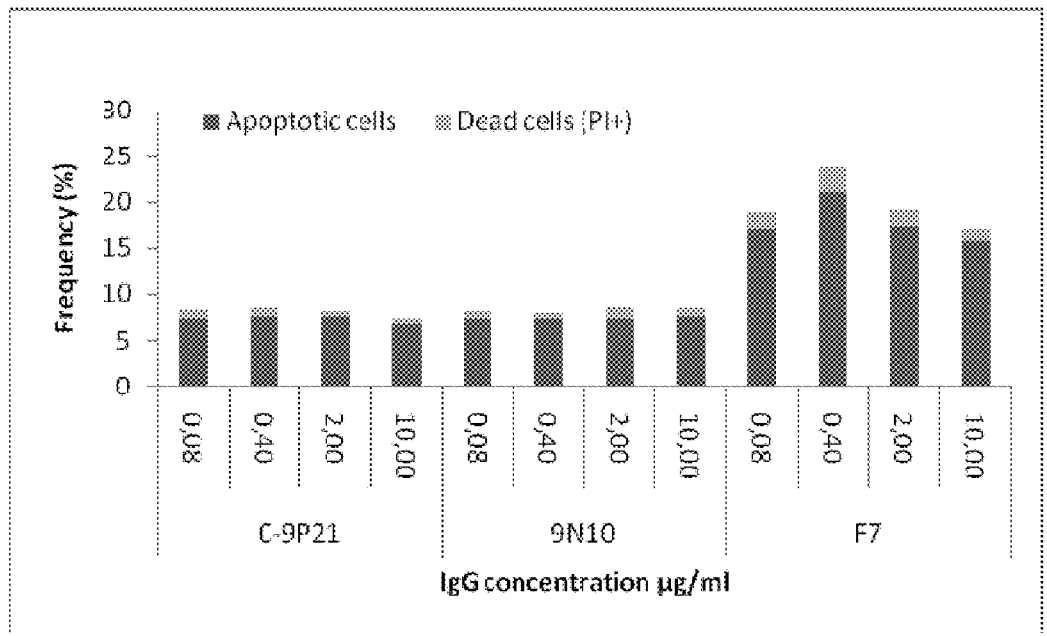

FIG. 16A shows an analysis of the apoptotic activity of anti-CXCR4 antibodies B-1M22, C-9P21, C-1I24, and D-1K21 with Annexin V. As controls, antibody F7 and Staurosporin (S; 25 nM) were used. The negative control (background level), where no antibody and no staurosporin is added is shown in the column 0. Light grey shading: Total amount of dead cells, positive both for Annexin V and PI, dark grey shading: apoptotic cells as defined by being positive for Annexin V but negative for PI. FIG. 16B shows an analysis of apoptotic activity of the anti-CXCR4 antibodies C-9P21 and 9N10 with Annexin V. As controls, antibody F7 was used. Light grey shading: Total amount of dead cells, positive both for Annexin V and PI, dark grey shading: apoptotic cells as defined by being positive for Annexin V but negative for PI.

EXAMPLES

Example 1

Novel Antibodies

Five human antibodies have been identified which can specifically bind to CXCR4. Single chain forms of the antibodies were cloned in the pHOG21 plasmid (Kipriyanov et al., 1997) which contains a c-myc and 6×His tag epitopes. TG1 bacteria were transformed, and the scFv was expressed upon IPTG induction. The binding of the purified scFv was confirmed by EasyCyte.

The nucleotide sequences of the heavy and light chain of the antibody producing clones were sequenced. The antibodies are designated as C-9P21, B-1M22, C-1I24, D-1K21 and 9N10. The nucleotide sequence and amino acid sequence of the light and heavy chain of C-9P21 are shown in FIG. 1. The CDR regions of the light and heavy chains of C-9P21 are shown in Table 1. The nucleotide sequence and amino acid sequence of the light and heavy chain of B-1M22 are shown in FIG. 2. The CDR regions of the light and heavy chains of B-1M22 are shown in Table 2. The nucleotide sequence and amino acid sequence of the light and heavy chain of C-1I24 are shown in FIG. 3. The CDR regions of the light and heavy chains of C-1I24 are shown in Table 3. The nucleotide sequence and amino acid sequence of the light and heavy chain of D-1K21 are shown in FIG. 4. The CDR regions of the light and heavy chains of D-1K21 are shown in Table 4. The nucleotide sequence and amino acid sequence of the light and heavy chain of 9N10 are shown in FIG. 5. The CDR regions of the light and heavy chains of 9N10 are shown in Table 5.

The IgG form of antibodies C-9P21, B-1M22, C-1I24, D-1K21 and 9N10 have also been made. The IgG form is of the IgG1 isotype and it comprises two heavy chains and two light chains. Each heavy chain comprises a $V_H$ domain of SEQ ID NO: 69 (for C-9P21), SEQ ID NO: 71 (for B-1M22), SEQ ID NO:73 (for C-1I24), SEQ ID NO:75 (for D-1K21) or SEQ ID NO: 69 (for 9N10) and a human IgG1 constant region. Each light chain comprises a $V_L$ domain of SEQ ID NO: 70 (for C-9P21), SEQ ID NO: 72 (for B-1M22), SEQ ID NO: 74 (for C-1I24), SEQ ID NO: 76 (for D-1K21) or SEQ ID NO: 103 (for 9N10) and a human lambda light chain constant region (for B-1M22 and C1I24), or a human kappa light chain constant region (for C-9P21, D-1K21 and 9N10). The full IgG sequences of C-9P21, B-1M22, C-1I24, D-1K21 and 9N10 are shown in Tables 6, 7, 8, 9 and 10, respectively.

Cells and Cell Culture

CCRF-CEM (acute lymphoblastic leukemia, ATCC number CCL-119), HEK293T/17 (human kidney, ATCC number CRL-11268), Ramos (Burkitt's lymphoma, ATCC CRL-1596), Jurkat 6E-1 (Human T-cell leukemia, ATCC ECACC) and DT40 (chicken lymphoma, ATCC number CRL-2111) cell lines were obtained from the American Type Culture Collection (ATCC, Rockville, Md.). The CCRF-CEM, Ramos, Jurkat and DT40 cells were maintained in RPMI-1640 culture medium and the HEK293T cells were maintained in Dulbecco's Modified Eagle Medium (DMEM) culture medium. All cells were maintained with fetal calf serum, the concentration was 10% for DT40 and HEK293T cells and 20% for CCRF-CEM cells, Jurkat and Ramos. All media were supplemented with Penicillin and Streptomycin.

Ramos and Jurkat cells are split three times per week to $3 \times 10^5$ cell/ml for 48 hours growth and to $2 \times 10^5$ cells/ml over the weekend.

CCRF-CEM cells are split three times per week to $3 \times 10^5$ cell/ml for 48 hours growth and to $2 \times 10^5$ cells/ml over the weekend.

HEK293T/17 cells are split two to three times per week to $3.2 \times 10^5$ cell/ml for 48 hours growth and to $2.7 \times 10^5$ cells/ml over the weekend.

For transient transfection, HEK293T/17 cells are seeded as $2 \times 10^6$ cells in a T75 (Nunc) flask. 48 h after seeding, the cells are transfected with Fugene (Roche). 40 μl Fugene and 16 μg DNA are used per T75. The cells are used for assays 48 h after transfection.

Example 2

Specificity of Binding of Antibody Clones to CXCR4 Expressing Cells

The four antibodies B-1M22, C-9P21, C-1I24, and D-1K21 were tested at scFv level for their CXCR4 specificity by their ability to bind to CXCR4 transfected cells. The transfected cells differ from their untransfected counterpart only in the expression of CXCR4.

Material and Methods:

DT40 and HEK293T/17 cells were maintained as described above.

The DT40+CXCR4, HEK293+CXCR4, DT40 and HEK293 cells were harvested from culture flasks, washed 2 times with PBS (400×g, 5 min, 4° C.) and resuspended in PBS containing 0.2% BSA and 0.09% NaN$_3$. 1×10$^5$ cells per well were aliquoted into V-shaped 96-well plates (Greiner Bio-One, Frikenhausen, Germany). The cells were centrifuged (400×g, 5 min, 4° C.) and resuspended in 50 µl ScFvs (10 µg/ml) in PBS containing 0.2% BSA and 0.09% NaN$_3$. After 1 hour incubation (4° C.), the cells were washed three times with 100 µl PBS with 0.2% BSA and 0.09% NaN$_3$ and stained with an in-house produced murine anti-cMyc antibody (2.5 µg/ml). After 1 hour incubation (4° C.), the cells were washed three times with 100 µl PBS with 0.2% BSA and 0.09% NaN$_3$ and incubated for 30 minutes at 4° C. with RPE conjugated goat anti-mouse IgG (F0479, Dako, Denmark) diluted to 5 µg/ml in PBS with 0.2% BSA and 0.09% NaN$_3$. Cells were washed, resuspended in 200 µl PBS with 0.2% BSA and 0.09% NaN$_3$, and transferred to a U-shaped 96 well Costar (Corning, Schiphol-Rijik, The Netherlands) plate for flow cytometry using an Easy Cyte device (Guava Technologies, Hayward, Calif., USA).

Results:

All four clones show specific binding to the transfected cell lines, with the exception of B-1M22 on transformed HEK cells (see FIGS. 6A and 6B), (although the B-1M22 antibody does show specific binding to the DT40 transfected cells). It should be noted that it is long known that CXCR4 has a tendency to develop somewhat different conformations depending on the cell line expressing it (Baribaud et al, 2001). This fact is likely to be the cause for different results on different cell lines. In these experiments, clone C-9P21 was generally the best binder.

In addition, as described below, the clones 9N10, C-9P21 and F7 were tested at IgG level for their ability to bind to cells naturally expressing CXCR4 (Ramos, CCRF-CEM).

Material and Methods:

Ramos and CCRF-CEM cells were maintained as described above.

The cells were harvested from culture flasks, washed 2 times with PBS (350×g, 5 min, 4° C.) and resuspended in PBS containing 0.2% BSA and 0.09% NaN$_3$. 1×10$^5$ cells per well were aliquoted into V-shaped 96-well plates (Greiner Bio-One, Frikenhausen, Germany). The cells were centrifuged (350×g, 5 min, 4° C.) and resuspended in 50 µl IgG (50 µg/ml) in PBS containing 0.2% BSA and 0.09% NaN$_3$. Titration was done in twelve points and three fold dilution. After 1 hour incubation (4° C.), the cells were washed three times with 150 µl PBS with 0.2% BSA and 0.09% NaN$_3$ and incubated for 30 minutes at 4° C. with RPE conjugated goat anti-human IgG (AbD seroTec #204009) diluted to 2.5 µg/ml in PBS with 0.2% BSA and 0.09% NaN$_3$. Cells were washed, resuspended in 200 µl PBS with 0.2% BSA and 0.09% NaN$_3$, and transferred to a U-shaped 96 well Costar (Corning, Schiphol-Rijik, The Netherlands) plate for flow cytometry using an Easy Cyte device (Guava Technologies, Hayward, Calif., USA).

Results:

In this experiment, all three clones recognize the cell lines, in a dose dependent manner (see FIG. 6C). F7 appears to bind slightly better to both cell lines when compared to 9N10 and C-9P21.

Example 3

Anti-CXCR4 Antibodies Interference with Ligand Binding

The four antibodies B-1M22, C-9P21, C-1I24, and D-1K21 were tested on scFv level for their CXCR4 specificity by their ability to bind to CXCR4 transfected cells and to lymphoblastoid cells with constitutive expression of CXCR4 in the presence and absence of two molecules specifically binding to CXCR4. One molecule is SDF-1, the natural ligand to CXCR4, the other one is AMD3100, a peptide derived highly specific competitive inhibitor to SDF-1α binding to CXCR4.

Materials and Methods:

Jurkat and Ramos cells were maintained as described above.

The scFv clones were expressed in large scale and purified as monomer fraction by SEC fractionation. The natural CXCR4$^+$ expressing cell lines Jurkat and Ramos were harvested from the culture flasks, washed 2 times with PBS supplemented with 0.2% BSA and 0.09% NaN$_3$ buffer and aliquoted at 1×10$^5$ cells per well into V-shaped 96-well plates (Greiner Bio-One, Frickenhausen, Germany). Cells were pelleted by centrifugation (400 g, 5 min) and then incubated for 60 min at 4° C. with 1 µg SDF-1α (PeproTech EC, London, UK) and 50 µl scFv diluted to 10 µg/ml in PBS supplemented with 0.2% BSA and 0.09% NaN$_3$ buffer, both added at the same time to the cells. A sample without ligand or 157 µg AMD3100 served as control for the specificity of CXCR4 since AMD3100 only binds to this receptor. AMD3100 was added simultaneously with the scFv to the cells. The supernatants were aspirated after a centrifugation step at 400 g for 5 min and the cells were washed another two times with 100 µl PBS supplemented with 0.2% BSA and 0.09% NaN$_3$ and centrifugation steps (5 min at 400 g) before incubation for 1 hr at 4° C. with 50 µl of in-house produced anti-cMyc diluted to 2.5 µg/ml in PBS supplemented with 0.2% BSA and 0.09% NaN$_3$. After washing three times with PBS supplemented with 0.2% BSA and 0.09% NaN$_3$, the cells were stained with rPE-conjugated Goat anti-mouse IgG (BD Biosciences) diluted to 5 µg/ml in with PBS supplemented with 0.2% BSA and 0.09% NaN$_3$ and incubated for 30 minutes at 4° C. The cells were washed again and re-suspended in 200 µl PBS with 0.2% BSA and 0.09% NaN$_3$ and transferred to a U-shaped 96-well plate (Corning) for flow cytometry using an Easy-Cyte device (Guava Technologies, Hayward, Calif., USA).

Results:

Three of the four clones, B-1M22 being the exception, show specific binding to both cell lines. All three binding clones are also inhibited by both SDF-1 and AMD3100 although the degrees of competition are varying (see FIG. 7A (Jurkat cells) and FIG. 7B (Ramos cells). This suggests that the clones are binding to roughly the same binding sites as the natural ligand and may have a biological effect. For B-1M22, the level of binding is too low to allow statements on binding or competition. However, as shown in the following examples, B-1M22 is one of the best binders described herein in binding CXCR4 on CCRF-CEM cells (see Examples 4 and FIG. 8A). Again, it is believed that the tendency of CXCR4 to develop somewhat different conformations depending on the cell line expressing it, is the explanation behind the data obtained with B-1M22. It can be noted that C-9P21 and C1I24 show excellent binding to all cell types tested suggesting that they have the capability to bind to CXCR4 in multiple conformations which may well be advantageous.

In a further experiment, as described below, the three antibodies 9N10, C-9P21 and F7 were tested on IgG level for their CXCR4 specificity by their ability to bind to CCRF-CEM cells naturally expressing CXCR4 in the presence and absence of SDF-1, a molecule specifically binding to CXCR4.

Materials and Methods:

CCRF-CEM were maintained as described above.

Cells of the natural CXCR4$^+$ expressing cell line CCRF-CEM were harvested from the culture flasks, washed 2 times with PBS supplemented with 0.2% BSA and 0.09% NaN$_3$ buffer and aliquoted at 1×10$^5$ cells per well into V-shaped 96-well plates (Greiner Bio-One, Frickenhausen, Germany). Cells were pelleted by centrifugation (350 g, 5 min) and then incubated for 60 min at 4° C. with 4, 1, 0, 5 µg SDF-1α (PeproTech EC, London, UK) and 50 µl IgG diluted to 2 µg/ml in PBS supplemented with 0.2% BSA and 0.09% NaN₃ buffer, both added at the same time to the cells. Samples without ligand served as control. The supernatants were aspirated after a centrifugation step at 350 g for 5 min and the cells were washed another two times with 150 µl PBS supplemented with 0.2% BSA and 0.09% NaN₃ and centrifugation steps (5 min at 350 g) before being stained with RPE-conjugated goat anti-human IgG (AbD seroTec #204009) diluted to 2.5 µg/ml in with PBS supplemented with 0.2% BSA and 0.09% NaN₃ and incubated for 30 minutes at 4° C. The cells were washed again and re-suspended in 200 µl PBS with 0.2% BSA and 0.09% NaN₃ and transferred to a U-shaped 96-well plate (Corning) for flow cytometry using an EasyCyte device (Guava Technologies, Hayward, Calif., USA).

Results:

Both clones, C-9P21 and 9N10 show specific binding to CCRF-CEM cell line. Both clones are also inhibited by SDF-1 (see FIG. 7C). It should be noted that in this experiment, F7 shows the best binding to the cells as judged by the highest absolute signal.

Example 4

Conversion of Antibody Candidates into IgG Format

For comparison of the biological activity of the identified anti-CXCR4 antibodies, B-1M22, C-1I24, C-9P21 and D-1K21 and 9N10 were converted into full length IgG1 antibody format. As a control, antibody F7 was generated. The F7 antibody is described to bind to CXCR4 (see WO2008/060367 by Medarex). The sequence of the VH and VL chains of the F7 antibody are provided in SEQ ID NO: 25 and SEQ ID NO: 29 of WO2008/060367. In order to produce this antibody in an IgG1 format, an optimized nucleotide sequence was deduced from the amino acid sequence for the antibody F7 as it was described in patent WO2008/060367 (VH: SEQ ID NO: 25 and VL: SEQ ID NO: 29). This sequence was then synthesized, cloned into the Human IgG1/Kappa format as described by Norderhaug et al (JIM 204:27-87, 1997), expressed in HEK293 cells and subsequently purified by Protein A. To confirm that the IgGs were retaining their ability to bind to CXCR4 positive cells, all IgGs were assessed on CCRF-CEM cells which naturally express CXCR4.

Materials and Methods:

The genes encoding the corresponding variable domains were cloned into the mammalian expression vector pLNO comprising the genes for human constant domains (Norderhaug et al, supra).

The antibodies were expressed in a cell factory, and the first harvest was purified on a protein A column and fractionated into monomer by size exclusion chromatography.

The natural CXCR4⁺ expressing cell line CCRF-CEM was harvested from the culture flasks, washed 2 times with PBS supplemented with 0.2% BSA and 0.09% NaN₃ buffer and aliquoted at 1×10⁵ cells per well into V-shaped 96-well plates (Greiner Bio-One, Frickenhausen, Germany). Cells were pelleted by centrifugation (400 g, 5 min) and then incubated for 60 min at 4° C. with 50 µl IgGs diluted to 10 µg/ml in PBS supplemented with 0.2% BSA and 0.09% NaN₃ buffer. The supernatants were aspirated after a centrifugation step at 400 g for 5 min and the cells were washed another two times with 100 µl PBS supplemented with 0.2% BSA and 0.09% NaN₃ each wash was followed by a centrifugation step (5 min at 400 g). After, the cells were stained for 30 minutes at 4° C. with 50 µl of rPE-conjugated Goat anti-human IgG (AbD Serotec) diluted to 5 µg/ml in with PBS supplemented with 0.2% BSA and 0.09% NaN₃ and incubated for 30 minutes at 4° C. The cells were washed again and re-suspended in 200 µl PBS with 0.2% BSA and 0.09% NaN₃ and transferred to a U-shaped 96-well plate (Corning) for flow cytometry using an EasyCyte device (Guava Technologies, Hayward, Calif., USA).

Results:

All tested clones retained their capability to bind to CXCR4 positive cells (see FIG. 8A for C-1I24 and B-1M22 and FIG. 8B for D-1K21 and C-9P21; data for 9N10 not shown). It can also be noted from the EasyCyte curves of FIG. 8 that in these experiments the clones described herein show significantly better binding to CXCR4 expressing CCRF-CEM cells than the F7 antibody (median values 48.11 (F7), 179.03 (D-1K21), 626.43 (C-9P21), 910.58 (C-1I24) and 1077.33 (B-1H22) compared to 3.11 (PBS negative control)).

Example 5

Species Cross Reactivity

The antibody candidates were tested on scFv level for their ability to cross-react with CXCR4 from monkey and mouse.

Materials and Methods:

HEK293T/17 cells were maintained as described above. FACS-binding analyses (EasyCyte) were performed using HEK-293 cells transiently transfected with plasmids encoding either, mouse (Gene bank accession number BC031665) or monkey (*Macaca mulatta*) CXCR4 (NCBI Accession number NP_001036110). Two experiments were performed, one using α-cMyc and PE-labelled goat anti-mouse IgG antibody, the second using a directly conjugated RPE-c-Myc antibody for detection. In addition, cross-reactivity on IgG level was analysed. In the latter case, antibody binding was detected with PE-conjugated goat anti-human IgG antibody.

Results:

D-1K21 showed good cross-reactivity with both mouse and monkey CXCR4. The scFv variants B-1M22, C-9P21 and C-1I24 also showed good cross-reactivity with monkey antigen but low (B-1M22) to intermediate (C-1I24, C-9P21) reactivity with mouse CXCR4. (see FIG. 9). 9N10 was also tested, and showed to have the same cross-reactivity pattern as C-9P21, with slightly higher absolute values for binding.

Example 6

Inhibition of Ligand-Induced Signalling Via CXCR4

The anti-CXCR4 antibodies B-1M22, C-1I24, C-9P21 and D-1K21 were tested on both scFv and IgG level for their ability to influence SDF-1α ligand induced Ca⁺⁺ flux. 9N10 was only tested on IgG level. The experiment was performed using the naturally CXCR4⁺ positive cell line CCRF-CEM.

In a first step the optimal antibody concentrations were determined by titrating the antibodies on the CCRF-CEM cells.

Materials and Methods:

CCRF-CEM cells were maintained as described above.

The natural CXCR4⁺ expressing cell line CCRF-CEM was harvested from the culture flasks, washed 2 times with PBS supplemented with 0.2% BSA and 0.09% NaN₃ buffer and aliquoted at 1×10⁵ cells per well into V-shaped 96-well plates (Greiner Bio-One, Frickenhausen, Germany). Cells were pelleted by centrifugation (400 g, 5 min) and then incubated for 60 min at 4° C. with 50 µl IgGs diluted to a starting concentration of 10 µg/ml and further titrated with 2-fold dilutions 11 times in PBS supplemented with 0.2% BSA and 0.09% NaN$_3$ buffer. The supernatants were aspirated after a centrifugation step at 400 g for 5 min and the cells were washed another two times with 100 µl PBS supplemented with 0.2% BSA and 0.09% NaN$_3$ each wash was followed by a centrifugation step (5 min at 400 g). After, the cells were stained for 30 minutes at 4° C. with 50 µl of rPE-conjugated Goat anti-human IgG (AbD Serotec) diluted to 5 µg/ml in with PBS supplemented with 0.2% BSA and 0.09% NaN$_3$ and incubated for 30 minutes at 4° C. The cells were washed again and re-suspended in 200 µl PBS with 0.2% BSA and 0.09% NaN$_3$ and transferred to a U-shaped 96-well plate (Corning) for flow cytometry using an EasyCyte device (Guava Technologies, Hayward, Calif., USA).

Results:

As a result, the concentrations of antibodies determined for use in the competition experiment were 10 µg/ml or 100 µg/ml for IgGs (with the exception of 9N10 where the concentrations were 1 µg/ml or 10 µg/ml) (data not shown) and 4 µg/ml for scFvs (see FIG. 10).

After the correct concentrations were identified, the actual competition experiment was performed.

Materials and Methods:

The CCRF-CEM target cells, were harvested by centrifugation and washed twice in RPMI-1640 culture medium. Either 1 ml with 2.5×10$^6$ cells (for IgGs) or 10 ml with 2.5×10$^7$ cells (for scFvs) were mixed with Fluo-4-AM (acetoxymethyl ester; Invitrogen), Pluronic F-127 (Invitrogen) and Probenecid to final concentrations of 1 µM, 0.02% and 1 mM respectively. The cells were incubated at 37° C. for 60 min on a vertical rotating wheel (7 rpm). All subsequent steps were done in the presence of 1 mM Probenecid. The cells were washed twice in RPMI-1640 with 10% fetal calf serum (FCS), once in an assay buffer (145 mM NaCl, 4 mM KCl, 1 mM NaH$_2$PO$_4$, 0.8 mM MgCl$_2$, 25 mM Hepes, 22 mM glucose) and then resuspended to a final density of 4×10$^6$ cells/ml. Equal volumes of cells, assay buffer with or without antibodies and ligand (SDF-1α) were mixed. The first two components (cells and antibodies) were pre-incubated for 15 min prior to adding the ligand, SDF-1α (final concentration 50 ng/ml). The final concentrations of antibodies were 10 µg/ml or 100 µg/ml for IgGs and 4 µg/ml for scFvs. The samples were immediately analyzed using the 515-545 nm band pass filter on a FACSCanto II (BD Biosciences). The areas under the curves (AUC) were integrated using software Prism (GraphPad) and plotted as percentage of AUC for maximal stimulation with SDF-1α alone.

Results:

At the scFv level, strong antagonistic activity was demonstrated by the variants C-9P21 and D-1K21. C-1I24 displayed also some antagonistic effect. No activity was demonstrated by B-1M22 (FIG. 11A).

On the IgG level, inhibition of SDF-1α-induced signalling was demonstrated by four out of five tested antibodies: B-1M22, C-1I24, C-9P21 and 9N10 (FIGS. 11B, C, D and E). For unknown reasons, the variant D-1K21 appeared to be only marginally inhibitory at high concentration in IgG format.

In addition, none of the antibodies was able to induce signalling by itself, i.e. the antibodies did not show agonistic activity (data not shown).

In conclusion, it was shown that all the antibodies displayed an antagonistic effect on Ca$^{++}$ signalling induced by SDF1α binding to CXCR4. C-9P21 and 9N10 had the most prominent effect.

In a further experiment, 9N10 was assayed at the IgG level for the ability to reduce ligand induced calcium flux in comparison to C-9P21.

Material and Methods:

The experiment was performed as described above, but the antibodies were used in a titration series with concentrations of 100, 20, 4, 0.8, 0.16, 0.032, 0.064 and 0.00128 µg/ml.

Results:

The results show that 9N10 is approximately eight times more efficient in the inhibition of Calcium flux with an IC$_{50}$ (nM) of 3.85 compared to an IC$_{50}$ (nM) of 29 for C-9P21 (see FIG. 12A and FIG. 12B).

Example 7

Inhibition of Ligand-Induced Cell Migration

The ability of scFv C-9P21 to reduce ligand-induced cell migration was assessed in the CXCR4$^+$ CCRF-CEM cell line. The anti-GFP scFv fragment was used as a negative control and anti-cMyc antibody was used for cross-linking both scFvs to mimic the effect of the antibodies in IgG format.

Materials and Methods:

CCRF-CEM cells were maintained as described above.

CCRF-CEM target cells were sedimented by centrifugation and washed twice in RPMI-1640 culture medium without FCS. The cell density was then adjusted to 1×10$^6$ cells/ml and 60 ml of this suspension was mixed with 38 µl BATDA [bis(acetoxymethyl) 2,2':6',2"-terpyridine-6,6"-dicarboxylate] (Perkin Elmer, Waltham, Mass.). The cells were incubated with BATDA at 37° C. for 20 min with mixing by gently inverting the vessel every 10 min. The cells were washed three times in RPMI-1640 with 20% FCS, and then re-suspended in RPMI-1640/20% FCS to a final density 2×10$^7$ cells/ml. The labelled cells were mixed with an equal volume of medium containing 10% FCS, anti-c-myc antibody (clone 9E10) and serial ½ dilutions of scFv C-9P21, thus resulting in final antibody concentrations of 20 µg/ml and 32 µg/ml to 16 ng/ml for anti-cMyc IgG and scFv C-9P21, respectively. Anti-GFP scFv was used at 32 µg/ml as a negative control in combination with 20 µg/ml anti-cMyc antibody. In parallel, 30 µl of RPMI containing 0.15 nM SDF-1α ligand was added into the lower compartment of a ChemoTX 96 well Boyden chamber plate (Neuro Probe, Gaithersburg, Md.). 50 µl of the antibody-coated BATDA-labelled cells were then added to the upper compartment of the ChemoTX 96 chamber plate and incubated in presence at 37° C. for 2.5 hr. The cells above the filter were then removed and the filter was washed with PBS followed by centrifugation of the plate to collect all the cells in the lower chamber before removing the filter. The plate was then inverted on the top of a V-shaped plate followed by centrifugation. The cells in the V-shaped plate were washed with 100 µl PBS, sedimented by centrifugation and re-suspended in 35 µl PBS with 1.3% Triton X-100. The samples were transferred to a black 96-well microtiter plate, mixed with 200 µl Europium Solution (Perkin Elmer), and analyzed for fluorescence (excitation at 340 nm, emission at 613 nm, lag-time 0.4 ms and integration time 0.4 ms) using a TECAN M200 plate reader. For each antibody concentration, the ratio of signals in presence/absence of scFv and the percentage of migration inhibition was calculated. The data were plotted and analysed by non-linear regression curve fit using the "log(inhibitor) vs. response" model of software Prism (GraphPad).

Results:

The data demonstrates inhibition of SDF-1-induced chemotaxis of CCRF-CEM cells in the presence of anti- CXCR4 scFv C-9P21 (see FIG. 13). Under these conditions, the $IC_{50}$ value (antibody concentration leading to 50% inhibition of cell migration) was calculated as 2.9 µg/ml and 100% inhibition was reached at a scFv concentration 20 µg/ml. The anti-GFP scFv fragment (negative control) showed no inhibition of cell migration (data not shown).

Thus, the C-9P21 antibody in an scFv format inhibits ligand induced migration of CXCR4+ CCRF-CEM cells with an $IC_{50}$ value of 2.9 µg/ml (~100 nM) and demonstrates 100% inhibition at 20 µg/ml (0.7 µM).

Example 8

Induction of Antibody Dependent Cellular Cytotoxicity (ADCC)

One potential mechanism by which an antibody can be therapeutically useful is the ability to mediate ADCC of CXCR4 expressing target cells, if killing the target cell is the preferred mode of action. This was tested using CCRF-CEM cells which are derived from T cell lymphoma and have constitutive expression of CXCR4. The selected antibodies were tested both as scFv fragments cross-linked with anti-cMyc antibody and as fully human IgG1 antibodies.

Materials and Methods:

CCRF-CEM cells were maintained as described above.

CCRF-CEM target cells, were sedimented by centrifugation and washed twice in RPMI-1640 medium. $2.5 \times 10^6$ cells/ml was mixed with calcein-AM (Invitrogen) to a final concentration of 10 µM and incubated at 37° C. for 30 min. The cells were washed three times in RPMI-1640 medium supplemented with 10% FCS and the cell density was adjusted to $3 \times 10^5$ cells/ml. Human PBMCs were prepared from fresh donor blood by Lymphoprep (Axis-Shield, Liverpool, UK) density gradient centrifugation, washed in RPMI-1640/10% FCS and stored frozen in RPMI with 10% FCS and 10% DMSO at density $3 \times 10^7$ cells/ml in liquid nitrogen. The effector cells were thawed on day of the experiment, washed in RPMI with 10% FCS and resuspended at density $6 \times 10^6$ cells/ml. Fifty µl of each target and effector cells were mixed in the same wells of a 96-well microtiter plate thus providing an effector-to-target (E:T) cell ratio of 20:1. The antibodies in IgG1 format were added to the same wells in a volume of 100 µl resulting in a concentration range of 0.8 to 1000 ng/ml. Accordingly, the scFv fragments were added in 20 µl volume for final concentrations from 2.5 to $5 \times 10^4$ ng/ml, after having before being pre-mixed with an excess (20 µg/ml) of anti-cMyc chimeric (mouse variable/human constant) IgG1 antibody (derived from hybridoma 9E10). The microtiter plate was incubated for 4 hrs at 37° C. After 3 hrs and 45 min incubation, 20 µl 0.9% Triton-X100 was added to control wells to achieve complete lysis of the target cells (maximal lysis). 100 µl supernatant of each sample was then transferred into a black microtiter plate and the fluorescence (excitation at 488 nm, emission at 518 nm) was recorded using a TECAN M200 plate reader. Each experiment was carried out in quadruplicates. The fluorescence intensity of the samples without antibodies was subtracted as a background and the percentage of specific lysis in samples with antibodies was calculated. The dose-response curves were computed by nonlinear regression analysis and a three-parameter fit model using Prism software (GraphPad).

Results:

The results shown in FIG. 14 demonstrate that all tested anti-CXCR4 antibodies were able to induce ADCC both as scFv and full-length IgGs in the presence of human PBMCs with maximum killing approaching 100%. The tested scFvs and IgGs can be ranked according to their maximal killing as follows: C-9P21>D-1K21 (scFv); and B-1M22>C-1I24~C-9P21>D-1K21 (IgG) (see also Table A).

TABLE A

Comparative ADCC activity of the tested anti-CXCR4 antibodies.

| Antibody | Max killing (%) | | $EC_{50}$ (ng/mL) | |
|---|---|---|---|---|
| | scFv | IgG | scFv | IgG |
| B-1M22 | ND | 100 | ND | 115.7 (0.8 nM) |
| C-1I24 | ND | 65 | ND | 49.2 (0.3 nM) |
| C-9P21 | 96.4 | 63.5 | 2.7 (0.09 nM) | 1852.0 (12.3 nM) |
| D-1K21 | 68.6 | 25.7 | 18.8 (0.7 nM) | 79.9 (0.5 nM) |

ND, not done.

Thus, all anti-CXCR4 antibodies tested demonstrated ADCC activity against CCRF-CEM cells with B-1M22 and C-9P21 demonstrating the greatest maximum cell killing.

Example 9

Induction of Complement Dependent Cellular Cytotoxicity (CDC)

To test whether the anti-CXCR4 IgGs described herein are able to mediate complement dependent cytotoxicity, CDC experiments have been performed using Ramos cells which are derived from Burkitt's B-cell lymphoma and have constitutive expression of CXCR4.

Materials and Methods:

Ramos cells were maintained as described above.

The ability of B-1M22, C-1I24, C-9P21 and D-1K21 IgGs to induce CDC was assessed on the natural CXCR4+ Ramos cell line. The Ramos cells, were sedimented by centrifugation and washed twice in RPMI-1640 culture medium. $2.5 \times 10^6$ cells/ml was mixed with calcein-AM (Invitrogen) to a final concentration of 10 µM and then incubated at 37° C. for 30 min. The cells were washed three times in RPMI-1640 with 10% FCS and the cell density was adjusted to $4 \times 10^6$ cells/mL. A 25 µl aliquot of labelled target cells and 25 µl of human serum were mixed in the wells in a 96-well microtiter plate. Dilutions of the antibodies (all in IgG format) were added to the same wells in 50 µl volume thus resulting in a final antibody concentration ranging from $5 \times 10^{-5}$ to $5 \times 10^4$ ng/ml. Twenty µl 0.9% Triton-X100 was added to control wells to achieve complete lysis of the target cells (maximal lysis defining 100%). The microtiter plate was incubated for 1 hr at 37° C. One hundred µl RPMI-1640 with 10% FCS was added to all wells followed by centrifugation and transfer of 100 µl supernatant of each sample to a black microtiter plate. The fluorescence (excitation at 488 nm, emission at 518 nm) was recorded using a TECAN M200 plate reader. Each experiment was carried out in quadruplicates. The fluorescence intensity of the samples without antibodies was subtracted as a background and the percentage of specific lysis in samples with antibodies was calculated. The dose-response curves were computed by nonlinear regression analysis and a three-parameter fit model using Prism software (GraphPad).

Results:

The results shown in FIG. 15A and FIG. 15B demonstrated that the antibody C-1I24 was able to induce CDC in presence of human serum. C-1I24 showed an $EC_{50}$ value of 0.7 µg/mL and maximum killing of 100%. Some CDC activity was also observed for the variant B-1M22, however, only at very high concentration (100 μg/ml). F7 was used as a positive control antibody.

Thus, of the antibodies described herein, two antibodies, C-1I24 and B-1M22, demonstrated CDC activity against Ramos cells. C-1I24 showed superior CDC activity.

Example 10

Induction of Apoptosis

The ability of anti-CXCR4 antibodies to induce apoptosis was assessed on the CXCR4+ Ramos cell line.

Materials and Methods:

Ramos cells were cultivated as described above.

The Ramos cells were harvested by centrifugation, washed twice in RPMI-1640 culture medium with 10% FCS and resuspended in RPMI-1640 medium with 10% FCS to a density of $3 \times 10^5$ cells/ml. The cell suspension (250 μl) was mixed with the same volume of either antibody to be tested in dilutions (final concentration of 0.08 to 10 μg/ml) or staurosporin (25 nM) in wells of a 24-well plate and incubated at 37° C. for 48 hrs. The cells were collected by centrifugation and washed in Annexin V Binding Buffer (10 mM Hepes, 140 mM NaCl, 2.5 mM $CaCl_2$, 0.2% BSA, pH 7.4). The cells were harvested again and resuspended in 300 μl Annexin V Binding Buffer. Both FITC-conjugated Annexin V and propidium iodide (PI) were mixed with 240 μl cell suspension resulting in a final concentration of PI of 0.2 μg/ml. The samples were analyzed immediately after adding the ligand using the 515-545 nm and 610/20 nm band pass filters on a FACSCanto II flow cytometer (BD Biosciences). The apoptotic cells were defined as Annexin V positive/PI negative and the dead cells were defined as PI positive.

Results:

The results presented in FIG. 16A (B-1M22, C-1I24, C-9P21 and D-1K21) demonstrate that no apoptosis was induced above the background level (negative control level), marked 0 in FIG. 16A, in the presence of the antibodies B-1M22, C-1I24, C-9P21, and D-1K21. In contrast, the control IgG1 F7 induced apoptosis at all concentrations used in the assay. The results presented in FIG. 16B demonstrate that antibodies C-9P21 and 9N10 do not induce significant apoptosis.

Thus, these results demonstrate the antibodies described herein do not induce apoptosis of CXCR4-positive cells, which may provide a potentially superior side effect profile in comparison with F7.

TABLE 1

| SEQ ID NO: | | scFv C-9P21 |
|---|---|---|
| 25 | Heavy chain FR1: | QVQLQESGGGLVHPGGSLRLSCAASGFTFS |
| 1 | CDR 1: | SYWMH |
| 26 | FR 2 | WVRQAPGKGLVWVS |
| 2 | CDR 2: | RINSDGSSTSYADSVKG |
| 27 | FR 3: | RFTISRDNAKNTLYLQMNSLRAEDTAVYYCAR |
| 3 | CDR 3: | KILGVGARSRRYFDY |
| 28 | FR 4: | WGQGTMVTVSS |
| 29 | Linker: | KLSGSASAPKLEEGEFSEARV |
| 30 | Light chain FR1: | ETTLTQSPGTLSLSPGERATLSC |
| 4 | CDR 1: | RASQSVVSNYLA |
| 31 | FR 2 | WYQQKPGQAPRLLIS |
| 5 | CDR 2: | GASNRAT |
| 32 | FR 3: | GISDRFSGSGSGADFTLTISRVEPEDSAVYYC |
| 6 | CDR 3: | QQFDKSTWT |
| 33 | FR 4: | FGQGTKVEIK |
| 34 | scFv C-9P21 n.a. | CAGGTGCAGCTGCAGGAGTCCGGGGGAGGCTTAGTTCACCCTGGGGGGTC CCTGAGACTCTCCTGTGCAGCCTCTGGATTCACCTTCAGTAGCTACTGGA TGCACTGGGTCCGCCAAGCTCCAGGGAAGGGGCTGGTGTGGGTCTCACGT ATTAATAGTGATGGGAGTAGCACAAGCTACGCGGACTCCGTGAAGGGCCG ATTCACCATCTCCAGAGACAACGCCAAGAACACGCTGTATCTGCAAATGA ACAGTCTGAGAGCCGAGGACACGGCTGTGTATTACTGTGCGAGAAAAATC TTGGGGGTGGGAGCTAGGTCTCGTCGTTACTTTGACTACTGGGGCCAGGG AACAATGGTCACCGTCTCTTCAAAGCTTTCAGGGAGTGCATCCGCCCCAA AACTTGAAGAAGGTGAATTTTCAGAAGCACGCGTAGAAACGACACTCACG CAGTCTCCAGGCACCCTGTCTTTGTCTCCAGGGGAAAGAGCCACCCTCTC CTGCAGGGCCAGTCAGAGTGTTGTCAGCAACTATTTAGCCTGGTACCAGC |

TABLE 1-continued

| SEQ ID NO: | | scFv C-9P21 |
|---|---|---|
| | | AGAAGCCTGGCCAGGCTCCCAGGCTCCTCATCTCTGGTGCATCCAACAGG GCCACTGGCATCTCAGACAGGTTCAGTGGCAGTGGGTCTGGGGCAGACTT CACTCTCACCATCAGCAGAGTCGAGCCTGAAGACTCAGCAGTGTATTACT GTCAACAGTTTGATAAGTCCACGTGGACGTTCGGCCAAGGGACCAAGGTG GAAATCAAA |
| 35 | scFv C-9P21 a.a. | QVQLQESGGGLVHPGGSLRLSCAASGFTFSSYWMHWVRQAPGKGLVWVSR INSDGSSTSYADSVKGRFTISRDNAKNTLYLQMNSLRAEDTAVYYCARKI LGVGARSRRYFDYWGQGTMVTVSSKLSGSASAPKLEEGEFSEARVETTLT QSPGTLSLSPGERATLSCRASQSVVSNYLAWYQQKPGQAPRLLISGASNR ATGISDRFSGSGSGADFTLTISRVEPEDSAVYYCQQFDKSTWTFGQGTKV EIK |
| 69 | $V_{H(aa)}$ | QVQLQESGGGLVHPGGSLRLSCAASGFTFSSYWMHWVRQAPGKGLVWVSR INSDGSSTSYADSVKGRFTISRDNAKNTLYLQMNSLRAEDTAVYYCARKI LGVGARSRRYFDYWGQGTMVTVSS |
| 70 | $V_{L(aa)}$ | ETTLTQSPGTLSLSPGERATLSCRASQSVVSNYLAWYQQKPGQAPRLLIS GASNRATGISDRFSGSGSGADFTLTISRVEPEDSAVYYCQQFDKSTWTFG QGTKVEIK |
| 77 | VH domain (nt) | CAGGTGCAGCTGCAGGAGTCCGGGGGAGGCTTAGTTCACCCTGGGGGGTC CCTGAGACTCTCCTGTGCAGCCTCTGGATTCACCTTCAGTAGCTACTGGA TGCACTGGGTCCGCCAAGCTCCAGGGAAGGGGCTGGTGTGGGTCTCACGT ATTAATAGTGATGGGAGTAGCACAAGCTACGCGGACTCCGTGAAGGGCCG ATTCACCATCTCCAGAGACAACGCCAAGAACACGCTGTATCTGCAAATGA ACAGTCTGAGAGCCGAGGACACGGCTGTGTATTACTGTGCGAGAAAAATC TTGGGGGTGGGAGCTAGGTCTCGTCGTTACTTTGACTACTGGGGCCAGGG AACAATGGTCACCGTCTCTTCA |
| 78 | VL domain (nt) | GAAACGACACTCACGCAGTCTCCAGGCACCCTGTCTTTGTCTCCAGGGGA AAGAGCCACCCTCTCCTGCAGGGCCAGTCAGAGTGTTGTCAGCAACTATT TAGCCTGGTACCAGCAGAAGCCTGGCCAGGCTCCCAGGCTCCTCATCTCT GGTGCATCCAACAGGGCCACTGGCATCTCAGACAGGTTCAGTGGCAGTGG GTCTGGGGCAGACTTCACTCTCACCATCAGCAGAGTCGAGCCTGAAGACT CAGCAGTGTATTACTGTCAACAGTTTGATAAGTCCACGTGGACGTTCGGC CAAGGGACCAAGGTGGAAATCAAA |

TABLE 2

| SEQ ID NO: | | scFv B-1M22 |
|---|---|---|
| 36 | Heavy chain FR1: | QVQLVQSGAEVKKPGSSVKVSCKASGGTFS |
| 7 | CDR 1: | SYAIS |
| 37 | FR 2 | WVRQAPGQGLEWMG |
| 8 | CDR 2: | GIIPIFGTANYAQKFQG |
| 38 | FR 3: | RVTITADESTSTAYMELRSLRSDDTAVYYCAR |
| 9 | CDR 3: | DRERWLQSAGDY |
| 39 | FR 4: | WGQGTLVTVSS |
| 40 | Linker: | KLSGSASAPKLEEGEFSEARV |
| 41 | Light chain FR1: | QPVLTQSPSVSVAPGQTARITC |
| 10 | CDR 1: | GGNNIGSKSVH |
| 42 | FR 2 | WYQQKPGQAPVLVVY |
| 11 | CDR 2: | DDSDRPS |
| 43 | FR 3: | GIPERFSGSNSGNTATLTISRVEAGDEADYYC |

TABLE 2-continued

| SEQ ID NO: | | scFv B-1M22 |
|---|---|---|
| 12 | CDR 3: | QVWDSSSDHWV |
| 44 | FR 4: | FGGGTKLTVL |
| 45 | scFv B-1M22 n.a. | CAGGTCCAGCTTGTGCAGTCTGGGGCTGAGGTGAAGAAGCCTGGGTCCTCGG<br>TGAAGGTCTCCTGCAAGGCTTCTGGAGGCACCTTCAGCAGCTATGCTATCAG<br>CTGGGTGCGACAGGCCCCTGGACAAGGGCTTGAGTGGATGGGAGGGATCATC<br>CCTATCTTTGGTACAGCAAACTACGCACAGAAGTTCCAGGGCAGAGTCACGA<br>TTACCGCGGACGAATCCACGAGCACAGCCTACATGGAGCTGAGGAGCCTGAG<br>ATCTGACGACACGGCCGTGTATTACTGTGCGAGAGATCGGGAGAGATGGCTA<br>CAATCCGCGGGCGACTACTGGGGCCAGGGAACCCTGGTCACTGTCTCCTCAA<br>AGCTTTCAGGGAGTGCATCCGCCCCAAAACTTGAAGAAGGTGAATTTTCAGA<br>AGCACGCGTACAGCCTGTGCTGACTCAGTCACCCTCGGTGTCAGTGGCCCCA<br>GGACAGACGGCCAGGATTACCTGTGGGGGAAACAACATTGGAAGTAAAAGTG<br>TGCACTGGTACCAGCAGAAGCCAGGCCAGGCCCCTGTGCTGGTCGTCTATGA<br>TGATAGCGACCGGCCCTCAGGGATCCCTGAGCGATTCTCTGGCTCCAACTCT<br>GGGAACACGGCCACCCTGACCATCAGCAGGGTCGAAGCCGGGGATGAGGCCG<br>ACTATTACTGTCAGGTGTGGGATAGTAGTAGTGATCATTGGGTGTTCGGCGG<br>AGGGACCAAGCTGACCGTCCTA |
| 46 | scFv B-1M22 a.a. | QVQLVQSGAEVKKPGSSVKVSCKASGGTFSSYAISWVRQAPGQGLEWMGGII<br>PIFGTANYAQKFQGRVTITADESTSTAYMELRSLRSDDTAVYYCARDRER<br>WLQSAGDYWGQGTLVTVSSKLSGSASAPKLEEGEFSEARVQPVLTQSPSV<br>SVAPGQTARITCGGNNIGSKSVHWYQQKPGQAPVLVVYDDSDRPSGIPER<br>FSGSNSGNTATLTISRVEAGDEADYYCQVWDSSSDHWVFGGGTKLTVL |
| 71 | V$_{H(aa)}$ | QVQLVQSGAEVKKPGSSVKVSCKASGGTFSSYAISWVRQAPGQGLEWMGGII<br>PIFGTANYAQKFQGRVTITADESTSTAYMELRSLRSDDTAVYYCARDRER<br>WLQSAGDYWGQGTLVTVSS |
| 72 | V$_{L(aa)}$ | QPVLTQSPSVSVAPGQTARITCGGNNIGSKSVHWYQQKPGQAPVLVVYDD<br>SDRPSGIPERFSGSNSGNTATLTISRVEAGDEADYYCQVWDSSSDHWVFG<br>GGTKLTVL |
| 79 | VH domain (nt) | CAGGTCCAGCTTGTGCAGTCTGGGGCTGAGGTGAAGAAGCCTGGGTCCTCGG<br>TGAAGGTCTCCTGCAAGGCTTCTGGAGGCACCTTCAGCAGCTATGCTATCAG<br>CTGGGTGCGACAGGCCCCTGGACAAGGGCTTGAGTGGATGGGAGGGATCATC<br>CCTATCTTTGGTACAGCAAACTACGCACAGAAGTTCCAGGGCAGAGTCACGA<br>TTACCGCGGACGAATCCACGAGCACAGCCTACATGGAGCTGAGGAGCCTGAG<br>ATCTGACGACACGGCCGTGTATTACTGTGCGAGAGATCGGGAGAGATGGCTA<br>CAATCCGCGGGCGACTACTGGGGCCAGGGAACCCTGGTCACTGTCTCCTCA |
| 80 | VL domain (nt) | CAGCCTGTGCTGACTCAGTCACCCTCGGTGTCAGTGGCCCCAGGACAGAC<br>GGCCAGGATTACCTGTGGGGGAAACAACATTGGAAGTAAAAGTGTGCACT<br>GGTACCAGCAGAAGCCAGGCCAGGCCCCTGTGCTGGTCGTCTATGATGAT<br>AGCGACCGGCCCTCAGGGATCCCTGAGCGATTCTCTGGCTCCAACTCTGG<br>GAACACGGCCACCCTGACCATCAGCAGGGTCGAAGCCGGGGATGAGGCCG<br>ACTATTACTGTCAGGTGTGGGATAGTAGTAGTGATCATTGGGTGTTCGGC<br>GGAGGGACCAAGCTGACCGTCCTA |

TABLE 3

| SEQ ID NO: | | scFv C-1124 |
|---|---|---|
| 47 | Heavy chain FR1: | QVQLVQSGGGVVQPGRSLRLSCAASGFTFS |
| 13 | CDR 1: | SYGMH |
| 48 | FR 2 | WVRQAPGKGLEWVA |
| 14 | CDR 2: | VISYDGSNKYYADSVKG |
| 49 | FR 3: | RFTISRDNSKNTLYLQMNSLRAEDTAVYYCAK |
| 15 | CDR 3: | DLPITRGTGADY |
| 50 | FR 4: | WGQGTLVTVSS |
| 51 | Linker: | KLSGSASAPKLEEGEFSEARV |
| 52 | Light chain FR1: | QSVLIQPASVSGSPGQSITISC |

TABLE 3-continued

| SEQ ID NO: | | scFv C-1124 |
|---|---|---|
| 16 | CDR 1: | TGTSSDVGGYNYVS |
| 53 | FR 2 | WYQQHPGKAPRLMIY |
| 17 | CDR 2: | DVTSRPS |
| 54 | FR 3: | GVSNRFSGSKSGNTASLTISGLQAEDEADYYC |
| 18 | CDR 3: | SSYAGSYSVV |
| 55 | FR 4: | FGGGTKVTVL |
| 56 | scFv C-1124 n.a. | CAGGTCCAGCTGGTACAGTCTGGGGGAGGCGTGGTCCAGCCTGGGA GGTCCCTGAGACTCTCCTGTGCAGCCTCTGGATTCACCTTCAGTAG CTATGGCATGCACTGGGTCCGCCAGGCTCCAGGCAAGGGGCTGGAG TGGGTGGCAGTTATATCATATGATGGAAGTAATAAATACTATGCAG ACTCCGTGAAGGGCCGATTCACCATCTCCAGAGACAATTCCAAGAA CACGCTGTATCTGCAAATGAACAGCCTGAGAGCTGAGGACACGGCT GTGTATTACTGTGCGAAAGATCTTCCGATTACCCGCGGGACAGGGG CTGACTACTGGGGCCAGGGAACCCTGGTCACTGTCTCCTCAAAGCT TTCAGGGAGTGCATCCGCCCCAAAACTTGAAGAAGGTGAATTTTCA GAAGCACGCGTACAGTCTGTCCTGATTCAGCCTGCCTCCGTGTCTG GGTCTCCTGGACAGTCGATCACCATCTCCTGCACTGGAACCAGCAG TGACGTTGGTGGTTATAACTATGTCTCCTGGTATCAACAACACCCA GGCAAAGCCCCCAGACTCATGATTTACGATGTCACTAGTCGGCCCT CAGGGGTTTCGAATCGCTTCTCTGGCTCCAAGTCTGGCAACACGGC CTCCCTGACCATCTCTGGGCTCCAGGCTGAGGACGAGGCTGATTAT TACTGCAGTTCATATGCAGGCAGCTACAGCGTGGTATTCGGCGGAG GGACCAAGGTCACCGTCCTA |
| 57 | scFv C-1124 a.a. | QVQLVQSGGGVVQPGRSLRLSCAASGFTFSSYGMHWVRQAPGKGLE WVAVISYDGSNKYYADSVKGRFTISRDNSKNTLYLQMNSLRAEDTA VYYCAKDLPITRGTGADYWGQGTLVTVSSKLSGSASAPKLEEGEFS EARVQSVLIQPASVSGSPGQSITISCTGTSSDVGGYNYVSWYQQHP GKAPRLMIYDVTSRPSGVSNRFSGSKSGNTASLTISGLQAEDEADY YCSSYAGSYSVVFGGGTKVTVL |
| 73 | V$_{H(aa)}$ | QVQLVQSGGGVVQPGRSLRLSCAASGFTFSSYGMHWVRQAPGKGLE WVAVISYDGSNKYYADSVKGRFTISRDNSKNTLYLQMNSLRAEDTA VYYCAKDLPITRGTGADYWGQGTLVTVSS |
| 74 | V$_{L(aa)}$ | QSVLIQPASVSGSPGQSITISCTGTSSDVGGYNYVSWYQQHPGKAP RLMIYDVTSRPSGVSNRFSGSKSGNTASLTISGLQAEDEADYYCSS YAGSYSVVFGGGTKVTVL |
| 81 | VH domain (nt) | CAGGTCCAGCTGGTACAGTCTGGGGGAGGCGTGGTCCAGCCTGGGA GGTCCCTGAGACTCTCCTGTGCAGCCTCTGGATTCACCTTCAGTAG CTATGGCATGCACTGGGTCCGCCAGGCTCCAGGCAAGGGGCTGGAG TGGGTGGCAGTTATATCATATGATGGAAGTAATAAATACTATGCAG ACTCCGTGAAGGGCCGATTCACCATCTCCAGAGACAATTCCAAGAA CACGCTGTATCTGCAAATGAACAGCCTGAGAGCTGAGGACACGGCT GTGTATTACTGTGCGAAAGATCTTCCGATTACCCGCGGGACAGGGG CTGACTACTGGGGCCAGGGAACCCTGGTCACTGTCTCCTCA |
| 82 | VL domain (nt) | CAGTCTGTCCTGATTCAGCCTGCCTCCGTGTCTGGGTCTCCTGGAC AGTCGATCACCATCTCCTGCACTGGAACCAGCAGTGACGTTGGTGG TTATAACTATGTCTCCTGGTATCAACAACACCCAGGCAAAGCCCCC AGACTCATGATTTACGATGTCACTAGTCGGCCCTCAGGGGTTTCGA ATCGCTTCTCTGGCTCCAAGTCTGGCAACACGGCCTCCCTGACCAT CTCTGGGCTCCAGGCTGAGGACGAGGCTGATTATTACTGCAGTTCA TATGCAGGCAGCTACAGCGTGGTATTCGGCGGAGGGACCAAGGTCA CCGTCCTA |

TABLE 4

| SEQ ID NO: | | scFv D-1K21 |
|---|---|---|
| 58 | Heavy chain FR1: | QVQLVQSGAEVKKPGASVKVSCKASGYTFT |
| 19 | CDR 1: | GYYMH |

TABLE 4-continued

| SEQ ID NO: | scFv D-1K21 | |
|---|---|---|
| 59 | FR 2 | WVRQAPGQGLEWMG |
| 20 | CDR 2: | RINPNSGGTNYAQKFQG |
| 60 | FR 3: | RVTMTRDTSISTAYMELSRLRSDDTAVYYCAR |
| 21 | CDR 3: | RNLIAARPRNRGRDAFDI |
| 61 | FR 4: | WGQGTMVTVSS |
| 62 | Linker: | KLSGSASAPKLEEGEFSEARV |
| 63 | Light chain FR1: | DIQMTQSPSTLSASVGDRVTITC |
| 22 | CDR 1: | RASQSIGGSLA |
| 64 | FR 2 | WYQQKPGKPNLLIY |
| 23 | CDR 2: | AASTLQS |
| 65 | FR 3: | GVPSRFSGSGSGTEFTLTISSLQPEDSATYYC |
| 24 | CDR 3: | QHYESYPLS |
| 66 | FR 4: | FGGGTKLEIK |
| 67 | scFv D-1K21 n.a. | CAGGTCCAGCTTGTGCAGTCTGGGGCTGAGGTGAAGAAGCCTGGGGCCTC<br>AGTGAAGGTCTCCTGCAAGGCTTCTGGATACACCTTCACCGGCTACTATA<br>TGCACTGGGTGCGACAGGCCCCTGGACAAGGGCTTGAGTGGATGGGACGG<br>ATCAACCCTAACAGTGGTGGCACAAACTATGCACAGAAGTTTCAGGGCAG<br>GGTCACCATGACCAGGGACACGTCCATCAGCACAGCCTACATGGAGCTGA<br>GCAGGCTGAGATCTGACGACACGGCCGTGTATTACTGCGCGAGGCGTAAC<br>CTGATAGCAGCTCGTCCCCGGAATCGGGGCAGGGATGCTTTTGATATCTG<br>GGGCCAAGGGACAATGGTCACCGTCTCTTCAAAGCTTTCAGGGAGTGCAT<br>CCGCCCCAAAACTTGAAGAAGGTGAATTTTCAGAAGCACGCGTAGACATC<br>CAGATGACCCAGTCTCCTTCCACCCTGTCTGCATCTGTAGGAGACAGAGT<br>CACCATCACTTGCCGGGCCAGTCAGAGTATTGGTGGCTCGTTGGCCTGGT<br>ATCAGCAGAAACCAGGGAAAGGCCCTAACCTCCTGATCTATGCTGCATCC<br>ACTTTGCAAAGTGGGGTCCCATCAAGGTTCAGCGGCAGTGGATCTGGGAC<br>AGAATTCACTCTCACAATCAGCAGCCTGCAGCCTGAAGATTCTGCAACTT<br>ACTACTGCCAACACTATGAAAGTTATCCCCTCTCTTTCGGCGGCGGGACC<br>AAGCTGGAGATCAAA |
| 68 | scFv D-1K21 a.a | QVQLVQSGAEVKKPGASVKVSCKASGYTFTGYYMHWVRQAPGQGLEWMGR<br>INPNSGGTNYAQKFQGRVTMTRDTSISTAYMELSRLRSDDTAVYYCARRN<br>LIAARPRNRGRDAFDIWGQGTMVTVSSKLSGSASAPKLEEGEFSEARVDI<br>QMTQSPSTLSASVGDRVTITCRASQSIGGSLAWYQQKPGKPNLLIYAAS<br>TLQSGVPSRFSGSGSGTEFTLTISSLQPEDSATYYCQHYESYPLSFGGGT<br>KLEIK |
| 75 | $V_{H(aa)}$ | QVQLVQSGAEVKKPGASVKVSCKASGYTFTGYYMHWVRQAPGQGLEWMGR<br>INPNSGGTNYAQKFQGRVTMTRDTSISTAYMELSRLRSDDTAVYYCARRN<br>LIAARPRNRGRDAFDIWGQGTMVTVSS |
| 76 | $V_{L(aa)}$ | DIQMTQSPSTLSASVGDRVTITCRASQSIGGSLAWYQQKPGKPNLLIYA<br>ASTLQSGVPSRFSGSGSGTEFTLTISSLQPEDSATYYCQHYESYPLSFGG<br>GTKLEIK |
| 83 | VH domain (nt) | CAGGTCCAGCTTGTGCAGTCTGGGGCTGAGGTGAAGAAGCCTGGGGCCTC<br>AGTGAAGGTCTCCTGCAAGGCTTCTGGATACACCTTCACCGGCTACTATA<br>TGCACTGGGTGCGACAGGCCCCTGGACAAGGGCTTGAGTGGATGGGACGG<br>ATCAACCCTAACAGTGGTGGCACAAACTATGCACAGAAGTTTCAGGGCAG<br>GGTCACCATGACCAGGGACACGTCCATCAGCACAGCCTACATGGAGCTGA<br>GCAGGCTGAGATCTGACGACACGGCCGTGTATTACTGCGCGAGGCGTAAC<br>CTGATAGCAGCTCGTCCCCGGAATCGGGGCAGGGATGCTTTTGATATCTG<br>GGGCCAAGGGACAATGGTCACCGTCTCTTCA |
| 84 | VL domain (nt) | GACATCCAGATGACCCAGTCTCCTTCCACCCTGTCTGCATCTGTAGGAGA<br>CAGAGTCACCATCACTTGCCGGGCCAGTCAGAGTATTGGTGGCTCGTTGG<br>CCTGGTATCAGCAGAAACCAGGGAAAGGCCCTAACCTCCTGATCTATGCT<br>GCATCCACTTTGCAAAGTGGGGTCCCATCAAGGTTCAGCGGCAGTGGATC<br>TGGGACAGAATTCACTCTCACAATCAGCAGCCTGCAGCCTGAAGATTCTG<br>CAACTTACTACTGCCAACACTATGAAAGTTATCCCCTCTCTTTCGGCGGC<br>GGGACCAAGCTGGAGATCAAA |

TABLE 5

| SEQ ID NO: | | scFv 9N10 |
|---|---|---|
| 25 or 91 | Heavy chain FR1: | QVQLQESGGGLVHPGGSLRLSCAASGFTFS |
| 1 or 85 | CDR 1: | SYWMH |
| 26 or 92 | FR 2 | WVRQAPGKGLVWVS |
| 2 or 86 | CDR 2: | RINSDGSSTSYADSVKG |
| 27 or 93 | FR 3: | RFTISRDNAKNTLYLQMNSLRAEDTAVYYCAR |
| 3 or 87 | CDR 3: | KILGVGARSRRYFDY |
| 28 or 94 | FR 4: | WGQGTMVTVSS |
| 95 | Linker: | KLSGSASAPKLEEGEFSEARV |
| 96 | Light chain FR1: | DIVLTQTPDSLAVSLGETTTINC |
| 88 | CDR 1: | KSSQSVLHSSNNKNYLA |
| 97 | FR 2 | WYQQKPGQPPKLLIY |
| 89 | CDR 2: | WASTRES |
| 98 | FR 3: | GVPDRFSGSGSGTDFTLTISNLQPEDVAFYYC |
| 90 | CDR 3: | LQYSTFPRT |
| 33 or 99 | FR 4: | FGQGTKVEIK |
| 100 | scFv 9N10 n.a. | CAGGTGCAGCTGCAGGAGTCCGGGGGAGGCTTAGTTCACCCTGGGGGGTC<br>CCTGAGACTCTCCTGTGCAGCCTCTGGATTCACCTTCAGTAGCTACTGGA<br>TGCACTGGGTCCGCCAAGCTCCAGGGAAGGGGCTGGTGTGGGTCTCACGT<br>ATTAATAGTGATGGGAGTAGCACAAGCTACGCGGACTCCGTGAAGGGCCG<br>ATTCACCATCTCCAGAGACAACGCCAAGAACACGCTGTATCTGCAAATGA<br>ACAGTCTGAGAGCCGAGGACACGGCTGTGTATTACTGTGCGAGAAAAATC<br>TTGGGGGTGGGAGCTAGGTCTCGTCGTTACTTTGACTACTGGGGCCAGGG<br>AACAATGGTCACCGTCTCTTCAAAGCTTTCAGGGAGTGCATCCGCCCAA<br>AACTTGAAGAAGGTGAATTTTCAGAAGCACGCGTAGATATTGTGCTGACC<br>CAGACTCCAGACTCCCTGGCTGTGTCTCTGGGCGACACCACCATCAA<br>CTGCAAGTCCAGCCAGAGTGTTTTACACAGCTCCAACAATAAGAACTACT<br>TAGCTTGGTACCAGCAGAAACCAGGACAGCCTCCTAAGCTGCTCATTTAC<br>TGGGCATCTACCCGGGAATCCGGGGTCCCTGACCGATTCAGTGGCAGCGG<br>GTCTGGGACAGATTTCACTCTCACCATCAGCAACCTGCAGCCTGAAGATG<br>TGGCTTTTTACTACTGTCTGCAATATTCTACTTTTCCTCGGACGTTCGGC<br>CAAGGGACCAAGGTGGAGATCAAA |
| 101 | scFv 9N10 a.a. | QVQLQESGGGLVHPGGSLRLSCAASGFTFSSYWMHWVRQAPGKGLVWVSR<br>INSDGSSTSYADSVKGRFTISRDNAKNTLYLQMNSLRAEDTAVYYCARKI<br>LGVGARSRRYFDYWGQGTMVTVSSKLSGSASAPKLEEGEFSEARVDIVLT<br>QTPDSLAVSLGETTTINCKSSQSVLHSSNNKNYLAWYQQKPGQPPKLLIY<br>WASTRESGVPDRFSGSGSGTDFTLTISNLQPEDVAFYYCLQYSTFPRTFG<br>QGTKVEIK |
| 69 or 102 | VH(aa) | QVQLQESGGGLVHPGGSLRLSCAASGFTFSSYWMHWVRQAPGKGLVWVSR<br>INSDGSSTSYADSVKGRFTISRDNAKNTLYLQMNSLRAEDTAVYYCARKI<br>LGVGARSRRYFDYWGQGTMVTVSS |
| 103 | VL(aa) | DIVLTQTPDSLAVSLGETTTINCKSSQSVLHSSNNKNYLAWYQQKPGQPP<br>KLLIYWASTRESGVPDRFSGSGSGTDFTLTISNLQPEDVAFYYCLQYSTF<br>PRTFGQGTKVEIK |

TABLE 5-continued

| SEQ ID NO: | scFv 9N10 | |
|---|---|---|
| 77 or 104 | VH domain (nt) | CAGGTGCAGCTGCAGGAGTCCGGGGGAGGCTTAGTTCACCCTGGGGGGTC<br>CCTGAGACTCTCCTGTGCAGCCTCTGGATTCACCTTCAGTAGCTACTGGA<br>TGCACTGGGTCCGCCAAGCTCCAGGGAAGGGGCTGGTGTGGGTCTCACGT<br>ATTAATAGTGATGGGAGTAGCACAAGCTACGCGGACTCCGTGAAGGGCCG<br>ATTCACCATCTCCAGAGACAACGCCAAGAACACGCTGTATCTGCAAATGA<br>ACAGTCTGAGAGCCGAGGACACGGCTGTGTATTACTGTGCGAGAAAAATC<br>TTGGGGGTGGGAGCTAGGTCTCGTCGTTACTTTGACTACTGGGGCCAGGG<br>AACAATGGTCACCGTCTCTTCA |
| 105 | VL domain (nt) | GATATTGTGCTGACCCAGACTCCAGACTCCCTGGCTGTGTCTCTGGGCGA<br>GACGACCACCATCAACTGCAAGTCCAGCCAGAGTGTTTTACACAGCTCCA<br>ACAATAAGAACTACTTAGCTTGGTACCAGCAGAAACCAGGACAGCCTCCT<br>AAGCTGCTCATTTACTGGGCATCTACCCGGGAATCCGGGGTCCCTGACCG<br>ATTCAGTGGCAGCGGGTCTGGGACAGATTTCACTCTCACCATCAGCAACC<br>TGCAGCCTGAAGATGTGGCTTTTTACTACTGTCTGCAATATTCTACTTTT<br>CCTCGGACGTTCGGCCAAGGGACCAAGGTGGAGATCAAA |

SEQ ID NO: 91 is identical to SEQ ID NO: 25
SEQ ID NO: 85 is identical to SEQ ID NO: 1
SEQ ID NO: 92 is identical to SEQ ID NO: 26
SEQ ID NO: 86 is identical to SEQ ID NO: 2
SEQ ID NO: 93 is identical to SEQ ID NO: 27

SEQ ID NO: 87 is identical to SEQ ID NO: 3
SEQ ID NO: 94 is identical to SEQ ID NO: 28
SEQ ID NO: 99 is identical to SEQ ID NO: 33
SEQ ID NO: 102 is identical to SEQ ID NO: 69
SEQ ID NO: 104 is identical to SEQ ID NO: 77

TABLE 6

| IgG sequences of C-9P21 | | |
|---|---|---|
| SEQ ID NO: 106 | IgG1 heavy chain (n) | CAGGTGCAGCTGCAGGAGTCCGGGGGAGGCTTAGTTCACCCTGGGGGGT<br>CCCTGAGACTCTCCTGTGCAGCCTCTGGATTCACCTTCAGTAGCTACTG<br>GATGCACTGGGTCCGCCAAGCTCCAGGGAAGGGGCTGGTGTGGGTCTCA<br>CGTATTAATAGTGATGGGAGTAGCACAAGCTACGCGGACTCCGTGAAGG<br>GCCGATTCACCATCTCCAGAGACAACGCCAAGAACACGCTGTATCTGCA<br>AATGAACAGTCTGAGAGCCGAGGACACGGCTGTGTATTACTGTGCGAGA<br>AAAATCTTGGGGGTGGGAGCTAGGTCTCGTCGTTACTTTGACTACTGGG<br>GCCAGGGAACAATGGTCACCGTCTCTTCAGCCTCCACCAAGGGCCCATC<br>GGTCTTCCCCCTGGCACCCTCCTCCAAGAGCACCTCTGGGGGCACAGCG<br>GCCCTGGGCTGCCTGGTCAAGGACTACTTCCCCGAACCGGTGACGGTGT<br>CGTGGAACTCAGGCGCCCTGACCAGCGGCGTGCACACCTTCCCGGCTGT<br>CCTACAGTCCTCAGGACTCTACTCCCTCAGCAGCGTGGTGACCGTGCCC<br>TCCAGCAGCTTGGGCACCCAGACCTACATCTGCAACGTGAATCACAAGC<br>CCAGCAACACCAAGGTGGACAAGAAAGTTGAGCCCAAATCTTGTGACAA<br>AACTCACACATGCCCACCGTGCCCAGCACCTGAACTCCTGGGGGGACCG<br>TCAGTCTTCCTCTTCCCCCCAAAACCCAAGGACACCCTCATGATCTCCC<br>GGACCCCTGAGGTCACATGCGTGGTGGTGGACGTGAGCCACGAAGACCC<br>TGAGGTCAAGTTCAACTGGTACGTGGACGGCGTGGAGGTGCATAATGCC<br>AAGACAAAGCCGCGGGAGGAGCAGTACAACAGCACGTACCGTGTGGTCA<br>GCGTCCTCACCGTCCTGCACCAGGACTGGCTGAATGGCAAGGAGTACAA<br>GTGCAAGGTCTCCAACAAAGCCCTCCCAGCCCCCATCGAGAAAACCATC<br>TCCAAAGCCAAAGGGCAGCCCCGAGAACCACAGGTGTACACCCTGCCCC<br>CATCCCGGGATGAGCTGACCAAGAACCAGGTCAGCCTGACCTGCCTGGT<br>CAAAGGCTTCTATCCCAGCGACATCGCCGTGGAGTGGGAGAGCAATGGG<br>CAGCCGGAGAACAACTACAAGACCACGCCTCCCGTGCTGGACTCCGACG<br>GCTCCTTCTTCCTCTACAGCAAGCTCACCGTGGACAAGAGCAGGTGGCA<br>GCAGGGGAACGTCTTCTCATGCTCCGTGATGCATGAGGCTCTGCACAAC<br>CACTACACGCAGAAGAGCCTCTCCCTGTCTCCGGGTAAA |
| SEQ ID NO: 107 | Kappa light chain (nt) | GAAACGACACTCACGCAGTCTCCAGGCACCCTGTCTTTGTCTCCAGGGG<br>AAAGAGCCACCCTCTCCTGCAGGGCCAGTCAGAGTGTTGTCAGCAACTA<br>TTTAGCCTGGTACCAGCAGAAGCCTGGCCAGGCTCCCAGGCTCCTCATC<br>TCTGGTGCATCCAACAGGGCCACTGGCATCTCAGACAGGTTCAGTGGCA<br>GTGGGTCTGGGACAGACTTCACTCTCACCATCAGCAGTCGAGCCTGA<br>AGACTCAGCAGTGTATTACTGTCAACAGTTTGATAAGTCCACGTGGACG<br>TTCGGCCAAGGGACCAAGGTGGAAATCAAACGAACTGTGGCTGCACCAT<br>CTGTCTTCATCTTCCCGCCATCTGATGAGCAGTTGAAATCTGGAACTGC<br>CTCTGTTGTGTGCCTGCTGAATAACTTCTATCCCAGAGAGGCCAAAGTA<br>CAGTGGAAGGTGGATAACGCCCTCCAATCGGGTAACTCCCAGGAGAGTG<br>TCACAGAGCAGGACAGCAAGGACAGCACCTACAGCCTCAGCAGCACCCT<br>GACGCTGAGCAAAGCAGACTACGAGAAACACAAAGTCTACGCCTGCGAA<br>GTCACCCATCAGGGCCTGAGCTCGCCCGTCACAAAGAGCTTCAACAGGG<br>GAGAGTGT |

TABLE 6-continued

IgG sequences of C-9P21

| SEQ ID NO: 108 | IgG1 heavy chain (aa) | QVQLQESGGGLVHPGGSLRLSCAASGFTFSSYWMHWVRQAPGKGLVWVS RINSDGSSTSYADSVKGRFTISRDNAKNTLYLQMNSLRAEDTAVYYCAR KILGVGARSRRYFDYWGQGTMVTVSSASTKGPSVFPLAPSSKSTSGGTA ALGCLVKDYFPEPVTVSWNSGALTSGVHTFPAVLQSSGLYSLSSVVTVP SSSLGTQTYICNVNHKPSNTKVDKKVEPKSCDKTHTCPPCPAPELLGGP SVFLFPPKPKDTLMISRTPEVTCVVVDVSHEDPEVKFNWYVDGVEVHNA KTKPREEQYNSTYRVVSVLTVLHQDWLNGKEYKCKVSNKALPAPIEKTI SKAKGQPREPQVYTLPPSRDELTKNQVSLTCLVKGFYPSDIAVEWESNG QPENNYKTTPPVLDSDGSFFLYSKLTVDKSRWQQGNVFSCSVMHEALHN HYTQKSLSLSPGK |
| --- | --- | --- |
| SEQ ID NO: 109 | Kappa light chain (aa) | ETTLTQSPGTLSLSPGERATLSCRASQSVVSNYLAWYQQKPGQAPRLLI SGASNRATGISDRFSGSGSGADFTLTISRVEPEDSAVYYCQQFDKSTWT FGQGTKVEIKRTVAAPSVFIFPPSDEQLKSGTASVVCLLNNFYPREAKV QWKVDNALQSGNSQESVTEQDSKDSTYSLSSTLTLSKADYEKHKVYACE VTHQGLSSPVTKSFNRGEC |

TABLE 7

IgG sequences of B-1M22

| SEQ ID NO: 110 | IgG1 heavy chain (nt) | CAGGTCCAGCTTGTGCAGTCTGGGGCTGAGGTGAAGAAGCCTGGGTCC TCGGTGAAGGTCTCCTGCAAGGCTTCTGGAGGCACCTTCAGCAGCTAT GCTATCAGCTGGGTGCGACAGGCCCCTGGACAAGGGCTTGAGTGGATG GGAGGGATCATCCCTATCTTTGGTACAGCAAACTACGCACAGAAGTTC CAGGGCAGAGTCACGATTACCGCGGACGAATCCACGAGCACAGCCTAC ATGGAGCTGAGGAGCCTGAGATCTGACGACACGGCCGTGTATTACTGT GCGAGAGATCGGGAGAGATGGCTACAATCCGCGGGCGACTACTGGGGC CAGGGAACCCTGGTCACTGTCTCCTCAGCCTCCACCAAGGGCCCATCG GTCTTCCCCCTGGCACCCTCCTCCAAGAGCACCTCTGGGGGCACAGCG GCCCTGGGCTGCCTGGTCAAGGACTACTTCCCCGAACCGGTGACGGTG TCGTGGAACTCAGGCGCCCTGACCAGCGGCGTGCACACCTTCCCGGCT GTCCTACAGTCCTCAGGACTCTACTCCCTCAGCAGCGTGGTGACCGTG CCCTCCAGCAGCTTGGGCACCCAGACCTACATCTGCAACGTGAATCAC AAGCCCAGCAACACCAAGGTGGACAAGAAAGTTGAGCCCAAATCTTGT GACAAAACTCACACATGCCCACCGTGCCCAGCACCTGAACTCCTGGGG GGACCGTCAGTCTTCCTCTTCCCCCCAAAACCCAAGGACACCCTCATG ATCTCCCGGACCCCTGAGGTCACATGCGTGGTGGTGGACGTGAGCCAC GAAGACCCTGAGGTCAAGTTCAACTGGTACGTGGACGGCGTGGAGGTG CATAATGCCAAGACAAAGCCGCGGGAGGAGCAGTACAACAGCACGTAC CGTGTGGTCAGCGTCCTCACCGTCCTGCACCAGGACTGGCTGAATGGC AAGGAGTACAAGTGCAAGGTCTCCAACAAAGCCCTCCCAGCCCCCATC GAGAAAACCATCTCCAAAGCCAAAGGGCAGCCCCGAGAACCACAGGTG TACACCCTGCCCCCATCCCGGGATGAGCTGACCAAGAACCAGGTCAGC CTGACCTGCCTGGTCAAAGGCTTCTATCCCAGCGACATCGCCGTGGAG TGGGAGAGCAATGGGCAGCCGGAGAACAACTACAAGACCACGCCTCCC GTGCTGGACTCCGACGGCTCCTTCTTCCTCTACAGCAAGCTCACCGTG GACAAGAGCAGGTGGCAGCAGGGGAACGTCTTCTCATGCTCCGTGATG CATGAGGCTCTGCACAACCACTACACGCAGAAGAGCCTCTCCCTGTCT CCGGGTAAA |
| --- | --- | --- |
| SEQ ID NO: 111 | Lambda light chain (nt) | CAGCCTGTGCTGACTCAGTCACCCTCGGTGTCAGTGGCCCCAGGACAG ACGGCCAGGATTACCTGTGGGGGAAACAACATTGGAAGTAAAAGTGTG CACTGGTACCAGCAGAAGCCAGGCCAGGCCCCTGTGCTGGTCGTCTAT GATGATAGCGACCGGCCCTCAGGGATCCCTGAGCGATTCTCTGGCTCC AACTCTGGGAACACGGCCACCCTGACCATCAGCAGGGTCGAAGCCGGG GATGAGGCCGACTATTACTGTCAGGTGTGGGATAGTAGTAGTGATCAT TGGGTGTTCGGCGGAGGGACCAAGCTGACCGTCCTAGGTCAGCCCAAG GCTGCCCCCTCGGTCACTCTGTTCCCGCCCTCCTCTGAGGAGCTTCAA GCCAACAAGGCCACACTGGTGTGTCTCATAAGTGACTTCTACCCGGGA GCCGTGACAGTGGCCTGGAAGGCAGATAGCAGCCCCGTCAAGGCGGGA GTGGAGACCACCACACCCTCCAAACAAAGCAACAACAAGTACGCGGCC AGCAGCTATCTGAGCCTGACGCCTGAGCAGTGGAAGTCCCACAGAAGC TACAGCTGCCAGGTCACGCATGAAGGGAGCACCGTGGAGAAGACAGTG GCCCCTACAGAATGTTCA |

TABLE 7-continued

IgG sequences of B-1M22

| SEQ ID NO: 112 | IgG1 heavy chain (aa) | QVQLVQSGAEVKKPGSSVKVSCKASGGTFSSYAISWVRQAPGQGLEWM GGIIPIFGTANYAQKFQGRVTITADESTSTAYMELRSLRSDDTAVYYC ARDRERWLQSAGDYWGQGTLVTVSSASTKGPSVFPLAPSSKSTSGGTA ALGCLVKDYFPEPVTVSWNSGALTSGVHTFPAVLQSSGLYSLSSVVTV PSSSLGTQTYICNVNHKPSNTKVDKKVEPKSCDKTHTCPPCPAPELLG GPSVFLFPPKPKDTLMISRTPEVTCVVVDVSHEDPEVKFNWYVDGVEV HNAKTKPREEQYNSTYRVVSVLTVLHQDWLNGKEYKCKVSNKALPAPI EKTISKAKGQPREPQVYTLPPSRDELTKNQVSLTCLVKGFYPSDIAVE WESNGQPENNYKTTPPVLDSDGSFFLYSKLTVDKSRWQQGNVFSCSVM HEALHNHYTQKSLSLSPGK |
| --- | --- | --- |
| SEQ ID NO: 113 | Lambda light chain (aa) | QPVLTQSPSVSVAPGQTARITCGGNNIGSKSVHWYQQKPGQAPVLVVY DDSDRPSGIPERFSGSNSGNTATLTISRVEAGDEADYYCQVWDSSSDH WVFGGGTKLTVLGQPKAAPSVTLFPPSSEELQANKATLVCLISDFYPG AVTVAWKADSSPVKAGVETTTPSKQSNNKYAASSYLSLTPEQWKSHRS YSCQVTHEGSTVEKTVAPTECS |

TABLE 8

IgG sequences of C-1I24

| SEQ ID NO: 114 | IgG1 heavy chain (nt) | CAGGTCCAGCTGGTACAGTCTGGGGGAGGCGTGGTCCAGCCTGGGAGGT CCCTGAGACTCTCCTGTGCAGCCTCTGGATTCACCTTCAGTAGCTATGG CATGCACTGGGTCCGCCAGGCTCCAGGCAAGGGGCTGGAGTGGGTGGCA GTTATATCATATGATGGAAGTAATAAATACTATGCAGACTCCGTGAAGG GCCGATTCACCATCTCCAGAGACAATTCCAAGAACACGCTGTATCTGCA AATGAACAGCCTGAGAGCTGAGGACACGGCTGTGTATTACTGTGCGAAA GATCTTCCGATTACCCGCGGGACAGGGGCTGACTACTGGGGCCAGGGAA CCCTGGTCACTGTCTCCTCAGCCTCCACCAAGGGCCCATCGGTCTTCCC CCTGGCACCCTCCTCAAGAGCACCTCTGGGGGCACAGCGGCCCTGGGC TGCCTGGTCAAGGACTACTTCCCCGAACCGGTGACGGTGTCGTGGAACT CAGGCGCCCTGACCAGCGGCGTGCACACCTTCCCGGCTGTCCTACAGTC CTCAGGACTCTACTCCCTCAGCAGCGTGGTGACCGTGCCCTCCAGCAGC TTGGGCACCCAGACCTACATCTGCAACGTGAATCACAAGCCCAGCAACA CCAAGGTGGACAAGAAAGTTGAGCCCAAATCTTGTGACAAAACTCACAC ATGCCCACCGTGCCCAGCACCTGAACTCCTGGGGGGACCGTCAGTCTTC CTCTTCCCCCCAAAACCCAAGGACACCCTCATGATCTCCCGGACCCCTG AGGTCACATGCGTGGTGGTGGACGTGAGCCACGAAGACCCTGAGGTCAA GTTCAACTGGTACGTGGACGGCGTGGAGGTGCATAATGCCAAGACAAAG CCGCGGGAGGAGCAGTACAACAGCACGTACCGTGTGGTCAGCGTCCTCA CCGTCCTGCACCAGGACTGGCTGAATGGCAAGGAGTACAAGTGCAAGGT CTCCAACAAAGCCCTCCCAGCCCCCATCGAGAAAACCATCTCCAAAGCC AAAGGGCAGCCCCGAGAACCACAGGTGTACACCCTGCCCCCATCCCGGG ATGAGCTGACCAAGAACCAGGTCAGCCTGACCTGCCTGGTCAAAGGCTT CTATCCCAGCGACATCGCCGTGGAGTGGGAGAGCAATGGGCAGCCGGAG AACAACTACAAGACCACGCCTCCCGTGCTGGACTCCGACGGCTCCTTCT TCCTCTACAGCAAGCTCACCGTGGACAAGAGCAGGTGGCAGCAGGGGAA CGTCTTCTCATGCTCCGTGATGCATGAGGCTCTGCACAACCACTACACG CAGAAGAGCCTCTCCCTGTCTCCGGGTAAA |
| --- | --- | --- |
| SEQ ID NO: 115 | Lambda light chain (nt) | CAGTCTGTCCTGATTCAGCCTGCCTCCGTGTCTGGGTCTCCTGGACAGT CGATCACCATCTCCTGCACTGGAACCAGCAGTGACGTTGGTGGTTATAA CTATGTCTCCTGGTATCAACAACACCCAGGCAAAGCCCCCAGACTCATG ATTTACGATGTCACTAGTCGGCCCTCAGGGGTTTCGAATCGCTTCTCTG GCTCCAAGTCTGGCAACACGGCCTCCCTGACCATCTCTGGGCTCCAGGC TGAGGACGAGGCTGATTATTACTGCAGTTCATATGCAGGCAGCTACAGC GTGGTATTCGGCGGAGGGACCAAGGTCACCGTCCTAGGTCAGCCCAAGG CTGCCCCCTCGGTCACTCTGTTCCCGCCCTCCTCTGAGGAGCTTCAAGC CAACAAGGCCACACTGGTGTGTCTCATAAGTGACTTCTACCCGGGAGCC GTGACAGTGGCCTGGAAGGCAGATAGCAGCCCCGTCAAGGCGGGAGTGG AGACCACCACACCCTCCAAACAAAGCAACAACAAGTACGCGGCCAGCAG CTATCTGAGCCTGACGCCTGAGCAGTGGAAGTCCCACAGAAGCTACAGC TGCCAGGTCACGCATGAAGGGAGCACCGTGGAGAAGACAGTGGCCCCTA CAGAATGTTCA |
| SEQ ID NO: 116 | IgG1 heavy chain (aa) | QVQLVQSGGGVVQPGRSLRLSCAASGFTFSSYGMHWVRQAPGKGLEWVA VISYDGSNKYYADSVKGRFTISRDNSKNTLYLQMNSLRAEDTAVYYCAK DLPITRGTGADYWGQGTLVTVSSASTKGPSVFPLAPSSKSTSGGTAALG CLVKDYFPEPVTVSWNSGALTSGVHTFPAVLQSSGLYSLSSVVTVPSSS LGTQTYICNVNHKPSNTKVDKKVEPKSCDKTHTCPPCPAPELLGGPSVF LFPPKPKDTLMISRTPEVTCVVVDVSHEDPEVKFNWYVDGVEVHNAKTK PREEQYNSTYRVVSVLTVLHQDWLNGKEYKCKVSNKALPAPIEKTISKA KGQPREPQVYTLPPSRDELTKNQVSLTCLVKGFYPSDIAVEWESNGQPE NNYKTTPPVLDSDGSFFLYSKLTVDKSRWQQGNVFSCSVMHEALHNHYT QKSLSLSPGK |

TABLE 8-continued

IgG sequences of C-1I24

| | | |
|---|---|---|
| SEQ ID NO: 117 | Lambda light chain (aa) | QSVLIQPASVSGSPGQSITISCTGTSSDVGGYNYVSWYQQHPGKAPRLM IYDVTSRPSGVSNRFSGSKSGNTASLTISGLQAEDEADYYCSSYAGSYS VVFGGGTKVTVLGQPKAAPSVTLFPPSSEELQANKATLVCLISDFYPGA VTVAWKADSSPVKAGVETTTPSKQSNNKYAASSYLSLTPEQWKSHRSYS CQVTHEGSTVEKTVAPTECS |

TABLE 9

IgG sequences of D-1K21

| | | |
|---|---|---|
| SEQ ID NO: 118 | IgG1 heavy chain (nt) | CAGGTCCAGCTTGTGCAGTCTGGGGCTGAGGTGAAGAAGCCTGGGGCCTC AGTGAAGGTCTCCTGCAAGGCTTCTGGATACACCTTCACCGGCTACTATA TGCACTGGGTGCGACAGGCCCCTGGACAAGGGCTTGAGTGGATGGGACGG ATCAACCCTAACAGTGGTGGCACAAACTATGCACAGAAGTTTCAGGGCAG GGTCACCATGACCAGGGACACGTCCATCAGCACAGCCTACATGGAGCTGA GCAGGCTGAGATCTGACGACACGGCCGTGTATTACTGCGCGAGGCGTAAC CTGATAGCAGCTCGTCCCCGGAATCGGGGCAGGGATGCTTTTGATATCTG GGGCCAAGGGACAATGGTCACCGTCTCTTCAGCCTCCACCAAGGGCCCAT CGGTCTTCCCCCTGGCACCCTCCTCCAAGAGCACCTCTGGGGGCACAGCG GCCCTGGGCTGCCTGGTCAAGGACTACTTCCCCGAACCGGTGACGGTGTC GTGGAACTCAGGCGCCCTGACCAGCGGCGTGCACACCTTCCCGGCTGTCC TACAGTCCTCAGGACTCTACTCCCTCAGCAGCGTGGTGACCGTGCCCTCC AGCAGCTTGGGCACCCAGACCTACATCTGCAACGTGAATCACAAGCCCAG CAACACCAAGGTGGACAAGAAAGTTGAGCCCAAATCTTGTGACAAAACTC ACACATGCCCACCGTGCCCAGCACCTGAACTCCTGGGGGGACCGTCAGTC TTCCTCTTCCCCCCAAAACCCAAGGACACCCTCATGATCTCCCGGACCCC TGAGGTCACATGCGTGGTGGTGGACGTGAGCCACGAAGACCCTGAGGTCA AGTTCAACTGGTACGTGGACGGCGTGGAGGTGCATAATGCCAAGACAAAG CCGCGGGAGGAGCAGTACAACAGCACGTACCGTGTGGTCAGCGTCCTCAC CGTCCTGCACCAGGACTGGCTGAATGGCAAGGAGTACAAGTGCAAGGTCT CCAACAAAGCCCTCCCAGCCCCCATCGAGAAAACCATCTCCAAAGCCAAA GGGCAGCCCCGAGAACCACAGGTGTACACCCTGCCCCCATCCCGGGATGA GCTGACCAAGAACCAGGTCAGCCTGACCTGCCTGGTCAAAGGCTTCTATC CCAGCGACATCGCCGTGGAGTGGGAGAGCAATGGGCAGCCGGAGAACAAC TACAAGACCACGCCTCCCGTGCTGGACTCCGACGGCTCCTTCTTCCTCTA CAGCAAGCTCACCGTGGACAAGAGCAGGTGGCAGCAGGGGAACGTCTTCT CATGCTCCGTGATGCATGAGGCTCTGCACAACCACTACACGCAGAAGAGC CTCTCCCTGTCTCCGGGTAAA |
| SEQ ID NO: 119 | Kappa light chain (nt) | GACATCCAGATGACCCAGTCTCCTTCCACCCTGTCTGCATCTGTAGGAGA CAGAGTCACCATCACTTGCCGGGCCAGTCAGAGTATTGGTGGCTCGTTGG CCTGGTATCAGCAGAAACAGGGAAAGGCCCTAACCTCCTGATCTATGCT GCATCCACTTTGCAAAGTGGGGTCCCATCAAGGTTCAGCGGCAGTGGATC TGGGACAGAATTCACTCTCACAATCAGCAGCCTGCAGCCTGAAGATTCTG CAACTTACTACTGCCAACACTATGAAAGTTATCCCCTCTCTTTCGGCGGC GGGACCAAGCTGGAGATCAAACGAACTGTGGCTGCACCATCTGTCTTCAT CTTCCCGCCATCTGATGAGCAGTTGAAATCTGGAACTGCCTCTGTTGTGT GCCTGCTGAATAACTTCTATCCCAGAGAGGCCAAAGTACAGTGGAAGGTG GATAACGCCCTCCAATCGGGTAACTCCCAGGAGAGTGTCACAGAGCAGGA CAGCAAGGACAGCACCTACAGCCTCAGCAGCACCCTGACGCTGAGCAAAG CAGACTACGAGAAACACAAAGTCTACGCCTGCGAAGTCACCCATCAGGGC CTGAGCTCGCCCGTCACAAAGAGCTTCAACAGGGGAGAGTGT |
| SEQ ID NO: 120 | IgG1 heavy chain (aa) | QVQLVQSGAEVKKPGASVKVSCKASGYTFTGYYMHWVRQAPGQGLEWMGR INPNSGGTNYAQKFQGRVTMTRDTSISTAYMELSRLRSDDTAVYYCARRN LIAARPRNRGRDAFDIWGQGTMVTVSSASTKGPSVFPLAPSSKSTSGGTA ALGCLVKDYFPEPVTVSWNSGALTSGVHTFPAVLQSSGLYSLSSVVTVPS SSLGTQTYICNVNHKPSNTKVDKKVEPKSCDKTHTCPPCPAPELLGGPSV FLFPPKPKDTLMISRTPEVTCVVVDVSHEDPEVKFNWYVDGVEVHNAKTK PREEQYNSTYRVVSVLTVLHQDWLNGKEYKCKVSNKALPAPIEKTISKAK GQPREPQVYTLPPSRDELTKNQVSLTCLVKGFYPSDIAVEWESNGQPENN YKTTPPVLDSDGSFFLYSKLTVDKSRWQQGNVFSCSVMHEALHNHYTQKS LSLSPGK |
| SEQ ID NO: 121 | Kappa light chain (aa) | DIQMTQSPSTLSASVGDRVTITCRASQSIGGSLAWYQQKPGKGPNLLIYA ASTLQSGVPSRFSGSGSGTEFTLTISSLQPEDSATYYCQHYESYPLSFGG GTKLEIKRTVAAPSVFIFPPSDEQLKSGTASVVCLLNNFYPREAKVQWKV DNALQSGNSQESVTEQDSKDSTYSLSSTLTLSKADYEKHKVYACEVTHQG LSSPVTKSFNRGEC |

TABLE 10

IgG sequences of 9N10

| | | |
|---|---|---|
| SEQ ID NO: 106 or 122 | IgG1 heavy chain (nt) | CAGGTGCAGCTGCAGGAGTCCGGGGGAGGCTTAGTTCACCCTGGGGGGTC<br>CCTGAGACTCTCCTGTGCAGCCTCTGGATTCACCTTCAGTAGCTACTGGA<br>TGCACTGGGTCCGCCAAGCTCCAGGGAAGGGGCTGGTGTGGGTCTCACGT<br>ATTAATAGTGATGGGAGTAGCACAAGCTACGCGGACTCCGTGAAGGGCCG<br>ATTCACCATCTCCAGAGACAACGCCAAGAACACGCTGTATCTGCAAATGA<br>ACAGTCTGAGAGCCGAGGACACGGCTGTGTATTACTGTGCAGAAAAATC<br>TTGGGGGTGGGAGCTAGGTCTCGTCGTTACTTTGACTACTGGGGCCAGGG<br>AACAATGGTCACCGTCTCTTCAGCCTCCACCAAGGGCCCATCGGTCTTCC<br>CCCTGGCACCCTCCTCCAAGAGCACCTCTGGGGGCACAGCGGCCCTGGGC<br>TGCCTGGTCAAGGACTACTTCCCCGAACCGGTGACGGTGTCGTGGAACTC<br>AGGCGCCCTGACCAGCGGCGTGCACACCTTCCCGGCTGTCCTACAGTCCT<br>CAGGACTCTACTCCCTCAGCAGCGTGGTGACCGTGCCCTCCAGCAGCTTG<br>GGCACCCAGACCTACATCTGCAACGTGAATCACAAGCCCAGCAACACCAA<br>GGTGGACAAGAAAGTTGAGCCCAAATCTTGTGACAAAACTCACACATGCC<br>CACCGTGCCCAGCACCTGAACTCCTGGGGGGACCGTCAGTCTTCCTCTTC<br>CCCCCAAAACCCAAGGACACCCTCATGATCTCCCGGACCCCTGAGGTCAC<br>ATGCGTGGTGGTGGACGTGAGCCACGAAGACCCTGAGGTCAAGTTCAACT<br>GGTACGTGGACGGCGTGGAGGTGCATAATGCCAAGACAAAGCCGCGGGAG<br>GAGCAGTACAACAGCACGTACCGTGTGGTCAGCGTCCTCACCGTCCTGCA<br>CCAGGACTGGCTGAATGGCAAGGAGTACAAGTGCAAGGTCTCCAACAAAG<br>CCCTCCCAGCCCCCATCGAGAAAACCATCTCCAAAGCCAAAGGGCAGCCC<br>CGAGAACCACAGGTGTACACCCTGCCCCCATCCCGGGATGAGCTGACCAA<br>GAACCAGGTCAGCCTGACCTGCCTGGTCAAAGGCTTCTATCCCAGCGACA<br>TCGCCGTGGAGTGGGAGAGCAATGGGCAGCCGGAGAACAACTACAAGACC<br>ACGCCTCCCGTGCTGGACTCCGACGGCTCCTTCTTCCTCTACAGCAAGCT<br>CACCGTGGACAAGAGCAGGTGGCAGCAGGGGAACGTCTTCTCATGCTCCG<br>TGATGCATGAGGCTCTGCACAACCACTACACGCAGAAGAGCCTCTCCCTG<br>TCTCCGGGTAAA |
| SEQ ID NO: 123 | Kappa light chain (nt) | GATATTGTGCTGACCCAGACTCCAGACTCCCTGGCTGTGTCTCTGGGCGA<br>GACGACCACCATCAACTGCAAGTCCAGCCAGAGTGTTTTACACAGCTCCA<br>ACAATAAGAACTACTTAGCTTGGTACCAGCAGAAACCAGGACAGCCTCCT<br>AAGCTGCTCATTTACTGGGCATCTACCCGGGAATCCGGGGTCCCTGACCG<br>ATTCAGTGGCAGCGGGTCTGGGACAGATTTCACTCTCACCATCAGCAACC<br>TGCAGCCTGAAGATGTGGCTTTTTACTACTGTCTGCAATATTCTACTTTT<br>CCTCGGACGTTCGGCCAAGGGACCAAGGTGGAGATCAAACGAACTGTGGC<br>TGCACCATCTGTCTTCATCTTCCCGCCATCTGATGAGCAGTTGAAATCTG<br>GAACTGCCTCTGTTGTGTGCCTGCTGAATAACTTCTATCCCAGAGAGGCC<br>AAAGTACAGTGGAAGGTGGATAACGCCCTCCAATCGGGTAACTCCCAGGA<br>GAGTGTCACAGAGCAGGACAGCAAGGACAGCACCTACAGCCTCAGCAGCA<br>CCCTGACGCTGAGCAAAGCAGACTACGAGAAACACAAAGTCTACGCCTGC<br>GAAGTCACCCATCAGGGCCTGAGCTCGCCCGTCACAAAGAGCTTCAACAG<br>GGGAGAGTGT |
| SEQ ID NO: 108 or 124 | IgG1 heavy chain (aa) | QVQLQESGGGLVHPGGSLRLSCAASGFTFSSYWMHWVRQAPGKGLVWVSR<br>INSDGSSTSYADSVKGRFTISRDNAKNTLYLQMNSLRAEDTAVYYCARKI<br>LGVGARSRRYFDYWGQGTMVTVSSASTKGPSVFPLAPSSKSTSGGTAALG<br>CLVKDYFPEPVTVSWNSGALTSGVHTFPAVLQSSGLYSLSSVVTVPSSSL<br>GTQTYICNVNHKPSNTKVDKKVEPKSCDKTHTCPPCPAPELLGGPSVFLF<br>PPKPKDTLMISRTPEVTCVVVDVSHEDPEVKFNWYVDGVEVHNAKTKPRE<br>EQYNSTYRVVSVLTVLHQDWLNGKEYKCKVSNKALPAPIEKTISKAKGQP<br>REPQVYTLPPSRDELTKNQVSLTCLVKGFYPSDIAVEWESNGQPENNYKT<br>TPPVLDSDGSFFLYSKLTVDKSRWQQGNVFSCSVMHEALHNHYTQKSLSL<br>SPGK |
| SEQ ID NO: 125 | Kappa light chain (aa) | DIVLTQTPDSLAVSLGETTTINCKSSQSVLHSSNNKNYLAWYQQKPGQPP<br>KLLIYWASTRESGVPDRFSGSGSGTDFTLTISNLQPEDVAFYYCLQYSTF<br>PRTFGQGTKVEIKRTVAAPSVFIFPPSDEQLKSGTASVVCLLNNFYPREA<br>KVQWKVDNALQSGNSQESVTEQDSKDSTYSLSSTLTLSKADYEKHKVYAC<br>EVTHQGLSSPVTKSFNRGEC |

TABLE 11

| SEQ ID NO | Description | Sequence |
|---|---|---|
| 126 | VH CDR1 | S/G Y X$_3$ M/I H/S |
| 127 | VH CDR1 | X$_1$ Y X$_3$ M H |
| 128 | VH CDR1 | S Y X$_3$ M H |
| 129 | VH CDR2 | X$_1$ I X$_3$ X$_4$ D G S X$_8$ X$_9$ X$_{10}$ Y A D S V K G |
| 130 | VH CDR2 | V/R I S/N Y/S D G S N/S K/T Y/S Y A D S V K G |
| 131 | VH CDR2 | X$_1$ I X$_3$ P X$_5$ X$_6$ G X$_8$ X$_9$ N Y A Q K F Q G |
| 132 | VH CDR2 | R/G I N/I P N/I S/F G G/T T/A N Y A Q K F Q G |

REFERENCES

The following references, to the extent that they provide exemplary procedural or other details supplementary to those set forth herein, are specifically incorporated herein by reference.

Altschul, Madden, Schaffer, Zhang, Zhang, Miller, Lipman, "Gapped BLAST and PSI-BLAST: a new generation of protein database search programs", *Nucleic Acids Res.*, 25:3389-3402, 1997.

Arbabi-Ghahroudi, Desmyter, Wyns, Hamers, Muyldermans, "Selection and identification of single domain antibody fragments from camel heavy-chain antibodies", *FEBS Lett.*, 414:521-526, 1997.

Baeverle and Gires, B J C, 96: 417-423, 2007.

Baldari, Murray, Ghiara, Cesareni, Galeotti, "A Novel Leader Peptide Which Allows Efficient Secretion of a Fragment of Human Interleukin 1 Beta in *Saccharomyces Cerevisiae*", *EMBO J.*, 6:229-234, 1987

Baribaud, Edwards, Sharron, Brelot, Heveker, Price, Mortari, Alizon, Tsang, Doms: "Antigenically Distinct Conformations of CXCR4" J. of Virology, 75(19): 8957-8967, 2001

Beckman, Weiner and Davis, "Antibody Constructs in Cancer Therapy", *Cancer*, 109(2):170-179, 2006.

Brinster, Chen, Trumbauer, Yagle, Palmiter, "Factors Affecting the Efficiency of Introducing Foreign DNA into Mice by Microinjecting Eggs", *Proc. Natl. Acad. Sci. USA*, 82(13):4438-4442, 1985.

Carillo and Lipton, "The Multiple Sequence Alignment Problem in Biology", *SIAM J. Applied Math.*, 48:1073, 1988.

Cullen, Gray, Wilson, Hayenga, Lamsa, Rey, Norton, Berka, "Controlled Expression and Secretion of Bovine Chymosin in *Aspergillus Nidulans*", *BioTechnology*, 5:369, 1987.

Davies and Cohen, "Interactions of protein antigens with antibodies," *Proc Natl. Acad. Sci. U.S.A.* 93:7-12, 1996.

Davies, Padlan, Sheriff, "Antibody-antigen complexes," *Annu. Rev. Biochem.* 59:439-473, 1990.

Davies and Riechmann, "Antibody VH domains as small recognition units", *Biotechnology* (NY), 13:475-479, 1995.

Devereux, Haeberli, Smithies, "A Comprehensive Set of Sequence Analysis Programs for the VAX", *Nucleic Acids Res.*, 12:387, 1984.

Di Paolo et al., "A recombinant immunotoxin derived from a humanized epithelial cell adhesion molecule-specific single-chain antibody fragment has potent and selective antitumor activity", Clin Cancer Res 9: 2837-48, 2003.

Frische, Meldal, Werdelin, Mouritsen, Jensen, Galli-Stampino, Bock, "Multiple Column Synthesis of a Library of T-Cell Stimulating Tn-Antigenic Glycopeptide Analogues for the Molecular Characterization of T-Cell-Glycan Specificity", *J. Pept. Sci.*, 2(4): 212-22, 1996.

Goeddel, "Gene Expression Technology: Methods in Enzymology 185, Academic Press, San Diego, Calif., 1990.

Guleng, Tateishi, Ohta, Kanai, Jazag, Ijichi, Tanaka, Washida, Morikane, Fukushima, Yamori, Tsuruo, Kawabe, Miyagishi, Taira, Sata, Omata. "Blockade of the stromal cell-derived factor-1/CXCR4 axis attenuates in vivo tumor growth by inhibiting angiogenesis in a vascular endothelial growth factor-independent manner". Cancer Res 65: 5864-71, 2005

Hamers-Casterman and Atarhouch, "Naturally Occurring antibodies Devoid of Light Chains", *Nature*, 363(6428): 446-448, 1993.

Hammer, Pursel, Rexroad, Wall, Bolt, Ebert, Palmiter, Brinster, "Production of Transgenic Rabbits, Sheep and Pigs by Microinjection", *Nature*, 315:680-683, 1985.

Henikoff and Henikoff, "Amino acid Substitution Matrices from Protein Blocks", *Proc. Natl. Acad. Sci. USA*, 89:10915-10919, 1992.

Hinnen, Hicks, Fink, "Transformation of Yeast", *Proc. Natl. Acad. Sci. USA*, 75:1929, 1978.

Holliger and Hudson, "Engineered Antibody Fragments and the Rise of Single Domains", *Nature Biotechnology*, 23(9): 1126-1136, 2005.

Holm, "Dali: a Network Tool for Protein Structure Comparison", *Trends in Biochemical Sciences*, 20:478-480, 1995.

Holm, "Protein Structure Comparison by Alignment of Distance Matrices", *J. Mol. Biol.*, 233:123-38, 1993

Holm, "Touring Protein Fold Space With Dali/FSSP", *Nucleic Acid Res.*, 26:316-9, 1998.

Hu, Deng, Bian, Li, Tong, Li, Wang, Xin, He, Zhou, Xie, Wang, Cao. "The expression of functional chemokine receptor CXCR4 is associated with the metastatic potential of human nasopharyngeal carcinoma." Clin Cancer Res 11: 4658-65, 2005

Ito, Fukuda, Murata, Kimura, "Transformation of Intact Yeast Cells Treated with Alkali Cations", *J. Bacteriol.*, 153:163-168, 1983.

Kabat, Wu, Perry, Gottesman, Foeller, "Sequences of Proteins of Immunological Interest", 5th Ed. Public Health Service, National Institutes of Health, Bethesda, Md., 647-669, 1991.

Kaufman, Murtha, Davies, "Translational Efficiency of Polycistronic Mrnas and Their Utilization to Express Heterologous Genes in Mammalian Cells", *EMBO J.*, 6:187-195, 1987.

Kim, Lee, Midura, Yeung, Mendoza, Hong, Ren, Wong, Korz, Merzouk, Salari, Zhang, Hwang, Khanna, Helman. "Inhibition of the CXCR4/CXCL12 chemokine pathway reduces the development of murine pulmonary metastases." Clin Exp Metastasis 25: 201-11, 2008

Kipriyanov, Moldenhauer, Little, "High level production of soluble single chain antibodies in small-scale *Escherichia coli* cultures." *J Immunol Methods* 200: 69-77, 1997

Kiss, Fisher, Pesavento, Dai, Valero, Ovecka, Nolan, Phipps, Velappan, Chasteen, Martinez, Waldo, Pavlik, Bradbury, "Antibody binding loop insertions as diversity elements", *Nucleic Acids Research*, 34(19):e132, 2006.

Kurjan and Herskowitz, "Structure of a Yeast Pheromone Gene (MFα): a Putative α-Factor Precursor Contains Four Tandem Copies of mature α-Factor", *Cell*, 30:933-943, 1982.

Kwong, Kulbe, Wong, Chakravarty, Balkwill. "An antagonist of the chemokine receptor CXCR4 induces mitotic catastrophe in ovarian cell cancer cells." Mol Cancer Ther 8(7), 1893-1905, 2009

Le Gall, Reusch, Little and Kipriyanov, "Effect of Linker Sequences Between the Antibody Variable Domains on the Formation, Stability and Biological Activity of a Bispecific Tandem Diabody", *Protein Engineering, Design & Selection*, 17(4):357-366, 2004.

Liang, Wu, Reddy, Zhu, Wang, Blevins, Yoon, Zhang, Shim. "Blockade of invasion and metastasis of breast cancer cells via targeting CXCR4 with an artificial microRNA." Biochem Biophys Res Commun 363: 542-6, 2007

Luckow and Summers, "High Level Expression of Nonfused Foreign Genes with *Autographa Californica* Nuclear Polyhedrosis Virus Expression Vectors", *Virology*, 170:31-39, 1989.

Marhaba et al., "CD44 and EpCAM: cancer-initiating cell markers", Curr Mol Med 8: 784-804, 2008.

Merrifield, "Solid Phase Peptide Synthesis 1. Synthesis of a Tetrapeptide", *J. Am. Chem. Assoc.*, 85:2149-2154, 1964.

Muller, Homey, Soto, Ge, Catron, Buchanan, McClanahan, Murphy, Yuan, Wagner, Barrera, Mohar, Verastegui, Zlotnik. "Involvement of chemokine receptors in breast cancer metastasis." Nature 410: 50-6, 2001

Munz et al., "The carcinoma-associated antigen EpCAM upregulates c-myc and induces cell proliferation", Oncogene 23: 5748-58, 2004.

Myers and Miller, "Optical Alignments in Linear Space", *CABIOS*, 4:11-17, 1988.

Needleman and Wunsch, "A General Method Applicable to the Search For Similarities in the Amino Acid Sequence of Two Proteins", *J. Mol. Biol.*, 48:443, 1970.

Neuberger and Milstein, "Somatic hypermutation," *Curr. Opin. Immunol.,* 7:248-254, 1995.

Nicaise, Valerio-Lepiniec, Minard, Desmadril, "Affinity transfer by CDR grafting on a nonimmunoglobulin scaffold", *Protein Sci.,* 13: 1882-1891, 2004.

O'Brien et al., "A human colon cancer cell capable of initiating tumour growth in immunodeficient mice", *Nature* 445: 106-10, 2007.

Orimo, Gupta, Sgroi, Arenzana-Seisdedos, Delaunay, Naeem, Carey, Richardson, Weinberg. "Stromal fibroblasts present in invasive human breast carcinomas promote tumor growth and angiogenesis through elevated SDF-1/CXCL12 secretion." *Cell* 121: 335-48, 2005

Palmiter and Brinster, "Transgenic Mice", *Cell,* 41:343-345, 1985.

Palmiter, Norstedt, Gelinas, Hammer, Brinster, "Metallothionein-Human GH Fusion Genes Stimulate Growth of Mice", *Science,* 222:809-814, 1983.

Pearson and Lipman, "Improved tools for biological sequence analysis", *Proc. Natl. Acad. Sci. USA,* 85:2444-2448, 1988.

Pearson, "Rapid and sensitive sequence comparison with FASTP and FASTA", *Methods in Enzymology,* 183:63-98, 1990.

Prang, Preithner, Brischwein, Göster, Wöppel, Müller, Steiger, Peters, Baeuerle, da Silva, "Cellular and complement-dependent cytotoxicity of Ep-CAM-specific monoclonal antibody MT201 against breast cancer cell lines", Br J Cancer, 92(2):342-349, 2005.

Qiu, Wang, Cai, Wang, Yue, "Small antibody mimetics comprising two complementarity-determining regions and a framework region for tumor targeting|, *Nature Biotechnology,* 25(8): 921-929, 2007.

Reff and Heard, "A Review of Modifications to Recombinant Antibodies: Attempt to Increase Efficacy in Oncology Applications", *Critical Reviews in Oncology Hematology,* 40:25-35, 2001.

Reiter, Ulrich Brinkmann, Lee and Pastan, "Engineering Antibody Fv Fragments for Cancer Detection and Therapy: Disulfide-Stabilized Fv Fragments", *Nature Biotechnology,* 14:1239-1245, 1996.

Schultz, Tanner, Hofmann, Emini, Condra, Jones, Kieff, Ellis, "Expression and Secretion in Yeast of a 400-Kda Envelope Glycoprotein Derived from Epstein-Barr Virus", *Gene,* 54:113-123, 1987.

Seed, "an LFA-3 Cdna Encodes a Phospholipid-Linked Membrane Protein Homologous to its Receptor CD2", *Nature,* 329:840, 1987.

Sinkar, White, Gordon, "Molecular Biology of Ri-Plasmid a Review", *J. Biosci (Bangalore),* 11:47-58, 1987.

Smith and Waterman, "Comparison of Biosequences", *Adv. Appl. Math.,* 2:482, 1981.

Smith, Summers, Fraser, "Production of Human Beta Interferon in Insect Cells Infected With Baculovirus Expression Vector", *Mol. Cell. Biol.,* 3:2156-2165, 1983.

Spizzo et al., "High Ep-CAM expression is associated with poor prognosis in node-positive breast cancer", Breast Cancer Res Treat 86: 207-13, 2004.

Spizzo et al., "Overexpression of epithelial cell adhesion molecule (Ep-CAM) is an independent prognostic marker for reduced survival of patients with epithelial ovarian cancer", Gynecol Oncol 103: 483-8, 2006.

Thompson, Higgins, Gibson, "CLUSTAL W: Improving the sensitivity of progressive multiple sequence alignment through sequence weighting, position-specific gap penalties and weight matrix choice", *Nucleic Acids Res.,* 22:4673-4680, 1994.

van den Beucken, Neer, Sablon, Desmet, Celis, Hoogenboom, Hufton, "Building novel binding ligands to B7.1 and B7.2 based on human antibody single variable light chain domains", *J. Mol. Biol.,* 310:591-601, 2001.

Varga et al., "Overexpression of epithelial cell adhesion molecule antigen in gallbladder carcinoma is an independent marker for poor survival", Clin Cancer Res 10: 3131-6, 2004.

Wagner, Milstein, Neuberger, "Codon bias targets mutation," *Nature,* 376:732, 1995.

Ward, Güssow, Griffiths, Jones, Winter, "Binding Activities of a Repertoire of Single Immunoglobulin Variable Domains Secreted from *Escherichia Coli", Nature,* 341 (6242):544-546, 1989.

Went et al., "Frequent high-level expression of the immunotherapeutic target Ep-CAM in colon, stomach, prostate and lung cancers", Br J Cancer 94: 128-35, 2006.

Xu, Duda, Di Tomaso, Ancukiewicz, Chung, Lauwers, Samuel, Shellito, Czito, Lin, Poleski, Bentley, Clark, Willett, Jain. "Direct Evidence that Bevacizumab, an Anti-VEGF Antibody, Up-regulates SDF1α, CXCR4, CXCL6 and Neuropilin 1 in Tumors from Patients with Rectal Cancer." Cancer Res 69(20) 7905-7910, 2009

Young, MacKenzie, Narang, Oomen and Baenziger, "Thermal Stabilization of a Single-Chain Fv Antibody Fragment by Introduction of a Disulphide Bond", *FEBS Letters,* 16396(377):135-139, 1995.

Zambryski, Herrera-Estreila, DeBlock, Van Montagu, Schell "Genetic Engineering, Principles and Methods", *Hollaender and Setlow* (eds.), Vol. VI, pp. 253-278, Plenum Press, New York, 1984.

Zapata, Ridgway, Mordenti, Osaka, Wong, Bennett, Carter, "Engineering Linear F(Ab')$_2$ Fragments For Efficient Production in *Escherichia Coli* and Enhanced Antiproliferative Activity", *Protein Eng.,* 8(10):1057-1062, 1995.

Zhang, Gildersleeve, Yang, Xu, Loo, Uryu, Wong, Schultz, "A New Strategy for the Synthesis of Glycoproteins", *Science,* 303(5656): 371-373, 2004.

The invention claimed is:

1. An isolated antibody which binds to CXC chemokine receptor 4 (CXCR4) and which does not induce significant apoptosis of CXCR4 expressing cells, wherein by the term not inducing significant apoptosis of CXCR4 expressing cells is meant that levels of apoptosis induced in the presence of an antibody are comparable to or not significantly different from levels of apoptosis induced in the absence of an antibody, and wherein said antibody comprises at least one heavy chain variable region that comprises three CDRs and at least one light chain variable region that comprises three CDRs,
wherein said heavy chain variable region comprises:
(i) a variable heavy (VH) CDR1 that has the amino acid sequence of S/G Y $X_3$ M/I H/S (SEQ ID NO: 126), or $X_1$ Y $X_3$ M H (SEQ ID NO: 127) or S Y $X_3$ M H (SEQ ID NO: 128);
wherein $X_1$ can be S or G, preferably S;
$X_3$ can be G or W or Y or A, preferably W;

(ii) a VH CDR2 that has the amino acid sequence of $X_1$ I $X_3$ $X_4$ D G S $X_8$ $X_9$ $X_{10}$ Y A D S V K G (SEQ ID NO:129);
wherein $X_1$ can be V or R, preferably R;
$X_3$ can be S or N, preferably N;
$X_4$ can be Y or S, preferably S;
$X_8$ can be N or S, preferably S;
$X_9$ can be K or T, preferably T; and
$X_{10}$ can be Y or S, preferably S;
or a VH CDR2 that has the amino acid sequence of $X_1$ I $X_3$ P $X_5$ $X_6$ G $X_8$ $X_9$ N Y A Q K F Q G (SEQ ID NO: 131);
wherein $X_1$, can be R or G, preferably R;
$X_3$ can be N or I, preferably N;
$X_5$ can be N or I, preferably N;
$X_6$ can be S or F, preferably S;
$X_8$ can be G or T, preferably G; and
$X_9$ can be T or A, preferably T; and
(iii) a VH CDR3 that has the amino acid sequence of SEQ ID NO:s 3, 9, 15 or 21.

2. The antibody of claim 1, wherein said antibody does not induce significant apoptosis of CXCR4 expressing cells if used at a concentration of ≥0.4 µg/ml.

3. The antibody of claim 1, wherein said antibody is capable of inhibiting the binding of a ligand to CXCR4, or is capable of inhibiting the ligand-induced migration of CXCR4 expressing cells, or is capable of inhibiting ligand-induced calcium flux in CXCR4 expressing cells.

4. An antibody according to claim 1, wherein said antibody comprises at least one heavy chain variable region that comprises three CDRs and at least one light chain variable region that comprises three CDRs,
wherein said heavy chain variable region comprises:
(i) a variable heavy (VH) CDR1 that has the amino acid sequence of SEQ ID NO: 1;
(ii) a VH CDR2 that has the amino acid sequence of SEQ ID NO: 2; and
(iii) a VH CDR3 that has the amino acid sequence of SEQ ID NO: 3; and/or
wherein said light chain variable region comprises:
(iv) a variable light (VL) CDR1 that has the amino acid sequence of SEQ ID NO: 4;
(v) a VL CDR2 that has the amino acid sequence of SEQ ID NO: 5; and
(vi) a VL CDR3 that has the amino acid sequence of SEQ ID NO: 6.

5. An antibody according to claim 1, wherein said antibody comprises at least one heavy chain variable region that comprises three CDRs and at least one light chain variable region that comprises three CDRs,
wherein said heavy chain variable region comprises:
(i) a variable heavy (VH) CDR1 that has the amino acid sequence of SEQ ID NO: 7;
(ii) a VH CDR2 that has the amino acid sequence of SEQ ID NO: 8; and
(iii) a VH CDR3 that has the amino acid sequence of SEQ ID NO: 9; and/or
wherein said light chain variable region comprises:
(iv) a variable light (VL) CDR1 that has the amino acid sequence of SEQ ID NO: 10;
(v) a VL CDR2 that has the amino acid sequence of SEQ ID NO: 11; and
(vi) a VL CDR3 that has the amino acid sequence of SEQ ID NO: 12.

6. An antibody according to claim 1, wherein said antibody comprises at least one heavy chain variable region that comprises three CDRs and at least one light chain variable region that comprises three CDRs,
wherein said heavy chain variable region comprises:
(i) a variable heavy (VH) CDR1 that has the amino acid sequence of SEQ ID NO: 13;
(ii) a VH CDR2 that has the amino acid sequence of SEQ ID NO: 14; and
(iii) a VH CDR3 that has the amino acid sequence of SEQ ID NO: 15; and/or
wherein said light chain variable region comprises:
(iv) a variable light (VL) CDR1 that has the amino acid sequence of SEQ ID NO: 16;
(v) a VL CDR2 that has the amino acid sequence of SEQ ID NO: 17; and
(vi) a VL CDR3 that has the amino acid sequence of SEQ ID NO: 18.

7. An antibody according to claim 1, wherein said antibody comprises at least one heavy chain variable region that comprises three CDRs and at least one light chain variable region that comprises three CDRs,
wherein said heavy chain variable region comprises:
(i) a variable heavy (VH) CDR1 that has the amino acid sequence of SEQ ID NO: 19;
(ii) a VH CDR2 that has the amino acid sequence of SEQ ID NO: 20; and
(iii) a VH CDR3 that has the amino acid sequence of SEQ ID NO: 21; and/or
wherein said light chain variable region comprises:
(iv) a variable light (VL) CDR1 that has the amino acid sequence of SEQ ID NO: 22;
(v) a VL CDR2 that has the amino acid sequence of SEQ ID NO: 23; and
(vi) a VL CDR3 that has the amino acid sequence of SEQ ID NO: 24.

8. An antibody according to claim 1, wherein said antibody comprises at least one heavy chain variable region that comprises three CDRs and at least one light chain variable region that comprises three CDRs,
wherein said heavy chain variable region comprises:
(i) a variable heavy (VH) CDR1 that has the amino acid sequence of SEQ ID NO: 1;
(ii) a VH CDR2 that has the amino acid sequence of SEQ ID NO: 2; and
(iii) a VH CDR3 that has the amino acid sequence of SEQ ID NO: 3; and/or
wherein said light chain variable region comprises:
(iv) a variable light (VL) CDR1 that has the amino acid sequence of SEQ ID NO: 88;
(v) a VL CDR2 that has the amino acid sequence of SEQ ID NO: 89; and
(vi) a VL CDR3 that has the amino acid sequence of SEQ ID NO: 90.

9. An antibody according to claim 4, comprising one of each of the VH CDR domains (i), (ii) and (iii), and one of each of the VL CDR domains (iv), (v) and (vi).

10. An antibody according to claim 5, comprising one of each of the VH CDR domains (i), (ii) and (iii), and one of each of the VL CDR domains (iv), (v) and (vi).

11. An antibody according to claim 6, comprising one of each of the VH CDR domains (i), (ii) and (iii), and one of each of the VL CDR domains (iv), (v) and (vi).

12. An antibody according to claim 7, comprising one of each of the VH CDR domains (i), (ii) and (iii), and one of each of the VL CDR domains (iv), (v) and (vi).

13. An antibody according to claim 8, comprising one of each of the VH CDR domains (i), (ii) and (iii), and one of each of the VL CDR domains (iv), (v) and (vi).

14. An antibody according to claim 1, wherein said antibody has (i) a VH domain of SEQ ID NO: 69, (ii) a VL domain of SEQ ID NO: 70 or (iii) a VH domain of SEQ ID NO: 69 and a VL domain of SEQ ID NO: 70.

15. An antibody according to claim 1, wherein said antibody has (i) a VH domain of SEQ ID NO: 71, (ii) a VL domain of SEQ ID NO: 72 or (iii) a VH domain of SEQ ID NO: 71 and a VL domain of SEQ ID NO: 72.

16. An antibody according to claim 1, wherein said antibody has (i) a VH domain of SEQ ID NO: 73, (ii) a VL domain of SEQ ID NO: 74 or (iii) a VH domain of SEQ ID NO: 73 and a VL domain of SEQ ID NO: 74.

17. An antibody according to claim 1, wherein said antibody has (i) a VH domain of SEQ ID NO: 75, (ii) a VL domain of SEQ ID NO: 76 or (iii) a VH domain of SEQ ID NO: 75 and a VL domain of SEQ ID NO: 76.

18. An antibody according to claim 1, wherein said antibody has (i) a VH domain of SEQ ID NO: 69, (ii) a VL domain of SEQ ID NO: 103 or (iii) a VH domain of SEQ ID NO: 69 and a VL domain of SEQ ID NO: 103.

19. An antibody according to claim 1, wherein said antibody is a human antibody, preferably a fully human antibody.

20. The antibody of claim 1, wherein said antibody comprises (i) all or a portion of an antibody heavy chain constant region, (ii) all or a portion of an antibody light chain constant region or (iii) all or a portion of an antibody heavy chain constant region and all or a portion of an antibody light chain constant region.

21. The antibody of claim 20, wherein said antibody is an IgG antibody, preferably an IgG1 antibody.

22. The antibody of claim 20, wherein said antibody comprises (i) a heavy chain that comprises the amino acid sequence of SEQ ID NO: 108, (ii) a light chain that comprises the amino acid sequence of SEQ ID NO: 109 or (iii) a heavy chain that comprises the amino acid sequence of SEQ ID NO: 108 and a light chain that comprises the amino acid sequence of SEQ ID NO: 109.

23. The antibody of claim 20, wherein said antibody comprises (i) a heavy chain that comprises the amino acid sequence of SEQ ID NO: 112, (ii) a light chain that comprises the amino acid sequence of SEQ ID NO: 113 or (iii) a heavy chain that comprises the amino acid sequence of SEQ ID NO: 112 and a light chain that comprises the amino acid sequence of SEQ ID NO: 113.

24. The antibody of claim 20, wherein said antibody comprises (i) a heavy chain that comprises the amino acid sequence of SEQ ID NO: 116, (ii) a light chain that comprises the amino acid sequence of SEQ ID NO: 117 or (iii) a heavy chain that comprises the amino acid sequence of SEQ ID NO: 116 and a light chain that comprises the amino acid sequence of SEQ ID NO: 117.

25. The antibody of claim 20, wherein said antibody comprises (i) a heavy chain that comprises the amino acid sequence of SEQ ID NO: 120, (ii) a light chain that comprises the amino acid sequence of SEQ ID NO: 121 or (iii) a heavy chain that comprises the amino acid sequence of SEQ ID NO: 120 and a light chain that comprises the amino acid sequence of SEQ ID NO: 121.

26. The antibody of claim 20, wherein said antibody comprises (i) a heavy chain that comprises the amino acid sequence of SEQ ID NO: 124, (ii) a light chain that comprises the amino acid sequence of SEQ ID NO: 125 or (iii) a heavy chain that comprises the amino acid sequence of SEQ ID NO: 124 and a light chain that comprises the amino acid sequence of SEQ ID NO: 125.

27. The antibody of claim 1, wherein said antibody is an antigen binding fragment of an antibody.

28. The antibody of claim 27, wherein said antigen binding fragment of said antibody is a Fab', Fab, F(ab')$_2$, single domain antibody, T and Abs dimer, Fv, scFv, dsFv, ds-scFv, Fd, linear antibody, minibody, diabody, bispecific antibody fragment, bibody, tribody, sc-diabody, kappa(lamda) body, BiTE, DVD-Ig, SIP, SMIP, DART or a small antibody mimetic comprising one or more CDRs.

29. The antibody of claim 1, wherein said antibody is a first diagnostic or therapeutic agent and is attached to at least a second diagnostic or therapeutic agent.

30. The antibody of claim 29, wherein said antibody is attached to at least a radiotherapeutic agent, chemotherapeutic agent, anti-angiogenic agent, apoptosis-inducing agent, anti-tubulin drug, anti-cellular or cytotoxic agent, steroid, cytokine antagonist, cytokine expression inhibitor, chemokine antagonist, chemokine expression inhibitor, ATPase inhibitor, anti-inflammatory agent, signalling pathway inhibitor, anti-cancer agent, other antibodies, coagulant or anti-viral agent, wherein said anti-viral agent is preferably selected from the group consisting of a nucleoside, a nucleoside reverse transcriptase inhibitor, a non-nucleoside reverse transcriptase inhibitor and a protease inhibitor.

31. An immunoconjugate comprising the antibody of claim 1 attached to at least a second therapeutic or diagnostic agent, wherein said antibody is a first therapeutic or diagnostic agent.

32. A composition comprising at least a first antibody according to claim 1 or an immunoconjugate thereof, wherein said composition is preferably a pharmaceutically acceptable composition.

33. The composition of claim 32, wherein said composition further comprises at least a second therapeutic agent.

34. A kit comprising, in at least a first container:
 (a) the antibody of claim 1;
 (b) the immunoconjugate of claim 31; or
 (c) the composition of claim 32.

35. A method of binding CXCR4, comprising contacting a composition comprising CXCR4 with the antibody of claim 1, or an immunoconjugate thereof.

36. A method of detecting CXCR4, comprising contacting a composition suspected of containing CXCR4 with the antibody of claim 1, or an immunoconjugate thereof, under conditions effective to allow the formation of complexes between said CXCR4 and said antibody and detecting said complexes so formed.

\* \* \* \* \*

SEQUENCE LISTING

```
<160> NUMBER OF SEQ ID NOS: 142

<210> SEQ ID NO 1
<211> LENGTH: 5
<212> TYPE: PRT
<213> ORGANISM: Artificial Sequence
<220> FEATURE:
<223> OTHER INFORMATION: antibody sequence
```

```
<400> SEQUENCE: 1

Ser Tyr Trp Met His
1               5

<210> SEQ ID NO 2
<211> LENGTH: 17
<212> TYPE: PRT
<213> ORGANISM: Artificial Sequence
<220> FEATURE:
<223> OTHER INFORMATION: antibody sequence

<400> SEQUENCE: 2

Arg Ile Asn Ser Asp Gly Ser Ser Thr Ser Tyr Ala Asp Ser Val Lys
1               5                   10                  15

Gly

<210> SEQ ID NO 3
<211> LENGTH: 15
<212> TYPE: PRT
<213> ORGANISM: Artificial Sequence
<220> FEATURE:
<223> OTHER INFORMATION: antibody sequence

<400> SEQUENCE: 3

Lys Ile Leu Gly Val Gly Ala Arg Ser Arg Arg Tyr Phe Asp Tyr
1               5                   10                  15

<210> SEQ ID NO 4
<211> LENGTH: 12
<212> TYPE: PRT
<213> ORGANISM: Artificial Sequence
<220> FEATURE:
<223> OTHER INFORMATION: antibody sequence

<400> SEQUENCE: 4

Arg Ala Ser Gln Ser Val Val Ser Asn Tyr Leu Ala
1               5                   10

<210> SEQ ID NO 5
<211> LENGTH: 7
<212> TYPE: PRT
<213> ORGANISM: Artificial Sequence
<220> FEATURE:
<223> OTHER INFORMATION: antibody sequence

<400> SEQUENCE: 5

Gly Ala Ser Asn Arg Ala Thr
1               5

<210> SEQ ID NO 6
<211> LENGTH: 9
<212> TYPE: PRT
<213> ORGANISM: Artificial Sequence
<220> FEATURE:
<223> OTHER INFORMATION: antibody sequence

<400> SEQUENCE: 6

Gln Gln Phe Asp Lys Ser Thr Trp Thr
1               5

<210> SEQ ID NO 7
<211> LENGTH: 5
<212> TYPE: PRT
<213> ORGANISM: Artificial Sequence
<220> FEATURE:
<223> OTHER INFORMATION: antibody sequence
```

```
<400> SEQUENCE: 7

Ser Tyr Ala Ile Ser
1               5

<210> SEQ ID NO 8
<211> LENGTH: 17
<212> TYPE: PRT
<213> ORGANISM: Artificial Sequence
<220> FEATURE:
<223> OTHER INFORMATION: antibody sequence

<400> SEQUENCE: 8

Gly Ile Ile Pro Ile Phe Gly Thr Ala Asn Tyr Ala Gln Lys Phe Gln
1               5                   10                  15

Gly

<210> SEQ ID NO 9
<211> LENGTH: 12
<212> TYPE: PRT
<213> ORGANISM: Artificial Sequence
<220> FEATURE:
<223> OTHER INFORMATION: antibody sequence

<400> SEQUENCE: 9

Asp Arg Glu Arg Trp Leu Gln Ser Ala Gly Asp Tyr
1               5                   10

<210> SEQ ID NO 10
<211> LENGTH: 11
<212> TYPE: PRT
<213> ORGANISM: Artificial Sequence
<220> FEATURE:
<223> OTHER INFORMATION: antibody sequence

<400> SEQUENCE: 10

Gly Gly Asn Asn Ile Gly Ser Lys Ser Val His
1               5                   10

<210> SEQ ID NO 11
<211> LENGTH: 7
<212> TYPE: PRT
<213> ORGANISM: Artificial Sequence
<220> FEATURE:
<223> OTHER INFORMATION: antibody sequence

<400> SEQUENCE: 11

Asp Asp Ser Asp Arg Pro Ser
1               5

<210> SEQ ID NO 12
<211> LENGTH: 11
<212> TYPE: PRT
<213> ORGANISM: Artificial Sequence
<220> FEATURE:
<223> OTHER INFORMATION: antibody sequence

<400> SEQUENCE: 12

Gln Val Trp Asp Ser Ser Ser Asp His Trp Val
1               5                   10

<210> SEQ ID NO 13
<211> LENGTH: 5
<212> TYPE: PRT
<213> ORGANISM: Artificial Sequence
<220> FEATURE:
<223> OTHER INFORMATION: antibody sequence
```

```
<400> SEQUENCE: 13

Ser Tyr Gly Met His
1               5

<210> SEQ ID NO 14
<211> LENGTH: 17
<212> TYPE: PRT
<213> ORGANISM: Artificial Sequence
<220> FEATURE:
<223> OTHER INFORMATION: antibody sequence

<400> SEQUENCE: 14

Val Ile Ser Tyr Asp Gly Ser Asn Lys Tyr Tyr Ala Asp Ser Val Lys
1               5                   10                  15

Gly

<210> SEQ ID NO 15
<211> LENGTH: 12
<212> TYPE: PRT
<213> ORGANISM: Artificial Sequence
<220> FEATURE:
<223> OTHER INFORMATION: antibody sequence

<400> SEQUENCE: 15

Asp Leu Pro Ile Thr Arg Gly Thr Gly Ala Asp Tyr
1               5                   10

<210> SEQ ID NO 16
<211> LENGTH: 14
<212> TYPE: PRT
<213> ORGANISM: Artificial Sequence
<220> FEATURE:
<223> OTHER INFORMATION: antibody sequence

<400> SEQUENCE: 16

Thr Gly Thr Ser Ser Asp Val Gly Gly Tyr Asn Tyr Val Ser
1               5                   10

<210> SEQ ID NO 17
<211> LENGTH: 7
<212> TYPE: PRT
<213> ORGANISM: Artificial Sequence
<220> FEATURE:
<223> OTHER INFORMATION: antibody sequence

<400> SEQUENCE: 17

Asp Val Thr Ser Arg Pro Ser
1               5

<210> SEQ ID NO 18
<211> LENGTH: 10
<212> TYPE: PRT
<213> ORGANISM: Artificial Sequence
<220> FEATURE:
<223> OTHER INFORMATION: antibody sequence

<400> SEQUENCE: 18

Ser Ser Tyr Ala Gly Ser Tyr Ser Val Val
1               5                   10

<210> SEQ ID NO 19
<211> LENGTH: 5
<212> TYPE: PRT
<213> ORGANISM: Artificial Sequence
<220> FEATURE:
<223> OTHER INFORMATION: antibody sequence
```

```
<400> SEQUENCE: 19

Gly Tyr Tyr Met His
1               5

<210> SEQ ID NO 20
<211> LENGTH: 17
<212> TYPE: PRT
<213> ORGANISM: Artificial Sequence
<220> FEATURE:
<223> OTHER INFORMATION: antibody sequence

<400> SEQUENCE: 20

Arg Ile Asn Pro Asn Ser Gly Gly Thr Asn Tyr Ala Gln Lys Phe Gln
1               5                   10                  15

Gly

<210> SEQ ID NO 21
<211> LENGTH: 18
<212> TYPE: PRT
<213> ORGANISM: Artificial Sequence
<220> FEATURE:
<223> OTHER INFORMATION: antibody sequence

<400> SEQUENCE: 21

Arg Asn Leu Ile Ala Ala Arg Pro Arg Asn Arg Gly Arg Asp Ala Phe
1               5                   10                  15

Asp Ile

<210> SEQ ID NO 22
<211> LENGTH: 11
<212> TYPE: PRT
<213> ORGANISM: Artificial Sequence
<220> FEATURE:
<223> OTHER INFORMATION: antibody sequence

<400> SEQUENCE: 22

Arg Ala Ser Gln Ser Ile Gly Gly Ser Leu Ala
1               5                   10

<210> SEQ ID NO 23
<211> LENGTH: 7
<212> TYPE: PRT
<213> ORGANISM: Artificial Sequence
<220> FEATURE:
<223> OTHER INFORMATION: antibody sequence

<400> SEQUENCE: 23

Ala Ala Ser Thr Leu Gln Ser
1               5

<210> SEQ ID NO 24
<211> LENGTH: 9
<212> TYPE: PRT
<213> ORGANISM: Artificial Sequence
<220> FEATURE:
<223> OTHER INFORMATION: antibody sequence

<400> SEQUENCE: 24

Gln His Tyr Glu Ser Tyr Pro Leu Ser
1               5

<210> SEQ ID NO 25
<211> LENGTH: 30
<212> TYPE: PRT
<213> ORGANISM: Artificial Sequence
<220> FEATURE:
```

<223> OTHER INFORMATION: antibody sequence

<400> SEQUENCE: 25

Gln Val Gln Leu Gln Glu Ser Gly Gly Gly Leu Val His Pro Gly Gly
1               5                   10                  15

Ser Leu Arg Leu Ser Cys Ala Ala Ser Gly Phe Thr Phe Ser
            20                  25                  30

<210> SEQ ID NO 26
<211> LENGTH: 14
<212> TYPE: PRT
<213> ORGANISM: Artificial Sequence
<220> FEATURE:
<223> OTHER INFORMATION: antibody sequence

<400> SEQUENCE: 26

Trp Val Arg Gln Ala Pro Gly Lys Gly Leu Val Trp Val Ser
1               5                   10

<210> SEQ ID NO 27
<211> LENGTH: 32
<212> TYPE: PRT
<213> ORGANISM: Artificial Sequence
<220> FEATURE:
<223> OTHER INFORMATION: antibody sequence

<400> SEQUENCE: 27

Arg Phe Thr Ile Ser Arg Asp Asn Ala Lys Asn Thr Leu Tyr Leu Gln
1               5                   10                  15

Met Asn Ser Leu Arg Ala Glu Asp Thr Ala Val Tyr Tyr Cys Ala Arg
            20                  25                  30

<210> SEQ ID NO 28
<211> LENGTH: 11
<212> TYPE: PRT
<213> ORGANISM: Artificial Sequence
<220> FEATURE:
<223> OTHER INFORMATION: antibody sequence

<400> SEQUENCE: 28

Trp Gly Gln Gly Thr Met Val Thr Val Ser Ser
1               5                   10

<210> SEQ ID NO 29
<211> LENGTH: 21
<212> TYPE: PRT
<213> ORGANISM: Artificial Sequence
<220> FEATURE:
<223> OTHER INFORMATION: antibody sequence

<400> SEQUENCE: 29

Lys Leu Ser Gly Ser Ala Ser Ala Pro Lys Leu Glu Glu Gly Glu Phe
1               5                   10                  15

Ser Glu Ala Arg Val
            20

<210> SEQ ID NO 30
<211> LENGTH: 23
<212> TYPE: PRT
<213> ORGANISM: Artificial Sequence
<220> FEATURE:
<223> OTHER INFORMATION: antibody sequence

<400> SEQUENCE: 30

Glu Thr Thr Leu Thr Gln Ser Pro Gly Thr Leu Ser Leu Ser Pro Gly
1               5                   10                  15

Glu Arg Ala Thr Leu Ser Cys
            20

<210> SEQ ID NO 31
<211> LENGTH: 15
<212> TYPE: PRT
<213> ORGANISM: Artificial Sequence
<220> FEATURE:
<223> OTHER INFORMATION: antibody sequence

<400> SEQUENCE: 31

Trp Tyr Gln Gln Lys Pro Gly Gln Ala Pro Arg Leu Leu Ile Ser
1               5                   10                  15

<210> SEQ ID NO 32
<211> LENGTH: 32
<212> TYPE: PRT
<213> ORGANISM: Artificial Sequence
<220> FEATURE:
<223> OTHER INFORMATION: antibody sequence

<400> SEQUENCE: 32

Gly Ile Ser Asp Arg Phe Ser Gly Ser Gly Ser Gly Ala Asp Phe Thr
1               5                   10                  15

Leu Thr Ile Ser Arg Val Glu Pro Glu Asp Ser Ala Val Tyr Tyr Cys
            20                  25                  30

<210> SEQ ID NO 33
<211> LENGTH: 10
<212> TYPE: PRT
<213> ORGANISM: Artificial Sequence
<220> FEATURE:
<223> OTHER INFORMATION: antibody sequence

<400> SEQUENCE: 33

Phe Gly Gln Gly Thr Lys Val Glu Ile Lys
1               5                   10

<210> SEQ ID NO 34
<211> LENGTH: 759
<212> TYPE: DNA
<213> ORGANISM: Artificial Sequence
<220> FEATURE:
<223> OTHER INFORMATION: antibody sequence

<400> SEQUENCE: 34
caggtgcagc tgcaggagtc cgggggaggc ttagttcacc ctgggggtc cctgagactc      60 tcctgtgcag cctctggatt caccttcagt agctactgga tgcactgggt ccgccaagct    120
ccagggaagg gctggtgtg gtctcacgt attaatagtg atgggagtag cacaagctac      180
gcggactccg tgaagggccg attcaccatc tccagagaca acgccaagaa cacgctgtat    240
ctgcaaatga acagtctgag agccgaggac acggctgtgt attactgtgc gagaaaaatc    300
ttgggggtgg gagctaggtc tcgtcgttac tttgactact ggggccaggg aacaatggtc    360
accgtctctt caaagctttc agggagtgca tccgccccaa aacttgaaga aggtgaattt    420
tcagaagcac gcgtagaaac gacactcacg cagtctccag gcaccctgtc tttgtctcca    480
ggggaaagag ccaccctctc ctgcagggcc agtcagagtg ttgtcagcaa ctatttagcc    540
tggtaccagc agaagcctgg ccaggctccc aggctcctca tctctggtgc atccaacagg    600
gccactggca tctcagacag gttcagtggc agtgggtctg ggcagactt cactctcacc    660 atcagcagag tcgagcctga agactcagca gtgtattact gtcaacagtt tgataagtcc    720
acgtggacgt tcggccaagg gaccaaggtg gaaatcaaa        759

<210> SEQ ID NO 35
<211> LENGTH: 253
<212> TYPE: PRT
<213> ORGANISM: Artificial Sequence
<220> FEATURE:
<223> OTHER INFORMATION: antibody sequence

<400> SEQUENCE: 35

```
Gln Val Gln Leu Gln Glu Ser Gly Gly Gly Leu Val His Pro Gly Gly
1               5                   10                  15

Ser Leu Arg Leu Ser Cys Ala Ala Ser Gly Phe Thr Phe Ser Ser Tyr
            20                  25                  30

Trp Met His Trp Val Arg Gln Ala Pro Gly Lys Gly Leu Val Trp Val
        35                  40                  45

Ser Arg Ile Asn Ser Asp Gly Ser Ser Thr Ser Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Lys Ile Leu Gly Val Gly Ala Arg Ser Arg Arg Tyr Phe Asp
            100                 105                 110

Tyr Trp Gly Gln Gly Thr Met Val Thr Val Ser Ser Lys Leu Ser Gly
        115                 120                 125

Ser Ala Ser Ala Pro Lys Leu Glu Glu Gly Glu Phe Ser Glu Ala Arg
    130                 135                 140

Val Glu Thr Thr Leu Thr Gln Ser Pro Gly Thr Leu Ser Leu Ser Pro
145                 150                 155                 160

Gly Glu Arg Ala Thr Leu Ser Cys Arg Ala Ser Gln Ser Val Val Ser
                165                 170                 175

Asn Tyr Leu Ala Trp Tyr Gln Gln Lys Pro Gly Gln Ala Pro Arg Leu
            180                 185                 190

Leu Ile Ser Gly Ala Ser Asn Arg Ala Thr Gly Ile Ser Asp Arg Phe
        195                 200                 205

Ser Gly Ser Gly Ser Gly Ala Asp Phe Thr Leu Thr Ile Ser Arg Val
    210                 215                 220

Glu Pro Glu Asp Ser Ala Val Tyr Tyr Cys Gln Gln Phe Asp Lys Ser
225                 230                 235                 240

Thr Trp Thr Phe Gly Gln Gly Thr Lys Val Glu Ile Lys
                245                 250
```

<210> SEQ ID NO 36
<211> LENGTH: 30
<212> TYPE: PRT
<213> ORGANISM: Artificial Sequence
<220> FEATURE:
<223> OTHER INFORMATION: antibody sequence

<400> SEQUENCE: 36

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser
            20                  25                  30
```

<210> SEQ ID NO 37
<211> LENGTH: 14
<212> TYPE: PRT

```
<213> ORGANISM: Artificial Sequence
<220> FEATURE:
<223> OTHER INFORMATION: antibody sequence

<400> SEQUENCE: 37

Trp Val Arg Gln Ala Pro Gly Gln Gly Leu Glu Trp Met Gly
1               5                   10

<210> SEQ ID NO 38
<211> LENGTH: 32
<212> TYPE: PRT
<213> ORGANISM: Artificial Sequence
<220> FEATURE:
<223> OTHER INFORMATION: antibody sequence

<400> SEQUENCE: 38

Arg Val Thr Ile Thr Ala Asp Glu Ser Thr Ser Thr Ala Tyr Met Glu
1               5                   10                  15

Leu Arg Ser Leu Arg Ser Asp Asp Thr Ala Val Tyr Tyr Cys Ala Arg
            20                  25                  30

<210> SEQ ID NO 39
<211> LENGTH: 11
<212> TYPE: PRT
<213> ORGANISM: Artificial Sequence
<220> FEATURE:
<223> OTHER INFORMATION: antibody sequence

<400> SEQUENCE: 39

Trp Gly Gln Gly Thr Leu Val Thr Val Ser Ser
1               5                   10

<210> SEQ ID NO 40
<211> LENGTH: 21
<212> TYPE: PRT
<213> ORGANISM: Artificial Sequence
<220> FEATURE:
<223> OTHER INFORMATION: antibody sequence

<400> SEQUENCE: 40

Lys Leu Ser Gly Ser Ala Ser Ala Pro Lys Leu Glu Glu Gly Glu Phe
1               5                   10                  15

Ser Glu Ala Arg Val
            20

<210> SEQ ID NO 41
<211> LENGTH: 22
<212> TYPE: PRT
<213> ORGANISM: Artificial Sequence
<220> FEATURE:
<223> OTHER INFORMATION: antibody sequence

<400> SEQUENCE: 41

Gln Pro Val Leu Thr Gln Ser Pro Ser Val Ser Val Ala Pro Gly Gln
1               5                   10                  15

Thr Ala Arg Ile Thr Cys
            20

<210> SEQ ID NO 42
<211> LENGTH: 15
<212> TYPE: PRT
<213> ORGANISM: Artificial Sequence
<220> FEATURE:
<223> OTHER INFORMATION: antibody sequence

<400> SEQUENCE: 42
```

Trp Tyr Gln Gln Lys Pro Gly Gln Ala Pro Val Leu Val Val Tyr
1               5                   10                  15

<210> SEQ ID NO 43
<211> LENGTH: 32
<212> TYPE: PRT
<213> ORGANISM: Artificial Sequence
<220> FEATURE:
<223> OTHER INFORMATION: antibody sequence

<400> SEQUENCE: 43

Gly Ile Pro Glu Arg Phe Ser Gly Ser Asn Ser Gly Asn Thr Ala Thr
1               5                   10                  15

Leu Thr Ile Ser Arg Val Glu Ala Gly Asp Glu Ala Asp Tyr Tyr Cys
            20                  25                  30

<210> SEQ ID NO 44
<211> LENGTH: 10
<212> TYPE: PRT
<213> ORGANISM: Artificial Sequence
<220> FEATURE:
<223> OTHER INFORMATION: antibody sequence

<400> SEQUENCE: 44

Phe Gly Gly Gly Thr Lys Leu Thr Val Leu
1               5                   10

<210> SEQ ID NO 45
<211> LENGTH: 750
<212> TYPE: DNA
<213> ORGANISM: Artificial Sequence
<220> FEATURE:
<223> OTHER INFORMATION: antibody sequence

<400> SEQUENCE: 45

```
caggtccagc ttgtgcagtc tggggctgag gtgaagaagc ctgggtcctc ggtgaaggtc      60
tcctgcaagg cttctggagg caccttcagc agctatgcta tcagctgggt gcgacaggcc     120
cctggacaag gcttgagtg gatgggaggg atcatcccta tctttggtac agcaaactac     180
gcacagaagt tccagggcag agtcacgatt accgcgacg aatccacgag cacagcctac     240
atggagctga ggagcctgag atctgacgac acggccgtgt attactgtgc gagagatcgg     300
gagagatggc tacaatccgc gggcgactac tggggccagg gaaccctggt cactgtctcc     360
tcaaagcttt cagggagtgc atccgcccca aaacttgaag aaggtgaatt ttcagaagca     420
cgcgtacagc ctgtgctgac tcagtcaccc tcggtgtcag tggccccagg acagacggcc     480
aggattacct gtgggggaaa caacattgga agtaaaagtg tgcactggta ccagcagaag     540
ccaggccagg cccctgtgct ggtcgtctat gatgatagcg accggccctc aggatccct     600
gagcgattct ctggctccaa ctctgggaac acggccaccc tgaccatcag cagggtcgaa     660
gccggggatg aggccgacta ttactgtcag gtgtgggata gtagtagtga tcattgggtg     720
ttcggcggag ggaccaagct gaccgtccta                                     750
```

<210> SEQ ID NO 46
<211> LENGTH: 250
<212> TYPE: PRT
<213> ORGANISM: Artificial Sequence
<220> FEATURE:
<223> OTHER INFORMATION: antibody sequence

<400> SEQUENCE: 46

Gln Val Gln Leu Val Gln Ser Gly Ala Glu Val Lys Lys Pro Gly Ser
1               5                   10                  15

```
Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
            35                  40                  45

Gly Gly Ile Ile Pro Ile Phe Gly Thr Ala Asn Tyr Ala Gln Lys Phe
50                  55                  60

Gln Gly Arg Val Thr Ile Thr Ala Asp Glu Ser Thr Ser Thr Ala Tyr
65                  70                  75                  80

Met Glu Leu Arg Ser Leu Arg Ser Asp Thr Ala Val Tyr Tyr Cys
                85                  90                  95

Ala Arg Asp Arg Glu Arg Trp Leu Gln Ser Ala Gly Asp Tyr Trp Gly
            100                 105                 110

Gln Gly Thr Leu Val Thr Val Ser Ser Lys Ser Gly Ser Ala Ser
            115                 120                 125

Ala Pro Lys Leu Glu Glu Gly Glu Phe Ser Glu Ala Arg Val Gln Pro
            130                 135                 140

Val Leu Thr Gln Ser Pro Ser Val Ser Val Ala Pro Gly Gln Thr Ala
145                 150                 155                 160

Arg Ile Thr Cys Gly Gly Asn Asn Ile Gly Ser Lys Ser Val His Trp
            165                 170                 175

Tyr Gln Gln Lys Pro Gly Gln Ala Pro Val Leu Val Val Tyr Asp Asp
            180                 185                 190

Ser Asp Arg Pro Ser Gly Ile Pro Glu Arg Phe Ser Gly Ser Asn Ser
            195                 200                 205

Gly Asn Thr Ala Thr Leu Thr Ile Ser Arg Val Glu Ala Gly Asp Glu
            210                 215                 220

Ala Asp Tyr Tyr Cys Gln Val Trp Asp Ser Ser Ser Asp His Trp Val
225                 230                 235                 240

Phe Gly Gly Gly Thr Lys Leu Thr Val Leu
                245                 250

<210> SEQ ID NO 47
<211> LENGTH: 30
<212> TYPE: PRT
<213> ORGANISM: Artificial Sequence
<220> FEATURE:
<223> OTHER INFORMATION: antibody sequence

<400> SEQUENCE: 47

Gln Val Gln Leu Val Gln Ser Gly Gly Val Val Gln Pro Gly Arg
1               5                   10                  15

Ser Leu Arg Leu Ser Cys Ala Ala Ser Gly Phe Thr Phe Ser
            20                  25                  30

<210> SEQ ID NO 48
<211> LENGTH: 14
<212> TYPE: PRT
<213> ORGANISM: Artificial Sequence
<220> FEATURE:
<223> OTHER INFORMATION: antibody sequence

<400> SEQUENCE: 48

Trp Val Arg Gln Ala Pro Gly Lys Gly Leu Glu Trp Val Ala
1               5                   10

<210> SEQ ID NO 49
<211> LENGTH: 32
<212> TYPE: PRT
<213> ORGANISM: Artificial Sequence
```

<220> FEATURE:
<223> OTHER INFORMATION: antibody sequence

<400> SEQUENCE: 49

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Lys
            20                  25                  30

<210> SEQ ID NO 50
<211> LENGTH: 11
<212> TYPE: PRT
<213> ORGANISM: Artificial Sequence
<220> FEATURE:
<223> OTHER INFORMATION: antibody sequence

<400> SEQUENCE: 50

Trp Gly Gln Gly Thr Leu Val Thr Val Ser Ser
1               5                   10

<210> SEQ ID NO 51
<211> LENGTH: 21
<212> TYPE: PRT
<213> ORGANISM: Artificial Sequence
<220> FEATURE:
<223> OTHER INFORMATION: antibody sequence

<400> SEQUENCE: 51

Lys Leu Ser Gly Ser Ala Ser Ala Pro Lys Leu Glu Glu Gly Glu Phe
1               5                   10                  15

Ser Glu Ala Arg Val
            20

<210> SEQ ID NO 52
<211> LENGTH: 22
<212> TYPE: PRT
<213> ORGANISM: Artificial Sequence
<220> FEATURE:
<223> OTHER INFORMATION: antibody sequence

<400> SEQUENCE: 52

Gln Ser Val Leu Ile Gln Pro Ala Ser Val Ser Gly Ser Pro Gly Gln
1               5                   10                  15

Ser Ile Thr Ile Ser Cys
            20

<210> SEQ ID NO 53
<211> LENGTH: 15
<212> TYPE: PRT
<213> ORGANISM: Artificial Sequence
<220> FEATURE:
<223> OTHER INFORMATION: antibody sequence

<400> SEQUENCE: 53

Trp Tyr Gln Gln His Pro Gly Lys Ala Pro Arg Leu Met Ile Tyr
1               5                   10                  15

<210> SEQ ID NO 54
<211> LENGTH: 32
<212> TYPE: PRT
<213> ORGANISM: Artificial Sequence
<220> FEATURE:
<223> OTHER INFORMATION: antibody sequence

<400> SEQUENCE: 54

Gly Val Ser Asn Arg Phe Ser Gly Ser Lys Ser Gly Asn Thr Ala Ser

```
1               5                  10                 15
Leu Thr Ile Ser Gly Leu Gln Ala Glu Asp Glu Ala Asp Tyr Tyr Cys
            20                 25                 30
```

<210> SEQ ID NO 55
<211> LENGTH: 10
<212> TYPE: PRT
<213> ORGANISM: Artificial Sequence
<220> FEATURE:
<223> OTHER INFORMATION: antibody sequence

<400> SEQUENCE: 55

```
Phe Gly Gly Gly Thr Lys Val Thr Val Leu
1               5                  10
```

<210> SEQ ID NO 56
<211> LENGTH: 756
<212> TYPE: DNA
<213> ORGANISM: Artificial Sequence
<220> FEATURE:
<223> OTHER INFORMATION: antibody sequence

<400> SEQUENCE: 56

```
caggtccagc tggtacagtc tgggggaggc gtggtccagc ctggagggtc cctgagactc      60
tcctgtgcag cctctggatt caccttcagt agctatggca tgcactgggt ccgccaggct     120
ccaggcaagg ggctggagtg ggtggcagtt atatcatatg atggaagtaa taaatactat     180
gcagactccg tgaagggccg attcaccatc tccagagaca attccaagaa cacgctgtat     240
ctgcaaatga acagcctgag agctgaggac acggctgtgt attactgtgc gaaagatctt     300
ccgattaccc gcgggacagg ggctgactac tggggccagg gaaccctggt cactgtctcc     360
tcaaagcttt cagggagtgc atccgcccca aaacttgaag aaggtgaatt ttcagaagca     420
cgcgtacagt ctgtcctgat tcagcctgcc tccgtgtctg ggtctcctgg acagtcgatc     480
accatctcct gcactggaac cagcagtgac gttggtggtt ataactatgt ctcctggtat     540
caacaacacc caggcaaagc ccccagactc atgatttacg atgtcactag tcggccctca     600
ggggtttcga atcgcttctc tggctccaag tctggcaaca cggcctccct gaccatctct     660
gggctccagg ctgaggacga ggctgattat tactgcagtt catatgcagg cagctacagc     720
gtggtattcg gcggagggac caaggtcacc gtccta                                756
```

<210> SEQ ID NO 57
<211> LENGTH: 252
<212> TYPE: PRT
<213> ORGANISM: Artificial Sequence
<220> FEATURE:
<223> OTHER INFORMATION: antibody sequence

<400> SEQUENCE: 57

```
Gln Val Gln Leu Val Gln Ser Gly Gly Gly Val Val Gln Pro Gly Arg
1               5                  10                 15

Ser Leu Arg Leu Ser Cys Ala Ala Ser Gly Phe Thr Phe Ser Ser Tyr
            20                 25                 30

Gly Met His Trp Val Arg Gln Ala Pro Gly Lys Gly Leu Glu Trp Val
        35                 40                 45

Ala Val Ile Ser Tyr Asp Gly Ser Asn Lys Tyr Tyr Ala Asp Ser Val
    50                 55                 60

Lys Gly Arg Phe Thr Ile Ser Arg Asp Asn Ser Lys Asn Thr Leu Tyr
65                 70                 75                 80

Leu Gln Met Asn Ser Leu Arg Ala Glu Asp Thr Ala Val Tyr Tyr Cys
```

```
                            85                  90                  95
Ala Lys Asp Leu Pro Ile Thr Arg Gly Thr Gly Ala Asp Tyr Trp Gly
                100                 105                 110

Gln Gly Thr Leu Val Thr Val Ser Ser Lys Leu Ser Gly Ser Ala Ser
            115                 120                 125

Ala Pro Lys Leu Glu Glu Gly Glu Phe Ser Glu Ala Arg Val Gln Ser
        130                 135                 140

Val Leu Ile Gln Pro Ala Ser Val Ser Gly Ser Pro Gly Gln Ser Ile
145                 150                 155                 160

Thr Ile Ser Cys Thr Gly Thr Ser Ser Asp Val Gly Gly Tyr Asn Tyr
                165                 170                 175

Val Ser Trp Tyr Gln Gln His Pro Gly Lys Ala Pro Arg Leu Met Ile
            180                 185                 190

Tyr Asp Val Thr Ser Arg Pro Ser Gly Val Ser Asn Arg Phe Ser Gly
        195                 200                 205

Ser Lys Ser Gly Asn Thr Ala Ser Leu Thr Ile Ser Gly Leu Gln Ala
    210                 215                 220

Glu Asp Glu Ala Asp Tyr Tyr Cys Ser Ser Tyr Ala Gly Ser Tyr Ser
225                 230                 235                 240

Val Val Phe Gly Gly Gly Thr Lys Val Thr Val Leu
                245                 250

<210> SEQ ID NO 58
<211> LENGTH: 30
<212> TYPE: PRT
<213> ORGANISM: Artificial Sequence
<220> FEATURE:
<223> OTHER INFORMATION: antibody sequence

<400> SEQUENCE: 58

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr
            20                  25                  30

<210> SEQ ID NO 59
<211> LENGTH: 14
<212> TYPE: PRT
<213> ORGANISM: Artificial Sequence
<220> FEATURE:
<223> OTHER INFORMATION: antibody sequence

<400> SEQUENCE: 59

Trp Val Arg Gln Ala Pro Gly Gln Gly Leu Glu Trp Met Gly
1               5                   10

<210> SEQ ID NO 60
<211> LENGTH: 32
<212> TYPE: PRT
<213> ORGANISM: Artificial Sequence
<220> FEATURE:
<223> OTHER INFORMATION: antibody sequence

<400> SEQUENCE: 60

Arg Val Thr Met Thr Arg Asp Thr Ser Ile Ser Thr Ala Tyr Met Glu
1               5                   10                  15

Leu Ser Arg Leu Arg Ser Asp Asp Thr Ala Val Tyr Tyr Cys Ala Arg
            20                  25                  30

<210> SEQ ID NO 61
<211> LENGTH: 11
```

```
<212> TYPE: PRT
<213> ORGANISM: Artificial Sequence
<220> FEATURE:
<223> OTHER INFORMATION: antibody sequence

<400> SEQUENCE: 61

Trp Gly Gln Gly Thr Met Val Thr Val Ser Ser
1               5                   10

<210> SEQ ID NO 62
<211> LENGTH: 21
<212> TYPE: PRT
<213> ORGANISM: Artificial Sequence
<220> FEATURE:
<223> OTHER INFORMATION: antibody sequence

<400> SEQUENCE: 62

Lys Leu Ser Gly Ser Ala Ser Ala Pro Lys Leu Glu Glu Gly Glu Phe
1               5                   10                  15

Ser Glu Ala Arg Val
            20

<210> SEQ ID NO 63
<211> LENGTH: 23
<212> TYPE: PRT
<213> ORGANISM: Artificial Sequence
<220> FEATURE:
<223> OTHER INFORMATION: antibody sequence

<400> SEQUENCE: 63

Asp Ile Gln Met Thr Gln Ser Pro Ser Thr Leu Ser Ala Ser Val Gly
1               5                   10                  15

Asp Arg Val Thr Ile Thr Cys
            20

<210> SEQ ID NO 64
<211> LENGTH: 15
<212> TYPE: PRT
<213> ORGANISM: Artificial Sequence
<220> FEATURE:
<223> OTHER INFORMATION: antibody sequence

<400> SEQUENCE: 64

Trp Tyr Gln Gln Lys Pro Gly Lys Gly Pro Asn Leu Leu Ile Tyr
1               5                   10                  15

<210> SEQ ID NO 65
<211> LENGTH: 32
<212> TYPE: PRT
<213> ORGANISM: Artificial Sequence
<220> FEATURE:
<223> OTHER INFORMATION: antibody sequence

<400> SEQUENCE: 65

Gly Val Pro Ser Arg Phe Ser Gly Ser Gly Ser Gly Thr Glu Phe Thr
1               5                   10                  15

Leu Thr Ile Ser Ser Leu Gln Pro Glu Asp Ser Ala Thr Tyr Tyr Cys
            20                  25                  30

<210> SEQ ID NO 66
<211> LENGTH: 10
<212> TYPE: PRT
<213> ORGANISM: Artificial Sequence
<220> FEATURE:
<223> OTHER INFORMATION: antibody sequence

<400> SEQUENCE: 66
```

Phe Gly Gly Gly Thr Lys Leu Glu Ile Lys
1               5                   10

<210> SEQ ID NO 67
<211> LENGTH: 765
<212> TYPE: DNA
<213> ORGANISM: Artificial Sequence
<220> FEATURE:
<223> OTHER INFORMATION: antibody sequence

<400> SEQUENCE: 67
caggtccagc ttgtgcagtc tggggctgag gtgaagaagc tggggcctc  agtgaaggtc    60
tcctgcaagg cttctggata caccttcacc ggctactata tgcactgggt gcgacaggcc   120
cctggacaag gcttgagtg gatgggacgg atcaaccctaa cagtggtgg cacaaactat   180
gcacagaagt tcagggcag ggtcaccatg accagggaca cgtccatcag cacagcctac   240
atggagctga gcaggctgag atctgacgac acggccgtgt attactgcgc gaggcgtaac   300
ctgatagcag ctcgtccccg gaatcggggc agggatgctt ttgatatctg gggccaaggg   360
acaatggtca ccgtctcttc aaagctttca gggagtgcat ccgccccaaa acttgaagaa   420
ggtgaatttt cagaagcacg cgtagacatc cagatgaccc agtctccttc caccctgtct   480
gcatctgtag gagacagagt caccatcact tgccgggcca gtcagagtat tggtggctcg   540
ttggcctggt atcagcagaa accagggaaa ggccctaacc tcctgatcta tgctgcatcc   600
actttgcaaa gtggggtccc atcaaggttc agcggcagtg gatctgggac agaattcact   660
ctcacaatca gcagcctgca gcctgaagat tctgcaactt actactgcca acactatgaa   720
agttatcccc tctctttcgg cggcgggacc aagctggaga tcaaa               765

<210> SEQ ID NO 68
<211> LENGTH: 255
<212> TYPE: PRT
<213> ORGANISM: Artificial Sequence
<220> FEATURE:
<223> OTHER INFORMATION: antibody sequence

<400> SEQUENCE: 68

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
                20                  25                  30

Tyr Met His Trp Val Arg Gln Ala Pro Gly Gln Gly Leu Glu Trp Met
            35                  40                  45

Gly Arg Ile Asn Pro Asn Ser Gly Gly Thr Asn Tyr Ala Gln Lys Phe
        50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Arg Asn Leu Ile Ala Ala Arg Pro Arg Asn Arg Gly Arg Asp
            100                 105                 110

Ala Phe Asp Ile Trp Gly Gln Gly Thr Met Val Thr Val Ser Ser Lys
        115                 120                 125

Leu Ser Gly Ser Ala Ser Ala Pro Lys Leu Glu Glu Gly Glu Phe Ser
    130                 135                 140

Glu Ala Arg Val Asp Ile Gln Met Thr Gln Ser Pro Ser Thr Leu Ser
145                 150                 155                 160

```
Ala Ser Val Gly Asp Arg Val Thr Ile Thr Cys Arg Ala Ser Gln Ser
                165                 170                 175

Ile Gly Gly Ser Leu Ala Trp Tyr Gln Gln Lys Pro Gly Lys Gly Pro
            180                 185                 190

Asn Leu Leu Ile Tyr Ala Ala Ser Thr Leu Gln Ser Gly Val Pro Ser
        195                 200                 205

Arg Phe Ser Gly Ser Gly Ser Gly Thr Glu Phe Thr Leu Thr Ile Ser
    210                 215                 220

Ser Leu Gln Pro Glu Asp Ser Ala Thr Tyr Tyr Cys Gln His Tyr Glu
225                 230                 235                 240

Ser Tyr Pro Leu Ser Phe Gly Gly Thr Lys Leu Glu Ile Lys
                245                 250                 255
```

<210> SEQ ID NO 69
<211> LENGTH: 124
<212> TYPE: PRT
<213> ORGANISM: Artificial Sequence
<220> FEATURE:
<223> OTHER INFORMATION: antibody sequence

<400> SEQUENCE: 69

```
Gln Val Gln Leu Gln Glu Ser Gly Gly Gly Leu Val His Pro Gly Gly
1               5                   10                  15

Ser Leu Arg Leu Ser Cys Ala Ala Ser Gly Phe Thr Phe Ser Ser Tyr
            20                  25                  30

Trp Met His Trp Val Arg Gln Ala Pro Gly Lys Gly Leu Val Trp Val
        35                  40                  45

Ser Arg Ile Asn Ser Asp Gly Ser Ser Thr Ser Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Lys Ile Leu Gly Val Gly Ala Arg Ser Arg Arg Tyr Phe Asp
            100                 105                 110

Tyr Trp Gly Gln Gly Thr Met Val Thr Val Ser Ser
        115                 120
```

<210> SEQ ID NO 70
<211> LENGTH: 108
<212> TYPE: PRT
<213> ORGANISM: Artificial Sequence
<220> FEATURE:
<223> OTHER INFORMATION: antibody sequence

<400> SEQUENCE: 70

```
Glu Thr Thr Leu Thr Gln Ser Pro Gly Thr Leu Ser Leu Ser Pro Gly
1               5                   10                  15

Glu Arg Ala Thr Leu Ser Cys Arg Ala Ser Gln Ser Val Val Ser Asn
            20                  25                  30

Tyr Leu Ala Trp Tyr Gln Gln Lys Pro Gly Gln Ala Pro Arg Leu Leu
        35                  40                  45

Ile Ser Gly Ala Ser Asn Arg Ala Thr Gly Ile Ser Asp Arg Phe Ser
    50                  55                  60

Gly Ser Gly Ser Gly Ala Asp Phe Thr Leu Thr Ile Ser Arg Val Glu
65                  70                  75                  80

Pro Glu Asp Ser Ala Val Tyr Tyr Cys Gln Gln Phe Asp Lys Ser Thr
                85                  90                  95
```

```
Trp Thr Phe Gly Gln Gly Thr Lys Val Glu Ile Lys
            100                 105

<210> SEQ ID NO 71
<211> LENGTH: 121
<212> TYPE: PRT
<213> ORGANISM: Artificial Sequence
<220> FEATURE:
<223> OTHER INFORMATION: antibody sequence

<400> SEQUENCE: 71

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Arg Glu Arg Trp Leu Gln Ser Ala Gly Asp Tyr Trp Gly
            100                 105                 110

Gln Gly Thr Leu Val Thr Val Ser Ser
        115                 120

<210> SEQ ID NO 72
<211> LENGTH: 108
<212> TYPE: PRT
<213> ORGANISM: Artificial Sequence
<220> FEATURE:
<223> OTHER INFORMATION: antibody sequence

<400> SEQUENCE: 72

Gln Pro Val Leu Thr Gln Ser Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Trp Val Phe Gly Gly Gly Thr Lys Leu Thr Val Leu
            100                 105

<210> SEQ ID NO 73
<211> LENGTH: 121
<212> TYPE: PRT
<213> ORGANISM: Artificial Sequence
<220> FEATURE:
<223> OTHER INFORMATION: antibody sequence

<400> SEQUENCE: 73

Gln Val Gln Leu Val Gln Ser Gly Gly Gly Val Val Gln Pro Gly Arg
1               5                   10                  15
```

```
Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Lys Asp Leu Pro Ile Thr Arg Gly Thr Gly Ala Asp Tyr Trp Gly
            100                 105                 110

Gln Gly Thr Leu Val Thr Val Ser Ser
            115                 120

<210> SEQ ID NO 74
<211> LENGTH: 110
<212> TYPE: PRT
<213> ORGANISM: Artificial Sequence
<220> FEATURE:
<223> OTHER INFORMATION: antibody sequence

<400> SEQUENCE: 74

Gln Ser Val Leu Ile Gln Pro Ala Ser Val Ser Gly Ser Pro Gly Gln
 1               5                  10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Arg Leu
            35                  40                  45

Met Ile Tyr Asp Val Thr Ser Arg Pro Ser Gly Val Ser Asn Arg Phe
 50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Ser Ser Tyr Ala Gly Ser
                85                  90                  95

Tyr Ser Val Val Phe Gly Gly Gly Thr Lys Val Thr Val Leu
            100                 105                 110

<210> SEQ ID NO 75
<211> LENGTH: 127
<212> TYPE: PRT
<213> ORGANISM: Artificial Sequence
<220> FEATURE:
<223> OTHER INFORMATION: antibody sequence

<400> SEQUENCE: 75

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
            35                  40                  45

Gly Arg Ile Asn Pro Asn Ser Gly Gly Thr Asn Tyr Ala Gln Lys Phe
 50                  55                  60

Gln Gly Arg Val Thr Met Thr Arg Asp Thr Ser Ile Ser Thr Ala Tyr
 65                  70                  75                  80

Met Glu Leu Ser Arg Leu Arg Ser Asp Asp Thr Ala Val Tyr Tyr Cys
                85                  90                  95
```

Ala Arg Arg Asn Leu Ile Ala Ala Arg Pro Arg Asn Arg Gly Arg Asp
            100                 105                 110

Ala Phe Asp Ile Trp Gly Gln Gly Thr Met Val Thr Val Ser Ser
            115                 120                 125

<210> SEQ ID NO 76
<211> LENGTH: 107
<212> TYPE: PRT
<213> ORGANISM: Artificial Sequence
<220> FEATURE:
<223> OTHER INFORMATION: antibody sequence

<400> SEQUENCE: 76

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Gly Gly Ser
            20                  25                  30

Leu Ala Trp Tyr Gln Gln Lys Pro Gly Lys Pro Asn Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65              70                  75                  80

Glu Asp Ser Ala Thr Tyr Tyr Cys Gln His Tyr Glu Ser Tyr Pro Leu
                85                  90                  95

Ser Phe Gly Gly Gly Thr Lys Leu Glu Ile Lys
            100                 105

<210> SEQ ID NO 77
<211> LENGTH: 372
<212> TYPE: DNA
<213> ORGANISM: Artificial Sequence
<220> FEATURE:
<223> OTHER INFORMATION: antibody sequence

<400> SEQUENCE: 77
caggtgcagc tgcaggagtc cggggggggc ttagttcacc ctggggggtc cctgagactc    60
tcctgtgcag cctctggatt caccttcagt agctactgga tgcactgggt ccgccaagct   120
ccagggaagg ggctggtgtg gtctcacgt attaatagtg atgggagtag cacaagctac   180
gcggactccg tgaagggccg attcaccatc tccagagaca acgccaagaa cacgctgtat   240
ctgcaaatga acagtctgag agccgaggac acggctgtgt attactgtgc gagaaaaatc   300
ttgggggtgg gagctaggtc tcgtcgttac tttgactact ggggccaggg aacaatggtc   360
accgtctctt ca                                                      372

<210> SEQ ID NO 78
<211> LENGTH: 324
<212> TYPE: DNA
<213> ORGANISM: Artificial Sequence
<220> FEATURE:
<223> OTHER INFORMATION: antibody sequence

<400> SEQUENCE: 78
gaaacgacac tcacgcagtc tccaggcacc ctgtctttgt ctccagggga aagagccacc    60
ctctcctgca gggccagtca gagtgttgtc agcaactatt tagcctggta ccagcagaag   120
cctggccagg ctcccaggct cctcatctct ggtgcatcca acagggccac tggcatctca   180
gacaggttca gtggcagtgg gtctgggaca gacttcactc tcaccatcag cagagtcgag   240

```
cctgaagact cagcagtgta ttactgtcaa cagtttgata agtccacgtg gacgttcggc    300
caagggacca aggtggaaat caaa                                           324
```

<210> SEQ ID NO 79
<211> LENGTH: 363
<212> TYPE: DNA
<213> ORGANISM: Artificial Sequence
<220> FEATURE:
<223> OTHER INFORMATION: antibody sequence

<400> SEQUENCE: 79

```
caggtccagc ttgtgcagtc tggggctgag gtgaagaagc ctgggtcctc ggtgaaggtc     60
tcctgcaagg cttctggagg caccttcagc agctatgcta tcagctgggt gcgacaggcc    120
cctggacaag gcttgagtg gatgggaggg atcatccta tctttggtac agcaaactac     180
gcacagaagt tccagggcag agtcacgatt accgcggacg aatccacgag cacagcctac    240
atggagctga ggagcctgag atctgacgac acggccgtgt attactgtgc gagagatcgg    300
gagagatggc tacaatccgc gggcgactac tggggccagg aaccctggt cactgtctcc    360 tca                                                                  363
```

<210> SEQ ID NO 80
<211> LENGTH: 324
<212> TYPE: DNA
<213> ORGANISM: Artificial Sequence
<220> FEATURE:
<223> OTHER INFORMATION: antibody sequence

<400> SEQUENCE: 80

```
cagcctgtgc tgactcagtc accctcggtg tcagtggccc caggacagac ggccaggatt     60
acctgtgggg gaaacaacat tggaagtaaa agtgtgcact ggtaccagca gaagccaggc    120
caggcccctg tgctggtcgt ctatgatgat agcgaccggc cctcagggat ccctgagcga    180
ttctctggct ccaactctgg gaacacggcc accctgacca tcagcaggt cgaagccggg    240 gatgaggccg actattactg tcaggtgtgg gatagtagta gtgatcattg ggtgttcggc    300
ggagggacca agctgaccgt ccta                                           324
```

<210> SEQ ID NO 81
<211> LENGTH: 363
<212> TYPE: DNA
<213> ORGANISM: Artificial Sequence
<220> FEATURE:
<223> OTHER INFORMATION: antibody sequence

<400> SEQUENCE: 81

```
caggtccagc tggtacagtc tgggggaggc gtggtccagc ctggggaggtc cctgagactc     60 tcctgtgcag cctctggatt caccttcagt agctatggca tgcactgggt ccgccaggct    120
ccaggcaagg gctggagtg ggtggcagtt atatcatatg atggaagtaa taaatactat    180
gcagactccg tgaagggccg attcaccatc tccagagaca attccaagaa cacgctgtat    240
ctgcaaatga acagcctgag agctgaggac acggctgtgt attactgtgc gaaagatctt    300
ccgattaccc gcgggacagg ggctgactac tggggccagg aaccctggt cactgtctcc    360 tca                                                                  363
```

<210> SEQ ID NO 82
<211> LENGTH: 330
<212> TYPE: DNA
<213> ORGANISM: Artificial Sequence
<220> FEATURE:

-continued

<223> OTHER INFORMATION: antibody sequence

<400> SEQUENCE: 82

| cagtctgtcc | tgattcagcc | tgcctccgtg | tctgggtctc | ctggacagtc | gatcaccatc | 60 |
| tcctgcactg | gaaccagcag | tgacgttggt | ggttataact | atgtctcctg | gtatcaacaa | 120 |
| cacccaggca | agcccccag | actcatgatt | tacgatgtca | ctagtcggcc | ctcaggggtt | 180 |
| tcgaatcgct | tctctggctc | caagtctggc | aacacggcct | ccctgaccat | ctctgggctc | 240 |
| caggctgagg | acgaggctga | ttattactgc | agttcatatg | caggcagcta | cagcgtggta | 300 |
| ttcggcggag | ggaccaaggt | caccgtccta | | | | 330 |

<210> SEQ ID NO 83
<211> LENGTH: 381
<212> TYPE: DNA
<213> ORGANISM: Artificial Sequence
<220> FEATURE:
<223> OTHER INFORMATION: antibody sequence

<400> SEQUENCE: 83

| caggtccagc | ttgtgcagtc | tggggctgag | gtgaagaagc | ctggggcctc | agtgaaggtc | 60 |
| tcctgcaagg | cttctggata | caccttcacc | ggctactata | tgcactgggt | gcgacaggcc | 120 |
| cctggacaag | ggcttgagtg | gatgggacgg | atcaacccta | acagtggtgg | cacaaactat | 180 |
| gcacagaagt | ttcagggcag | ggtcaccatg | accagggaca | cgtccatcag | cacagcctac | 240 |
| atggagctga | gcaggctgag | atctgacgac | acggccgtgt | attactgcgc | gaggcgtaac | 300 |
| ctgatagcag | ctcgtccccg | gaatcggggc | agggatgctt | tgatatctg | gggccaaggg | 360 |
| acaatggtca | ccgtctcttc | a | | | | 381 |

<210> SEQ ID NO 84
<211> LENGTH: 321
<212> TYPE: DNA
<213> ORGANISM: Artificial Sequence
<220> FEATURE:
<223> OTHER INFORMATION: antibody sequence

<400> SEQUENCE: 84

| gacatccaga | tgacccagtc | tccttccacc | ctgtctgcat | ctgtaggaga | cagagtcacc | 60 |
| atcacttgcc | gggccagtca | gagtattggt | ggctcgttgg | cctggtatca | gcagaaacca | 120 |
| gggaaaggcc | ctaacctcct | gatctatgct | gcatccactt | tgcaaagtgg | ggtcccatca | 180 |
| aggttcagcg | gcagtggatc | tgggacagaa | ttcactctca | caatcagcag | cctgcagcct | 240 |
| gaagattctg | caacttacta | ctgccaacac | tatgaaagtt | atcccctctc | tttcggcggc | 300 |
| gggaccaagc | tggagatcaa | a | | | | 321 |

<210> SEQ ID NO 85
<211> LENGTH: 5
<212> TYPE: PRT
<213> ORGANISM: Artificial Sequence
<220> FEATURE:
<223> OTHER INFORMATION: antibody sequence

<400> SEQUENCE: 85

Ser Tyr Trp Met His
1               5

<210> SEQ ID NO 86
<211> LENGTH: 17
<212> TYPE: PRT
<213> ORGANISM: Artificial Sequence

```
<220> FEATURE:
<223> OTHER INFORMATION: antibody sequence

<400> SEQUENCE: 86

Arg Ile Asn Ser Asp Gly Ser Ser Thr Ser Tyr Ala Asp Ser Val Lys
1               5                   10                  15

Gly

<210> SEQ ID NO 87
<211> LENGTH: 15
<212> TYPE: PRT
<213> ORGANISM: Artificial Sequence
<220> FEATURE:
<223> OTHER INFORMATION: antibody sequence

<400> SEQUENCE: 87

Lys Ile Leu Gly Val Gly Ala Arg Ser Arg Arg Tyr Phe Asp Tyr
1               5                   10                  15

<210> SEQ ID NO 88
<211> LENGTH: 17
<212> TYPE: PRT
<213> ORGANISM: Artificial Sequence
<220> FEATURE:
<223> OTHER INFORMATION: antibody sequence

<400> SEQUENCE: 88

Lys Ser Ser Gln Ser Val Leu His Ser Ser Asn Asn Lys Asn Tyr Leu
1               5                   10                  15

Ala

<210> SEQ ID NO 89
<211> LENGTH: 7
<212> TYPE: PRT
<213> ORGANISM: Artificial Sequence
<220> FEATURE:
<223> OTHER INFORMATION: antibody sequence

<400> SEQUENCE: 89

Trp Ala Ser Thr Arg Glu Ser
1               5

<210> SEQ ID NO 90
<211> LENGTH: 9
<212> TYPE: PRT
<213> ORGANISM: Artificial Sequence
<220> FEATURE:
<223> OTHER INFORMATION: antibody sequence

<400> SEQUENCE: 90

Leu Gln Tyr Ser Thr Phe Pro Arg Thr
1               5

<210> SEQ ID NO 91
<211> LENGTH: 30
<212> TYPE: PRT
<213> ORGANISM: Artificial Sequence
<220> FEATURE:
<223> OTHER INFORMATION: antibody sequence

<400> SEQUENCE: 91

Gln Val Gln Leu Gln Glu Ser Gly Gly Gly Leu Val His Pro Gly Gly
1               5                   10                  15

Ser Leu Arg Leu Ser Cys Ala Ala Ser Gly Phe Thr Phe Ser
            20                  25                  30
```

```
<210> SEQ ID NO 92
<211> LENGTH: 14
<212> TYPE: PRT
<213> ORGANISM: Artificial Sequence
<220> FEATURE:
<223> OTHER INFORMATION: antibody sequence

<400> SEQUENCE: 92

Trp Val Arg Gln Ala Pro Gly Lys Gly Leu Val Trp Val Ser
1               5                   10

<210> SEQ ID NO 93
<211> LENGTH: 32
<212> TYPE: PRT
<213> ORGANISM: Artificial Sequence
<220> FEATURE:
<223> OTHER INFORMATION: antibody sequence

<400> SEQUENCE: 93

Arg Phe Thr Ile Ser Arg Asp Asn Ala Lys Asn Thr Leu Tyr Leu Gln
1               5                   10                  15

Met Asn Ser Leu Arg Ala Glu Asp Thr Ala Val Tyr Tyr Cys Ala Arg
            20                  25                  30

<210> SEQ ID NO 94
<211> LENGTH: 11
<212> TYPE: PRT
<213> ORGANISM: Artificial Sequence
<220> FEATURE:
<223> OTHER INFORMATION: antibody sequence

<400> SEQUENCE: 94

Trp Gly Gln Gly Thr Met Val Thr Val Ser Ser
1               5                   10

<210> SEQ ID NO 95
<211> LENGTH: 21
<212> TYPE: PRT
<213> ORGANISM: Artificial Sequence
<220> FEATURE:
<223> OTHER INFORMATION: antibody sequence

<400> SEQUENCE: 95

Lys Leu Ser Gly Ser Ala Ser Ala Pro Lys Leu Glu Glu Gly Glu Phe
1               5                   10                  15

Ser Glu Ala Arg Val
            20

<210> SEQ ID NO 96
<211> LENGTH: 23
<212> TYPE: PRT
<213> ORGANISM: Artificial Sequence
<220> FEATURE:
<223> OTHER INFORMATION: antibody sequence

<400> SEQUENCE: 96

Asp Ile Val Leu Thr Gln Thr Pro Asp Ser Leu Ala Val Ser Leu Gly
1               5                   10                  15

Glu Thr Thr Thr Ile Asn Cys
            20

<210> SEQ ID NO 97
<211> LENGTH: 15
<212> TYPE: PRT
<213> ORGANISM: Artificial Sequence
<220> FEATURE:
```

<223> OTHER INFORMATION: antibody sequence

<400> SEQUENCE: 97

Trp Tyr Gln Gln Lys Pro Gly Gln Pro Pro Lys Leu Leu Ile Tyr
1               5                   10                  15

<210> SEQ ID NO 98
<211> LENGTH: 32
<212> TYPE: PRT
<213> ORGANISM: Artificial Sequence
<220> FEATURE:
<223> OTHER INFORMATION: antibody sequence

<400> SEQUENCE: 98

Gly Val Pro Asp Arg Phe Ser Gly Ser Gly Ser Gly Thr Asp Phe Thr
1               5                   10                  15
Leu Thr Ile Ser Asn Leu Gln Pro Glu Asp Val Ala Phe Tyr Tyr Cys
            20                  25                  30

<210> SEQ ID NO 99
<211> LENGTH: 10
<212> TYPE: PRT
<213> ORGANISM: Artificial Sequence
<220> FEATURE:
<223> OTHER INFORMATION: antibody sequence

<400> SEQUENCE: 99

Phe Gly Gln Gly Thr Lys Val Glu Ile Lys
1               5                   10

<210> SEQ ID NO 100
<211> LENGTH: 774
<212> TYPE: DNA
<213> ORGANISM: Artificial Sequence
<220> FEATURE:
<223> OTHER INFORMATION: antibody sequence

<400> SEQUENCE: 100

```
caggtgcagc tgcaggagtc cggggggaggc ttagttcacc ctgggggtc cctgagactc      60
tcctgtgcag cctctggatt caccttcagt agctactgga tgcactgggt ccgccaagct     120
ccagggaagg gctggtgtg gtctcacgt attaatagtg atgggagtag cacaagctac      180
gcggactccg tgaagggccg attcaccatc tccagagaca cgccaagaa cacgctgtat     240
ctgcaaatga acagtctgag agccgaggac acggctgtgt attactgtgc gagaaaaatc     300
ttggggggtgg gagctaggtc tcgtcgttac tttgactact ggggccaggg aacaatggtc     360
accgtctctt caaagctttc agggagtgca tccgccccaa aacttgaaga aggtgaattt     420
tcagaagcac gcgtagatat tgtgctgacc cagactccag actccctggc tgtgtctctg     480
ggcgagacga ccaccatcaa ctgcaagtcc agccagagtg ttttacacag ctccaacaat     540
aagaactact tagcttggta ccagcagaaa ccaggacagc ctcctaagct gctcatttac     600
tgggcatcta cccgggaatc cggggtccct gaccgattca gtggcagcgg gtctgggaca     660
gatttcactc tcaccatcag caacctgcag cctgaagatg tggcttttta ctactgtctg     720
caatattcta cttttcctcg acgttcggc caagggacca aggtggagat caaa            774
```

<210> SEQ ID NO 101
<211> LENGTH: 258
<212> TYPE: PRT
<213> ORGANISM: Artificial Sequence
<220> FEATURE:
<223> OTHER INFORMATION: antibody sequence

```
<400> SEQUENCE: 101

Gln Val Gln Leu Gln Glu Ser Gly Gly Gly Leu Val His Pro Gly Gly
1               5                   10                  15

Ser Leu Arg Leu Ser Cys Ala Ala Ser Gly Phe Thr Phe Ser Ser Tyr
            20                  25                  30

Trp Met His Trp Val Arg Gln Ala Pro Gly Lys Gly Leu Val Trp Val
        35                  40                  45

Ser Arg Ile Asn Ser Asp Gly Ser Ser Thr Ser Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Lys Ile Leu Gly Val Gly Ala Arg Ser Arg Arg Tyr Phe Asp
            100                 105                 110

Tyr Trp Gly Gln Gly Thr Met Val Thr Val Ser Ser Lys Leu Ser Gly
        115                 120                 125

Ser Ala Ser Ala Pro Lys Leu Glu Glu Gly Glu Phe Ser Glu Ala Arg
    130                 135                 140

Val Asp Ile Val Leu Thr Gln Thr Pro Asp Ser Leu Ala Val Ser Leu
145                 150                 155                 160

Gly Glu Thr Thr Thr Ile Asn Cys Lys Ser Ser Gln Ser Val Leu His
                165                 170                 175

Ser Ser Asn Asn Lys Asn Tyr Leu Ala Trp Tyr Gln Gln Lys Pro Gly
            180                 185                 190

Gln Pro Pro Lys Leu Leu Ile Tyr Trp Ala Ser Thr Arg Glu Ser Gly
        195                 200                 205

Val Pro Asp Arg Phe Ser Gly Ser Gly Ser Gly Thr Asp Phe Thr Leu
    210                 215                 220

Thr Ile Ser Asn Leu Gln Pro Glu Asp Val Ala Phe Tyr Tyr Cys Leu
225                 230                 235                 240

Gln Tyr Ser Thr Phe Pro Arg Thr Phe Gly Gln Gly Thr Lys Val Glu
                245                 250                 255

Ile Lys

<210> SEQ ID NO 102
<211> LENGTH: 124
<212> TYPE: PRT
<213> ORGANISM: Artificial Sequence
<220> FEATURE:
<223> OTHER INFORMATION: antibody sequence

<400> SEQUENCE: 102

Gln Val Gln Leu Gln Glu Ser Gly Gly Gly Leu Val His Pro Gly Gly
1               5                   10                  15

Ser Leu Arg Leu Ser Cys Ala Ala Ser Gly Phe Thr Phe Ser Ser Tyr
            20                  25                  30

Trp Met His Trp Val Arg Gln Ala Pro Gly Lys Gly Leu Val Trp Val
        35                  40                  45

Ser Arg Ile Asn Ser Asp Gly Ser Ser Thr Ser Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95
```

```
Ala Arg Lys Ile Leu Gly Val Gly Ala Arg Ser Arg Tyr Phe Asp
            100                 105                 110

Tyr Trp Gly Gln Gly Thr Met Val Thr Val Ser Ser
            115                 120
```

<210> SEQ ID NO 103
<211> LENGTH: 113
<212> TYPE: PRT
<213> ORGANISM: Artificial Sequence
<220> FEATURE:
<223> OTHER INFORMATION: antibody sequence

<400> SEQUENCE: 103

```
Asp Ile Val Leu Thr Gln Thr Pro Asp Ser Leu Ala Val Ser Leu Gly
1               5                  10                  15

Glu Thr Thr Thr Ile Asn Cys Lys Ser Ser Gln Ser Val Leu His Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Asn Leu Gln Pro Glu Asp Val Ala Phe Tyr Tyr Cys Leu Gln
                85                  90                  95

Tyr Ser Thr Phe Pro Arg Thr Phe Gly Gln Gly Thr Lys Val Glu Ile
            100                 105                 110

Lys
```

<210> SEQ ID NO 104
<211> LENGTH: 372
<212> TYPE: DNA
<213> ORGANISM: Artificial Sequence
<220> FEATURE:
<223> OTHER INFORMATION: antibody sequence

<400> SEQUENCE: 104

```
caggtgcagc tgcaggagtc cgggggaggc ttagttcacc ctggggggtc cctgagactc        60
tcctgtgcag cctctggatt caccttcagt agctactgga tgcactgggt ccgccaagct       120
ccagggaagg ggctggtgtg ggtctcacgt attaatagtg atgggagtag cacaagctac       180
gcggactccg tgaagggccg attcaccatc tccagagaca acgccaagaa cacgctgtat       240
ctgcaaatga acagtctgag agccgaggac acggctgtgt attactgtgc gagaaaaatc       300
ttgggggtgg gagctaggtc tcgtcgttac tttgactact ggggccaggg aacaatggtc       360
accgtctctt ca                                                           372
```

<210> SEQ ID NO 105
<211> LENGTH: 339
<212> TYPE: DNA
<213> ORGANISM: Artificial Sequence
<220> FEATURE:
<223> OTHER INFORMATION: antibody sequence

<400> SEQUENCE: 105

```
gatattgtgc tgacccagac tccagactcc ctggctgtgt ctctgggcga cgaccacc         60 atcaactgca gtccagcca gagtgtttta cacagctcca acaataagaa ctacttagct       120
tggtaccagc agaaaccagg acagcctcct aagctgctca tttactgggc atctacccgg      180
gaatccgggg tccctgaccg attcagtggc agcgggtctg ggacagattt cactctcacc      240
```

| | |
|---|---|
| atcagcaacc tgcagcctga agatgtggct ttttactact gtctgcaata ttctactttt | 300 |
| cctcggacgt tcggccaagg gaccaaggtg gagatcaaa | 339 |

<210> SEQ ID NO 106
<211> LENGTH: 1362
<212> TYPE: DNA
<213> ORGANISM: Artificial Sequence
<220> FEATURE:
<223> OTHER INFORMATION: antibody sequence

<400> SEQUENCE: 106

| | |
|---|---|
| caggtgcagc tgcaggagtc cgggggaggc ttagttcacc ctggggggtc cctgagactc | 60 |
| tcctgtgcag cctctggatt caccttcagt agctactgga tgcactgggt ccgccaagct | 120 |
| ccagggaagg ggctggtgtg ggtctcacgt attaatagtg atgggagtag cacaagctac | 180 |
| gcggactccg tgaagggccg attcaccatc tccagagaca acgccaagaa cacgctgtat | 240 |
| ctgcaaatga acagtctgag agccgaggac acggctgtgt attactgtgc gagaaaaatc | 300 |
| ttggggtgg gagctaggtc tcgtcgttac tttgactact ggggccaggg aacaatggtc | 360 |
| accgtctctt cagcctccac caagggccca tcggtcttcc cctggcacc ctcctccaag | 420 |
| agcacctctg ggggcacagc ggccctgggc tgcctggtca aggactactt ccccgaaccg | 480 |
| gtgacggtgt cgtggaactc aggcgccctg accagcggcg tgcacacctt cccggctgtc | 540 |
| ctacagtcct caggactcta ctccctcagc agcgtggtga ccgtgccctc agcagcttg | 600 |
| ggcacccaga cctacatctg caacgtgaat cacaagccca gcaacaccaa ggtggacaag | 660 |
| aaagttgagc ccaaatcttg tgacaaaact cacacatgcc caccgtgccc agcacctgaa | 720 |
| ctcctggggg gaccgtcagt cttcctcttc cccccaaaac ccaaggacac cctcatgatc | 780 |
| tcccggaccc ctgaggtcac atgcgtggtg gtggacgtga gccacgaaga ccctgaggtc | 840 |
| aagttcaact ggtacgtgga cggcgtggag gtgcataatg ccaagacaaa gccgcgggag | 900 |
| gagcagtaca acagcacgta ccgtgtggtc agcgtcctca ccgtcctgca ccaggactgg | 960 |
| ctgaatggca aggagtacaa gtgcaaggtc tccaacaaag ccctcccagc ccccatcgag | 1020 |
| aaaaccatct ccaaagccaa agggcagccc cgagaaccac aggtgtacac cctgccccca | 1080 |
| tcccgggatg agctgaccaa gaaccaggtc agcctgacct gcctggtcaa aggcttctat | 1140 |
| cccagcgaca tcgccgtgga gtgggagagc aatgggcagc cggagaacaa ctacaagacc | 1200 |
| acgcctcccg tgctggactc cgacggctcc ttcttcctct acagcaagct caccgtggac | 1260 |
| aagagcaggt ggcagcaggg gaacgtcttc tcatgctccg tgatgcatga ggctctgcac | 1320 |
| aaccactaca cgcagaagag cctctccctg tctccgggta aa | 1362 |

<210> SEQ ID NO 107
<211> LENGTH: 645
<212> TYPE: DNA
<213> ORGANISM: Artificial Sequence
<220> FEATURE:
<223> OTHER INFORMATION: antibody sequence

<400> SEQUENCE: 107

| | |
|---|---|
| gaaacgacac tcacgcagtc tccaggcacc ctgtctttgt ctccagggga aagagccacc | 60 |
| ctctcctgca gggccagtca gagtgttgtc agcaactatt tagcctggta ccagcagaag | 120 |
| cctggccagg ctcccaggct cctcatctct ggtgcatcca cagggccac tggcatctca | 180 |
| gacaggttca gtggcagtgg gtctggggca gacttcactc tcaccatcag cagagtcgag | 240 |
| cctgaagact cagcagtgta ttactgtcaa cagtttgata agtccacgtg gacgttcggc | 300 |

```
caagggacca aggtggaaat caaacgaact gtggctgcac catctgtctt catcttcccg    360
ccatctgatg agcagttgaa atctggaact gcctctgttg tgtgcctgct gaataacttc    420
tatcccagag aggccaaagt acagtggaag gtggataacg ccctccaatc gggtaactcc    480
caggagagtg tcacagagca ggacagcaag gacagcacct acagcctcag cagcaccctg    540
acgctgagca agcagactac gagaaacac  aaagtctacg cctgcgaagt cacccatcag    600
ggcctgagct cgcccgtcac aaagagcttc aacagggag  agtgt                    645
```

<210> SEQ ID NO 108
<211> LENGTH: 454
<212> TYPE: PRT
<213> ORGANISM: Artificial Sequence
<220> FEATURE:
<223> OTHER INFORMATION: antibody sequence

<400> SEQUENCE: 108

```
Gln Val Gln Leu Gln Glu Ser Gly Gly Gly Leu Val His Pro Gly Gly
1               5                   10                  15

Ser Leu Arg Leu Ser Cys Ala Ala Ser Gly Phe Thr Phe Ser Ser Tyr
            20                  25                  30

Trp Met His Trp Val Arg Gln Ala Pro Gly Lys Gly Leu Val Trp Val
        35                  40                  45

Ser Arg Ile Asn Ser Asp Gly Ser Ser Thr Ser Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Lys Ile Leu Gly Val Gly Ala Arg Ser Arg Tyr Phe Asp
            100                 105                 110

Tyr Trp Gly Gln Gly Thr Met Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Lys Val Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300
```

```
Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
            325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Asp Glu Leu Thr Lys Asn
            355                 360                 365

Gln Val Ser Leu Thr Cys Leu Val Lys Gly Phe Tyr Pro Ser Asp Ile
        370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly Lys
    450

<210> SEQ ID NO 109
<211> LENGTH: 215
<212> TYPE: PRT
<213> ORGANISM: Artificial Sequence
<220> FEATURE:
<223> OTHER INFORMATION: antibody sequence

<400> SEQUENCE: 109

Glu Thr Thr Leu Thr Gln Ser Pro Gly Thr Leu Ser Leu Ser Pro Gly
1               5                   10                  15

Glu Arg Ala Thr Leu Ser Cys Arg Ala Ser Gln Ser Val Val Ser Asn
            20                  25                  30

Tyr Leu Ala Trp Tyr Gln Gln Lys Pro Gly Gln Ala Pro Arg Leu Leu
        35                  40                  45

Ile Ser Gly Ala Ser Asn Arg Ala Thr Gly Ile Ser Asp Arg Phe Ser
    50                  55                  60

Gly Ser Gly Ser Gly Ala Asp Phe Thr Leu Thr Ile Ser Arg Val Glu
65                  70                  75                  80

Pro Glu Asp Ser Ala Val Tyr Tyr Cys Gln Gln Phe Asp Lys Ser Thr
                85                  90                  95

Trp Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
```

<210> SEQ ID NO 110
<211> LENGTH: 1353
<212> TYPE: DNA
<213> ORGANISM: Artificial Sequence
<220> FEATURE:
<223> OTHER INFORMATION: antibody sequence

<400> SEQUENCE: 110

```
caggtccagc ttgtgcagtc tggggctgag gtgaagaagc ctgggtcctc ggtgaaggtc      60
tcctgcaagg cttctggagg cacccttcagc agctatgcta tcagctgggt gcgacaggcc    120
cctggacaag ggcttgagtg gatgggaggg atcatcccta tctttggtac agcaaactac    180
gcacagaagt tccagggcag agtcacgatt accgcggacg aatccacgag cacagcctac    240
atggagctga ggagcctgag atctgacgac acggccgtgt attactgtgc gagagatcgg    300
gagagatggc tacaatccgc gggcgactac tggggccagg gaaccctggt cactgtctcc    360
tcagcctcca ccaagggccc atcggtcttc cccctggcac cctcctccaa gagcacctct    420
gggggcacag cggccctggg ctgcctggtc aaggactact tccccgaacc ggtgacggtg    480
tcgtggaact caggcgccct gaccagcggc gtgcacacct tcccggctgt cctacagtcc    540
tcaggactct actccctcag cagcgtggtg accgtgccct ccagcagctt gggcacccag    600
acctacatct gcaacgtgaa tcacaagccc agcaacacca aggtggacaa gaaagttgag    660
cccaaatctt gtgacaaaac tcacacatgc ccaccgtgcc cagcacctga actcctgggg    720
ggaccgtcag tcttcctctt ccccccaaaa cccaaggaca cctcatgat ctcccggacc     780
cctgaggtca catgcgtggt ggtggacgtg agccacgaag accctgaggt caagttcaac    840
tggtacgtgg acggcgtgga ggtgcataat gccaagacaa agccgcggga ggagcagtac    900
aacagcacgt accgtgtggt cagcgtcctc accgtcctgc accaggactg gctgaatggc    960
aaggagtaca agtgcaaggt ctccaacaaa gccctcccag cccccatcga gaaaaccatc   1020
tccaaagcca aagggcagcc ccgagaacca caggtgtaca ccctgccccc atcccgggat   1080
gagctgacca agaaccaggt cagcctgacc tgcctggtca aaggcttcta tcccagcgac   1140
atcgccgtgg agtgggagag caatgggcag ccggagaaca actacaagac cacgcctccc   1200
gtgctggact ccgacggctc cttcttcctc tacagcaagc tcaccgtgga caagagcagg   1260
tggcagcagg ggaacgtctt ctcatgctcc gtgatgcatg aggctctgca caaccactac   1320
acgcagaaga gcctctccct gtctccgggt aaa                                1353
```

<210> SEQ ID NO 111
<211> LENGTH: 642
<212> TYPE: DNA
<213> ORGANISM: Artificial Sequence
<220> FEATURE:
<223> OTHER INFORMATION: antibody sequence

<400> SEQUENCE: 111

```
cagcctgtgc tgactcagtc accctcgtg tcagtggccc caggacagac ggccaggatt       60
acctgtgggg gaaacaacat tggaagtaaa agtgtgcact ggtaccagca gaagccaggc    120
caggcccctg tgctggtcgt ctatgatgat agcgaccggc cctcagggat ccctgagcga    180
ttctctggct ccaactctgg gaacacggcc accctgacca tcagcagggt cgaagccggg    240
gatgaggccg actattactg tcaggtgtgg gatagtagta gtgatcattg ggtgttcggc    300
ggagggacca agctgaccgt cctaggtcag cccaaggctg ccccctcggt cactctgttc    360
```

```
ccgccctcct ctgaggagct tcaagccaac aaggccacac tggtgtgtct cataagtgac    420
ttctacccgg gagccgtgac agtggcctgg aaggcagata gcagcccgt caaggcggga     480 gtggagacca ccacaccctc caaacaaagc aacaacaagt acgcggccag cagctatctg    540
agcctgacgc ctgagcagtg gaagtcccac agaagctaca gctgccaggt cacgcatgaa    600
gggagcaccg tggagaagac agtggcccct acagaatgtt ca                       642
```

<210> SEQ ID NO 112
<211> LENGTH: 451
<212> TYPE: PRT
<213> ORGANISM: Artificial Sequence
<220> FEATURE:
<223> OTHER INFORMATION: antibody sequence

<400> SEQUENCE: 112

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Arg Glu Arg Trp Leu Gln Ser Ala Gly Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320
```

```
Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 113
<211> LENGTH: 214
<212> TYPE: PRT
<213> ORGANISM: Artificial Sequence
<220> FEATURE:
<223> OTHER INFORMATION: antibody sequence

<400> SEQUENCE: 113

Gln Pro Val Leu Thr Gln Ser Pro Ser Val Ser Val Ala Pro Gly Gln
1               5                   10                  15

Thr Ala Arg Ile Thr Cys Gly Gly Asn Asn Ile Gly Ser Lys Ser Val
            20                  25                  30

His Trp Tyr Gln Gln Lys Pro Gly Gln Ala Pro Val Leu Val Val Tyr
        35                  40                  45

Asp Asp Ser Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ser Asp His
                85                  90                  95

Trp Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
    210
```

```
<210> SEQ ID NO 114
<211> LENGTH: 1353
<212> TYPE: DNA
<213> ORGANISM: Artificial Sequence
<220> FEATURE:
<223> OTHER INFORMATION: antibody sequence

<400> SEQUENCE: 114
caggtccagc tggtacagtc tggggggaggc gtggtccagc ctgggaggtc cctgagactc      60
tcctgtgcag cctctggatt caccttcagt agctatggca tgcactgggt ccgccaggct     120
ccaggcaagg ggctggagtg ggtggcagtt atatcatatg atggaagtaa taaatactat     180
gcagactccg tgaagggccg attcaccatc tccagagaca attccaagaa cacgctgtat     240
ctgcaaatga acagcctgag agctgaggac acggctgtgt attactgtgc gaaagatctt     300
ccgattaccc gcgggacagg ggctgactac tggggccagg gaaccctggt cactgtctcc     360
tcagcctcca ccaagggccc atcggtcttc cccctggcac cctcctccaa gagcacctct     420
gggggcacag cggccctggg ctgcctggtc aaggactact tccccgaacc ggtgacggtg     480
tcgtggaact caggcgccct gaccagcggc gtgcacacct tcccggctgt cctacagtcc     540
tcaggactct actccctcag cagcgtggtg accgtgccct ccagcagctt gggcacccag     600
acctacatct gcaacgtgaa tcacaagccc agcaacacca aggtggacaa gaaagttgag     660
cccaaatctt gtgacaaaac tcacacatgc ccaccgtgcc cagcacctga actcctgggg     720
ggaccgtcag tcttcctctt ccccccaaaa cccaaggaca ccctcatgat ctcccggacc     780
cctgaggtca catgcgtggt ggtggacgtg agccacgaag accctgaggt caagttcaac     840
tggtacgtgg acggcgtgga ggtgcataat gccaagacaa agccgcggga ggagcagtac     900
aacagcacgt accgtgtggt cagcgtcctc accgtcctgc accaggactg gctgaatggc     960
aaggagtaca agtgcaaggt ctccaacaaa gccctcccag cccccatcga gaaaaccatc    1020
tccaaagcca aagggcagcc ccgagaacca caggtgtaca ccctgccccc atcccgggat    1080
gagctgacca agaaccaggt cagcctgacc tgcctggtca aaggcttcta tcccagcgac    1140
atcgccgtgg agtgggagag caatgggcag ccggagaaca actacaagac cacgcctccc    1200
gtgctggact ccgacggctc cttcttcctc tacagcaagc tcaccgtgga caagagcagg    1260
tggcagcagg ggaacgtctt ctcatgctcc gtgatgcatg aggctctgca caaccactac    1320
acgcagaaga gcctctccct gtctccgggt aaa                                  1353

<210> SEQ ID NO 115
<211> LENGTH: 648
<212> TYPE: DNA
<213> ORGANISM: Artificial Sequence
<220> FEATURE:
<223> OTHER INFORMATION: antibody sequence

<400> SEQUENCE: 115
cagtctgtcc tgattcagcc tgcctccgtg tctgggtctc ctggacagtc gatcaccatc      60
tcctgcactg gaaccagcag tgacgttggt ggttataact atgtctcctg gtatcaacaa     120
cacccaggca aagcccccag actcatgatt tacgatgtca ctagtcggcc ctcagggggtt    180 tcgaatcgct tctctggctc caagtctggc aacacggcct ccctgaccat ctctgggctc     240
caggctgagg acgaggctga ttattactgc agttcatatg caggcagcta cagcgtggta    300
ttcggcggag ggaccaaggt caccgtccta ggtcagccca aggctgcccc ctcggtcact     360
ctgttcccgc cctcctctga ggagcttcaa gccaacaagg ccacactggt gtgtctcata     420
agtgacttct acccgggagc cgtgacagtg gcctggaagg cagatagcag ccccgtcaag     480
```

```
gcgggagtgg agaccaccac accctccaaa caaagcaaca acaagtacgc ggccagcagc      540
tatctgagcc tgacgcctga gcagtggaag tcccacagaa gctacagctg ccaggtcacg      600
catgaaggga gcaccgtgga gaagacagtg gcccctacag aatgttca                   648
```

<210> SEQ ID NO 116
<211> LENGTH: 451
<212> TYPE: PRT
<213> ORGANISM: Artificial Sequence
<220> FEATURE:
<223> OTHER INFORMATION: antibody sequence

<400> SEQUENCE: 116

```
Gln Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Leu Pro Ile Thr Arg Gly Thr Gly Ala Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335
```

```
Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
            355                 360                 365

Leu Thr Cys Leu Val Lys Gly Phe Tyr Pro Ser Asp Ile Ala Val Glu
            370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
            405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly Lys
    450

<210> SEQ ID NO 117
<211> LENGTH: 216
<212> TYPE: PRT
<213> ORGANISM: Artificial Sequence
<220> FEATURE:
<223> OTHER INFORMATION: antibody sequence

<400> SEQUENCE: 117

Gln Ser Val Leu Ile Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Arg Leu
            35                  40                  45

Met Ile Tyr Asp Val Thr Ser Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Ala Gly Ser
                85                  90                  95

Tyr Ser Val Val Phe Gly Gly Gly Thr Lys Val Thr Val Leu Gly Gln
            100                 105                 110

Pro Lys Ala Ala Pro Ser Val Thr Leu Phe Pro Pro Ser Ser Glu Glu
            115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
            195                 200                 205

Thr Val Ala Pro Thr Glu Cys Ser
    210                 215

<210> SEQ ID NO 118
<211> LENGTH: 1371
<212> TYPE: DNA
```

<213> ORGANISM: Artificial Sequence
<220> FEATURE:
<223> OTHER INFORMATION: antibody sequence

<400> SEQUENCE: 118

```
caggtccagc ttgtgcagtc tggggctgag gtgaagaagc tggggcctc agtgaaggtc      60
tcctgcaagg cttctggata caccttcacc ggctactata tgcactgggt gcgacaggcc    120
cctggacaag gcttgagtg gatgggacgg atcaaccctta acagtggtgg cacaaactat    180
gcacagaagt ttcagggcag ggtcaccatg accagggaca cgtccatcag cacagcctac    240
atggagctga gcaggctgag atctgacgac acggccgtgt attactgcgc gaggcgtaac    300
ctgatagcag ctcgtccccg gaatcggggc agggatgctt ttgatatctg gggccaaggg    360
acaatggtca ccgtctcttc agcctccacc aagggcccat cggtcttccc cctggcaccc    420
tcctccaaga gcacctctgg gggcacagcg gccctgggct gcctggtcaa ggactacttc    480
cccgaaccgg tgacggtgtc gtggaactca ggcgccctga ccagcggcgt gcacaccttc    540
ccggctgtcc tacagtcctc aggactctac tccctcagca gcgtggtgac cgtgccctcc    600
agcagcttgg gcacccagac ctacatctgc aacgtgaatc acaagcccag caacaccaag    660
gtggacaaga agttgagcc caatcttgt gacaaaactc acacatgccc accgtgccca    720
gcacctgaac tcctgggggg accgtcagtc ttcctcttcc ccccaaaaccc caaggacacc    780
ctcatgatct cccggacccc tgaggtcaca tgcgtggtgg tggacgtgag ccacgaagac    840
cctgaggtca agttcaactg gtacgtggac ggcgtggagg tgcataatgc caagacaaag    900
ccgcgggagg agcagtacaa cagcacgtac cgtgtggtca gcgtcctcac cgtcctgcac    960
caggactggc tgaatggcaa ggagtacaag tgcaaggtct ccaacaaagc cctcccagcc   1020
cccatcgaga aaaccatctc caaagccaaa gggcagcccc gagaaccaca ggtgtacacc   1080
ctgccccat cccgggatga gctgaccaag aaccaggtca gcctgacctg cctggtcaaa   1140
ggcttctatc ccagcgacat cgccgtggag tgggagagca atgggcagcc ggagaacaac   1200
tacaagacca cgcctcccgt gctggactcc gacggctcct tcttcctcta cagcaagctc   1260
accgtggaca agagcaggtg gcagcagggg aacgtcttct catgctccgt gatgcatgag   1320
gctctgcaca accactacac gcagaagagc ctctccctgt ctccgggtaa a            1371
```

<210> SEQ ID NO 119
<211> LENGTH: 642
<212> TYPE: DNA
<213> ORGANISM: Artificial Sequence
<220> FEATURE:
<223> OTHER INFORMATION: antibody sequence

<400> SEQUENCE: 119

```
gacatccaga tgacccagtc tccttccacc ctgtctgcat ctgtaggaga cagagtcacc     60
atcacttgcc gggccagtca gagtattggt ggctcgttgg cctggtatca gcagaaacca    120
gggaaaggcc ctaacctcct gatctatgct gcatccactt tgcaaagtgg ggtcccatca    180
aggttcagcg gcagtggatc tgggacagaa ttcactctca caatcagcag cctgcagcct    240
gaagattctg caacttacta ctgccaacac tatgaaagtt atccccctctc tttcggcggc    300
gggaccaagc tggagatcaa acgaactgtg gctgcaccat ctgtcttcat cttcccgcca    360
tctgatgagc agttgaaatc tggaactgcc tctgttgtgt gcctgctgaa taacttctat    420
cccagagagg ccaaagtaca gtggaaggtg gataacgccc tccaatcggg taactcccag    480
gagagtgtca cagagcagga cagcaaggac agcacctaca gcctcagcag cacccctgacg    540
```

```
ctgagcaaag cagactacga gaaacacaaa gtctacgcct gcgaagtcac ccatcagggc    600
ctgagctcgc ccgtcacaaa gagcttcaac aggggagagt gt                       642
```

<210> SEQ ID NO 120
<211> LENGTH: 457
<212> TYPE: PRT
<213> ORGANISM: Artificial Sequence
<220> FEATURE:
<223> OTHER INFORMATION: antibody sequence

<400> SEQUENCE: 120

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Arg Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Arg Asn Leu Ile Ala Ala Arg Pro Arg Asn Arg Gly Arg Asp
            100                 105                 110

Ala Phe Asp Ile Trp Gly Gln Gly Thr Met Val Thr Val Ser Ser Ala
        115                 120                 125

Ser Thr Lys Gly Pro Ser Val Phe Pro Leu Ala Pro Ser Ser Lys Ser
    130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Leu Gly Thr Gln Thr Tyr
        195                 200                 205

Ile Cys Asn Val Asn His Lys Pro Ser Asn Thr Lys Val Asp Lys Lys
    210                 215                 220

Val Glu Pro Lys Ser Cys Asp Lys Thr His Thr Cys Pro Pro Cys Pro
225                 230                 235                 240

Ala Pro Glu Leu Leu Gly Gly Pro Ser Val Phe Leu Phe Pro Pro Lys
                245                 250                 255

Pro Lys Asp Thr Leu Met Ile Ser Arg Thr Pro Glu Val Thr Cys Val
            260                 265                 270

Val Val Asp Val Ser His Glu Asp Pro Glu Val Lys Phe Asn Trp Tyr
        275                 280                 285

Val Asp Gly Val Glu Val His Asn Ala Lys Thr Lys Pro Arg Glu Glu
    290                 295                 300

Gln Tyr Asn Ser Thr Tyr Arg Val Val Ser Val Leu Thr Val Leu His
305                 310                 315                 320

Gln Asp Trp Leu Asn Gly Lys Glu Tyr Lys Cys Lys Val Ser Asn Lys
                325                 330                 335

Ala Leu Pro Ala Pro Ile Glu Lys Thr Ile Ser Lys Ala Lys Gly Gln
            340                 345                 350
```

-continued

```
Pro Arg Glu Pro Gln Val Tyr Thr Leu Pro Pro Ser Arg Asp Glu Leu
        355                 360                 365

Thr Lys Asn Gln Val Ser Leu Thr Cys Leu Val Lys Gly Phe Tyr Pro
370                 375                 380

Ser Asp Ile Ala Val Glu Trp Glu Ser Asn Gly Gln Pro Glu Asn Asn
385                 390                 395                 400

Tyr Lys Thr Thr Pro Pro Val Leu Asp Ser Asp Gly Ser Phe Phe Leu
            405                 410                 415

Tyr Ser Lys Leu Thr Val Asp Lys Ser Arg Trp Gln Gln Gly Asn Val
            420                 425                 430

Phe Ser Cys Ser Val Met His Glu Ala Leu His Asn His Tyr Thr Gln
            435                 440                 445

Lys Ser Leu Ser Leu Ser Pro Gly Lys
    450                 455

<210> SEQ ID NO 121
<211> LENGTH: 214
<212> TYPE: PRT
<213> ORGANISM: Artificial Sequence
<220> FEATURE:
<223> OTHER INFORMATION: antibody sequence

<400> SEQUENCE: 121

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Gly Gly Ser
            20                  25                  30

Leu Ala Trp Tyr Gln Gln Lys Pro Gly Lys Pro Asn Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Ser Ala Thr Tyr Tyr Cys Gln His Tyr Glu Ser Tyr Pro Leu
                85                  90                  95

Ser Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 122
<211> LENGTH: 1362
<212> TYPE: DNA
<213> ORGANISM: Artificial Sequence
<220> FEATURE:
<223> OTHER INFORMATION: antibody sequence
```

<400> SEQUENCE: 122

```
caggtgcagc tgcaggagtc cgggggaggc ttagttcacc ctgggggtc cctgagactc       60
tcctgtgcag cctctggatt caccttcagt agctactgga tgcactgggt ccgccaagct      120
ccagggaagg ggctggtgtg ggtctcacgt attaatagtg atgggagtag cacaagctac      180
gcggactccg tgaagggccg attcaccatc tccagagaca acgccaagaa cacgctgtat      240
ctgcaaatga acagtctgag agccgaggac acggctgtgt attactgtgc gagaaaaatc      300
ttggggggtgg gagctaggtc tcgtcgttac tttgactact ggggccaggg aacaatggtc      360
accgtctctt cagcctccac caagggccca tcggtcttcc ccctggcacc ctcctccaag      420
agcacctctg gggcacagc ggccctgggc tgcctggtca aggactactt ccccgaaccg       480
gtgacggtgt cgtggaactc aggcgccctg accagcggcg tgcacacctt cccggctgtc      540
ctacagtcct caggactcta ctccctcagc agcgtggtga ccgtgccctc cagcagcttg      600
ggcacccaga cctacatctg caacgtgaat cacaagccca gcaacaccaa ggtggacaag      660
aaagttgagc ccaaatcttg tgacaaaact cacacatgcc caccgtgccc agcacctgaa      720
ctcctggggg gaccgtcagt cttcctcttc cccccaaaac ccaaggacac cctcatgatc      780
tcccggaccc ctgaggtcac atgcgtggtg gtggacgtga gccacgaaga ccctgaggtc      840
aagttcaact ggtacgtgga cggcgtggag gtgcataatg ccaagacaaa gccgcgggag      900
gagcagtaca acagcacgta ccgtgtggtc agcgtcctca ccgtcctgca ccaggactgg      960
ctgaatggca aggagtacaa gtgcaaggtc tccaacaaag ccctcccagc ccccatcgag     1020
aaaaccatct ccaaagccaa agggcagccc cgagaaccac aggtgtacac cctgccccca     1080
tcccgggatg agctgaccaa gaaccaggtc agcctgacct gcctggtcaa aggcttctat     1140
cccagcgaca tcgccgtgga gtgggagagc aatgggcagc cggagaacaa ctacaagacc     1200
acgcctcccg tgctggactc cgacggctcc ttcttcctct acagcaagct caccgtggac     1260
aagagcaggt ggcagcaggg gaacgtcttc tcatgctccg tgatgcatga ggctctgcac     1320
aaccactaca cgcagaagag cctctccctg tctccgggta aa                        1362
```

<210> SEQ ID NO 123
<211> LENGTH: 660
<212> TYPE: DNA
<213> ORGANISM: Artificial Sequence
<220> FEATURE:
<223> OTHER INFORMATION: antibody sequence

<400> SEQUENCE: 123

```
gatattgtgc tgacccagac tccagactcc ctggctgtgt ctctgggcga gacgaccacc       60
atcaactgca agtccagcca gagtgtttta cacactccaa acaataagaa ctacttagct      120
tggtaccagc agaaaccagg acagcctcct aagctgctca tttactgggc atctacccgg      180
gaatccgggg tccctgaccg attcagtggc agcgggtctg gacagattt cactctcacc       240
atcagcaacc tgcagcctga agatgtggct ttttactact gtctgcaata ttctactttt      300
cctcggacgt tcggccaagg gaccaaggtg gagatcaaac gaactgtggc tgcaccatct      360
gtcttcatct tcccgccatc tgatgagcag ttgaaatctg gaactgcctc tgttgtgtgc      420
ctgctgaata acttctatcc cagagaggcc aaagtacagt ggaaggtgga taacgccctc      480
caatcgggta actcccagga gagtgtcaca gagcaggaca gcaaggacag cacctacagc      540
ctcagcagca ccctgacgct gagcaaagca gactacgaga aacacaaagt ctacgcctgc      600
gaagtcaccc atcagggcct gagctcgccc gtcacaaaga gcttcaacag gggagagtgt      660
```

<210> SEQ ID NO 124
<211> LENGTH: 454
<212> TYPE: PRT
<213> ORGANISM: Artificial Sequence
<220> FEATURE:
<223> OTHER INFORMATION: antibody sequence

<400> SEQUENCE: 124

```
Gln Val Gln Leu Gln Glu Ser Gly Gly Gly Leu Val His Pro Gly Gly
1               5                   10                  15

Ser Leu Arg Leu Ser Cys Ala Ala Ser Gly Phe Thr Phe Ser Ser Tyr
            20                  25                  30

Trp Met His Trp Val Arg Gln Ala Pro Gly Lys Gly Leu Val Trp Val
        35                  40                  45

Ser Arg Ile Asn Ser Asp Gly Ser Ser Thr Ser Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Lys Ile Leu Gly Val Gly Ala Arg Ser Arg Arg Tyr Phe Asp
            100                 105                 110

Tyr Trp Gly Gln Gly Thr Met Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Lys Val Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Asp Glu Leu Thr Lys Asn
        355                 360                 365
```

```
Gln Val Ser Leu Thr Cys Leu Val Lys Gly Phe Tyr Pro Ser Asp Ile
        370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly Lys
    450

<210> SEQ ID NO 125
<211> LENGTH: 220
<212> TYPE: PRT
<213> ORGANISM: Artificial Sequence
<220> FEATURE:
<223> OTHER INFORMATION: antibody sequence

<400> SEQUENCE: 125

Asp Ile Val Leu Thr Gln Thr Pro Asp Ser Leu Ala Val Ser Leu Gly
1               5                   10                  15

Glu Thr Thr Thr Ile Asn Cys Lys Ser Ser Gln Ser Val Leu His Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Asn Leu Gln Pro Glu Asp Val Ala Phe Tyr Tyr Cys Leu Gln
                85                  90                  95

Tyr Ser Thr Phe Pro Arg Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 126
<211> LENGTH: 5
<212> TYPE: PRT
<213> ORGANISM: Artificial Sequence
<220> FEATURE:
<223> OTHER INFORMATION: antibody sequence
<220> FEATURE:
<221> NAME/KEY: Xaa
<222> LOCATION: (1)..(1)
```

```
<223> OTHER INFORMATION: Xaa can be S or G
<220> FEATURE:
<221> NAME/KEY: Xaa
<222> LOCATION: (3)..(3)
<223> OTHER INFORMATION: Xaa can be any amino acid, preferably G or W or
      Y or A, most preferably W
<220> FEATURE:
<221> NAME/KEY: Xaa
<222> LOCATION: (4)..(4)
<223> OTHER INFORMATION: Xaa can be M or I
<220> FEATURE:
<221> NAME/KEY: Xaa
<222> LOCATION: (5)..(5)
<223> OTHER INFORMATION: Xaa can be H or S

<400> SEQUENCE: 126

Xaa Tyr Xaa Xaa Xaa
1               5

<210> SEQ ID NO 127
<211> LENGTH: 5
<212> TYPE: PRT
<213> ORGANISM: Artificial Sequence
<220> FEATURE:
<223> OTHER INFORMATION: antibody sequence
<220> FEATURE:
<221> NAME/KEY: Xaa
<222> LOCATION: (1)..(1)
<223> OTHER INFORMATION: Xaa can be S or G, preferably S
<220> FEATURE:
<221> NAME/KEY: Xaa
<222> LOCATION: (3)..(3)
<223> OTHER INFORMATION: Xaa can be any amino acid, preferably G or W or
      Y or A, most preferably W.

<400> SEQUENCE: 127

Xaa Tyr Xaa Met His
1               5

<210> SEQ ID NO 128
<211> LENGTH: 5
<212> TYPE: PRT
<213> ORGANISM: Artificial Sequence
<220> FEATURE:
<223> OTHER INFORMATION: antibody sequence
<220> FEATURE:
<221> NAME/KEY: Xaa
<222> LOCATION: (3)..(3)
<223> OTHER INFORMATION: Xaa can be any amino acid, preferably G or W or
      Y or A, most preferably W

<400> SEQUENCE: 128

Ser Tyr Xaa Met His
1               5

<210> SEQ ID NO 129
<211> LENGTH: 17
<212> TYPE: PRT
<213> ORGANISM: Artificial Sequence
<220> FEATURE:
<223> OTHER INFORMATION: antibody sequence
<220> FEATURE:
<221> NAME/KEY: Xaa
<222> LOCATION: (1)..(1)
<223> OTHER INFORMATION: Xaa can be any amino acid
<220> FEATURE:
<221> NAME/KEY: Xaa
<222> LOCATION: (3)..(4)
<223> OTHER INFORMATION: Xaa can be any amino acid
<220> FEATURE:
<221> NAME/KEY: Xaa
<222> LOCATION: (8)..(10)
<223> OTHER INFORMATION: Xaa can be any amino acid
```

```
<400> SEQUENCE: 129

Xaa Ile Xaa Xaa Asp Gly Ser Xaa Xaa Xaa Tyr Ala Asp Ser Val Lys
1               5                   10                  15

Gly

<210> SEQ ID NO 130
<211> LENGTH: 17
<212> TYPE: PRT
<213> ORGANISM: Artificial Sequence
<220> FEATURE:
<223> OTHER INFORMATION: antibody sequence
<220> FEATURE:
<221> NAME/KEY: Xaa
<222> LOCATION: (1)..(1)
<223> OTHER INFORMATION: Xaa can be V or R
<220> FEATURE:
<221> NAME/KEY: Xaa
<222> LOCATION: (3)..(3)
<223> OTHER INFORMATION: Xaa can be S or N
<220> FEATURE:
<221> NAME/KEY: Xaa
<222> LOCATION: (4)..(4)
<223> OTHER INFORMATION: Xaa can be Y or S
<220> FEATURE:
<221> NAME/KEY: Xaa
<222> LOCATION: (8)..(8)
<223> OTHER INFORMATION: Xaa can be N or S
<220> FEATURE:
<221> NAME/KEY: Xaa
<222> LOCATION: (9)..(9)
<223> OTHER INFORMATION: Xaa can be K or T
<220> FEATURE:
<221> NAME/KEY: Xaa
<222> LOCATION: (10)..(10)
<223> OTHER INFORMATION: Xaa can be Y or S

<400> SEQUENCE: 130

Xaa Ile Xaa Xaa Asp Gly Ser Xaa Xaa Xaa Tyr Ala Asp Ser Val Lys
1               5                   10                  15

Gly

<210> SEQ ID NO 131
<211> LENGTH: 17
<212> TYPE: PRT
<213> ORGANISM: Artificial Sequence
<220> FEATURE:
<223> OTHER INFORMATION: antibody sequence
<220> FEATURE:
<221> NAME/KEY: Xaa
<222> LOCATION: (1)..(1)
<223> OTHER INFORMATION: Xaa can be any amino acid
<220> FEATURE:
<221> NAME/KEY: Xaa
<222> LOCATION: (3)..(3)
<223> OTHER INFORMATION: Xaa can be any amino acid
<220> FEATURE:
<221> NAME/KEY: Xaa
<222> LOCATION: (5)..(6)
<223> OTHER INFORMATION: Xaa can be any amino acid
<220> FEATURE:
<221> NAME/KEY: Xaa
<222> LOCATION: (8)..(9)
<223> OTHER INFORMATION: Xaa can be any amino acid

<400> SEQUENCE: 131

Xaa Ile Xaa Pro Xaa Xaa Gly Xaa Xaa Asn Tyr Ala Gln Lys Phe Gln
1               5                   10                  15

Gly

<210> SEQ ID NO 132
<211> LENGTH: 17
```

<212> TYPE: PRT
<213> ORGANISM: Artificial Sequence
<220> FEATURE:
<223> OTHER INFORMATION: antibody sequence
<220> FEATURE:
<221> NAME/KEY: Xaa
<222> LOCATION: (1)..(1)
<223> OTHER INFORMATION: Xaa can be R or G
<220> FEATURE:
<221> NAME/KEY: Xaa
<222> LOCATION: (3)..(3)
<223> OTHER INFORMATION: Xaa can be N or I
<220> FEATURE:
<221> NAME/KEY: Xaa
<222> LOCATION: (5)..(5)
<223> OTHER INFORMATION: Xaa can be N or I
<220> FEATURE:
<221> NAME/KEY: Xaa
<222> LOCATION: (6)..(6)
<223> OTHER INFORMATION: Xaa can be S or F
<220> FEATURE:
<221> NAME/KEY: Xaa
<222> LOCATION: (8)..(8)
<223> OTHER INFORMATION: Xaa can be G or T
<220> FEATURE:
<221> NAME/KEY: Xaa
<222> LOCATION: (9)..(9)
<223> OTHER INFORMATION: Xaa can be T or A

<400> SEQUENCE: 132

Xaa Ile Xaa Pro Xaa Xaa Gly Xaa Xaa Asn Tyr Ala Gln Lys Phe Gln
1               5                   10                  15

Gly

<210> SEQ ID NO 133
<211> LENGTH: 836
<212> TYPE: DNA
<213> ORGANISM: Artificial Sequence
<220> FEATURE:
<223> OTHER INFORMATION: antibody sequence

<400> SEQUENCE: 133
ccatggccca ggtgcagctg caggagtccg ggggaggctt agttcaccct ggggggtccc     60
tgagactctc ctgtgcagcc tctggattca ccttcagtag ctactggatg cactgggtcc    120
gccaagctcc agggaagggg ctggtgtggg tctcacgtat taatagtgat gggagtagca    180
caagctacgc ggactccgtg aagggccgat tcaccatctc cagagacaac gccaagaaca    240
cgctgtatct gcaaatgaac agtctgagag ccgaggacac ggctgtgtat tactgtgcga    300
gaaaaatctt gggggtggga gctaggtctc gtcgttactt tgactactgg ggccaggaa     360 caatggtcac cgtctcttca aagctttcag ggagtgcatc cgccccaaaa cttgaagaag    420
gtgaattttc agaagcacgc gtagaaacga cactcacgca gtctccaggc accctgtctt    480
tgtctccagg ggaaagagcc accctctcct gcagggccag tcagagtgtt gtcagcaact    540
atttagcctg gtaccagcag aagcctggcc aggctcccag gctcctcatc tctggtgcat    600
ccaacagggc cactggcatc tcagacaggt tcagtggcag tgggtctggg acagacttca    660
ctctcaccat cagcagagtc gagcctgaag actcagcagt gtattactgt caacagtttg    720
ataagtccac gtggacgttc ggccaaggga ccaaggtgga aatcaaagcg gccgctggat    780
ccgaacaaaa gctgatctca gaagaagacc taaactcaca tcaccatcac catcac       836

<210> SEQ ID NO 134
<211> LENGTH: 276
<212> TYPE: PRT
<213> ORGANISM: Artificial Sequence
<220> FEATURE:

<223> OTHER INFORMATION: antibody sequence

<400> SEQUENCE: 134

Gln Val Gln Leu Gln Glu Ser Gly Gly Gly Leu Val His Pro Gly Gly
1               5                   10                  15

Ser Leu Arg Leu Ser Cys Ala Ala Ser Gly Phe Thr Phe Ser Ser Tyr
            20                  25                  30

Trp Met His Trp Val Arg Gln Ala Pro Gly Lys Gly Leu Val Trp Val
        35                  40                  45

Ser Arg Ile Asn Ser Asp Gly Ser Ser Thr Ser Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Lys Ile Leu Gly Val Gly Ala Arg Ser Arg Tyr Phe Asp
            100                 105                 110

Tyr Trp Gly Gln Gly Thr Met Val Thr Val Ser Ser Lys Leu Ser Gly
        115                 120                 125

Ser Ala Ser Ala Pro Lys Leu Glu Glu Gly Glu Phe Ser Glu Ala Arg
    130                 135                 140

Val Glu Thr Thr Leu Thr Gln Ser Pro Gly Thr Leu Ser Leu Ser Pro
145                 150                 155                 160

Gly Glu Arg Ala Thr Leu Ser Cys Arg Ala Ser Gln Ser Val Val Ser
                165                 170                 175

Asn Tyr Leu Ala Trp Tyr Gln Gln Lys Pro Gly Gln Ala Pro Arg Leu
            180                 185                 190

Leu Ile Ser Gly Ala Ser Asn Arg Ala Thr Gly Ile Ser Asp Arg Phe
        195                 200                 205

Ser Gly Ser Gly Ser Gly Ala Asp Phe Thr Leu Thr Ile Ser Arg Val
    210                 215                 220

Glu Pro Glu Asp Ser Ala Val Tyr Tyr Cys Gln Gln Phe Asp Lys Ser
225                 230                 235                 240

Thr Trp Thr Phe Gly Gln Gly Thr Lys Val Glu Ile Lys Ala Ala Ala
                245                 250                 255

Gly Ser Glu Gln Lys Leu Ile Ser Glu Glu Asp Leu Asn Ser His His
            260                 265                 270

His His His His
        275

<210> SEQ ID NO 135
<211> LENGTH: 827
<212> TYPE: DNA
<213> ORGANISM: Artificial Sequence
<220> FEATURE:
<223> OTHER INFORMATION: antibody sequence

<400> SEQUENCE: 135
ccatggccca ggtccagctt gtgcagtctg ggctgaggt gaagaagcct gggtcctcgg      60
tgaaggtctc ctgcaaggct tctggaggca ccttcagcag ctatgctatc agctgggtgc     120
gacaggcccc tggacaaggg cttgagtgga tgggagggat catccctatc tttggtacag     180
caaactacgc acagaagttc cagggcagag tcacgattac cgcggacgaa tccacgagca     240
cagcctacat ggagctgagg agcctgagat ctgacgacac ggccgtgtat tactgtgcga     300
gagatcggga gagatggcta caatccgcgg gcgactactg gggccaggga accctggtca     360

-continued

```
ctgtctcctc aaagctttca gggagtgcat ccgccccaaa acttgaagaa ggtgaatttt    420
cagaagcacg cgtacagcct gtgctgactc agtcaccctc ggtgtcagtg gccccaggac    480
agacggccag gattacctgt gggggaaaca acattggaag taaaagtgtg cactggtacc    540
agcagaagcc aggccaggcc cctgtgctgg tcgtctatga tgatagcgac cggccctcag    600
ggatccctga gcgattctct ggctccaact ctgggaacac ggccaccctg accatcagca    660
gggtcgaagc cggggatgag gccgactatt actgtcaggt gtgggatagt agtagtgatc    720
attgggtgtt cggcggaggg accaagctga ccgtcctagc ggccgctgga tccgaacaaa    780
agctgatctc agaagaagac ctaaactcac atcaccatca ccatcac                  827
```

<210> SEQ ID NO 136
<211> LENGTH: 273
<212> TYPE: PRT
<213> ORGANISM: Artificial Sequence
<220> FEATURE:
<223> OTHER INFORMATION: antibody sequence

<400> SEQUENCE: 136

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Arg Glu Arg Trp Leu Gln Ser Ala Gly Asp Tyr Trp Gly
            100                 105                 110

Gln Gly Thr Leu Val Thr Val Ser Ser Lys Leu Ser Gly Ser Ala Ser
        115                 120                 125

Ala Pro Lys Leu Glu Glu Gly Glu Phe Ser Glu Ala Arg Val Gln Pro
    130                 135                 140

Val Leu Thr Gln Ser Pro Ser Val Ser Val Ala Pro Gly Gln Thr Ala
145                 150                 155                 160

Arg Ile Thr Cys Gly Gly Asn Asn Ile Gly Ser Lys Ser Val His Trp
                165                 170                 175

Tyr Gln Gln Lys Pro Gly Gln Ala Pro Val Leu Val Val Tyr Asp Asp
            180                 185                 190

Ser Asp Arg Pro Ser Gly Ile Pro Glu Arg Phe Ser Gly Ser Asn Ser
        195                 200                 205

Gly Asn Thr Ala Thr Leu Thr Ile Ser Arg Val Glu Ala Gly Asp Glu
    210                 215                 220

Ala Asp Tyr Tyr Cys Gln Val Trp Asp Ser Ser Ser Asp His Trp Val
225                 230                 235                 240

Phe Gly Gly Gly Thr Lys Leu Thr Val Leu Ala Ala Ala Gly Ser Glu
                245                 250                 255

Gln Lys Leu Ile Ser Glu Glu Asp Leu Asn Ser His His His His His
            260                 265                 270

His
```

<210> SEQ ID NO 137
<211> LENGTH: 833
<212> TYPE: DNA
<213> ORGANISM: Artificial Sequence
<220> FEATURE:
<223> OTHER INFORMATION: antibody sequence

<400> SEQUENCE: 137

```
ccatggccca ggtccagctg gtacagtctg ggggaggcgt ggtccagcct gggaggtccc      60
tgagactctc ctgtgcagcc tctggattca ccttcagtag ctatggcatg cactgggtcc     120
gccaggctcc aggcaagggg ctggagtggg tggcagttat atcatatgat ggaagtaata     180
aatactatgc agactccgtg aagggccgat tcaccatctc cagagacaat tccaagaaca     240
cgctgtatct gcaaatgaac agcctgagag ctgaggacac ggctgtgtat tactgtgcga     300
aagatcttcc gattacccgc gggacagggg ctgactactg gggccaggga accctggtca     360
ctgtctcctc aaagctttca gggagtgcat ccgccccaaa acttgaagaa ggtgaatttt     420
cagaagcacg cgtacagtct gtcctgattc agcctgcctc cgtgtctggg tctcctggac     480
agtcgatcac catctcctgc actggaacca gcagtgacgt tggtggttat aactatgtct     540
cctggtatca acaacaccca ggcaaagccc ccagactcat gatttacgat gtcactagtc     600
ggccctcagg ggtttcgaat cgcttctctg ctccaagtc tggcaacacg gcctccctga     660
ccatctctgg gctccaggct gaggacgagg ctgattatta ctgcagttca tatgcaggca     720
gctacagcgt ggtattcggc ggagggacca aggtcaccgt cctagcggcc gctggatccg     780
aacaaaagct gatctcagaa gaagacctaa actcacatca ccatcaccat cac            833
```

<210> SEQ ID NO 138
<211> LENGTH: 275
<212> TYPE: PRT
<213> ORGANISM: Artificial Sequence
<220> FEATURE:
<223> OTHER INFORMATION: antibody sequence

<400> SEQUENCE: 138

```
Gln Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Leu Pro Ile Thr Arg Gly Thr Gly Ala Asp Tyr Trp Gly
            100                 105                 110

Gln Gly Thr Leu Val Thr Val Ser Ser Lys Leu Ser Gly Ser Ala Ser
        115                 120                 125

Ala Pro Lys Leu Glu Glu Gly Glu Phe Ser Glu Ala Arg Val Gln Ser
    130                 135                 140

Val Leu Ile Gln Pro Ala Ser Val Ser Gly Ser Pro Gly Gln Ser Ile
145                 150                 155                 160

Thr Ile Ser Cys Thr Gly Thr Ser Ser Asp Val Gly Gly Tyr Asn Tyr
                165                 170                 175
```

```
Val Ser Trp Tyr Gln Gln His Pro Gly Lys Ala Pro Arg Leu Met Ile
            180                 185                 190

Tyr Asp Val Thr Ser Arg Pro Ser Gly Val Ser Asn Arg Phe Ser Gly
            195                 200                 205

Ser Lys Ser Gly Asn Thr Ala Ser Leu Thr Ile Ser Gly Leu Gln Ala
            210                 215                 220

Glu Asp Glu Ala Asp Tyr Tyr Cys Ser Ser Tyr Ala Gly Ser Tyr Ser
225                 230                 235                 240

Val Val Phe Gly Gly Gly Thr Lys Val Thr Val Leu Ala Ala Ala Gly
                245                 250                 255

Ser Glu Gln Lys Leu Ile Ser Glu Glu Asp Leu Asn Ser His His His
            260                 265                 270

His His His
        275

<210> SEQ ID NO 139
<211> LENGTH: 842
<212> TYPE: DNA
<213> ORGANISM: Artificial Sequence
<220> FEATURE:
<223> OTHER INFORMATION: antibody sequence

<400> SEQUENCE: 139
ccatggccca ggtccagctt gtgcagtctg gggctgaggt gaagaagcct ggggcctcag      60
tgaaggtctc ctgcaaggct tctggataca ccttcaccgg ctactatatg cactgggtgc     120
gacaggcccc tggacaaggg cttgagtgga tgggacggat caaccctaac agtggtggca     180
caaactatgc acagaagttt cagggcaggg tcaccatgac cagggacacg tccatcagca     240
cagcctacat ggagctgagc aggctgagat ctgacgacac ggccgtgtat tactgcgcga     300
ggcgtaacct gatagcagct cgtccccgga tcggggcag ggatgctttt gatatctggg      360
gccaagggac aatggtcacc gtctcttcaa gctttcagg gagtgcatcc gccccaaaac     420
ttgaagaagg tgaattttca gaagcacgcg tagacatcca gatgacccag tctccttcca     480
ccctgtctgc atctgtagga gacagagtca ccatcacttg ccgggccagt cagagtattg     540
gtggctcgtt ggcctggtat cagcagaaac cagggaaagg ccctaacctc ctgatctatg     600
ctgcatccac tttgcaaagt ggggtcccat caaggttcag cggcagtgga tctgggacag     660
aattcactct cacaatcagc agcctgcagc ctgaagattc tgcaacttac tactgccaac     720
actatgaaag ttatccctc tctttcggcg gcgggaccaa gctggagatc aaagcggccg     780
ctggatccga acaaaagctg atctcagaag aagacctaaa ctcacatcac catcaccatc     840
ac                                                                    842

<210> SEQ ID NO 140
<211> LENGTH: 278
<212> TYPE: PRT
<213> ORGANISM: Artificial Sequence
<220> FEATURE:
<223> OTHER INFORMATION: antibody sequence

<400> SEQUENCE: 140

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45
```

Gly Arg Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Arg Asn Leu Ile Ala Ala Arg Pro Arg Asn Arg Gly Arg Asp
            100                 105                 110

Ala Phe Asp Ile Trp Gly Gln Gly Thr Met Val Thr Val Ser Ser Lys
        115                 120                 125

Leu Ser Gly Ser Ala Ser Ala Pro Lys Leu Glu Glu Gly Glu Phe Ser
    130                 135                 140

Glu Ala Arg Val Asp Ile Gln Met Thr Gln Ser Pro Ser Thr Leu Ser
145                 150                 155                 160

Ala Ser Val Gly Asp Arg Val Thr Ile Thr Cys Arg Ala Ser Gln Ser
                165                 170                 175

Ile Gly Gly Ser Leu Ala Trp Tyr Gln Gln Lys Pro Gly Lys Gly Pro
            180                 185                 190

Asn Leu Leu Ile Tyr Ala Ala Ser Thr Leu Gln Ser Gly Val Pro Ser
        195                 200                 205

Arg Phe Ser Gly Ser Gly Ser Gly Thr Glu Phe Thr Leu Thr Ile Ser
    210                 215                 220

Ser Leu Gln Pro Glu Asp Ser Ala Thr Tyr Tyr Cys Gln His Tyr Glu
225                 230                 235                 240

Ser Tyr Pro Leu Ser Phe Gly Gly Thr Lys Leu Glu Ile Lys Ala
                245                 250                 255

Ala Ala Gly Ser Glu Gln Lys Leu Ile Ser Glu Glu Asp Leu Asn Ser
            260                 265                 270

His His His His His His
        275

<210> SEQ ID NO 141
<211> LENGTH: 851
<212> TYPE: DNA
<213> ORGANISM: Artificial Sequence
<220> FEATURE:
<223> OTHER INFORMATION: antibody sequence

<400> SEQUENCE: 141
ccatggccca ggtgcagctg caggagtccg ggggaggctt agttcaccct ggggggtccc        60
tgagactctc ctgtgcagcc tctggattca ccttcagtag ctactggatg cactgggtcc       120
gccaagctcc agggaagggg ctggtgtggg tctcacgtat taatagtgat gggagtagca       180
caagctacgc ggactccgtg aagggccgat tcaccatctc cagagacaac gccaagaaca       240
cgctgtatct gcaaatgaac agtctgagag ccgaggacac ggctgtgtat tactgtgcga       300
gaaaaatctt gggggtggga ctaggtctc gtcgttactt tgactactgg ggccagggaa       360
caatggtcac cgtctcttca aagctttcag ggagtgcatc cgccccaaaa cttgaagaag       420
gtgaattttc agaagcacgc gtagatattg tgctgaccca gactccagac tccctggctg       480
tgtctctggg cgagacgacc accatcaact gcaagtccag ccagagtgtt ttacacagct       540
ccaacaataa gaactactta gcttggtacc agcagaaacc aggacagcct cctaagctgc       600
tcatttactg ggcatctacc cgggaatccg ggtccctga ccgattcagt ggcagcgggt       660
ctgggacaga tttcactctc accatcagca acctgcagcc tgaagatgtg gcttttact       720 actgtctgca atattctact tttcctcgga cgttcggcca aggaccaag gtggagatca       780

```
aagcggccgc tggatccgaa caaaagctga tctcagaaga agacctaaac tcacatcacc    840
atcaccatca c                                                        851
```

<210> SEQ ID NO 142
<211> LENGTH: 281
<212> TYPE: PRT
<213> ORGANISM: Artificial Sequence
<220> FEATURE:
<223> OTHER INFORMATION: antibody sequence

<400> SEQUENCE: 142

```
Gln Val Gln Leu Gln Glu Ser Gly Gly Gly Leu Val His Pro Gly Gly
1               5                   10                  15

Ser Leu Arg Leu Ser Cys Ala Ala Ser Gly Phe Thr Phe Ser Ser Tyr
            20                  25                  30

Trp Met His Trp Val Arg Gln Ala Pro Gly Lys Gly Leu Val Trp Val
        35                  40                  45

Ser Arg Ile Asn Ser Asp Gly Ser Ser Thr Ser Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Lys Ile Leu Gly Val Gly Ala Arg Ser Arg Tyr Phe Asp
            100                 105                 110

Tyr Trp Gly Gln Gly Thr Met Val Thr Val Ser Ser Lys Leu Ser Gly
            115                 120                 125

Ser Ala Ser Ala Pro Lys Leu Glu Glu Gly Glu Phe Ser Glu Ala Arg
        130                 135                 140

Val Asp Ile Val Leu Thr Gln Thr Pro Asp Ser Leu Ala Val Ser Leu
145                 150                 155                 160

Gly Glu Thr Thr Thr Ile Asn Cys Lys Ser Ser Gln Ser Val Leu His
                165                 170                 175

Ser Ser Asn Asn Lys Asn Tyr Leu Ala Trp Tyr Gln Gln Lys Pro Gly
            180                 185                 190

Gln Pro Pro Lys Leu Leu Ile Tyr Trp Ala Ser Thr Arg Glu Ser Gly
        195                 200                 205

Val Pro Asp Arg Phe Ser Gly Ser Gly Ser Gly Thr Asp Phe Thr Leu
    210                 215                 220

Thr Ile Ser Asn Leu Gln Pro Glu Asp Val Ala Phe Tyr Tyr Cys Leu
225                 230                 235                 240

Gln Tyr Ser Thr Phe Pro Arg Thr Phe Gly Gln Gly Thr Lys Val Glu
                245                 250                 255

Ile Lys Ala Ala Ala Gly Ser Glu Gln Lys Leu Ile Ser Glu Glu Asp
            260                 265                 270

Leu Asn Ser His His His His His
            275                 280
```